(12) United States Patent
Platzek et al.

(10) Patent No.: US 6,818,203 B2
(45) Date of Patent: Nov. 16, 2004

(54) USE OF PERFLUOROALKYL-CONTAINING METAL COMPLEXES AS CONTRAST MEDIA IN MR-IMAGING FOR VISUALIZATION OF PLAQUE, TUMORS AND NECROSES

(75) Inventors: Johannes Platzek, Berlin (DE); Peter Mareski, Berlin (DE); Ulrich Niedballa, Berlin (DE); Bernd Raduechel, Berlin (DE); Hanns-Joachim Weinmann, Berlin (DE); Bernd Misselwitz, Glienicke (DE)

(73) Assignee: Schering Aktiengesellschaft, Berlin (DE)

( * ) Notice: Subject to any disclaimer, the term of this patent is extended or adjusted under 35 U.S.C. 154(b) by 23 days.

(21) Appl. No.: 09/925,618

(22) Filed: Aug. 10, 2001

(65) Prior Publication Data

US 2003/0072713 A1 Apr. 17, 2003

Related U.S. Application Data

(60) Provisional application No. 60/235,958, filed on Sep. 26, 2000.

(30) Foreign Application Priority Data

Aug. 11, 2000 (DE) .......................................... 100 40 380

(51) Int. Cl.$^7$ ................................................. A61B 5/055
(52) U.S. Cl. .................... 424/9.363; 424/9.3; 424/9.32; 424/9.323; 424/9.36; 424/9.364; 424/9.365
(58) Field of Search ................................ 424/9.3, 9.35, 424/9.36, 9.361, 9.363, 9.364, 9.365, 9.37, 9.32, 9.323; 600/420

(56) References Cited

U.S. PATENT DOCUMENTS 6,019,959 A  *  2/2000  Platzek et al. ............. 424/9.36
6,468,502 B1 * 10/2002  Platzek et al. ............. 424/1.65

FOREIGN PATENT DOCUMENTS

WO   WO-97/26017   *  7/1997
WO   WO-99/101161  *  1/1999

* cited by examiner

Primary Examiner—Michael G. Hartley
(74) Attorney, Agent, or Firm—Millen, White, Zelano & Branigan, P.C.

(57) ABSTRACT

The invention relates to the use of perfluoroalkyl-containing metal complexes that have a critical micelle formation concentration $<10^{-3}$ mol/l, a hydrodynamic micelle diameter (2 Rh)>1 nm and a proton relaxivity in plasma ($R^1$)>10 l/mmol·s) as contrast media in MR imaging for visualization of plaque, lymph nodes, infarcted and necrotic tissue and for independent visualization of necrotic tissue and tumor tissue.

35 Claims, 18 Drawing Sheets

24 h p. i. in vivo, axial    24 h p. i. post mortem, axial    24 h p. i. post mortem, coronar Metallkomplex XV, 200 µmol/kg i.v.; 3D-T1-MPRange, TR/TE 11.1/4.3 ms, α 15°; (Pfeil: Metastase; T: Tumor)

Metallkomplex XV, 200 µmol/kg i.v.; TR/TE 11.1/4.3 ms, α 15°; Primärtumor

[Key to Fig. 5:]

Metalkomplex = Metal complex

Pfeil: Metastase = Arrow: Metastasis

Primärtumor = Primary tumor

USE OF PERFLUOROALKYL-CONTAINING METAL COMPLEXES AS CONTRAST MEDIA IN MR-IMAGING FOR VISUALIZATION OF PLAQUE, TUMORS AND NECROSES

This application claims the benefit of Provisional Application No. 60/235,958 filed Sep. 26, 2000.

DESCRIPTION

The invention relates to the use of perfluoroalkyl-containing metal complexes that have a critical micelle formation concentration of <$10^{-3}$ mol/l, a hydrodynamic micelle diameter (2 Rh)>1 nm and a proton relaxivity in plasma ($R^1$)>10 l/mmol·s as contrast media in MR-imaging both for visualization of plaque, lymph nodes, infarcted and necrotic tissue and for independent visualization of necrotic tissue and tumor tissue. It has been shown that perfluoroalkyl-containing metal complexes with the above-mentioned properties are extremely well suited for the independent visualization of plaque, tumors and necroses with the aid of MR-imaging and simultaneously can also cover the diagnostically important area of infarction and necrosis imaging.

Arteriosclerosis is the most important and most frequent pathological alteration of arteries with hardening, thickening, loss of elasticity and lumen constriction. It represents the most frequent cause of death in Western industrialized countries. Vascular wall alterations are produced by lipid retention, connective tissue reproduction and calcification with irregular dispersion for wall instability, vascular stenosis and for storage of clots. Causes of disease are numerous exogenic and endogenic noxae or diseases, e.g., hypertonia, hyperlipidemia, hyperfibrinogenemia, diabetes mellitus, toxins, nicotine, antigen-antibody complexes, inflammations, hypoxia, mental stress, age and family stress. The latter result in the disruption of the integrity of the vascular inside wall, in the disruption of growth control of smooth muscle cells of the vascular wall and in impairing the degradation of aged cell components. Treatment of arteriosclerosis itself is not possible; the target of medical efforts is prevention by reducing risk factors, e.g., using lipid reducing agents.

The diagnosis of arteriosclerosis in clinical practice is currently carried out mainly by angiography as a gold standard. The limitation in all processes that are based on the measurement of the reduction of the vascular lumen is, however, the early stage of the disease, which is characterized by a thickening of the vascular wall in the case of a normal vascular lumen (Glagov, S., Zarins, C. K. Quantitating Atherosclerosis. In: Bond, M. G.; Insull, W.; Glagov, S.; Chandler, A. B.; Cornhill, J. F. (eds.). Clinical Diagnosis of Atherosclerosis. Quantitative Methods of Evaluation. New York: Springer-Verlag, 1983, 11–35). Another method for diagnostic assessment of vascular wall and vascular lumen is the intravascular or percutaneous ultrasound.

Magnetic nuclear spin resonance tomography (MRT) is a modem, non-invasive radiological process, which makes possible the visualization of physiological and pathophysiological structures with a very good space and time resolution. The use of specific contrast media with selective concentration in certain tissues and organs can increase the diagnostic value considerably in this case. Contrast medium preparations with selective concentration in arteriosclerotic plaque were able to detect location and degree of the disease at an early time and thus to make possible a targeted therapy and prophylaxis, and therefore the search for suitable contrast media began early.

Thus, hematoporphyrin derivatives are claimed in U.S. Pat. No. 4,577,636 as contrast media for the detection of atherosclerotic plaque. As methods, scintigraphy, radiography, fluorescence and, for paramagnetic metalloporphyrins, even NMR-spectrometry, are mentioned. As paramagnetic ions, Gd, Cr, Co, Ni, Ag and Eu are cited.

The disadvantage to these compounds is that the porphyrins are stored in the skin and cause discolorations that can last up to several weeks. Moreover, they result in a photosensitization. In addition, the danger exists that in a long retention time in vivo, the metalloporphyrin loses the metal.

In Application WO 95/09856, metalloporphyrins (deuteroporphyrins) are claimed for diagnosis and therapy of plaque. As a diagnostic method, MRI is mentioned. These porphyrins also cause discolorations of the skin. in Application WO 95/09013, conjugates that consist of specifically binding polypeptides and metal complexes are claimed. These compounds are also to bind to plaque and thus make possible their diagnosis and therapy. As diagnostic methods, scintigraphy, computer tomography, and MRI are mentioned. While scintigraphy is confirmed by experiment, data is lacking for MRI.

Labeled phycocyanines are claimed as contrast media for the imaging of plaque in U.S. Pat. No. 5,807,536. As diagnostic methods, radiography, computer tomography, scintigraphy, SPECT and MRI are mentioned here. Scintigraphy is confirmed by experiment.

Numerous contrast media for infarction and necrosis imaging are known from the literature. Tests were carried out early on to improve the localization of infarctions and necroses by use of contrast media in noninvasive processes such as scintigraphy or nuclear spin tomography. The literature devotes a great deal of space to attempts to use porphyrins for necrosis imaging. The results that are achieved paint a contradictory picture, however. Winkelman and Hoyes thus describe in Nature, 200, 903 (1967) that manganese-5,10,15,20-tetrakis(4-sulfonatophenyl)-porphyrin (TPPS) selectively accumulates in the necrotic portion of a tumor.

Lyon et al. (Magn. Res. Med. 4, 24 (1987)) observed, however, that manganese-TPPS is dispersed into the body, specifically into the kidney, liver, tumor and only in a small portion to the muscles. It is advantageous in this case that the concentration in the tumor reach its maximum only on the fourth day and also only after the authors have increased the dose from 0.12 mmol/kg to 0.2 mmol/kg. The authors therefore also speak of a non-specific uptake of TPPS in the tumor. Bockhurst et al. in turn report in Acta Neurochir 60, 347 (1994, Suppl.) that MnTPPS binds selectively to tumor cells.

Foster et al. (J. Nucl. Med. 26, 756 (1985)) in turn found that $^{111}$In-5,10,15,20-tetrakis-(4-N-methyl-pyridinium)-porphyrin (TMPyP) does not accumulate in the necrotic portion, but rather in the living edge areas. It follows from the above that a porphyrin-tissue interaction exists, is obvious but not necessary.

In Circulation Vol. 90, No. 4, part 2, page 1468, Abstract No. 2512 (1994), Ni et al. report that they can visualize infarction areas with a manganese-tetraphenyl-porphyrin (Mn-TPP) and a gadolinium-mesoporphyrin (Gd-MP). In International Patent Application WO 95/31219, both substances were used for infarction and necrosis imaging. The authors Marchal and Ni write (see Example 3) that for the compound Gd-MP, the metal content of the infarcted kidney was as high as that of the non-infarcted organ, but that for the myocardium in the infarcted tissue (Example 1), it was nine times as high. It was surprising that the ratio of the signal intensities during MRI for infarcted tissue in comparison to healthy tissue was comparatively high in both cases, at 2.10 or 2.19. Other metalloporphyrins were described in Application DE 19835082 (Schering AG).

Porphyrins tend to be stored in the skin, which results in photosensitization. The sensitization can last for days, and indeed even weeks. This is an undesirable side effect when using porphyrins as diagnostic agents. In addition, the therapeutic index for porphyrins is only very small, since, e.g., for Mn-TPPS, an action starts only at a dose of 0.2 mmol/kg, but the $LD_{50}$ is already approximately 0.5 mmol/kg.

Contrast media for necrosis and infarction imaging not derived from the porphyrin skeleton have been described in DE 19744003 (Schering AG), DE 19744004 (Schering AG) and WO 99/17809 (EPIX).

In DE 19744003, oligomeric compounds, which consist of a nucleus and are bonded to the 1–3 metal complexes, are claimed.

In Application 19744004, lipophilic metal complexes for necrosis and infarction imaging are claimed. These compounds include metal complexes of polyaminopolycarboxylic acids, polyaminopolyphosphonic acids, porphyrins, texaphyrins, sapphyrins, and peptides.

In EPIX-Application WO 99/17809, the use of DTPA derivatives for necrosis imaging is claimed. The most prominent compound is the gadolinium complex of a phosphodiester of hydroxymethyl-DTPA (MS-325).

Perfluoroalkyl-containing metal complexes are also known as contrast media for MR-imaging. WO 97/26017 (Schering) and WO 99/01161 (Schering) thus disclose the use of perfluoroalkyl-containing metal complexes as lymphographic agents. In addition, WO 99/01161 also describes the suitability of these compounds for visualizing the vascular space (blood-pool agents).

Contrast media were also described for the individual visualization of tumors and necroses using MR-imaging.

In EP 417870 A1, compounds for tumor diagnosis and therapy are disclosed. It is stated that infarctions and ischemias can also be visualized. An experimental confirmation of this information cannot be derived from the application, however. The claimed compounds are chelates of complexes of N2S2 and N3S types with radioisotopes. Scintigraphy is used as a diagnostic method.

In DE 19646762, scintigraphy is also used as a diagnostic method. In the publication, metal chelates are claimed as radiosensitizers for therapy of hypoxic tumors and for diagnosis of hypoxic conditions and necroses. In the descriptive part, NMR-diagnosis, x-ray diagnosis and radiodiagnosis are mentioned as diagnostic processes.

In German Application DE 19824653, porphyrins are claimed as necrosis-affine substances for the therapy of tumors. In the application, it is explained that the compounds are concentrated in the necrotic and hypoxic areas of the tumors. The compounds can be used for diagnostic purposes in the form of their metal derivatives with paramagnetic ions or radioisotopes.

It is common to both applications—DE 19646762 and DE 19824653—that the visualization of necroses and tumors does not take place independently of one another, but rather that the necrosis is part of the tumor.

The object of this invention was to make available contrast media for MR-imaging, which are suitable both for visualization of plaque, lymph nodes, infarcted and necrotic tissue and for independent visualization of necroses and tumors.

Surprisingly enough, it was now found that perfluoroalkyl-containing metal complexes, which have a critical micelle formation concentration of $<10^{-3}$ mol/l, a hydrodynamic micelle diameter (2 Rh)>1 nm and a proton relaxivity in plasma ($R^1$)>10 l/mmol·s, are very well suited as contrast media in MR imaging for visualization of plaque. In addition, these compounds can be used both for visualization of lymph nodes, infarcted and necrotic tissue and for independent visualization of necrotic tissue and tumor tissue.

Amphiphilic compounds, which have a perfluoroalkyl side chain in the molecule as a nonpolar portion that is optionally connected to the total molecule via a lipophilic linker, are defined as perfluoroalkyl-containing metal complexes that are suitable for use according to the invention. The polar portion of the compounds according to the invention is formed by one or more metal complexes and optionally other existing polar groups.

In aqueous systems, these amphiphilic molecules show the properties that are characteristic of standard surfactants (such as, e.g., sodium dodecylsulfate, SDS). They thus reduce the surface tension of water. By tensiometry, the so-called CMC (critical micelle formation concentration in mol/l) can be determined. In this respect, the surface tension is determined based on the concentration of the substance to be measured. The CMC can be calculated from the plot of the surface tension function (c) that is obtained. The critical micelle formation concentration of the compounds according to the invention must be $<10^{-3}$ mol/l, preferably $<10^{-4}$ mol/l.

The amphiphilic compounds according to the invention are combined in solution and are present as aggregates. The size (2 Rh) of such aggregates (e.g., micelles, rods, wafers, etc.) can be determined with the aid of photon-correction spectroscopy (PCS).

As a second criterion, the hydrodynamic micelle diameter 2 Rh, which must be >1 nm, is therefore used. Those perfluoroalkyl-containing metal complexes according to the invention whose 2 RH is $\geq 3$, quite especially preferably >4 nm, are especially suitable.

Both the determination of the CMC and the photon correlation spectroscopy are described in H.-D. Dörfler, "Grenzflächen- und Kolloidchemie [Interface and Colloid Chemistry]," Weinheim, New York, Basel, Cambridge, Tokyo, VSH 1994.

As a third criterion, the proton-relaxivity in plasma ($R^1$) at 40° C. and a field strength of 0.47 tesla is used. The relaxivity, which is indicated in [l/mmol·s], is the quantitative measurement for the shortening of relaxation time $T^1$ of the protons. For the purpose according to the invention, the relaxivity must be as high as possible and >10 l/mmol·s, preferably >13 l/mmol·s, especially preferably >15 l/mmol·s.

Relaxivity $R^1$ [l/mmol·s] of the MR-contrast media according to the invention was determined with the Minispec P 20 device of the Bruker Company. The measurements were taken at 40° C. and a field strength of 0.47 tesla. Eight measuring points were recorded by each T1-sequence: 180°-TI-90°, inversion recovery. As a medium, bovine plasma of the Kraeber Company was used. The contrast medium concentrations [mmol/l] in the batches were between 0.30 and 1.16.

In an embodiment of this invention, the compounds of general formula I according to claims 8 to 11 are used as preferred compounds. In this case, these are known compounds that are described in WO 97/26017. Their production can also be found in this WO publication. Surprisingly enough, it has been shown that these compounds are also very well suited as MRI-contrast media for visualization of plaque. As quite especially preferred compounds, metal complexes I–IV, VI and XI–XIII (cf. also Table 1) are used.

In another embodiment of this invention, those compounds of general formula Ia according to claims 12 to 21 are used as preferred compounds. These compounds are known and are described in WO 99/01161. Their use as MRI contrast media for visualization of plaque still had not been described to date. Of these compounds, quite especially preferably metal complex XIV (cf. Table 1) is used.

The present invention includes a method for MRI imaging comprising administering to a patient an MRI contrast agent, comprising a perfluoroalkyl-containing metal complex that has a critical micelle formation concentration $<10^{-3}$ mol/l, a hydrodynamic micelle diameter (2 Rh)>1 nm and a proton relaxivity in plasma ($R^1$)>10 l/mmol·s and conducting MRI imaging whereby plaque, or necrotic tissue are visualized or necroses and tumors are independently visualized.

In an embodiment the metal complex has a micelle formation concentration of $<10^{-4}$ mol/l.

In an embodiment the metal complex has a hydrodynamic micelle diameter of >3 nm.

In an embodiment the metal complex has a proton relaxivity in plasma of >13 l/mmol·s.

In an embodiment the perfluoroalkyl-containing metal complex is a compound of formula I $$R^F\text{—}L\text{—}K \qquad \text{I}$$

in which
$R^F$ is a perfluorinated, straight-chain or branched carbon chain with formula —$C_nF_{2n}E$, in which
E is a terminal fluorine, chlorine, bromine, iodine or hydrogen atom and n is a number from 4–30,
L is a direct bond, a methylene group, an —NHCO— group, a group

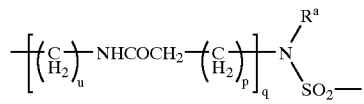

whereby p is a number from 0 to 10, and q and n, independently of one another, are 0 or 1, and $R^a$ is a hydrogen atom, a methyl group, a —$CH_2$—OH group, a —$CH_2$—$CO_2H$ group or a $C_2$-$C_{15}$ alkyl, which optionally is interrupted by 1 to 3 oxygen atoms, 1 to 2 CO groups or an optionally substituted aryl group and/or is substituted with 1 to 4 hydroxyl groups, 1 to 2 $C_1$-$C_4$ alkoxy groups, 1 to 2 carboxy groups, or a group —$SO_3H$, or
L is a straight-chain, branched, saturated or unsaturated $C_2$-$C_{30}$ carbon chain, which optionally contains 1 to 10 oxygen atoms, 1 to 3 —$NR^a$ groups, 1 to 2 sulfur atoms, a piperazine group, a —$CONR^a$ group, an —$NR^aCO$ group, an —$SO_2$ group, an —$NR^a$—$CO_2$ group, 1 to 2 CO groups, a group —CO—N—T—N($R^a$)—$SO_2$—$R^F$, or 1 to 2 optionally substituted aryls and/or is interrupted by these groups and/or is optionally substituted with 1 to 3 —$OR^a$ groups, 1 to 2 oxo groups, 1 to 2 —NH—$COR^a$ groups, 1 to 2 —$CONHR^a$ groups, 1 to 2 —$(CH_2)_p$—$CO_2H$ groups, 1 to 2 groups —$(CH_2)_p$—$(O)_q$—$CH_2CH_2$—$R^F$, whereby
$R^a$, $R^F$ and p and q have the above-indicated meanings, and T is a $C_2$-$C_{10}$ chain, which optionally is interrupted by 1 to 2 oxygen atoms or 1 to 2 —NHCO groups, K is a complexing agent or metal complex of formula II

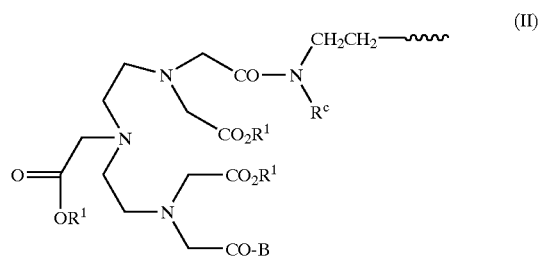

in which $R^c$, $R^1$ and B are independent of one another, and $R^c$ is $R^a$ or is —$(CH_2)$m-L—$R^F$, whereby m is 0, 1 or 2, and L and $R^F$ have the above-mentioned meaning, $R^1$, independently of one another, is a hydrogen atom or a metal ion equivalent of atomic numbers 22–29, 42–46 or 58–70, B is —$OR^1$,

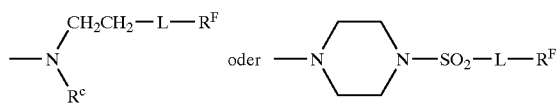

whereby $R^1$, L, $R^F$ and $R^c$ have the above-mentioned meanings, or

K is a complexing agent or complex of formula III

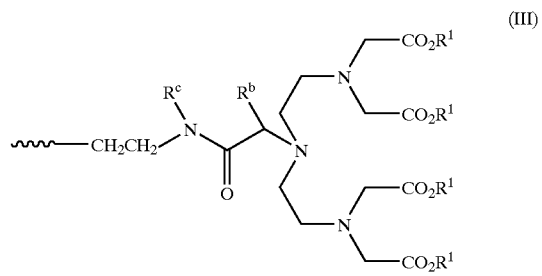

in which $R^c$ and $R^1$ have the above-mentioned meanings and $R^b$ has the meaning of $R^a$ or K is a complexing agent or complex of formula IV

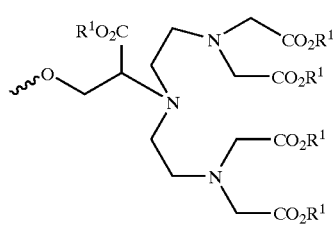

in which R¹ has the above-mentioned meaning
or
K is a complexing agent or complex of formula V

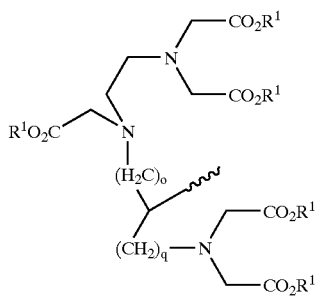

in which R¹ has the above-mentioned meaning, and o and q stand for numbers 0 or 1, and yields the sum o+q=1,
or
K is a complexing agent or complex of formula VI

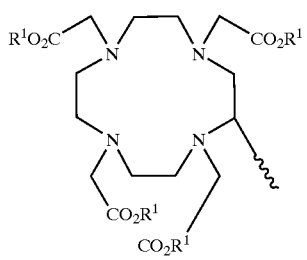

in which R¹ has the above-mentioned meaning or
K is a complexing agent or complex of formula VII

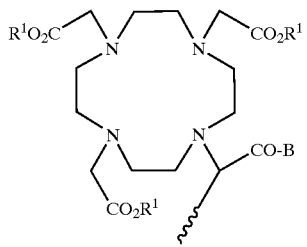

in which R¹ and B have the above-mentioned meanings
or

K is a complexing agent or complex of formula VIII

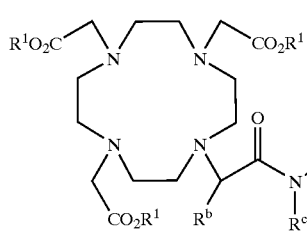

in which $R^c$ and $R^1$ have the above-mentioned meanings, and $R^b$ is $R^a$
or
K is a complexing agent or complex of formula IX

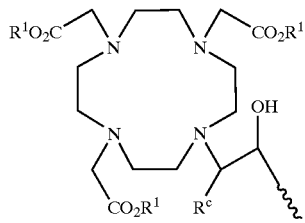

in which $R^c$ and $R^1$ have the above-mentioned meanings,
or

K is a complexing agent or complex of formula X

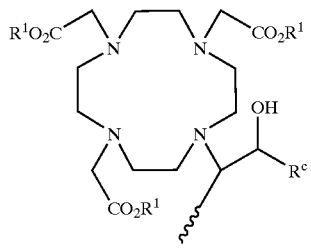

in which $R^c$ and $R^1$ have the above-mentioned meanings,
or
K is a complexing agent or complex of formula XI

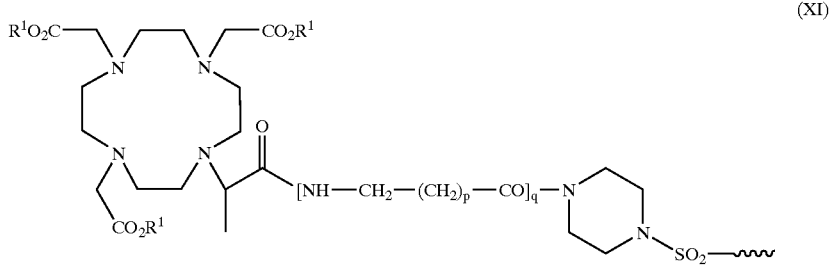

(XI)

in which $R^1$, p and q have the above-mentioned meanings,
and $R^b$ has the meaning of $R^a$,
or
K is a complexing agent or complex of formula XII

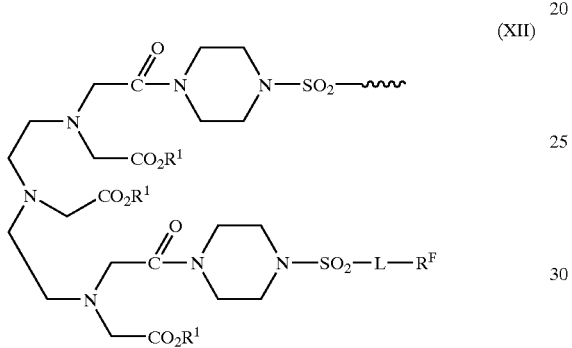

(XII)

in which L, $R^F$ and $Z^1$ have the above-mentioned meanings,
or
K is a complexing agent or complex of formula XIII

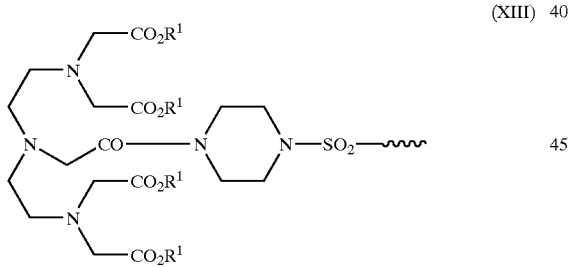

(XIII)

in which $R^1$ has the above-mentioned meaning, or
K is a salt of one of the complexing agents or complexes of fomula II to XIII with an organic and/or inorganic base or amino acid or amino acid amide.

In an embodiment the compound of formula I, is a compound in which

L is
α-$CH_2$-β
α-$CH_2CH_2$-β
α-$(CH_2)_s$-β s=3–15
α-$CH_2$—O—$CH_2CH_2$-β
α-$CH_2$—(O—$CH_2$—$CH_2$—)$_t$-β t=2–6
α-$CH_2$—NH—CO-β
α-$CH_2$—NH—CO—$CH_2$—N($CH_2COOH$)—$SO_2$-β
α-$CH_2$—NH—CO—$CH_2$—N($C_2H_5$)—$SO_2$-β
α-$CH_2$—NH—CO—$CH_2$—N($C_{10}H_{21}$)—$SO_2$-β
α-$CH_2$—NH—CO—$CH_2$—N($C_6H_{13}$)—$SO_2$-β
α-$CH_2$—NH—CO—$(CH_2)_{10}$—N($C_2H_5$)—$SO_2$-β
α-$CH_2$—NH—CO—$CH_2$—N(—$CH_2$—$C_6H_5$)—$SO_2$-β
α-$CH_2$—NH—CO—$CH_2$—N(—$CH_2$—$CH_2$—OH)$SO_2$-β
α-$CH_2$—NHCO—$(CH_2)_{10}$—S—$CH_2CH_2$-β
α-$CH_2NHCOCH_2$—O—$CH_2CH_2$-β
α-$CH_2NHCO(CH_2)_{10}$—O—$CH_2CH_2$-β
α-$CH_2$—$C_6H_4$—O—$CH_2CH_2$-β
α-$CH_2$—O—$CH_2$—C($CH_2$—$OCH_2CH_2$—$C_6F_{13}$)$_2$—$CH_2$—$OCH_2$—$CH_2$-β
α-$CH_2$—NHCO$CH_2CH_2$CON—$CH_2CH_2NHCOCH_2N(C_2H_5)SO_2C_8F_{17}CH_2$—$CH_2NHCOCH_2N(C_2H_5)$—$SO_2$-β
α-$CH_2O$—$CH_2$—CH($OC_{10}H_{21}$)—$CH_2$—O—$CH_2CH_2$-β
α-$(CH_2NHCO)_4$—$CH_2O$—$CH_2CH_2$-β
α-$(CH_2NHCO)_3$—$CH_2O$—$CH_2CH_2$-β
α-$CH_2$—$OCH_2C(CH_2OH)_2$—$CH_2$—O—$CH_2CH_2$-β

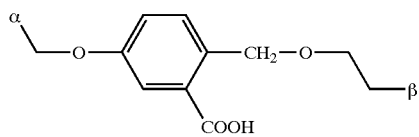

α-$CH_2NHCOCH_2N(C_6H_5)$—$SO_2$-β
α-NHCO—$CH_2$—$CH_2$-β
α-NHCO—$CH_2$—O—$CH_2CH_2$-β
α-NH—CO-β
α-NH—CO—$CH_2$—N($CH_2COOH$)—$SO_2$-β
α-NH—CO—$CH_2$—N($C_2H_5$)—$SO_2$-β
α-NH—CO—$CH_2$—N($C_{10}H_{21}$)—$SO_2$-β
α-NH—CO—$CH_2$—N($C_6H_{13}$)—$SO_2$-β
α-NH—CO—$(CH_2)_{10}$—N($C_2H_5$)—$SO_2$-β
α-NH—CO—$CH_2$—N(—$CH_2$-$C_6H_5$)—$SO_2$-β
α-NH—CO—$CH_2$—N(—$CH_2$—$CH_2$—OH)$SO_2$-β
α-NH—CO—$CH_2$-β
α-$CH_2$—O—$C_6H_4$—O—$CH_2$—$CH_2$-β
α-$CH_2$—$C_6H_4$—O—$CH_2$—$CH_2$-β
α-N($C_2H_5$)—$SO_2$-β
α-N($C_6H_5$)—$SO_2$-β
α-N($C_{10}H_{21}$)—$SO_2$-β
α-N($C_6H_{13}$)—$SO_2$-β
α-N($C_2H_4OH$)—$SO_2$-β
α-N($CH_2COOH$)—$SO_2$-β
α-N($CH_2C_6H_5$)—$SO_2$-β
α-N-[$CH(CH_2OH)_2$]—$SO_2$-β or
α-N-[$CH(CH_2OH)CH(CH_2OH)$]—$SO_2$-β, in which α is the binding site to the complexing agent or metal complex K, and β is the binding site to the fluorine radical.

In an embodiment the compound of formula I, is a compound in which n in formula —$C_nF_{2n}E$ is a number from 4–15 and/or E is a fluorine atom.

Also preferred are the following compounds of formula I:

Gadolinium complex of 10-[1-methyl-2-oxo-3-aza-5-oxo-{4-perfluorooctylsulfonyl-piperazin-1-yl}-pentyl]-1,4,7-tris(carboxymethyl)-1,4,7,10-tetraazacyclododecane, Gadolinium complex of 10-[2-hydroxy-4-aza-5-oxo-7-oxa-10,10,11,11,12,12,13,13,14,14,15,15,16,16,17,17-heptadecafluoroheptadecyl]-1,4,7-tris(carboxymethyl)-1,4,7,10-tetraazacyclododecane, Gadolinium complex of 10-[2-hydroxy-4-aza-5,9-dioxo-9-{4-perfluorooctyl)-piperazin-1-yl}-nonyl]-1,4,7-tris(carboxymethyl)-1,4,7,10-tetraazacyclododecane, Gadolinium complex of 10-[2-hydroxy-4-aza-5-oxo-7-aza-7-(perfluorooctylsulfonyl)-nonyl]-1,4,7-tris(carboxymethyl)-1,4,7,10-tetraazacyclododecane, Gadolinium complex of 10-[2-hydroxy-4-oxa-1H,1H,2H,3H,3H,5H,5H,6H,6H-perfluorotetradecyl]-1,4,7-tris(carboxymethyl)-1,4,7,10-tetraazacyclododecane, Gadolinium complex of 10-[2-hydroxy-4-aza-5-oxo-7-oxa-10,10,11,11,12,12,13,13,14,14,15,15,–16,16,17,17,18,18,19,19-henicosafluorononadecyl]-1,4,7-tris(carboxymethyl)-1,4,7,10-tetraazacyclododecane, Gadolinium complex of 10-[2-hydroxy-4-aza-5-oxo-11-aza-11-(perfluorooctylsulfonyl)-tridecyl]-1,4,7-tris(carboxymethyl)-1,4,7,10-tetraazacyclododecane, or Gadolinium complex of 10-[2-hydroxy-4-aza-5-oxo-7-aza-7-(perfluorooctylsulfonyl)-8-phenyl-octyl]-1,4,7-tris(carboxymethyl)-1,4,7,10-tetraaza-cyclododecane.

In an embodiment the perfluoroalkyl-containing metal complex, is a compound of formula Ia

A—$R^F$             (Ia)

in which

A is a group that contains 2 to 6 metal complexes, which are bonded directly or via a linker to a nitrogen atom of an annular skeleton chain, and $R^F$ is a perfluorinated, straight-chain or branched carbon chain with formula —$C_nF_{2n}E$, in which E is a terminal fluorine, chlorine, bromine, iodine or hydrogen atom, and n is a number from 4–30, whereby A has the following structure:

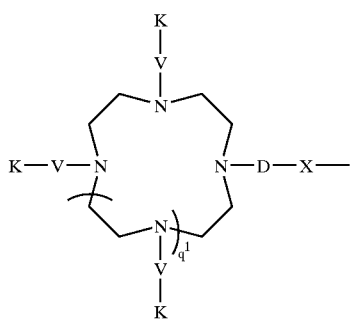

whereby $q^1$ is 0, 1, 2 or 3,

K is a complexing agent or metal complex or a salts thereof with an organic and/or inorganic base or amino acid or amino acid amide, X as the point of attachment to $R^F$, is a direct bond, a phenylene group or a $C_1$–$C_{10}$ alkylene chain, which optionally contains 1–15 oxygen atoms, 1–5 sulfur atoms, 1–10 carbonyl groups, 10—10 ($NR^d$) groups, 1–2 $NR^dSO_2$ groups, 1–10 $CONR^d$ groups, 1 piperidine group, 1–3 $SO_2$ groups and/or 1–2 phenylene groups or optionally is substituted by 1–3 radicals $R^F$, in which $R^d$ is a hydrogen atom, a phenyl group, benzyl group or a $C_1$–$C_{15}$ alkyl group, which optionally contains 1–2 NHCO, 1–2 CO groups, 1–5 oxygen atoms and optionally is substituted by 1–5 hydroxy, 1–5 methoxy, 1–3 carboxy, or 1–3 $R^F$ radicals, V is a direct bond or a chain of formula IIa or IIIa:

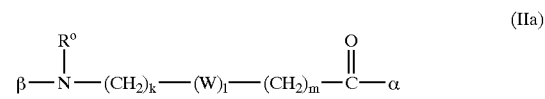

(IIa)

(IIIa)

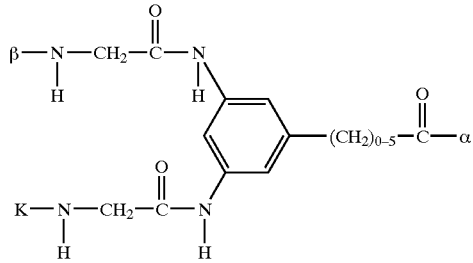

in which $R^e$ is a hydrogen atom, a phenyl group, a benzyl group or a $C_1$–$C_7$ alkyl group, which optionally is substituted with a carboxy group, a methoxy group or a hydroxy group, W is a direct bond, a polyglycol ether group with up to 5 glycol units, or a group of formula IVa —CH($R^h$)—            (IVa)

in which $R^h$ is a $C_1$–$C_7$ carboxylic acid, a phenyl group, a benzyl group or a —$(CH_2)_{1-5}$—NH—K group, α is the binding to the nitrogen atom of the skeleton chain, β is the binding to complexing agent or metal complex K, and in which variables k and m stand for natural numbers between 0 and 10, and I is 0 or 1 and whereby

D is a CO or $SO_2$ group.

Also preferred are compounds of formula Ia in which $q^1$ is the number 1.

In an embodiment the compound of formula Ia is a compound in which X is an alkylene chain, which contains 1–10 —$CH_2CH_2O$— groups or 1–5 —$COCH_2NH$— groups, a direct bond or one of the following structures

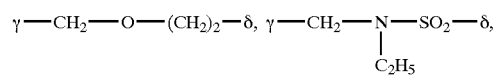

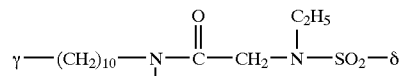

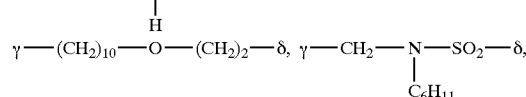

-continued

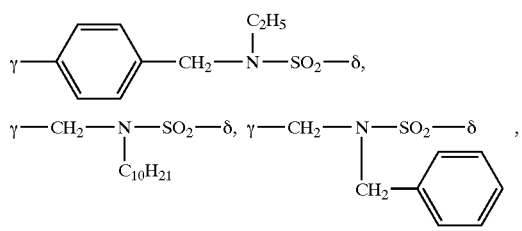

whereby

γ binds to D, and δ binds to $R^F$.

In an embodiment the compound of formula Ia, is a compound in which V is a group with one of the following structures

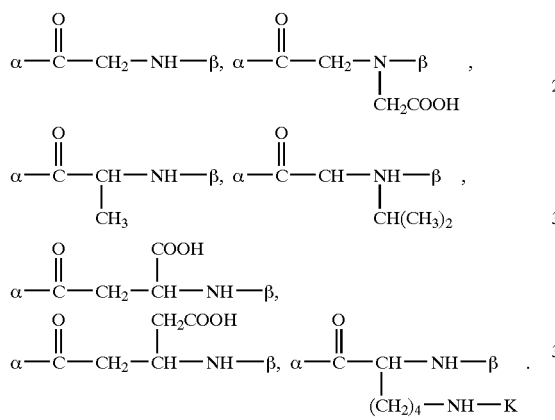

In an embodiment the compound of formula Ia, is a compound in which K is a complexing agent or complex of formula Va, VIa, VIIa or VIIIa, (Va)

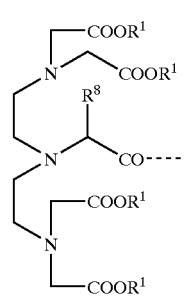

(VIa)

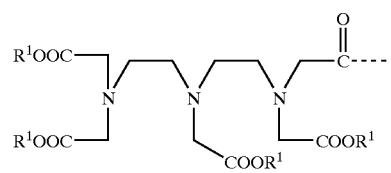

(VIIa)

(VIIIa)

whereby $R^1$, independently of one another, are a hydrogen atom or a metal ion equivalent of the elements of atomic numbers 23–29, 42–46 or 58–70, $R^8$ is a hydrogen atom or a straight-chain, branched, saturated or unsaturated $C_1$–$C_{30}$ alkyl chain, which optionally is substituted by 1–5 hydroxy, 1–3 carboxy or 1 phenyl group(s) and/or optionally is interrupted by 1–10 oxygen atoms, 1 phenylene group or 1 phenylenoxy group, $R^6$ are independently a hydrogen atom, a straight-chain or branched $C_1$–$C_7$ alkyl radical, a phenyl radical or benzyl radical, $R^7$ is a hydrogen atom, a methyl group or ethyl group, which optionally is substituted by a hydroxy group or carboxy group, $U^3$ is a straight-chain, branched, saturated or unsaturated $C_1$–$C_{20}$ alkylene group optionally containing 1–5 imino groups, 1–3 phenylene groups, 1–3 phenylenoxy groups, 1–3 phenylenimino groups, 1–5 amide groups, 1–2 hydrazide groups, 1–5 carbonyl groups, 1–5 ethylenoxy groups, 1 urea group, 1 thiourea group, 1–2 carboxyalkylimino groups, 1–2 ester groups, 1-1-0 oxygen atoms, 1–5 sulfur atoms and/or 1–5 nitrogen atoms, and/or optionally substituted by 1–5 hydroxy groups, 1–2 mercapto groups, 1–5 oxo groups, 1–5 thioxo groups, 1–3 carboxy groups, 1–5 carboxyalkyl groups, 1–5 ester groups and/or 1–3 amino groups, whereby the optionally contained phenylene groups can be substituted by 1–2 carboxy groups, 1–2 sulfone groups or 1–2 hydroxy groups $T^1$ is a —CO-β, —NHCO-β or —NHCS-β group, whereby β is the binding site to V.

In an embodiment the compound of formula Ia is a $C_1$–$C_{20}$ alkylene chain that is $U^3$ contains the group —$CH_2NHCO$—, —$NHCOCH_2O$—, —$NHCOCH_2OC_6H_4$—, —$N(CH_2CO_2H)$—, —$CH_2OCH_2$—, —$NHCOCH_2C_6H_4$—, —$NHCSNHC_6H_4$—, —$CH_2OC_6H_4$—, or —$CH_2CH_2O$— and/or is substituted by the group —COOH and/or —$CH_2COOH$.

In an embodiment the compound of formula Ia, $U^3$ is a —$CH_2$—, —$CH_2CH_2$—, —$CH_2CH_2CH_2$—, —$C_6H_4$—, —$C_6H_{10}$—, —$CH_2C_6H_4$—, —$CH_2NHCOCH_2CH(CH_2CO_2H)$—$C_6H_4$—, —$CH_2NHCOCH_2OCH_2$—, or —$CH_2NHCOCH_2C_6H_4$— group, In an embodiment the compound of formula Ia, is a compound in which K has one of the following structures:

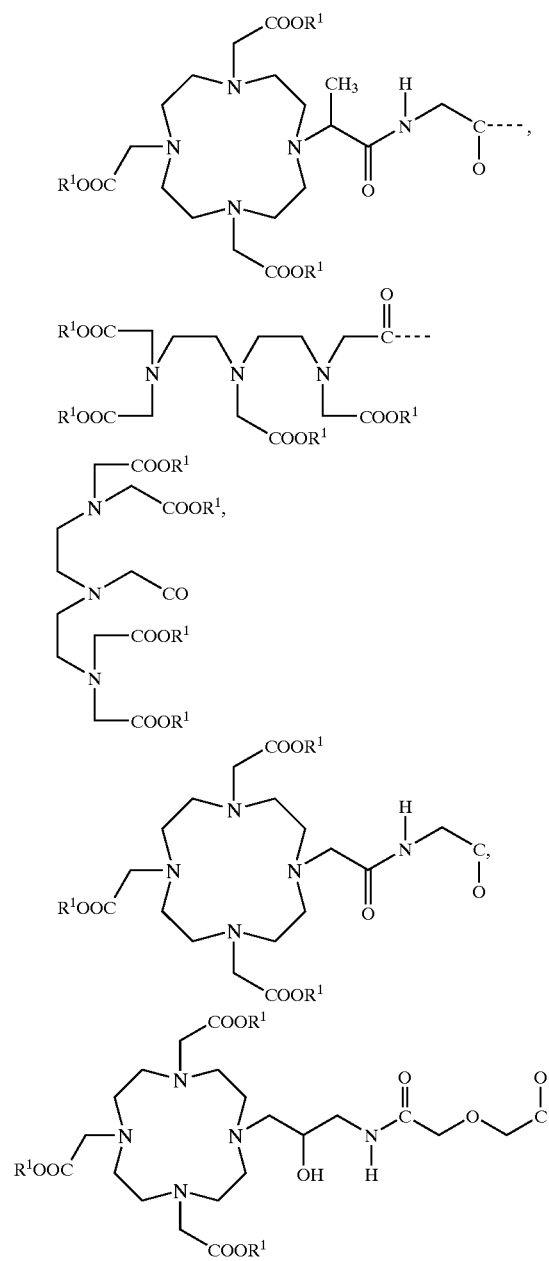

In an embodiment the compound of formula Ia is a compound in which the perfluoroalkyl chain is $R^F$ is $-C_6F_{13}$, $-C_8F_{17}$, $-C_{10}F_{21}$ or $-C_{12}F_{25}$.

In an embodiment the compound of formula Ia is 1,4,7-tris{1,4,7-tris(N-(carboxylatomethyl)-10-[N-1-methyl-3,6-diaza-2,5,8-trioxooctane-1,8-diyl)]-1,4,7,10-tetraazacyclododecane, Gd complex}-10-[N-2H,2H,4H,4H,5H,5H-3-oxa-perfluorotridecanoyl]-1,4,7,10-tetraazacyclododecane.

In an embodiment the metal complex has a hydrodynamic micelle diameter of >4 nm.

In an embodiment the metal complex has a proton relaxivity in plasma of >15 l/mmol·s.

In an embodiment the perfluoroalkyl-containing metal complex is in a galenical formulation that contains a paramagnetic, perfluoroalkyl-containing metal complex of formula Ia and diamagnetic perfluoroalkyl-containing substance, optionally dissolved in an aqueous solvent.

In an embodiment the perfluoroalkyl-containing metal complex is in a galenical formulations that contains a paramagnetic, perfluoroalkyl-containing metal complex of formula Ib, and a diamagnetic perfluoroalkyl-containing substance, optionally dissolved in an aqueous solvent.

In another preferred embodiment of the invention, the macrocyclic perfluoroalkyl compounds of general formula Ib

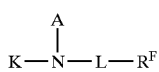

(Ib)

in which
K means a complexing agent or a metal complex of general formula IIb

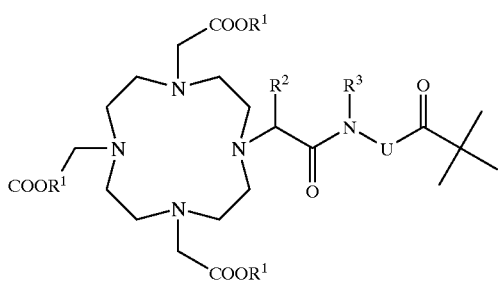

(IIb)

whereby
$R^1$ stands for a hydrogen atom or a metal ion equivalent of atomic numbers 23–29, 42–46 or 58–70,
$R^2$ and $R^3$ stand for a hydrogen atom, a $C_1$–$C_7$ alkyl group, a benzyl group, a phenyl group, —$CH_2OH$ or —$CH_2$—$OCH_3$, and
$U^2$ stands for radical $L^1$, whereby $L^1$ and $U^2$, independently of one another, can be the same or different,
$A^1$ means a hydrogen atom, a straight-chain or branched $C_1$–$C_{30}$-alkyl group, which optionally is interrupted by 1–15 oxygen atoms, and/or optionally is substituted with 1–10 hydroxy groups, 1–2 COOH groups, a phenyl group, a benzyl group and/or 1–5 —$OR^9$ groups, with $R^9$ in the meaning of a hydrogen atom or a $C_1$–$C_7$-alkyl radical, or —$L^1$—$R^F$,
$L^1$ means a straight-chain or branched $C_1$–$C_{30}$-alkylene group, which optionally is interrupted by 1–10 oxygen atoms, 1–5 —NH—CO groups, 1–5 —CO—NH groups, by a phenylene group optionally substituted by a COOH group, 1–3 sulfur atoms, 1–2 —N($B^1$)—$SO_2$ groups and/or 1–2 —$SO_2$—N($B^1$) groups with $B^1$ in the meaning of $A^1$, an NHCO group, a CONH group, an N($B^1$)—$SO_2$ group or an —$SO_2$—N($B^1$) group and/or optionally is substituted with radical $R^F$, and
$R^F$ means a straight-chain or branched perfluorinated alkyl radical of formula $C_nF_{2n}E$, whereby n stands for numbers 4–30, and
E stands for a terminal fluorine atom, chlorine atom, bromine atom, iodine atom or a hydrogen atom,
and optionally present acid groups optionally can be present as salts of organic and/or inorganic bases or amino acids or amino acid amides, can be used.

Since the compounds according to the invention are intended for use in NMR diagnosis, the metal ion of the signaling group must be paramagnetic. These are in particular the divalent and trivalent ions of the elements of atomic numbers 23–29, 42–46 and 58–70. Suitable ions are, for example, the chromium(III), iron(II), cobalt(II), nickel(II), copper(II), praseodymium(III), neodymium(III), samarium (III) and ytterbium(III) ions. Because of their strong magnetic moments, gadolinium(III), terbium(III), dysprosium (III), holmium(III), erbium(III), iron(III) and manganese(II) ions are especially preferred.

Preferred are manganese(II), iron(II), iron(III), praseodymium(III), neodymium(III), samarium(III), gadolinium(III) and ytterbium(III) ions, especially dysprosium(III) ions.

Alkyl groups $R^2$, $R^3$, and $R^9$ can be straight-chain or branched. By way of example, methyl, ethyl, propyl, isopropyl, n-butyl, 1-methylpropyl, 2-methylpropyl, n-pentyl, 1-methylbutyl, 2-methylbutyl, 3-methylbutyl, and 1,2-dimethylpropyl can be mentioned.

Hydrogen and $C_1$–$C_4$ alkyl groups are preferred for $R^2$, $R^3$ and $R^9$; hydrogen and the methyl group are especially preferred.

The benzyl group and phenyl group $R^2$, $A^1$ and $B^1$ can be substituted in the phenyl ring. The COOH group is suitable as a substituent.

If the compound of formula Ib contains radicals $L^1$ and $U^2$ at the same time, $L^1$ and $U^2$ can be different from one another.

$C_1$–$C_{30}$ alkylene groups U2 can be straight-chain or branched. By way of example, methylene, ethylene, propylene, isopropylene, n-butylene, 1-methylpropylene, 2-methylpropylene, n-pentylene, 1-methylbutylene, 2-methylbutylene, 3-methylbutylene, and 1,2-dimethylpropylene can be mentioned.

For $U^2$ in the meaning of alkylene, $C_1$–$C_{10}$ alkylene groups are preferred; $C_1$–$C_4$ alkylene groups are especially preferred.

$C_1$–$C_{30}$ alkyl groups $A^1$ can be straight-chain or branched. By way of example, methyl, ethyl, propyl, isopropyl, n-butyl, 1-methylpropyl, 2-methylpropyl, n-pentyl, 1-methylbutyl, 2-methylbutyl, 3-methylbutyl, 1,2-dimethylpropyl, and n-hexyl can be mentioned.

$C_1$–$C_{30}$ alkyl groups $A^1$ can be interrupted by 1–15 oxygen atoms and/or substituted with 1–10 hydroxy groups, 1–5 alkoxy groups or 1–2 COOH groups, such as, e.g., $C_2H_4$—O—$CH_3$, $C_3H_6$—O—$CH_3$,
$C_2H_4$—O—($C_2H_4$—O)$_t$—$C_2H_4$—OH, $C_2H_4$—O—($C_2H_4$—O)$_t$—$C_2H_4$—$OCH_3$ with t=0 to 13
$C_2H_4OH$, $C_3H_6OH$, $C_4H_8OH$, $C_5H_{10}OH$, $C_6H_{12}OH$, $C_7H_{14}OH$, as well as their branched isomers,
$CH(OH)CH_2OH$,
$CH(OH)CH(OH)CH_2OH$, $CH_2[CH(OH)]_{u^1}CH_2OH$, with $u^1=1$–10
$CH[CH_2(OH)]CH(OH)CH_2OH$,
$C_2H_4CH(OH)CH_2OH$,
$(CH_2)_sCOOH$ with s=1 to 15,
$C_2H_4$—O—($C_2H_4$—O)$_t$—$CH_2COOH$ with t=0 to 13,
$C_2H_4$—O—($C_2H_4$—O)$_t$—$C_2H_4$—$C_nF_{2n}E$ with t=0 to 13, n=4 to 20 and E=a fluorine, hydrogen, chlorine, bromine or iodine atom.
Preferred meanings of $A^1$ are hydrogen, $C_1$–$C_{10}$-alkyl,
$C_2H_4$—O—$CH_3$, $C_3H_6$—O—$CH_3$,
$C_2H_4$—O—($C_2H_4$—O)$_x$—$C_2H_4$—OH, $C_2H_4$—O—($C_2H_4$—O)$_x$—$C_2H_4$—$OCH_3$ with x=0 to 5,
$C_2H_4OH$, $C_3H_6OH$,
$CH_2[CH(OH)]_yCH_2OH$, with y=1–6
$CH[CH_2(OH)]CH(OH)CH_2OH$,
$(CH_2)_wCOOH$ with w=1 to 10,
$C_2H_4$—O—($C_2H_4$—O)$_x$—$CH_2COOH$ with x=0 to 5,
$C_2H_4$—O—($C_2H_4$—O)$_x$—$C_2H_4$—$C_nF_{2n}E$ with x=0 to 5, n=4 to 15, and E=a fluorine atom.
If the compound of general formula Ib contains two radicals $L^1$—$R^F$, these radicals can be different from one another.

For radicals $L^1$, there can be mentioned by way of example, whereby α stands for the binding to the nitrogen atom and β stands for the binding to radical $R^F$:

α-$(CH_2)_s$-β with s=1–15
α-$CH_2$—$CH_2$—(O—$CH_2$—$CH_2$—)$_y$-β with y=1–6
α-$CH_2$—(O—$CH_2$—$CH_2$—)$_y$-β with y=1–6
α-$CH_2$—NH—CO-β
α-$CH_2$—$CH_2$—NH—$SO_2$-β
α-$CH_2$—NH—CO—$CH_2$—N($CH_2COOH$)—$SO_2$-β
α-$CH_2$—NH—CO—$CH_2$—N($C_2H_5$)—$SO_2$-β
α-$CH_2$—NH—CO—$CH_2$—N($C_{10}H_{21}$)—$SO_2$-β
α-$CH_2$—NH—CO—$CH_2$—N($C_6H_{13}$)—$SO_2$-β
α-$CH_2$—NH—CO—$(CH_2)_{10}$—N($C_2H_5$)—$SO_2$-β
α-$CH_2$—NH—CO—$CH_2$—N(—$CH_2$—$C_6H_5$)—$SO_2$-β
α-$CH_2$—NH—CO—$CH_2$—N(—$CH_2$—$CH_2$—OH) $SO_2$-β
α-$CH_2$—NHCO—$(CH_2)_{10}$—S—$CH_2CH_2$-β
α-$CH_2NHCOCH_2$—O—$CH_2CH_2$-β
α-$CH_2$—$CH_2NHCOCH_2$—O—$CH_2CH_2$-β
α-$CH_2$—($CH_2$—$CH_2$—O)$_y$—$(CH_2)_3NHCO$—$CH_2$—O—$CH_2CH_2$-β with y=1–6
α-$CH_2NHCO(CH_2)_{10}$—O—$CH_2CH_2$-β
α-$CH_2CH_2NHCO(CH_2)_{10}$—O—$CH_2CH_2$-β
α-$CH_2$—$C_6H_4$—O—$CH_2CH_2$-β, whereby the phenylene group 1,4 or 1,3 is linked
α-$CH_2$—O—$CH_2$—C($CH_2$—$OCH_2CH_2$—$C_6F_{13}$)$_2$—$CH_2$—$OCH_2$—$CH_2$-β
α-$CH_2$—$NHCOCH_2CH_2CON$—$CH_2CH_2NHCOCH_2N$ ($C_2H_5$)$SO_2C_8F_{17}$β
α-$CH_2$—$CH_2NHCOCH_2N(C_2H_5)$—$SO_2$-β
α-$CH_2$—O—$CH_2$—CH(O$C_{10}H_{21}$)—$CH_2$—O—$CH_2CH_2$-β
α-$(CH_2NHCO)_4$—$CH_2O$—$CH_2CH_2$-β
α-$(CH_2NHCO)_3$—$CH_2O$—$CH_2CH_2$-β
α-$CH_2$—$OCH_2C(CH_2OH)_2$—$CH_213$ O—$CH_2CH_2$-β

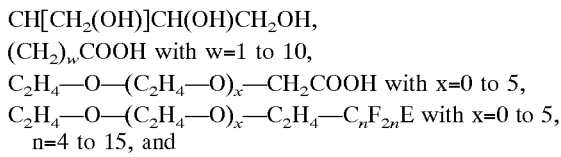

α-$CH_2NHCOCH_2N(C_6H_5)$—$SO_2$-β
α-NHCO—$CH_2$—$CH_2$-β
α-NHCO—$CH_2$—O—$CH_2CH_2$-β
α-NH—CO-β
α-NH—CO—$CH_2$—N($CH_2COOH$)—$SO_2$-β
α-NH—CO—$CH_2$—N($C_2H_5$)—$SO_2$-β
α-NH—CO—$CH_2$—N($C_{10}H_{21}$)—$SO_2$-β
α-NH—CO—$CH_2$—N($C_6H_{13}$)—$SO_2$-β
α-NH—CO—$(CH_2)_{10}$—N($C_2H_5$)—$SO_2$-β

α-NH—CO—CH$_2$—N(—CH$_2$—C$_6$H$_5$)—SO$_2$-β
α-NH—CO—CH$_2$—N(—CH$_2$—CH$_2$—OH)SO$_2$-β
α-NH—CO—CH$_2$-β
α-CH$_2$—O—C$_6$H$_4$—O—CH$_2$—CH$_2$-β
α-CH$_2$—C$_6$H$_4$—O—CH$_2$—CH$_2$-β
α-N(C$_2$H$_5$)—SO$_2$-β
α-N(C$_6$H$_5$)—SO$_2$-β
α-N(C$_{10}$H$_{21}$)—SO$_2$-β
α-N(C$_6$H$_{13}$)—SO$_2$-β
α-N(C$_2$H$_4$OH)—SO$_2$-β
α-N(CH$_2$COOH)—SO$_2$-β
α-N(CH$_2$C$_6$H$_5$)—SO$_2$-β
α-N—[CH(CH$_2$OH)$_2$]—SO$_2$-β
α-N—[CH(CH$_2$OH)CH(OH)(CH$_2$OH)]—SO$_2$-β
Preferred are:
α-CH$_2$—O—CH$_2$CH$_2$-β
α-CH$_2$—CH$_2$—(O—CH$_2$—CH$_2$—)$_y$-β with y=1–6
α-CH$_2$—(O—CH$_2$—CH$_2$—)$_y$-β with y=1–6
α-CH$_2$—CH$_2$—NH—SO$_2$-β Example 10
α-CH$_2$NHCOCH$_2$—O—CH$_2$CH$_2$-β
α-CH$_2$—CH$_2$NHCOCH$_2$—O—CH$_2$CH$_2$-β
α-CH$_2$—(CH$_2$—CH$_2$—O)$_y$—(CH$_2$)$_3$NHCO—CH$_2$—O—CH$_2$CH$_2$-β with y=1–6
α-CH$_2$NHCO(CH$_2$)$_{10}$—O—CH$_2$CH$_2$-β
α-CH$_2$CH$_2$NHCO(CH$_2$)$_{10}$—O—CH$_2$CH$_2$-β
α-CH$_2$—O—CH$_2$—CH(OC$_{10}$H$_{21}$)—CH$_2$—O—CH$_2$CH$_2$-β
α-CH$_2$—O—C$_6$H$_4$—O—CH$_2$—CH$_2$-β
α-CH$_2$—C$_6$H$_4$—O—CH$_2$—CH$_2$-β

According to the invention, radicals L$^1$ of the compounds mentioned in the examples of the description of this invention are quite especially preferred.

U$^2$ is considered to stand for the above-cited radicals for L$^1$ and the radicals that are characterized as preferred and especially preferred, and the above-cited and optionally preferred and especially preferred radicals are considered to stand for the meaning of alkylene, provided that no α-position nitrogen atom and no terminal (β-position) SO$_2$ or CO group must be present.

Preferred radicals B$^1$ are hydrogen, straight-chain or branched C$_1$–C$_{10}$-alkyl radicals, which optionally are interrupted by 1–5 oxygen atoms and/or optionally are substituted with 1–5 hydroxy groups, 1–2 COOH groups, a phenyl group optionally substituted by a COOH group, a benzyl group and/or 1–5 OR$^9$ groups, with R$^9$ in the meaning of a hydrogen atom or a C$_1$–C$_3$ alkyl radical.

Preferred radicals R$^F$ are straight-chain or branched perfluorinated alkyl radicals of formula C$_n$F$_{2n}$E, whereby n stands for numbers 4 to 15 and E stands for a terminal fluorine atom.

The production of the compounds of general formula Ib according to the invention

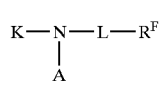
(Ib)

with

K in the meaning of a complexing agent or a metal complex of general formula IIb

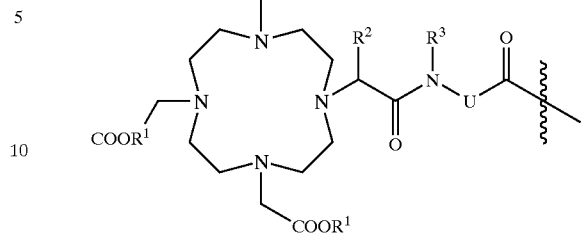
(IIb)

can be carried out according to the following process:
Process A.

The carboxylic acid of Formula IIIb already contains metal ion equivalent R$^1$.

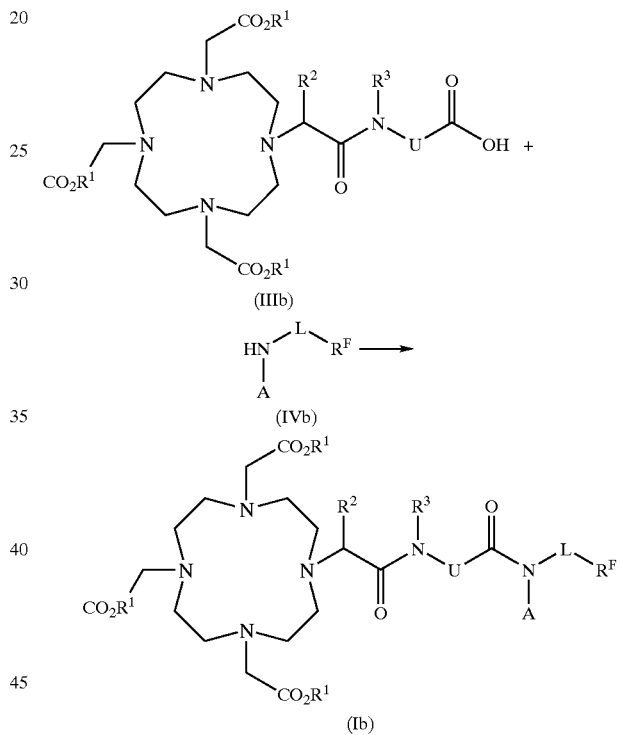

Carboxylic acid IIIb that is optionally activated in situ with R$^1$ in the meaning of a metal ion equivalent is reacted with an amine IVb in a coupling reaction to form an amide Ib.

This process for the production of metal complex carboxylic acid amides is known from DE 196 52 386.

The mixture of metal complex carboxylic acid IIIb that is used in the coupling reaction and that contains optionally present carboxy and/or hydroxy groups in protected form and at least one solubilizing substance in an amount up to 5, preferably 0.5–2 molar equivalents relative to the metal complex carboxylic acid, can both be produced in an upstream reaction stage and isolated (e.g., by concentration by evaporation, freeze-drying or spray-drying of an aqueous or water-miscible solution of components or by precipitation with an organic solvent from such a solution) and then can be reacted in DMSO with dehydrating reagent and optionally a coupling adjuvant and can be formed in situ optionally by the addition of solubilizing substance(s) for DMSO-suspension of metal complex carboxylic acid, dehydrating reagent and optionally a coupling adjuvant.

The reaction solution that is produced according to one of these processes is kept for pretreatment (acid activation) for 1 to 24 hours, preferably 3 to 12 hours at temperatures of 0 to 50° C., preferably at room temperature.

Then, an amine of general formula IVb

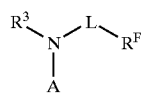
(IVb)

in which radicals $R^3$, $L^1$, $R^F$ and A have the above-indicated meanings, is added without solvent or dissolved in, for example, dimethyl sulfoxide, alcohols, such as, e.g., methanol, ethanol, isopropanol or mixtures thereof, formamide, dimethylformamide, water or mixtures of the cited solvents, preferably in dimethyl sulfoxide, in water or in solvents that are mixed with water. For amide coupling, the thus obtained reaction solution is kept at temperatures of 0 to 70° C., preferably 30 to 60° C., for 1 to 48 hours, preferably 8 to 24 hours.

In some cases, it has proven advantageous to use the amine in the form of its salts, e.g., as hydrobromide or hydrochloride, in the reaction. To release the amine, a base such as, e.g., triethylamine, diisopropylethylamine, N-methylmorpholine, pyridine, tripropylamine, tributylamine, lithium hydroxide, lithium carbonate, sodium hydroxide or sodium carbonate is added.

The optionally still present protective groups are then cleaved off.

The isolation of the reaction product is carried out according to the methods that are known to one skilled in the art, preferably by precipitation with organic solvents, preferably acetone, 2-butanone, diethyl ether, ethyl acetate, methyl-t-butylether, isopropanol or mixtures thereof. Further purification can be carried out by, for example, chromatography, crystallization or ultrafiltration.

As solubilizing substances, alkali salts, alkaline-earth salts, trialkylammonium salts, tetraalkylammonium salts, ureas, N-hydroxyimides, hydroxyaryltriazoles, substituted phenols and salts of heterocyclic amines are suitable. By way of example, there can be mentioned: lithium chloride, lithium bromide, lithium iodide, sodium bromide, sodium iodide, lithium methanesulfonate, sodium methanesulfonate, lithium-p-toluenesulfonate, sodium-p-toluenesulfonate, potassium bromide, potassium iodide, sodium chloride, magnesium bromide, magnesium chloride, magnesium iodide, tetraethylammonium-p-toluenesulfonate, tetramethylammonium-p-toluenesulfonate, pyridinium-p-toluenesulfonate, triethylammonium-p-toluenesulfonate, 2-morpholinoethylsulfonic acid, 4-nitrophenol, 3,5-dinitrophenol, 2,4-dichlorophenol, N-hydroxysuccinimide, N-hydroxyphthalimide, urea, tetramethylurea, N-methylpyrrolidone, formamide, as well as cyclic ureas, whereby the five first-mentioned are preferred.

As dehydrating reagents, all agents that are known to one skilled in the art are used. By way of example, carbodiimides and onium reagents, such as, e.g., dicyclohexylcarbodiimide (DCCI), 1-ethyl-3-(3-dimethylaminopropyl)-carbodiimide-hydroxychloride (EDC), benzotriazol-1-yloxytris (dimethylamino)-phosphonium hexafluorophosphate (BOP) and O-(benzotriazol-1-yl)-1,1,3,3-tetramethyluroniumhexafluorophosphate (HBTU), preferably DCCI, can be mentioned.

In the literature, for example, the following suitable processes are described:

Aktivierung von Carbonsäuren. Übersicht in Houben-Weyl, Methoden der Organischen Chemie [Activation of Carboxylic Acids. Survey in Houben-Weyl, Methods of Organic Chemistry], Volume XV/2, Georg Thieme Verlag Stuttgart, 1974 (and J. Chem. Research (S) 1996, 302).

Aktivierung mit Carbodiimiden [Activation with Carbodiimides]. R. Schwyzer and H. Kappeler, Helv. 46: 1550 (1963).

E. Wünsch et al., Vol. 100: 173 (1967).

Aktivierung mit Carbodiimiden/Hydroxysuccinimid [Activation with Carbodiimides/Hydroxysuccinimide]: J. Am. Chem. Soc. 86: 1839 (1964) and J. Org. Chem. 53: 3583 (1988). Synthesis 453 (1972).

Anhydridmethode, 2-Ethoxy-1-ethoxycarbonyl-1,2-dihydrochinolin [Anhydride Methods, 2-Ethoxy-1-ethoxycarbonyl-1,2-dihydroquinoline]: B. Belleau et al., J. Am. Chem. Soc., 90: 1651 (1986), H. Kunz et al., Int. J. Pept. Prot. Res., 26: 493 (1985) and J. R. Voughn, Am. Soc. 73: 3547 (1951).

Imidazolid-Methode [Imidazolide Methods]: B. F. Gisin; R. B. Menifield; D. C. Tosteon, Am. Soc. 91: 2691 (1969).

Säurechlorid-Methoden, Thionylchlorid [Acid Chloride Methods, Thionyl Chloride]: Helv., 42: 1653 (1959).

Oxalylchlorid [Oxalyl Chloride]: J. Org. Chem., 29: 843 (1964).

As coupling adjuvants that are optionally to be used, all that are known to one skilled in the art are suitable (Houben-Weyl, Methoden der organischen Chemie, Volume XV/2, Georg Thieme-Verlag, Stuttgart, 1974). By way of example, 4-nitrophenol, N-hydroxysuccinimide, 1-hydroxybenzotriazole, 1-hydroxy-7-aza-benzotriazole, 3,5-dinitrophenol and pentafluorophenol can be mentioned. Preferred are 4-nitrophenol and N-hydroxysuccinimide; especially preferred in this case is the first-mentioned reagent.

The cleavage of the protective groups is carried out according to the processes that are known to one skilled in the art, for example by hydrolysis, hydrogenolysis, alkaline saponification of esters with alkali in aqueous-alcoholic solution at temperatures of 0° to 50° C., acid saponification with mineral acids or in the case of, e.g., tert-butylesters with the aid of trifluoroacetic acid [Protective Groups in Organic Synthesis, 2nd Edition, T. W. Greene and P. G. M. Wuts, John Wiley and Sons, Inc. New York, 1991], in the case of benzyl ethers with hydrogen/palladium/carbon.

The production of the starting material, the compounds of Formula IIIb,

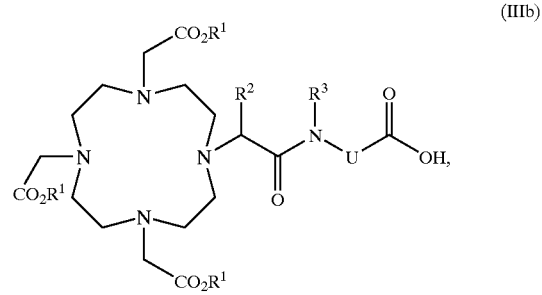
(IIIb)

is known from DE 196 52 386.

The amines of general formula IVb

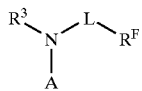
(IVb)

are commercially available products (Fluorochem, ABCR) or can be obtained according to the following process from compounds of general formula Vb by reaction with an amine of general formula VIb and subsequent reduction of the compounds of general formula VIIb:

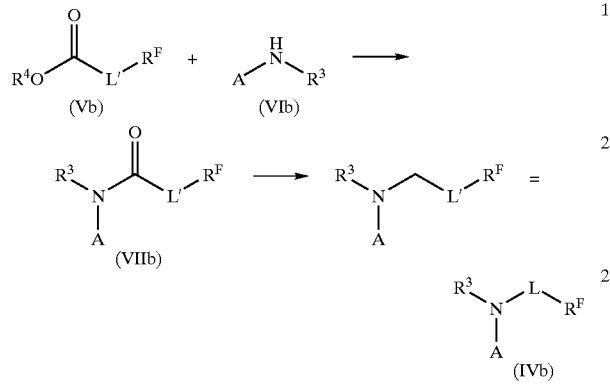

in which

R$^F$, A$^1$, L$^1$ and R$^3$ have the above-mentioned meaning, and L' has the meaning of group L$^1$, in which the α-CH$_2$-group is still missing, and R$^9$ stands for hydrogen or a methyl group.

According to the process described in the literature that was already disclosed above for the activation of carboxylic acid IIIb, acid Vb is activated with amine VIb before the reaction. For R$^9$ in the meaning of a methyl group, an aminolysis is performed.

The compounds of general formula Vb are commercially available products (Fluorochem, ABCR) or are produced as disclosed in DE 196 03 033.

The compounds of general formula VIb are commercially available products (Fluorochem, ABCR) or can be produced as described in Houben-Weyl, Methoden der organischen Chemie, XI/2 Stickstoffverbindungen [XI/2 Nitrogen Compounds], Georg Thieme Verlag Stuttgart, 1957, p. 680; J. E. Rickman and T. Atkins, Am. Chem. Soc., 96:2268, 1974, 96: 2268; F. Chavez and A. D. Sherry. J. Org. Chem. 1989, 54: 2990.

The compounds of general formula IVb are obtained in a way that is known in the art [Helv. Chim. Acta. 77: 23 (1994)] by reduction of the compounds of general formula VII, for example, with diborane or lithium aluminum hydride and cleavage of the protective groups.

Process B.

As starting material, the carboxylic acid of formula IIIx is used with R$^1$ in the meaning of hydrogen—it still does not contain any metal ion equivalent R$^1$. The carboxyl groups are protected according to the processes that are known to one skilled in the art, and a compound of Formula IIIy is obtained, whereby R$^5$ stands for any protective group and R$^{5'}$ stands for its precursor.

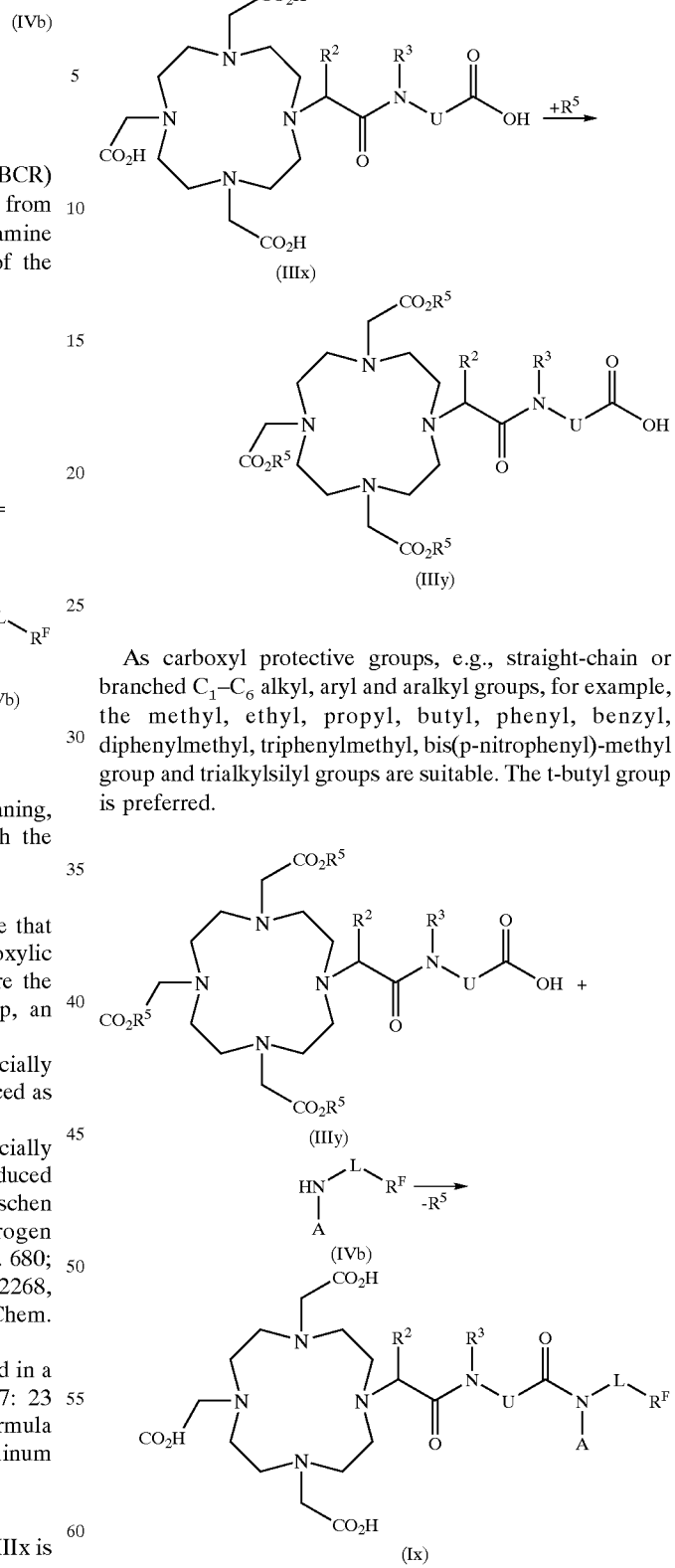

As carboxyl protective groups, e.g., straight-chain or branched C$_1$–C$_6$ alkyl, aryl and aralkyl groups, for example, the methyl, ethyl, propyl, butyl, phenyl, benzyl, diphenylmethyl, triphenylmethyl, bis(p-nitrophenyl)-methyl group and trialkylsilyl groups are suitable. The t-butyl group is preferred.

The reaction of the protected carboxylic acid IIIy with the amine of formula IVb and the cleavage of the protective groups is carried out as described under process A and in a subsequent step, the obtained carboxylic acid Ix is reacted with at least one metal oxide or metal salt of an element of the desired atomic number as is disclosed in, e.g., DE 195 25 924.

If the metal complex that is obtained from process A or B still contains free COOH groups, these groups can also be present as salts of physiologically compatible inorganic or organic bases.

The neutralization of optionally still present free carboxy groups is then carried out with the aid of inorganic bases (for example, hydroxides, carbonates or bicarbonates) of, for example, sodium, potassium, lithium, magnesium, or calcium and/or organic bases such as, i.a., primary, secondary and tertiary amines, such as, for example, ethanolamine, morpholine, glucamine, N-methyl- and N,N-dimethylglucamine, as well as basic amino acids, such as, for example, lysine, arginine, and ornithine, or amides of originally neutral or acidic amino acids.

According to the invention, quite especially preferably metal complexes V, VII, VIII, IX and X (cf. Table 1) are used.

These compounds of general formula Ib are very well suited as MRI contrast media for visualization of plaque.

In another preferred embodiment of the invention, the perfluoroalkyl-containing complexes with sugar radicals of general formula Ic

(Ic)

in which
R represents a mono- or oligosaccharide radical bonded by the 1-OH— or 1-SH-position,
$R^F$ is a perfluorinated, straight-chain or branched carbon chain with the formula —$C_nF_{2n}E$, in which E represents a terminal fluorine, chlorine, bromine, iodine or hydrogen atom, and n stands for numbers 4–30,
K stands for a metal complex of general formula IIc,

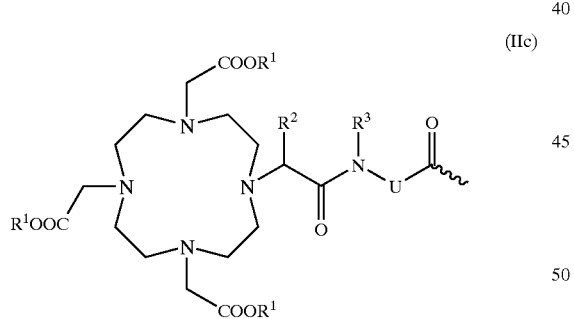

(IIc)

in which
$R^1$ means a hydrogen atom or a metal ion equivalent of atomic numbers 23–29, 42–46 or 58–70,
provided that at least two $R^1$ stand for metal ion equivalents,
$R^2$ and $R^3$, independently of one another, represent hydrogen, $C_1$–$C_7$ alkyl, benzyl, phenyl, —$CH_2OH$ or —$CH_2OCH_3$, and
U represents —$C_6H_4$—O—$CH_2$-ω, —$(CH_2)_{1-5}$-ω, a phenylene group, —$CH_2$—NHCO—$CH_2$—CH($CH_2COOH$)—$C_6H_4$-ω, —$C_6H_4$—($OCH_2CH_2$)$_{0-1}$—N($CH_2COOH$)—$CH_2$-ω, or a $C_1$–$C_{12}$ alkylene group or $C_7$–$C_{12}$—$C_6H_4$—O group optionally interrupted by one or more oxygen atoms, 1 to 3 —NHCO groups or 1 to 3 —CONH groups and/or substituted with 1 to 3 —$(CH_2)_{0-5}COOH$ groups, whereby ω stands for the binding site to —CO—, or of general formula IIIc

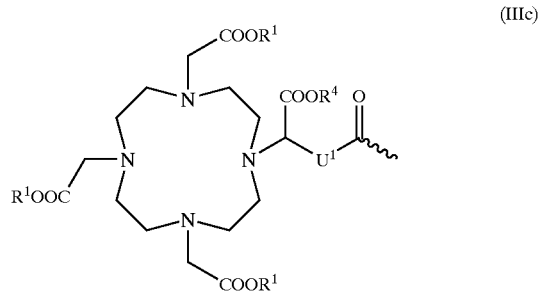

(IIIc)

in which $R^1$ has the above-mentioned meaning, $R^4$ represents hydrogen or a metal ion equivalent mentioned under $R^1$, and $U^1$ represents —$C_6H_4$—O—$CH_2$-ω, whereby ω means the binding site to —CO—, or of general formula IVc

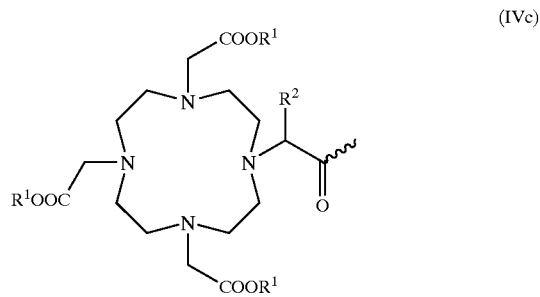

(IVc)

in which $R^1$ and $R^2$ have the above-mentioned meaning or of general formula VcA or VcB

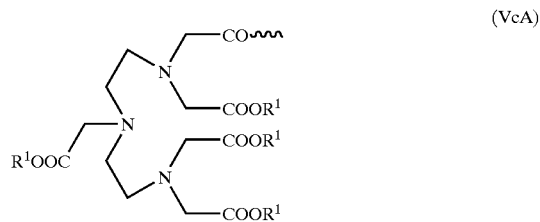

(VcA)

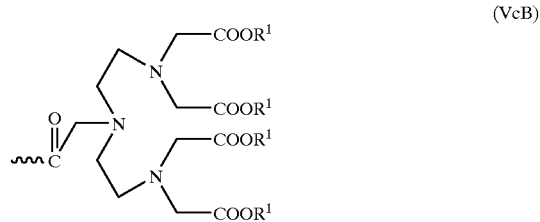

(VcB)

in which $R^1$ has the above-mentioned meaning,
or of general formula VIc

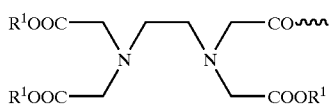
(VIc)

in which $R^1$ has the above-mentioned meaning,
or of general formula VIIc

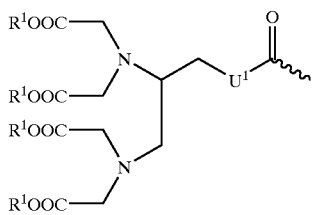
(VIIc)

in which $R^1$ has the above-mentioned meaning, and
$U^1$ represents $-C_6H_4-O-CH_2-\omega$, whereby $\omega$ means the binding site to $-CO-$ or of general formula VIIIc

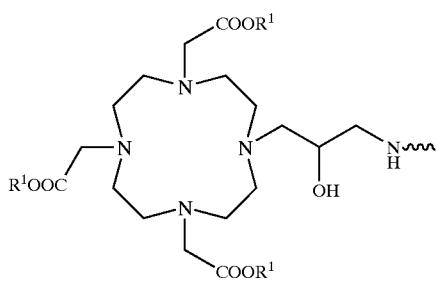
(VIIIc)

in which $R^1$ has the above-mentioned meaning,
and in radical K, optionally present free acid groups optionally can be present as salts of organic and/or inorganic bases or amino acids or amino acid amides, G for the case that K means metal complexes IIc to VIIc, represents a radical that is functionalized in at least three places and is selected from the following radicals a) to j)

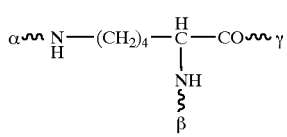
(a)

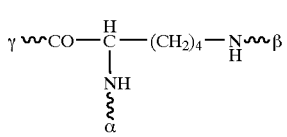
(b)

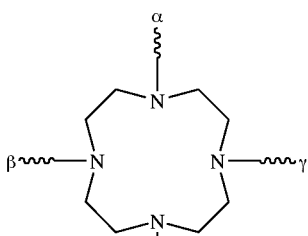
(c)

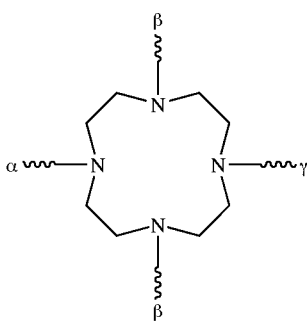
(d)

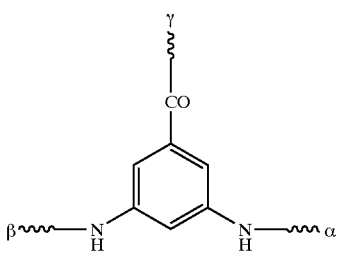
(e)

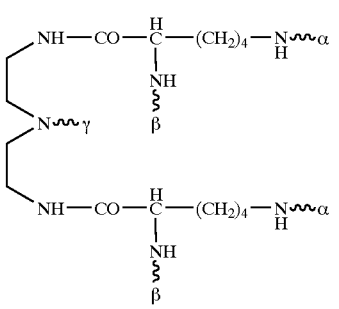
(f)

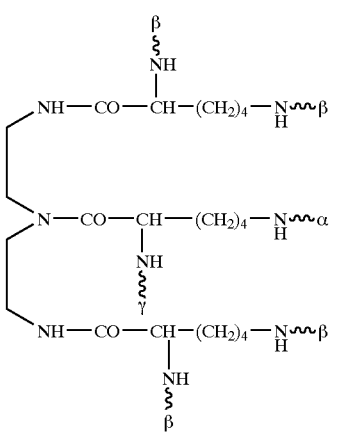
(g)

-continued

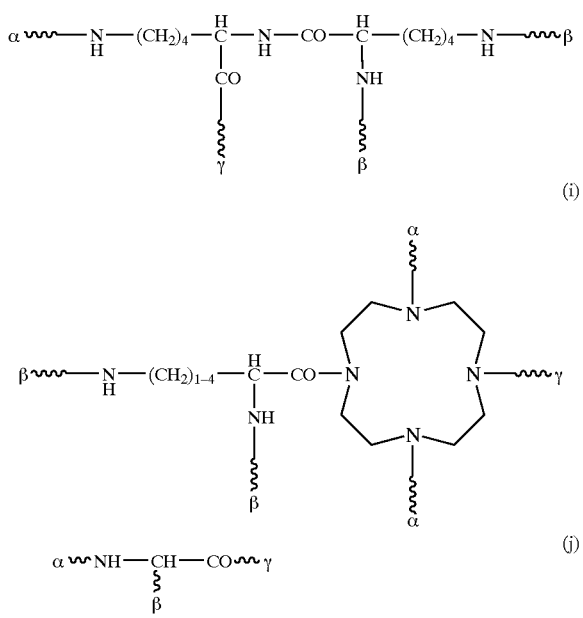

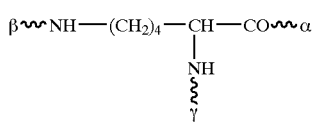

and

G for the case that K means metal complex VIIIc, represents a radical that is functionalized in at least three places and is selected from k) or l)

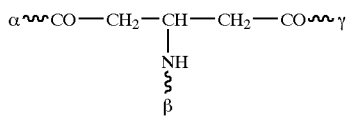

whereby a means the binding site of G to complex K, β is the binding site of G to radical Y, and γ represents the binding site of G to radical Z, Y means —$CH_2$—, δ-$(CH_2)_{1-5}$CO-β, δ-$CH_2$—CHOH—CO-β or δ-CH(CHOH—$CH_2$OH)—CHOH—CHOH—CO-β, whereby δ represents the binding site to sugar radical R, and β is the binding site to radical G, Z stands for

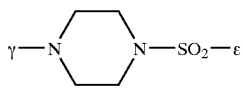

γ-COCH$_2$—N(C$_2$H$_5$)—SO$_2$-ε,
γ-COCH$_2$—O—(CH$_2$)$_2$—SO$_2$-ε,

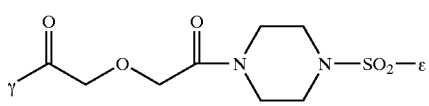

or
γ-NHCH$_2$CH$_2$—O—CH$_2$CH$_2$-ε whereby γ represents the binding site of Z to radical G, and ε means the binding site of Z to perfluorinated radical $R^F$ and $l^1$, $m^1$, independently of one another, mean integer 1 or 2, and $p^1$ means integers 1 to 4, can be used.

Since the compounds according to the invention are intended for use in NMR-diagnosis, the metal ion of the signaling group must be paramagnetic. These are especially the divalent and trivalent ions of the elements of atomic numbers 23–29, 42–46 and 58–70. Suitable ions are, for example, the chromium(III), iron(II), cobalt(II), nickel(II), copper(II), praseodymium(III), neodymium(III), samarium (II) and ytterbium(III) ion. Because of their strong magnetic moment, gadolinium(III), terbium(III), dysprosium(III), holmium(III), erbium(III), iron(III) and manganese(II) ions are especially preferred.

Preferred are manganese(II), iron(II), iron(III), praseodymium(III), neodymium(III), samarium(III), gadolinium(III) and ytterbium(III) ions, especially dysprosium(III) ions.

In $R^1$, optionally present acidic hydrogen atoms, i.e., those that have not been substituted by the central ion, can optionally be replaced completely or partially by cations of inorganic and/or organic bases or amino acids or amino acid amides.

Suitable inorganic cations are, for example, the lithium ion, the potassium ion, the calcium ion and especially the sodium ion. Suitable cations of organic bases are, i.a., those of primary, secondary or tertiary amines, such as, for example, ethanolamine, diethanolamine, morpholine, glucamine, N,N-dimethylglucamine and especially N-methylglucamine. Suitable cations of amino acids are, for example, those of lysine, arginine, and ornithine as well as the amides of otherwise acidic or neutral amino acids.

Especially preferred compounds of general formula Ic are those with macrocyclic compound K of general formula IIc.

Radical U in metal complex K means preferably —$CH_2$— or $C_6H_4$—O—$CH_2$-ω, whereby ω stands for the binding site to —CO—.

Alkyl groups $R^2$ and $R^3$ in the macrocyclic compound of general formula IIc can be straight-chain or branched. By way of example, methyl, ethyl, propyl, isopropyl, n-butyl, 1-methylpropyl, 2-methylpropyl, n-pentyl, 1-methylbutyl, 2-methylbutyl, 3-methylbutyl, and 1,2-dimethylpropyl can be mentioned. $R^2$ and $R^3$, independently of one another, preferably mean hydrogen or $C_1$–$C_4$-alkyl. In a quite especially preferred embodiment, $R^2$ stands for methyl and $R^3$ stands for hydrogen.

The benzyl group or phenyl group $R^2$ or $R^3$ in macrocyclic compound K of general formula IIc can also be substituted in the ring.

Radical R in general formula Ic means a mono- or oligosaccharide radical or thiosugar radical that is bonded via the 1-OH— or 1-SH-position, whereby in this connection according to the invention, this can be a deoxy sugar, which contains an H atom instead of one or more OH groups. In a preferred embodiment of the invention, R means a monosaccharide radical with 5 or 6 C atoms, preferably glucose, mannose, galactose, ribose, arabinose or xylose or their deoxy sugars, such as, for example, 6-deoxygalactose (fucose) or 6-deoxymannose (rhamnose) or their thiosugars, whereby glucose, mannose and galactose are especially preferred.

Of the compounds of general formula Ic according to the invention, in addition those are preferred in which $R^F$ means —$C_nF_{2n+1}$. n preferably stands for numbers 4–15. Quite especially preferred are radicals —$C_4F_9$, —$C_6F_{13}$, —$C_8F_{17}$, —$C_{12}F_{25}$ and 13 $C_{14}F_{29}$ as well as the radicals of the compounds that are mentioned in the examples.

Radical G that is functionalized in at least three places in general formula Ic, which represents the "skeleton," means lysine radical (a) or (b) in a preferred embodiment of the invention.

Y and Z mean the linkers indicated in general formula Ic, whereby independently of one another, radical

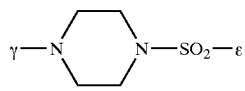

is preferred for Z, and radical δ-$CH_2CO$-β is preferred for Y.

The perfluoroalkyl-containing metal complexes with sugar radicals of general formula Ic

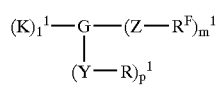

(Ic)

with K in the meaning of a metal complex of general formulas IIc to VIIc and G in the meaning of formulas a) to j), whereby Y, Z, R, $R^F$, $m^1$, $p^1$ and $1^1$ have the above-mentioned meaning, are produced by a carboxylic acid of general formula IIi

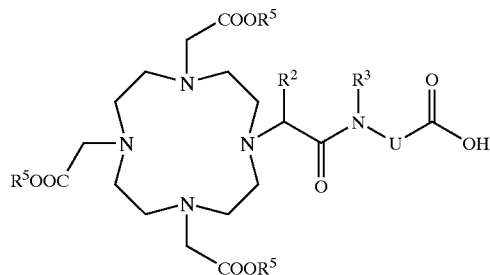

(IIi)

in which $R^5$ means a metal ion equivalent of atomic numbers 23–29, 42–46, or 58–70 or a carboxyl protective group, and $R^2$, $R^3$ and U have the above-mentioned meaning, or a carboxylic acid of general formula IIIi

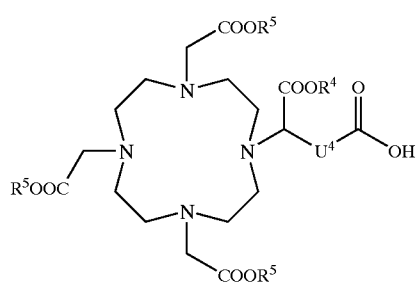

(IIIi)

in which $R^4$, $R^5$ and $U^1$ have the above-mentioned meaning or a carboxylic acid of general formula IVi

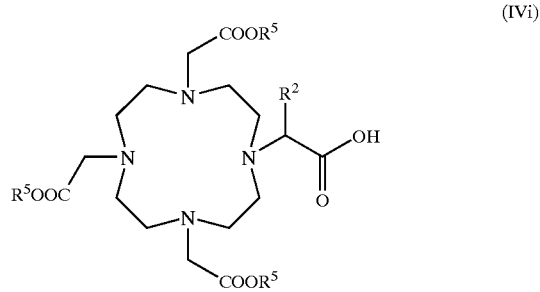

(IVi)

in which $R^5$ and $R^2$ have the above-mentioned meaning or a carboxylic acid of general formula Vi or Vii

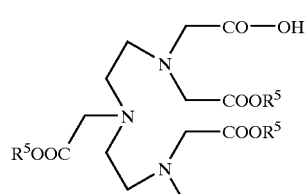

(Vi)

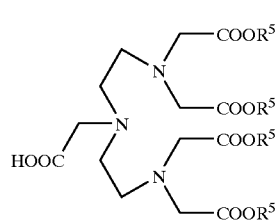

(Vii)

in which $R^5$ has the above-mentioned meaning or a carboxylic acid of general formula VIi

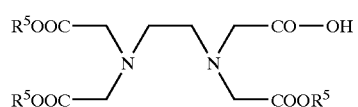

(VIi)

in which $R^5$ has the above-mentioned meaning or a carboxylic acid of general formula VIIi

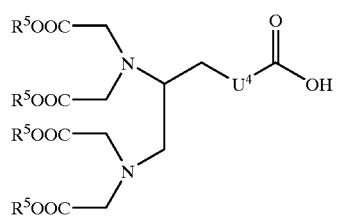

(VIIi)

in which $R^5$ and $U^1$ have the above-mentioned meanings, being reacted in a way that is known in the art in optionally activated form with an amine of general formula IXc

in which G has the meaning of formulas a) to j), and R, $R^F$, Y, Z, $m^1$ and $p^1$ have the indicated meaning, in a coupling reaction and optionally subsequent cleavage of optionally present protective groups to form a metal complex of general formula Ic or if $R^5$ has the meaning of a protective group, after cleavage of these protective groups in a subsequent step being reacted in a way that is known in the art with at least one metal oxide or metal salt of an element of atomic numbers 23–29, 42–46 or 58–70, and then, if desired, optionally present acidic hydrogen atoms being substituted by cations of inorganic and/or organic bases, amino acids or amino acid amides.

The compounds of general formula Ic according to the invention with K in the meaning of a metal complex of general formula VIIIc and G in the meaning of formulas k) or l) are produced by an amine of general formula VIIIi

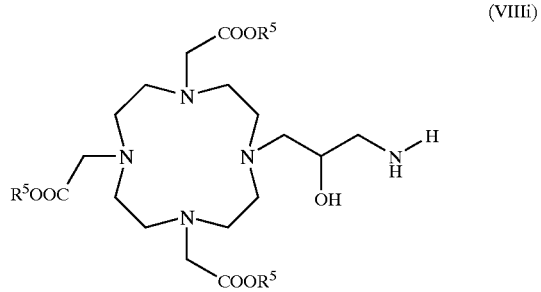

in which $R^5$ means a metal ion equivalent of atomic numbers 23–29, 42–46 or 58–70 or a carboxyl protective group, being reacted in a way that is known in the art with an optionally activated carboxylic acid of general formula Xc

in which G has the meaning of formula k) or l) and R, $R^F$, Y, Z, $m^1$ nand $p^1$ have the indicated meanings, in a coupling reaction and optionally subsequent cleavage of optionally present protective groups to form a metal complex of general formula Ic or if $R^5$ has the meaning of a protective group, after cleavage of these protective groups in a subsequent step, being reacted in a way that is known in the art with at least one metal oxide or metal salt of an element of atomic numbers 23–29, 42–46 or 58–70, and then, if desired, optionally present acidic hydrogen atoms being substituted by cations of inorganic and/or organic bases, amino acids or amino acid amides.

The carboxylic acids of general formulas IIi to VIIi that are used are either known compounds or are produced according to the processes that are described in the examples. Thus, the production of carboxylic acids of general formula IIi is known from DE 196 52 386. The production of the carboxylic acids of general formula IVi can be found in DE 197 28 954.

A precursor for compounds of general formula VcA is the $N^3$-(2,6-dioxomorpholinoethyl)-$N^6$-(ethoxycarbonylmethyl)-3,6-diaza-octanedioic acid, which is described in EP 263 059.

The compounds of general formula VcB are derived from the isomeric diethylenetriamine-pentaacetic acid, which binds via acetic acid on the center N atom. This DTPA is described in Patents DE 195 07 819 and DE 195 08 058.

Compounds of general formula VIc are derived from N-(carboxymethyl)-N-[2-(2,6-dioxo-4-morpholinyl)-ethyl]-glycine, whose production is described in J. Am. Oil. Chem. Soc. (1982), 59(2), 104–107.

Compounds of general formula VIIc are derived from the 1-(4-carboxymethoxybenzyl)ethylenediamine-tetraacetic acid, which is described in U.S. Pat. No. 4,622,420.

The perbenzylated sugar acids that are used as starting substances can be produced analogously to Lockhoff; Angew. Chem. 1998, 110 No. 24, p. 3634 ff. For example, the production of 1-O-acetic acid from perbenzyl-glucose is carried out over 2 stages, via trichloroacetimidate and reaction with hydroxyacetic acid ethyl ester, $BF_3$-catalysis in THF and subsequent saponification with NaOH in MeOH/THF.

In a more advantageous process, the perbenzylated sugar acids that are used as starting substances can also be produced by the perbenzylated I—OH-sugar being dissolved in a water-immiscible organic solvent and being reacted with an alkylating reagent of general formula XIc $$\text{Nu-L—COO-Sg} \quad \text{(XIc)},$$

in which Nu means a nucleofuge, L is —$(CH_2)_{(1-5)}$, —$CH_2$—CHOH—, —CH(CHOH—$CH_2$OH)—CHOH—CHOH—, and Sg represents a protective group, in the presence of a base and optionally a phase transfer catalyst. As a nucleofuge, for example, the radicals —Cl, —Br, —I, —OTs, —OMs, —$OSO_2CF_3$, —$OSO_2C_4F_9$ or —$OSO_2C_8F_{17}$ can be contained in the alkylating reagent of general formula XIc.

The protective group is a common acid protective group. These protective groups are well known to one skilled in the art (Protective Groups in Organic Syntheses, Second Edition, T. W. Greene and P. G. M. Wuts, John Wiley & Sons, Inc., New York 1991).

The reaction according to the invention can be carried out at temperatures from 0–50° C., preferably from 0° C. to room temperature. The reaction times are 10 minutes to 24 hours, preferably 20 minutes to 12 hours.

The base is added either in solid form, preferably fine-powder, or as 10–70%, preferably 30–50%, aqueous solution. NaOH and KOH are used as preferred bases.

As organic, water-immiscible solvent, for example, toluene, benzene, $CF_3$-benzene, hexane, cyclohexane, diethyl ether, tetrahydrofuran, dichloromethane, MTB or mixtures thereof can be used in the alkylating process according to the invention.

As phase-transfer catalysts, the quaternary ammonium or phosphonium salts or else crown ethers, such as, e.g., [15]-crown-5 or [18]-crown-6, that are known for this purpose are used in the process according to the invention. Quaternary ammonium salts with four identical or different hydrocarbon groups at the.cation, selected from methyl, ethyl, propyl, isopropyl, butyl or isobutyl, are preferably suitable. The hydrocarbon groups at the cation must be large enough to ensure good solubility of the alkylating reagent in the organic solvent. According to the invention, $N(butyl)_4^+$—$Cl^-$, $N(butyl)_4^+$—$HSO_4^-$, but also $N(methyl)_4^+$—$Cl^-$ are especially preferably used.

As quite especially preferred compounds of general formula Ic, metal complex XV of Table 1 (Example 1) according to the invention is used.

In another preferred embodiment of the invention, the perfluoroalkyl-containing complexes with polar radicals of general formula Id are used

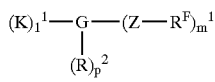

(Id)

in which
R$^F$ is a perfluorinated, straight-chain or branched carbon chain with formula —C$_n$F$_{2n}$E, in which E represents a terminal fluorine, chlorine, bromine, iodine or hydrogen atom, and n stands for numbers 4–30,
K stands for a metal complex of general formula IId,

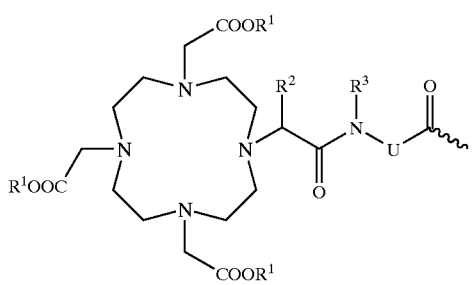

(IId)

in which
R$^1$ means a hydrogen atom or a metal ion equivalent of atomic numbers 23–29, 42–46 or 58–70, provided that at least two R$^1$ stand for metal ion equivalents,
R$^2$ and R$^3$, independently of one another, represent hydrogen, C$_1$–C$_7$-alkyl, benzyl, phenyl, —CH$_2$OH or —CH$_2$OCH$_3$, and
U represents —C$_6$H$_4$—O—CH$_2$-ω-, —(CH$_2$)$_{1,5}$-ω, a phenylene group, —CH$_2$—NHCO—CH$_2$—CH (CH$_2$COOH)—C$_6$H$_4$-ω-, —C$_6$H$_4$—(OCH$_2$CH$_2$)$_{0-1}$-N(CH$_2$COOH)—CH$_2$-ω, or a C$_1$–C$_{12}$-alkylene group or C$_7$–C$_{12}$—C$_6$H$_4$—O group optionally interrupted by one or more oxygen atoms, 1 to 3 —NHCO groups, 1 to 3 —CONH groups and/or substituted with 1 to 3 —(CH$_2$)$_{0-5}$COOH groups, whereby ω stands for the binding site to —CO—,
or
of general formula IIId

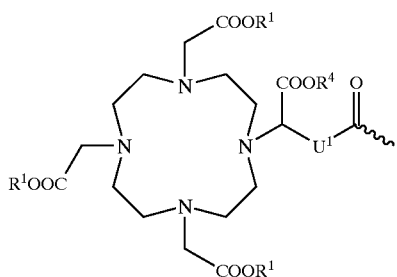

(IIId)

in which R$^1$ has the above-mentioned meaning, R$^4$ represents hydrogen or a metal ion equivalent mentioned under R$^1$, and U$^1$ represents —C$_6$H$_4$—O—CH$_2$-ω-, whereby ω means the binding site to —CO—,
or of general formula IVd

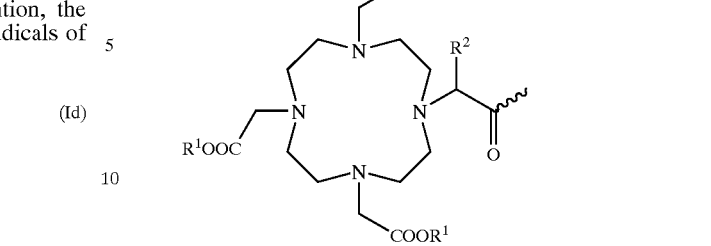

(IVd)

in which R$^1$ and R$^2$ have the above-mentioned meaning,
or of general formula VdA or VdB

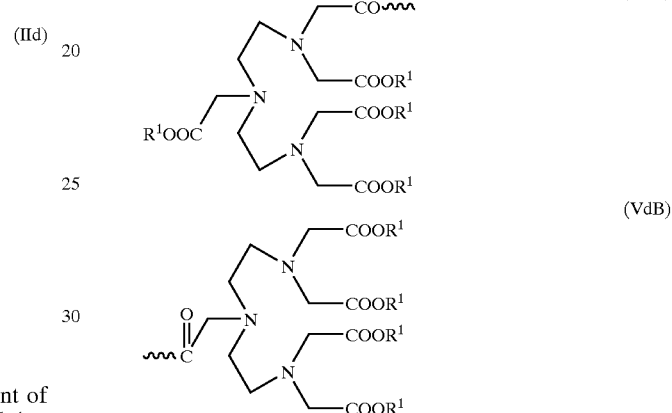

(VdA)

(VdB)

in which R$^1$ has the above-mentioned meaning,
or of general formula VId

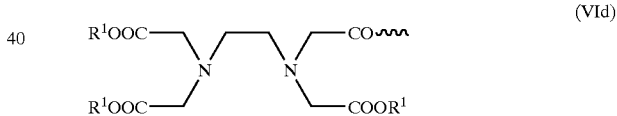

(VId)

in which R$^1$ has the above-mentioned meaning,
or of general formula VIId

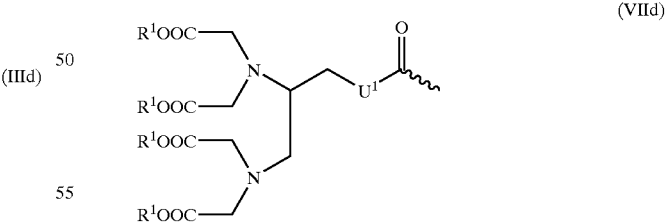

(VIId)

in which R$^1$ has the above-mentioned meaning, and
U$^1$ represents —C$_6$H$_4$—O—CH$_2$-ω-, whereby ω means the binding site to —CO—,
and in radical K, optionally present free acid groups optionally can be present as salts of organic and/or inorganic bases or amino acids or amino acid amides,
G represents a radical that is functionalized in at least three places and is selected from the following radicals a) to g)

(a) 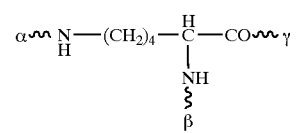

(b) 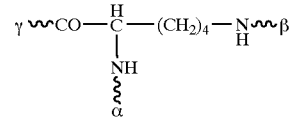

(c) 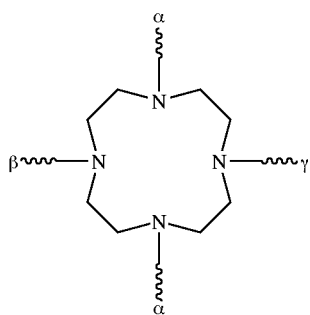

(d) 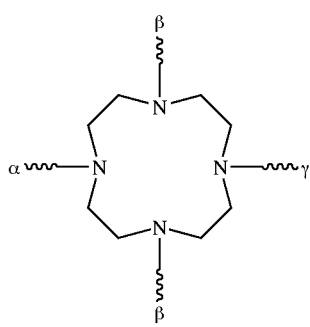

(e) 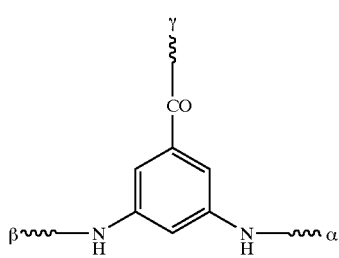

(f) 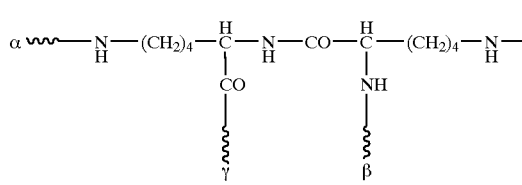

(g) 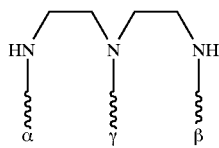

(h) 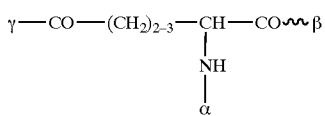

-continued (i) 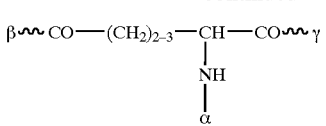

whereby α means the binding site of G to complex K, β is the binding site of G to radical R, and γ represents the binding site of G to radical Z Z stands for

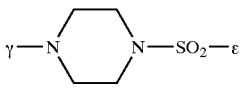

γ-C(O)CH$_2$O(CH$_2$)$_2$-ε, whereby γ represents the binding site of Z to radical G and ε means the binding site of Z to perfluorinated radical R$^F$, R represents a polar radical that is selected from complexes K of general formulas IId to VIId, whereby R$^1$ here means a hydrogen atom or a metal ion equivalent of atomic numbers 20, 23–29, 42–46 or 58–70, and radicals R$^2$, R$^3$, R$^4$, U and U$^1$ have the above-indicated meaning, or the folic acid radical or R means a carbon chain with 2–30 C atoms that is bonded to radical G via —CO— or SO$_2$— and is straight or branched, saturated or unsaturated, optionally interrupted by 1–10 oxygen atoms, 1–5 —NHCO groups, 1–5 —CONH groups, 1–2 sulfur atoms, 1–5 —NH groups or 1–2 phenylene groups, which optionally can be substituted with 1–2 OH groups, 1–2 NH$_2$ groups, 1–2 —COOH groups, or 1–2 —SO$_3$H groups, or optionally substituted with 1–8 OH groups, 1–5 —COOH groups, 1–2 SO$_3$H groups, 1–5 NH$_2$ groups, 1–5 C$_1$–C$_4$-alkoxy groups, and l$^1$, m$^1$, p$^2$, independently of one another, mean integer 1 or 2.

Since the compounds according to the invention are intended for use in NMR diagnosis, the metal ion of the signaling group must be paramagnetic. These are in particular the divalent and trivalent ions of the elements of atomic numbers 23–29, 42–46 and 58–70. Suitable ions are, for example, the chromium(III), iron(II), cobalt(II), nickel(II), copper(II), praseodymium(III), neodymium(III), samarium (III) and ytterbium(III) ions. Because of their strong magnetic moment, gadolinium(III), terbium(III), dysprosium (III), holmium(III), erbium(III), iron(III) and manganese(II) ions are especially preferred.

Preferred are manganese(II), iron(II), iron(III), praseodymium(III), neodymium(III), samarium(III), gadolinium(III) and ytterbium(III) ions, especially dysprosium(III) ions.

In R$^1$, optionally present acidic hydrogen atoms, i.e., those that have not been substituted by the central ion, can be replaced optionally completely or partially by cations of inorganic and/or organic bases or amino acids or amino acid amides.

Suitable inorganic cations are, for example, the lithium ion, the potassium ion, the calcium ion and especially the sodium ion. Suitable cations of organic bases are, i.a., those of primary, secondary or tertiary amines, such as, for example, ethanolamine, diethanolamine, morpholine, glucamine, N,N-dimethylglucamine, and especially N-methylglucamine. Suitable cations of amino acids are, for example, those of lysine, arginine, and ornithine as well as the amides of otherwise acidic or neutral amino acids.

Especially preferred compounds of general formula Id are those with macrocyclic compound K of general formulas IId, IIId, VdB or VIId.

Radical U in metal complex K preferably means —$CH_2$— or $C_6H_4$—O—$CH_2$-ω, whereby ω stands for the binding site to —CO—.

Alkyl groups $R^2$ and $R^3$ in the macrocyclic compound of general formula IId can be straight-chain or branched. By way of example, methyl, ethyl, propyl, isopropyl, n-butyl, 1-methylpropyl, 2-methylpropyl, n-pentyl, 1-methylbutyl, 2-methylbutyl, 3-methylbutyl, and 1,2-dimethylpropyl can be mentioned. $R^2$ and $R^3$, independently of one another, preferably mean hydrogen or $C_1$–$C_4$-alkyl.

In a quite especially preferred embodiment, $R^2$ stands for methyl and $R^3$ stands for hydrogen.

The benzyl group or phenyl group $R^2$ or $R^3$ in macrocyclic compound K of general formula IId can also be substituted in the ring.

In a preferred embodiment, polar radical R in general formula Id means complex K, whereby the latter preferably in addition to a $Gd^{3+}$- or $Mn^{2+}$ complex also can be a $Ca^{2+}$ complex. As polar radicals R, complexes K of general formulas IId, IIId, VdA or VIId are especially preferred. The latter as $R^1$ quite especially preferably have a metal ion equivalent of atomic numbers 20, 25, 39 or 64.

In another preferred embodiment, polar radical R has the following meanings:

—C(O)$CH_2CH_2SO_3H$
—C(O)$CH_2OCH_2CH_2OCH_2CH_2OH$
—C(O)$CH_2OCH_2CH_2OH$
—C(O)$CH_2OCH_2CH(OH)CH_2OH$
—C(O)$CH_2NH$—C(O)$CH_2COOH$
—C(O)$CH_2CH(OH)CH_2OH$
—C(O)$CH_2OCH_2COOH$
—$SO_2CH_2CH_2COOH$
—C(O)—$C_6H_3$-(m-COOH)$_2$
—C(O)$CH_2O(CH_2)_2$—$C_6H_3$-(m-COOH)$_2$
—C(O)$CH_2O$—$C_6H_4$-m-$SO_3H$
—C(O)$CH_2NHC(O)CH_2NHC(O)CH_2OCH_2COOH$
—C(O)$CH_2OCH_2CH_2OCH_2COOH$
—C(O)$CH_2OCH_2CH(OH)CH_2O$—$CH_2CH_2OH$
—C(O)$CH_2OCH_2CH(OH)CH_2OCH_2$—CH(OH)—$CH_2OH$
—C(O)$CH_2SO_3H$
—C(O)$CH_2CH_2COOH$
—C(O)CH(OH)CH(OH)$CH_2OH$
—C(O)$CH_2O[(CH_2)_2O]_{1-9}$—$CH_3$
—C(O)$CH_2O[(CH_2)_2O]_{1-9}$—H
—C(O)$CH_2OCH(CH_2OH)_2$
—C(O)$CH_2OCH(CH_2OCH_2COOH)_2$
—C(O)—$C_6H_3$-(m-O$CH_2$COOH)$_2$ —CO—$CH_2$O—($CH_2$)$_2$O($CH_2$)$_2$O—($CH_2$)$_2$O($CH_2$)$_2$O$CH_3$
preferably —C(O)$CH_2O[(CH_2)_2O]_4$—$CH_3$.

In another preferred embodiment, polar radical R means the folic acid radical.

Of the compounds of general formula Id according to the invention, in addition those are preferred in which $R^F$ means —$C_nF_{2n+1}$. n preferably stands for numbers 4–15. Quite especially preferred are the radicals —$C_4F_9$, —$C_6F_{13}$, —$C_8F_{17}$, —$C_{12}F_{25}$ and —$C_{14}F_{29}$.

Radical G that is functionalized in at least three places in general formula Id, which represents the "skeleton," means lysine radical (a) or (b) in a preferred embodiment of the invention.

Z means the linker that is indicated in general formula Id, whereby radical

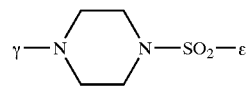

is preferred.

The perfluoroalkyl-containing metal complexes with polar radicals of general formula Id

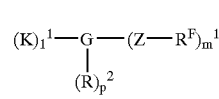

(Id)

in which K, G, R, Z, $R^F$, $I^1$, $m^1$, and $p^2$ have the above-indicated meaning, are produced by a carboxylic acid of general formula IIk

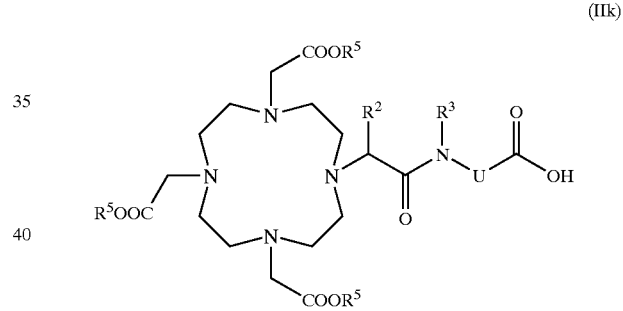

(IIk)

in which $R^5$ means a metal ion equivalent of atomic numbers 23–29, 42–46 or 58–70 or a carboxyl protective group, and $R^2$, $R^3$ and U have the above-mentioned meaning, or a carboxylic acid of general formula IIIk

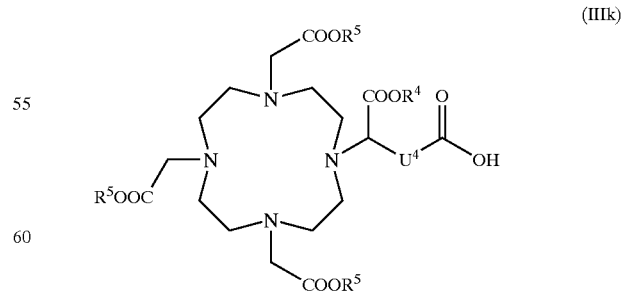

(IIIk)

in which $R^4$, $R^5$ and $U^1$ have the above-mentioned meaning or a carboxylic acid of general formula IVk

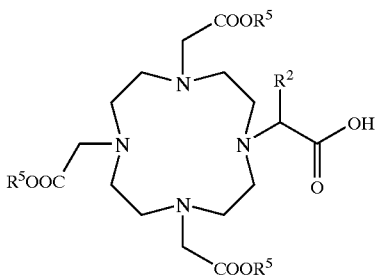

(IVk)

in which $R^5$ and $R^2$ have the above-mentioned meaning or a carboxylic acid of general formula Vk or Vm

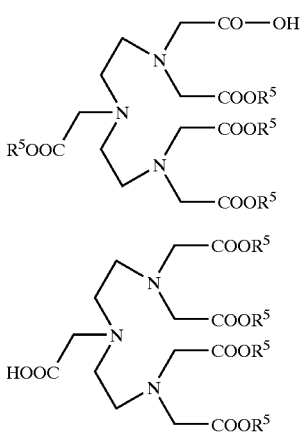

(Vk)

(Vm)

in which $R^5$ has the above-mentioned meaning or a carboxylic acid of general formula VIk

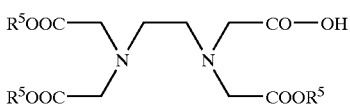

(VIk)

in which $R^5$ has the above-mentioned meaning or a carboxylic acid of general formula VIIk

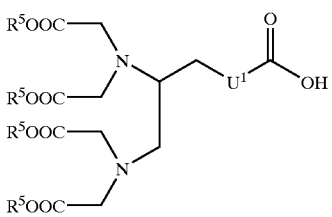

(VIIk)

in which $R^5$ and $U^1$ have the above-mentioned meanings, being reacted in a way that is known in the art in optionally activated form with an amine of general formula VIIId

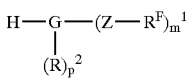

(VIIId)

in which G, R, Z, $R^F$, $m^1$ and $p^2$ have the above-indicated meaning, in a coupling reaction and optionally subsequent cleavage of optionally present protective groups to form a metal complex of general formula Id or if $R^5$ has the meaning of a protective group, being reacted after cleavage of these protective groups in a subsequent step in a way that is known in the art with at least one metal oxide or metal salt of an element of atomic numbers 23–29, 42–46 or 58–70, and then, if desired, optionally present acidic hydrogen atoms being substituted by cations of inorganic and/or organic bases, amino acids or amino acid amides.

The carboxylic acids of general formulas IIk to VIIk that are used are either known compounds or are produced according to the processes that are described in the examples. Thus, the production of the carboxylic acids of general formula IIk is known from DE 196 52 386. The production of the carboxylic acids of general formula IVk can be found in DE 197 28 954.

A precursor of compounds of general formula VdA is the $N^3$-(2,6-dioxomorpholinoethyl)-$N^6$-(ethoxycarbonylmethyl)-3,6-diaza-octanedioic acid, which is described in EP 263 059.

The compounds of general formula VdB are derived from the isomeric diethylenetriamine-pentaacetic acid, which binds via acetic acid on the center N-atom. This DTPA is described in Patents DE 195 07 819 and DE 195 08 058.

Compounds of general formula VId are derived from N-(carboxymethyl)-N-[2-(2,6-dioxo-4-morpholinyl)-ethyl]-glycine, whose production is described in J. Am. Oil. Chem. Soc. (1982), 59 (2), 104–107.

Compounds of general formula VIId are derived from 1-(4-carboxymethoxybenzyl)ethylenediamine-tetraacetic acid, whose production was described in U.S. Pat. No. 4,622,420.

Metal complex XVI of Table 1 according to the invention is used as a quite especially preferred compound of general formula Id.

In another preferred embodiment of the invention, galenical formulations can be used that contain paramagnetic and diamagnetic perfluoroalkyl-containing substances. The paramagnetic and diamagnetic substances are preferably present in a dissolved state in an aqueous solvent.

As paramagnetic, perfluoroalkyl-containing compounds, all above-mentioned metal complexes of general formulas I, Ia, Ib, Ic and/or Id according to the invention can be used in the formulations.

The diamagnetic perfluoroalkyl-containing substances are those of general formula XX:

$$R^F—L^2—B^2 \qquad (XX)$$

in which $R^F$ represents a straight-chain or branched perfluoroalkyl radical with 4 to 30 carbon atoms, $L^2$ stands for a linker and $B^2$ stands for a hydrophilic group. Linker $L^2$ is a direct bond, an —$SO_2$ group, or a straight-chain or branched carbon chain with up to 20 carbon atoms, which can be substituted with one or more —OH, —COO—, —$SO_3$ groups and/or optionally contains one or more —O—, —S—, —CO—, —CONH—, —NHCO—, —$CONR^9$—, —$NR^9CO$—, —$SO_2$—, —$PO_4$—, —NH— or —$NR^9$ groups, an aryl ring or a piperazine, whereby $R^9$ stands for a $C_1$- to $C_{20}$-alkyl radical, which in turn can contain one or more O atoms, and/or can be substituted with —$COO^-$ or $SO_3$ groups.

Hydrophilic group $B^2$ is a mono- or disaccharide, one or more adjacent —$COO^-$ or —$SO_3$ groups, a dicarboxylic acid, an isophthalic acid, a picolinic acid, a benzenesulfonic acid, a tetrahydropyrandicarboxylic acid, a 2,6-pyridinedicarboxylic acid, a quaternary ammonium ion, an aminopolycarboxylic acid, an aminodipolyethylene glycol-sulfonic acid, an aminopolyethylene glycol group, an $SO_2$—$(CH_2)_2$—OH group, a polyhydroxyalkyl chain with at least two hydroxyl groups or one or more polyethylene glycol chains with at least two glycol units, whereby the polyethylene glycol chains are terminated by an —OH or —$OCH_3$ group. Such substances are partially already known; such substances for the production of formulations according to the invention were partially newly synthesized. Known perfluoroalkyl-containing substances and their production are described in the following publications:

- J. G. Riess, Journal of Drug Targeting, 1994, Vol. 2, pp. 455–468;
- J. B. Nivet et al., Eur. J. Med. Chem., 1991, Vol. 26, pp. 953–960;
- M.-P. Krafft et al., Angew. Chem., 1994, Vol. 106, No. 10, pp. 1146–1148;
- M. Lanier et al., Tetrahedron Letters, 1995, Vol. 36, No. 14, pp. 2491–2492;
- F. Guillod et al., Carbohydrate Research, 1994, Vol. 261, pp. 37–55;
- S. Achilefu et al., Journal of Fluorine Chemistry, 1995, Vol. 70, pp.19–26;
- L. Clary et al., Tetrahedron, 1995, Vol. 51, No. 47, pp. 13073–13088;
- F. Szoni et al., Journal of Fluorine Chemistry, 1989, Vol. 42, pp. 59–68;
- H. Wu et al., Supramolecular Chemistry, 1994, Vol.3, pp. 175–180;
- F. Guileri et al., Angew. Chem. 1994, Vol. 106, No. 14, pp. 1583–1585;
- M.-P. Krafft et al., Eur. J. Med. Chem., 1991, Vol. 26, pp.545–550;
- J. Greiner et al., Journal of Fluorine Chemistry, 1992, Vol. 56, pp. 285–293;
- A. Milius et al., Carbohydrate Research, 1992, Vol. 229, pp. 323–336;
- J. Riess et al., Colloids and Surfaces A, 1994, Vol. 84, pp. 33–48;
- G. Merhi et al., J. Med. Chem., 1996, Vol. 39, pp. 4483–4488;
- V. Cirkva et al., Journal of Fluorine Chemistry, 1997, Vol. 83, pp. 151–158;
- A. Ould Amanetoullah et al., Journal of Fluorine Chemistry, 1997, Vol. 84, pp. 149–153;
- J. Chen et al., Inorg. Chem., 1996, Vol. 35, pp. 1590–161;
- L. Clary et al., Tetrahedron Letters, 1995, Vol. 36, No. 4, pp.539–542;
- M. M. Chaabouni ct al., Journal of Fluorine Chemistry, 1990, Vol. 46, pp.307–315;
- A. Milius et al., New J. Chem., 1991, Vol. 15, pp.337–344;
- M.-P. Krafft et al., New J. Chem., 1990, Vol. 14, pp. 869–875;
- J.-B. Nivet et al., New J. Chem., 1994, Vol. 18, pp. 861–869;
- C. Santaella et al., New J. Chem., 1991, Vol. 15, pp. 685–692;
- C. Santaella et al., New J. Chem., 1992, Vol. 16, pp. 399–404;
- A. Milius et al., New J. Chem., 1992, Vol. 16, pp. 771–773;
- F. Szönyi et al., Journal of Fluorine Chemistry, 1991, Vol. 55, pp. 85–92;
- C. Santaella et al., Angew. Chem., 1991, Vol. 103, No. 5, pp. 584–586;
- M.-P. Krafft et al., Angew. Chem., 1993, Vol. 105, No. 5, pp. 783–785;
- EP 0 548 096 B1.

The production of the new perfluoroalkyl-containing substances is carried out analogously to the above-mentioned compounds that are known in the literature and is described in the examples. In this case, these are substances of general formula XXI $$R^F-X^1 \quad\quad\quad (XXI)$$

in which $R^F$ represents a straight-chain or branched perfluoroalkyl radical with 4 to 30 carbon atoms, and $X^1$ is a radical that is selected from the group of the following radicals (n in this case is a number between 1 and 10):

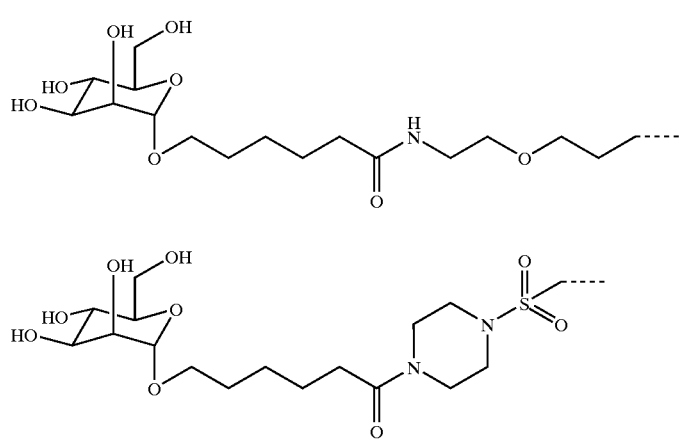
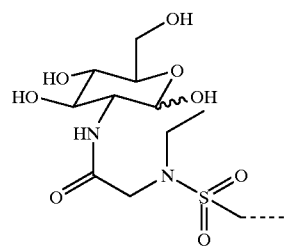

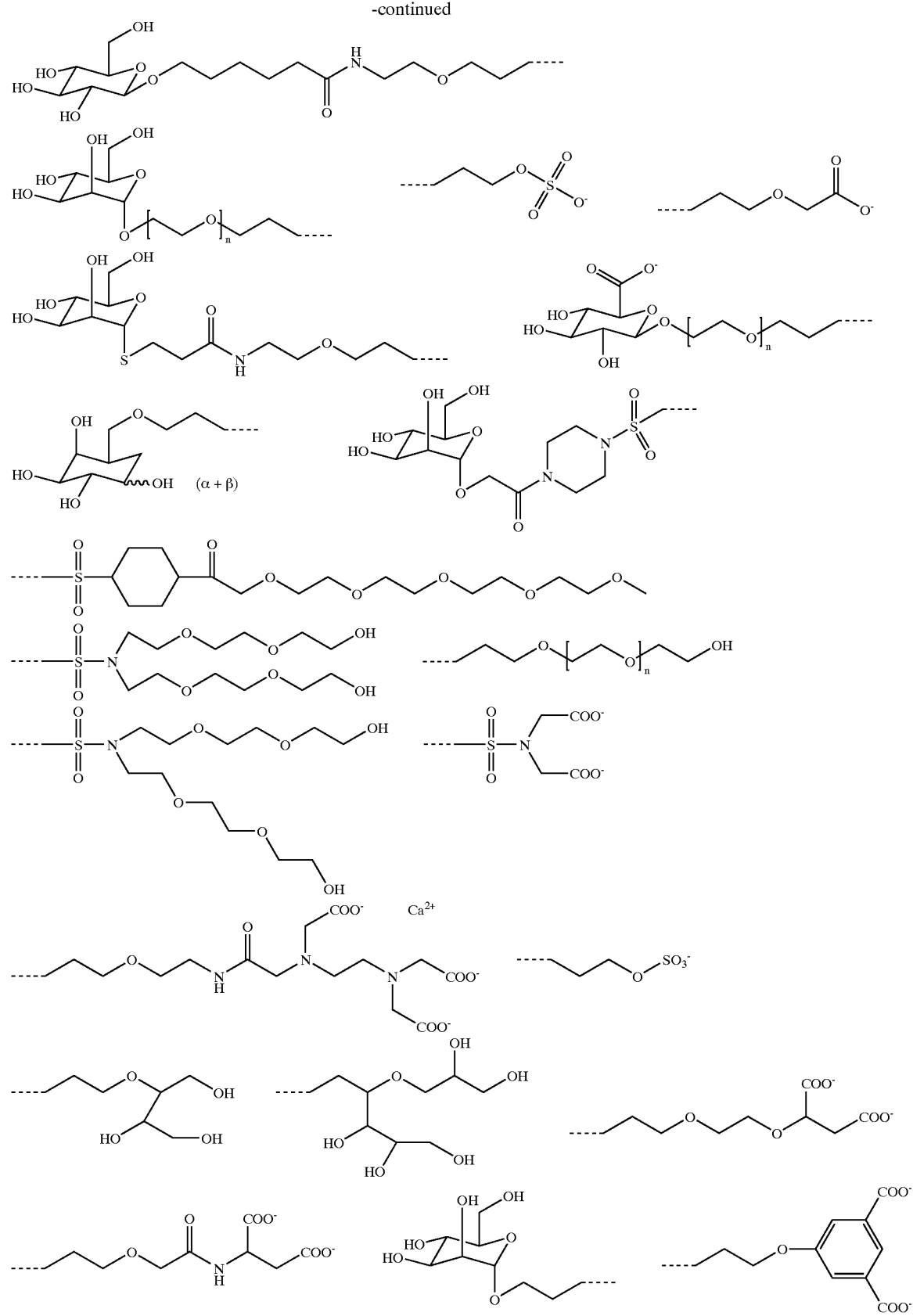

Preferred diamagnetic perfluoroalkyl-containing substances are those with a monosaccharide as hydrophilic group $B^2$.

Especially preferred diamagnetic perfluoroalkyl-containing compounds contain a perfluoroalkyl radical $R_f$ with 6 to 12 carbon atoms, a linker $L^2$, which represents an —$SO_2$ group, or a straight-chain or branched carbon chain with up to 20 carbon atoms, which in turn contains one or more —O—, —CO—, —CONH—, —NHCO—, —CONR—, —NRCO—, or —$SO_2$ groups or a piperazine, in which R has the above-indicated meaning, and a monosaccharide as hydrophilic group $B^2$.

Other suitable diamagnetic perfluoroalkyl-containing compounds are conjugates that consist of cyclodextrin and perfluoroalkyl-containing compounds. These conjugates consist of α-, β- or γ-cyclodextrin and compounds of general formula XXII $$A^1—L^3—R^F \qquad (XXII)$$

in which $A^1$ stands for an adamantan, biphenyl or anthracene molecule, $L^3$ stands for a linker, and $R^F$ stands for a straight-chain or branched perfluoroalkyl radical with 4 to 30 carbon atoms. Linker $L^3$ is a straight-chain hydrocarbon chain with 1 to 20 carbon atoms, which can be interrupted by one or more oxygen atoms, one or more CO—, $SO_2$—, CONH—, NHCO—, CONR—, NRCO—, NH— or NR groups or a piperazine, whereby R is a $C_1$–$C_5$-alkyl radical.

Preferred compounds are the following compounds:

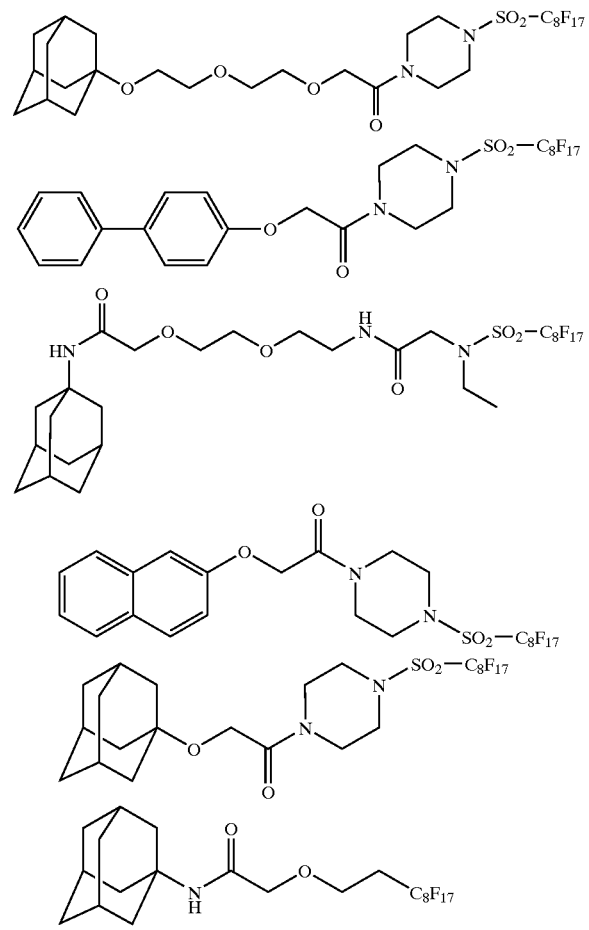

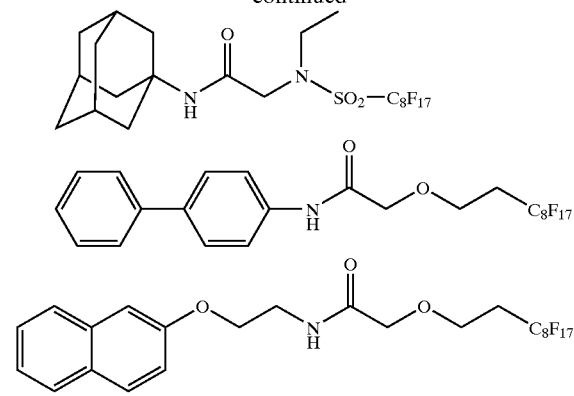

The galenical formulations of this invention contain the paramagnetic and diamagnetic perfluoroalkyl-containing compounds in a mixing ratio of between 5:95 and 95:5. Preferred are mixing ratios of between 40:60 and 60:40 of the two substances. Both substances are used in millimolar concentrations. Concentrations of between 0.5 and 1000 mmol/l of solvent are achieved. The solvent is preferably water. The metal concentration of the formulations is preferably in a range of 50–250 mmol/l.

Preferred are mixtures that consist of paramagnetic and diamagnetic perfluoroalkyl-containing compounds, in which the perfluoroalkyl chains have a length of 6 to 12 carbon atoms. Especially preferred are mixtures in which both the paramagnetic and the diamagnetic perfluoroalkyl-containing compounds have a perfluoroalkyl chain with 8 carbon atoms.

The production of the galenical formulations is carried out in that the paramagnetic perfluoroalkyl-containing compounds (components A) and the diamagnetic perfluoroalkyl-containing substances (components B) are weighed in fractions of a mol of between 0.05 and 0.95 in components A or B and are dissolved in a suitable solvent. An especially well suited solvent is water. Common galenical additives, such as, e.g., buffer solutions and the Ca-salt of the complexing agent, are then added in excess to this solution. At 10 to 100° C., the solutions are stirred vigorously. As an alterative, the solutions can be treated in an ultrasound bath at 10 to 100° C. Another alternative consists in that the solutions are treated with microwaves.

In substances that do not dissolve in water as individual components, it proves advantageous to add a solubilizer such as alcohol (e.g., methanol or ethanol) or another water-miscible solvent, and the latter can then be distilled off slowly. The distillation can be carried out under a vacuum. The residue is then dissolved in water, and the solution is filtered. It is also possible to dissolve each component separately in one solvent each, then to combine them and proceed as indicated above. It has proven advantageous to introduce a relatively strongly concentrated solution (>100 mmol) of the metal complex (component A) and then to add component B in the pure state, and, as mentioned above, to stir the solution or to treat it with ultrasound or microwaves.

In summary, it has been determined that as quite especially preferred compounds, gadolinium complexes I–XVI that are presented in Table 1 meet the criteria according to the invention. The physical parameters of these metal complexes I–XVI are presented in Table 2.

Both the paramagnetic compounds of general formulas I, Ia, Ib, Ic and Id according to the invention and the formulations that consist of paramagnetic and diamagnetic perfluoroalkyl-containing substances according to the invention are extremely well suited as contrast media in MR-imaging for visualization of plaque, tumors and necroses.

TABLE 1

Figure 1:
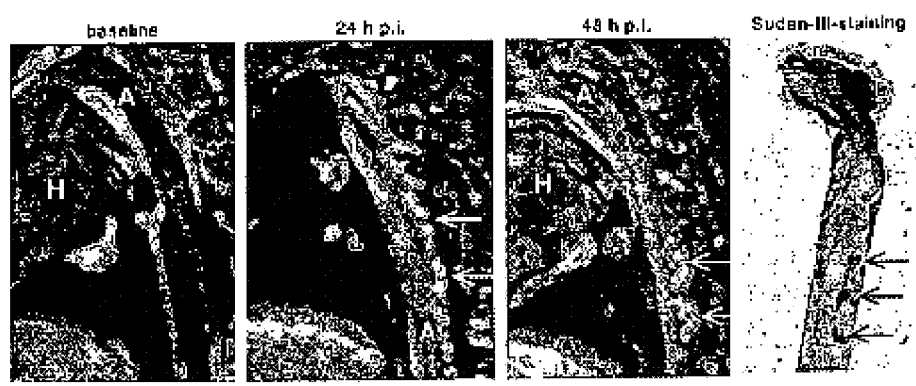
FIG. 1 depicts the localization of plaque at baseline, 24 hours p.i and 48 hours p.i, especially in aortic arches and in vascular passages by means of Sudan-III staining, with visualization after administration of metal complex XV 25 µmol/kg.; 3D-T1-MPRage, TR/TE 11.1/4.3 ms, α 15°. (Watanabe rabbits; A:Aorta; H: Heart; Arrow: vascular passages; MPR Projection:)

Metal Complexes that are Quite Especially Preferably Used According to the Invention

| Complex | Bibliographic Reference, Name |
| --- | --- |
| I | WO 97/26017, Example 33f<br>Gadolinium complex of 10-[1-methyl-2-oxo-3-aza-5-oxo-{4-perfluorooctyl-sulfonyl-piperazin-1-yl}-pentyl]-1,4,7-tris(carboxymethyl)-1,4,7,10-tetraazacyclododecane |
| II | WO 97/26017, Example 2c<br>Gadolinium complex of 10-[2-hydroxy-4-aza-5-oxo-7-oxa-10,10,11,11,12,12,13,13,14,14,15,15,16,16,17,17-heptadecafluoroheptadecyl]-1,4,7-tris (carboxy-methyl)-1,4,7,10-tetraazacyclododecane |
| III | WO 97/26017, Example 34b<br>Gadolinium complex of 10-[2-hydroxy-4-aza-5,9-dioxo-9-{4-perfluorooctyl)-piperazin-1-yl}-nonyl]-1,4,7-tris(carboxymethyl)-1,4,7,10-tetraazacyclododecane |
| IV | WO 97/26017, Example 1c<br>Gadolinium complex of 10-[2-hydroxy-4-aza-5-oxo-7-aza-7-(perfluorooctyl-sulfonyl)-nonyl]-1,4,7-tris (carboxymethyl)-1,4,7,10-tetraazacyclododecane |
| V | Example 2c, this application<br>1,4,7-Tris(carboxylatomethyl)-10-(3-aza-4-oxo-hexan-5-ylic)-acid-N-(2,3-dihydroxypropyl)-N-(1H,1H,2H,2H,4H,4H,5H,5H-3-oxa)-perfluorotridecyl)-amide]-1,4,7,10-tetraazacyclododecane, gadolinium complex |
| VI | WO 97/26017, Example 3c<br>Gadolinium complex of 10-[2-hydroxy-4-oxa-1H,1H,2H,2H,3H,3H,5H,5H,6H,6H-perfluorotetradecyl]-1,4,7-tris(carboxymethyl)-1,4,7,10-tetraazacyclododecane |
| VII | Example 5e, this application<br>1,4,7-Tris(carboxylatomethyl)-10-{(3-aza-4-oxo-hexan-5-ylic)acid-[N- (3,6,9,12,15-pentaoxa)-hexadecyl)-N-(1H,1H,2H,2H,4H,4H,5H,5H-3-oxa)-perfluorotridecyl]-amide}-1,4,7,10-tetraazacyclododecane, gadolinium complex |
| VIII | Example 3c, this application<br>1,4,7-Tris(carboxylatomethyl)-10-{(3-aza-4-oxo-hexan-5-ylic)-acid-N-(5-hydroxy-3-oxa-pentyl)-N-(1H,1H,2H,2H,4H,4H,5H,5H-3-oxa)-perfluorotridecyl]-amide}-1,4,7,10-tetraazacyclododecane, gadolinium complex |
| IX | Example 6b, this application<br>1,4,7-Tris(carboxylatomethyl)-10-{(3-aza-4-oxo-hexan-5-ylic)-acid-[N-3,6,9,16-tetraoxa-13-aza-14-oxo-$C_{19}$–$C_{26}$-hepta-decafluoro)hexacosyl]-amide}-1,4,7,10-tetraazacyclododecane, gadolinium complex |
| X | Example 1c, this application<br>1,4,7-Tris(carboxylatomethyl)-10-[(3-aza-4-oxo-hexan-5-ylic)-acid-N-(2-methoxyethyl)-N-(1H,1H,2H,2H,4H,4H,5H,5H-3-oxa)-perfluorotridecyl]-amide}-1,4,7,10-tetraazacyclododecane, gadolinium complex |
| XI | WO 97/26017, Example 32c<br>Gadolinium complex of 10-[2-hydroxy-4-aza-5-oxo-7-oxa-10,10,11,11,12,12,13,13,14,14,15,15, 16,16,17,17,18,18,19,19-henicosafluoro-nonadecyl]-1,4,7-tris(carboxymethyl)-1,4,7,10-tetraazacyclododecane |

TABLE 1-continued

Metal Complexes that are Quite Especially Preferably Used According to the Invention

| Complex | Bibliographic Reference, Name |
|---|---|
| XII | WO 97/26017, Example 38d<br>Gadolinium complex of 10-[2-hydroxy-4-aza-5-oxo-11-aza-11-(perfluorooctyl-sulfonyl)-tridecyl]-1,4,7-tris(carboxymethyl) 1,4,7,10-tetraazacyclododecane |
| XIII | WO 97/26017, Example 35d<br>Gadolinium complex of 10-[2-hydroxy-4-aza-5-oxo-7-aza-7-(perfluorooctyl-sulfonyl)-8-phenyl-octyl]-1-4-7-tris(carboxymethyl)-1,4,7,10-tetraaza cyclododecane |
| XIV | WO 99/01161, Example 1g<br>1,4,7-Tris{1,4,7-tris(N-(carboxylatomethyl)-10-[N-1-methyl-3,6-diaza-2,5,8-trioxooctane-1,8-diyl]-1,4,7,10-tetraazacyclododecane, Gd complex}-10-N-2H,2H,4H,4H,5H,5H-3-oxa-perfluoro-tridecanoyl]-1,4,7,10-tetraazacyclo-dodecane, Gd complex |
| XV | Example 21f, this application<br>6-N-[1,4,7-Tris(carboxylatomethyl)-1,4,7,10-tetraazacyclododecane-10-N-(pentanoyl-3-aza-4-oxo-5-methyl-5-yl)]-2-N-[1-O-α-D-carbonylmethyl-mannopyranose]-L-lysine-[1-(4-perfluorooctylsulfonyl)-piperazine]-amide, Gd complex |
| XVI | Example 54b, this application<br>2,6-N,N'-Bis[1,4,7-tris(carboxylatomethyl)-1,4,7,10-tetraazacyclododecane-10-(pentanoyl-3-aza-4-oxo-5-methyl-5-yl)]-lysine-[1-(4-perfluorooctylsulfonyl-piperazine]-amide, Gd complex |

TABLE 2

Physicochemical Parameters of the Complexes of Table 1 that are Used According to the Invention

| Complex No. | CMC (mol/l) | 2 Rh (nm) | $R^1$ Plasma (1/mmol · s) |
|---|---|---|---|
| I | 1.86 · 10$^{-6}$ | 4.6 | 35.7 |
| II | 2.30 · 10$^{-5}$ | 14 | 33 |
| III | 7.06 · 10$^{-6}$ | 3.2 | 24.9 |
| IV | 1.0 · 10$^{-6}$ | 31.5 | 29.7 |
| V | 3.9 · 10$^{-6}$ | 4.4 | 19.6 |
| VI | 1.44 · 10$^{-5}$ | 3.2 | 27.5 |
| VII | 5.20 · 10$^{-5}$ | 3.0 | 30.3 |
| VIII | 2.92 · 10$^{-5}$ | 25 | 21.2 |
| IX | 2.65 · 10$^{-6}$ | 6.0 | 13.3 |
| X | 7.90 · 10$^{-6}$ | 5.4 | 25.7 |
| XI | 2.88 · 10$^{-6}$ | 35.5 | 24.8 |
| XII | 1.07 · 10$^{-5}$ | 7.4 | 30.5 |
| XIII | 3.25 · 10$^{-6}$ | 4.3 | 34.0 |
| XIV | 8.90 · 10$^{-4}$ | 2.2 | 19.5 |
| XV | 2.50 · 10$^{-6}$ | 4.4 | 15.9 |
| XVI | 3.90 · 10$^{-5}$ | 4.9 | 21.3 |

CMC: Critical micelle formation concentration
2 Rh: Hydrodynamic micelle diameter
$R^1$: Relaxivity

EMBODIMENTS

EXAMPLE 1 a) 2H,2H,4H,4H,5H,5 H-3-Oxa-perfluorotridecanoic acid-N-(2-methoxy)-ethyl-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 4.51 g (60 mmol) of 2-methoxyethylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethanelacetone=20:1).

Yield: 30.28 g (91% of theory) of a colorless solid.

Elementary analysis: Cld: C, 31.10; H, 2.44; N, 2.42; F, 55.76. Fnd: C, 30.87; H, 2.58; N, 2.35; F, 55.51.

b) N-(2-Methoxyethyl)-N-(1H,1H,2H,2H,4H,4H,5H,5H-3-oxa)-perfluorotridecylamine 30 g (51.79 mmol) of the title compound of Example 1a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 300 ml of ethanol/50 ml of 10% aqueous hydrochloric acid, and it is stirred for 8 hours at 40° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 26.93 g (92% of theory) of a colorless solid.

Elementary analysis (relative to anhydrous substance): Cld: C, 31.87; H, 2.85; N, 2.48; F, 57.14. Fnd: C, 31.69; H, 3.10; N, 2.27; F, 56.88.

c) 1,4,7-Tris(carboxylatomethyl)-10-[(3-aza-4-oxo-hexan-5-ylic)-acid-N-2-methoxyethyl)-N-(1H,1H,2H,2H,4H,4H,5H,5H-3-oxa)-perfluorotridecyl)-amide]-1,4,7,10-tetraazacyclododecane, gadolinium complex (metal complex X)

10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 8.98 g (15.88 mmol) of the title compound of Example 1b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-18 (mobile solvent: gradient that consists of tetrahydrofuran/acetonitrile/water).

Yield: 15.14 g(81% of theory) of a colorless, amorphous powder.

Water content: 5.7%.

Elementary analysis (relative to anhydrous substance): Cld: C, 34.70; H, 3.77; N, 7.14; F, 27.44; Gd, 13.36. Fnd: C, 34.51; H, 3.94; N, 7.02; F, 27.25; Gd, 13.18.

EXAMPLE 2 a) 2H,2H,4H,4H,5H,5H-3-Oxa)-perfluorotridecanoic acid-N-(2,3-dihydroxypropyl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 5.47 g (60 mmol) of 2,3-dihydroxypropylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/ethanol=15:1).

Yield: 29.70 g (87% of theory) of a colorless solid.

Elementary analysis: Cld: C, 30.32; H, 2.20; N, 2.36; F, 54.35. Fnd: C, 30.12; H, 2.41; N, 2.18; F, 54.15.

b) N-(2,3-Dihydroxypropyl)-N-(1H,1H,2H,2H,4H,4H,5H,5H-3-oxa-perfluorotridecyl)-amine 30 g (48.8 mmol) of the title compound of Example 2a is dissolved in 300 ml of tetrahydrofuran, and 50 ml of 10 M boranedimethyl sulfide (in tetrahydrofuran) is added. It is refluxed for 16 hours. It is cooled to 0° C., and 300 ml of methanol is added in drops, then it is evaporated to the dry state in a vacuum. The residue is taken up in a mixture that consists of 300 ml of ethanol/50 ml of 10% aqueous hydrochloric acid, and it is stirred for 8 hours at 60° C. It is evaporated to the dry state in a vacuum, the residue is taken up in 300 ml of 5% aqueous sodium hydroxide solution and extracted 3 times with 300 ml of dichloromethane each. The organic phases are dried on magnesium sulfate, evaporated to the dry state in a vacuum, and the residue is chromatographed on silica gel (mobile solvent: dichloromethane/methanol=15:1).

Yield: 24.07 g (85% of theory) of a colorless solid.

Elementary analysis: Cld: C, 31.05; H, 2.61; N, 2.41; F, 55.66. Fnd: C, 31.91; H, 2.78; N, 2.33; F, 55.47.

c) 1,4,7-Tris(carboxylatomethyl)-10-[(3-aza-4-oxo-hexan-5-ylic)-acid-N-(2,3-dihydroxypropyl)-N-(1H,1H,2H,2H,4H,4H,5H,5H-3-oxa)-perfluorotridecyl)-amide]-1,4,7,10-tetraazacyclododecane, gadolinium complex (metal complex V)

10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved in 100 ml of dimethyl sulfoxide at 60° C. It is cooled to 15° C., and 9.21 g (1 5.88 mmol) of the title compound of Example 2b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-18 (mobile solvent: gradient that consists of tetrahydrofuran/acetonitrile/water).

Yield: 16.09 g (85% of theory) of a colorless, amorphous powder.

Water content: 6.3%.

Elementary analysis (relative to anhydrous substance): Cld: C, 34.26; H, 3.64; N, 7.05; F, 27.10; Gd, 13.19. Fnd: C, 34.12; H, 3.83; N, 6.91; F, 26.88; Gd, 12.93.

EXAMPLE 3 a) 2H,2H,4H,4H,5H,5H-3-Oxa-perfluorotridecanoic acid-N-(5-hydroxy-3-oxa-pentyl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 6.25 g (60 mmol) of 5-hydroxy-3-oxa-pentylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=15:1).

Yield: 32.20 g (92% of theory) of a colorless solid.

Elementary analysis: Cld: C, 31.54; H, 2.65; N, 2.30; F, 53.01. Fnd: C, 31.61; H, 2.84; N, 2.14; F, 52.85.

b) N-(5-Hydroxy-3-oxa-pentyl)-N-(1H,1H,2H ,2H,4H,4H,5H,5H-3-oxa-perfluorotridecyl)-amine 30 g (49.24 mmol) of the title compound of Example 3a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 300 ml of ethanol/50 ml of 10% aqueous hydrochloric acid, and it is stirred for 10 hours at 50° C. It is evaporated to the dry state in a vacuum, the residue is taken up in 300 ml of 5% aqueous sodium hydroxide solution and extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol 20:1).

Yield: 26.09 g (89% of theory) of a colorless solid.

Elementary analysis: Cld: C, 32.28; H, 3.05; N, 2.35; F, 54.25. Fnd: C, 32.12; H, 3.21; N, 2.18; F, 54.09.

c) 1,4,7-Tris(carboxylatomethyl)-10-[(3-aza4-oxo-hexan-5-ylic)-acid-N-(5-hydroxy-3-oxa-pentyl)-N-(1H,1H,2H,2H,4H,4H,5H,5H-3-oxa)-perfluorotridecyl)-amide]-1,4,7,10-tetraazacyclododecane, gadolinium complex (metal complex VIII)

10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.45 g (15.88 mmol) of the title compound of Example 3b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-18 (mobile solvent: gradient that consists of tetrahydrofuran/acetonitrile/water).

Yield: 16.10 g (84% of theory) of a colorless, amorphous powder.

Water content: 5.7%.

Elementary analysis (relative to anhydrous substance): Cld: C, 34.83; H, 3.84; N, 6.96; F, 26.76; Gd, 13.03. Fnd: C, 34.65; H, 3.96; N, 6.84; F, 26.62; Gd, 12.91.

EXAMPLE 4 a) 2H,2H,4H,4H,5H,5H-3-Oxa-perfluorotridecanoic acid-N-(2-hydroxyethyl)-amide 8.90 g (70 mmol) of oxalyl chloride is added to 30 g (57.45 mmol) of 2H,2H,4H,4H,5H,5H-3-oxaperfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 3.66 g (60 mmol) of 2-aminoethanol and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

Yield: 28.90 g (89% of theory).

Elementary analysis: Cld: C, 29.75; H, 2.14; N, 2.48; F, 57.14. Fnd: C, 29.61; H, 2.29; N, 2.37; F, 57.01.

b) N-(2-Hydroxyethyl)-N-(1H,1H,2H,2H,4H,4H,5H,5H-3-oxa)-perfluorotridecyl)-amine 28 g (49.54 mmol) of the title compound of Example 4a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 300 ml of ethanol/50 ml of 10% aqueous hydrochloric acid, and it is stirred for 10 hours at 50° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol=15:1).

Yield: 25.12 g (92% of theory) of a colorless solid.

Elementary analysis (relative to anhydrous substance): Cld: C, 30.50; H, 2.56; N, 2.54; F, 58.59. Fnd: C, 30.32; H, 2.71; N, 2.48; F, 58.43.

c) 1,4,7-Tris(carboxylatomethyl)-10-[(3-aza-4-oxo-hexan-5-ylic)-acid-N-(2-hydroxyethyl)-N-(1H,1H,2H,2H,4H,4H,5H,5H-3-oxa)-perfluorotridecyl)-amine-amide]-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 8.75 g (15.88 mmol) of the title compound of Example 4b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-1 8 (mobile solvent: gradient that consists of tetrahydrofuran/acetonitrile/water).

Yield: 16.81 g (91% of theory) of a colorless, amorphous powder.

Water content: 7.2%.

Elementary analysis (relative to anhydrous substance): Cld: C, 34.08; H, 3.64; N, 7.23; F, 27.77; Gd; 13.52. Fnd: C, 33.91; H, 3.82; N, 7.14; F, 27.58; Gd, 13.41.

EXAMPLE 5 a) 2H,2H,4H,4H,5H,5H-3-Oxa-perfluorotridecanoic acid amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 200 ml of dichloromethane. Ammonia gas is then directed into the solution for about 2 hours at 0° C. It is stirred for 4 more hours at 0° C., then for 2 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

Yield: 27.85 g (93% of theory).

Elementary analysis: Cld: C, 27.66; H, 1.55; N, 2.69; F, 61.97. Fnd: C, 27.49; H, 1.72; N, 2.54; F, 61.81.

b) 1H,1H,2H,2H,4H,4H,5H,5H-3-Oxa-perfluorotridecylamine, hydrochloride 27 g (51.8 mmol) of the title compound of Example 5a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added, then it is evaporated to the dry state in a vacuum. The residue is taken up in a mixture that consists of 400 ml of ethanol/100 ml of 10% aqueous hydrochloric acid, and it is stirred for 8 hours at 60° C. It is evaporated to the dry state in a vacuum, and the residue is recrystallized from a little ethanol/diethyl ether.

Yield: 26.75 g (95% of theory) of a colorless, crystalline solid.

Elementary analysis: Cld: C, 26.51; H, 2.04; N, 2.58; F, 59.41; Cl, 6.52. Fnd: C, 26.37; H, 2.21; N, 2.46; F, 59.25; Cl, 6.38.

c) 3,6,9,12,15-Pentaoxahexadecanoic acid-N-(1H,1H,2H,2H,4H,4H,5H,5H-3-oxa)-perfluorotridecyl)-amide 14.24 g (50 mmol) of 3,6,9,12,15-pentaoxahexadecanoic acid chloride is added at 0° C. to 26.5 g (48.74 mmol) of the title compound of Example 5b and 14.8 g (146.2 mmol) of triethylamine, dissolved in 300 ml of dichloromethane, and it is stirred for 3 hours at 0° C. 300 ml of 5% aqueous hydrochloric acid is added, and it is thoroughly stirred for 30 minutes. The organic phase is separated, dried on magnesium sulfate and evaporated to the dry state in a vacuum. The residue is chromatographed on silica gel (mobile solvent: dichloromethane/acetone: 20:1).

Yield: 32.03 g (87% of theory) of a colorless oil.

Elementary analysis: Cld: C, 36.57; H, 4.00; N, 1.85; F, 42.75. Fnd: C, 36.46; H, 4.12; N, 1.76; F, 42.53.

d) N-(3,6,9,12,15-Pentaoxahexadecyl)-N-(1H,1H,2H,2H,4H,4H-3-oxa)-perfluorotridecyl)-amine 31 g (41.03 mmol) of the title compound of Example 5c is dissolved in 300 ml of tetrahydrofuran, and 25 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 300 ml of ethanol/50 ml of 10% aqueous hydrochloric acid, and it is stirred for 8 hours at 40° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol=15:1).

Yield: 27.68g(91% of theory).

Elementary analysis: Cld: C, 37.26; H, 4.35; N, 1.89; F, 43.56. Fnd: C, 37.11; H, 4.51; N, 1.73; F, 43.41.

e) 1,4,7-Tris(carboxylatomethyl)-10-{(3-aza-4-oxo-hexan-5-ylic)-acid-[N-3,6,9,12,15-pentaoxa)-hexadecyl)-N-(1H, 1H,2H,2H,4H,4H,5H,5H-3-oxa)-perfluorotridecyl]-amide}-1,4,7,10-tetraazacyclododecane, gadolinium complex (metal complex VII)

10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 11.77 g (15.88 mmol) of the title compound of Example 5d is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/300 ml of diethyl ether, and it is stirred for 2 hours at room temperature. The deposited precipitate is filtered off, it is dissolved in a mixture that consists of a little ethanol/water and chromatographed on silica gel RP-18 (mobile solvent: gradient that consists of tetrahydrofuran/acetonitrile/water).

Yield: 18.05 g (84% of theory) of a colorless, amorphous powder.

Water content: 6.2%.

Elementary analysis (relative to anhydrous substance):
Cld: C, 37.29; H, 4.47; N, 6.21; F, 23.87; Gd, 11.62. Fnd: C, 37.11; H, 4.61; N, 6.03; F, 23.64; Gd, 11.42.

EXAMPLE 6 a) 1,4,7-Tris(carboxylatomethyl)-10-[(3-aza-4-oxo-hexan-5-ylic)-acid-N-(12-amino-3,6,9-trioxa-dodecyl)-amide]-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride and 3.66 g (31.76 mmol) of N-hydroxysuccinimide are dissolved at 60° C. in 100 ml of dimethyl sulfoxide. It is cooled to 15° C., and 3.51 g (17 mmol) of N,N'-dicyclohexyl-carbodiimide is added, and it is stirred for 5 hours at 15° C. To separate the urea, the solution is filtered. 14.66 g (60 mmol) of 1,12-diamino-3,6,9-trioxa-dodecane and 2.02 g (20 mmol) of triethylamine are added to the filtrate, and it is stirred for 12 hours at room temperature. The solution is poured into 1500 ml of diethyl ether/50 ml of n-butanol, and it is stirred for 30 minutes. The precipitated solid is filtered and chromatographed on silica gel RP-18 (mobile solvent: gradient that consists of tetrahydrofuran/acetonitrile/water).

Yield: 12.66 g (69% of theory) of a colorless, amorphous powder.

Water content: 3.5%.

Elementary analysis (relative to anhydrous substance):
Cld: C, 30.16; H, 4.54; N, 8.49; F, 27.96; Gd, 13.61. Fnd: C, 30.02; H, 4.68; N, 8.35; F, 27.81; Gd, 13.45.

b) 1,4,7-Tris(carboxylatomethyl)-10-{(3-aza-4-oxo-hexan-5-ylic)-acid-[N-3,6,9,16-tetraoxa-13-aza-14-oxo-$C_{19}$–$C_{26}$-hepta-decafluoro)-hexacosyl]-amide}-1,4,7,10-tetraazacyclododecane, gadolinium complex (metal complex IX)

11.3 g (21.64 mmol) of 2H,2H,4H,4H,5H,5H-3-oxa-perfluorotridecanoic acid, 0.85 g (20 mmol) of lithium chloride and 4.95 g (43 mmol) of N-hydroxysuccinimide are dissolved at 25° C. in 150 ml of dimethyl sulfoxide. It is cooled to 15° C., and 6.19 g (30 mmol) of N,N'-dicyclohexylcarbodiimide is added, and it is stirred for 5 hours at 15° C. To separate the urea, the solution is filtered. 12.5 g (10.82 mmol) of the title compound of Example 6a and 3.29 g (32.47 mmol) of triethylamine are added to the filtrate, and it is stirred for 12 hours at room temperature. The solution is poured into 1300 ml of diethyl ether/100 ml of acetone, and it is stirred for 30 minutes. The precipitated solid is filtered off and chromatographed on silica gel RP-18 (mobile solvent: gradient that consists of tetrahydrofuran/acetonitrile/water).

Yield: 13.01 g (90% of theory).

Water content: 6.7%.

Elementary analysis (relative to anhydrous substance):
Cld: C, 36.86; H, 4.30; N, 7.34; F, 24.17; Gd, 11.77. Fnd: C, 36.68; H, 4.41; N, 7.25; F, 24.03; Gd, 11.55.

EXAMPLE 7

1,4,7-Tris(carboxylatomethyl)-10-[(3-aza4-oxo-hexan-5-ylic)-acid-N-(1H,1H,2H,2H,4H,4H,5H,5H-3-oxa-perfluorotridecyl)-amide]-1,4,7,10-tetraaza-cyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride and 3.66 g (31.76 mmol) of N-hydroxysuccinimide are dissolved at 60° C. in 100 ml of dimethyl sulfoxide. It is cooled to 15° C., and 3.51 g (17 mmol) of N,N'-dicyclohexylcarbodiimide is added, and it is stirred for 5 hours at 15° C. To separate the urea, the solution is filtered. 8.63 g (15.88 mmol) of the title compound of Example 5b and 5.06 g (50 mmol) of triethylamine are added to the filtrate, and it is stirred for 12 hours at room temperature. The solution is poured into 1500 ml of diethyl ether/100 ml of acetone, and it is stirred for 30 minutes. The precipitated solid is filtered off and chromatographed on silica gel RP-18 (mobile solvent: gradient that consists of tetrahydrofuran/acetonitrile/water).

Yield: 13.86 g (78% of theory) of a colorless, amorphous powder.

Water content: 9.3%.

Elementary analysis (relative to anhydrous substance):
Cld: C, 33.28; H, 3.42; N, 7.51; F, 28.87; Gd, 14.05. Fnd: C, 33.12; H, 3.61; N, 7.37; F, 28.69; Gd, 13.89.

EXAMPLE 8 a) 2H,2H,4H,4H,5H,5H-3-Oxa-perfluorotridecanoic acid-N-(2,3,4,5,6-pentahydroxy)-hexylamide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 10.87 g (60 mmol) of glucamine and 6.07 g (60 mmol) of triethylamine, dissolved in 150 ml of dichloromethane/150 dioxane. It is stirred for 3 hours at 0° C., then for 8 hours at room temperature. 400 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/methanol=5:1).

Yield: 30.71 g (78% of theory).

Elementary analysis: Cld: C, 31.55; H, 2.94; N, 2.04; F, 47.13. Fnd: C, 31.44; H, 3.09; N, 1.97; F, 47.01.

b) N-2,3,4,5,6-Pentahydroxyhexyl)-N-1H,1H,2H,2H,4H,4H,5H,5H-3-oxa-perfluorotridecyl)-amine 30 g (43.77 mmol) of the title compound of Example 8a is dissolved in 300 ml of tetrahydrofuran, and 50 ml of 10 M boranedimethyl sulfide (in tetrahydrofuran) is added. It is refluxed for 48 hours. It is cooled to 0° C., and 500 ml of methanol is added in drops, then it is evaporated to the dry state in a vacuum. The residue is taken up in a mixture that consists of 500 ml of ethanol/100 ml of 10% aqueous hydrochloric acid, and it is stirred for 15 hours at 60° C. It is evaporated to the dry state in a vacuum, the residue is taken up in 400 ml of 5% aqueous sodium hydroxide solution and extracted 5 times with 400 ml of chloroform each. The organic phases are dried on magnesium sulfate, evaporated to the dry state in a vacuum, and the residue is chromatographed on silica gel (mobile solvent: dichloromethane/methanol=3:1).

Yield: 19.69 g (67% of theory) of a colorless solid.
Elementary analysis: Cld: C, 32.20; H, 3.30; N, 2.09; F, 48.11. Fnd: C, 32.05; H, 3.43; N, 1.97; F, 47.93.

c) 1,4,7-Tris(carboxylatomethyl)-10-{(3-aza-4-oxo-hexan-5-ylic)-acid-[N-2,3,5,6-pentahydroxy)-hexyl-N-(1H,1H,2H, 2H,4H,4H,5H,5H-3-oxa-perfluorotridecyl]-amide}-1,4,7, 10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 15.88 g (15.88 mmol) of the title compound of Example 8b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-18 (mobile solvent: gradient that consists of tetrahydrofuran/acetonitrile/water).

Yield: 16.10 g (79% of theory) of a colorless, amorphous powder.
Water content: 6.3%.
Elementary analysis (relative to anhydrous substance): Cld: C, 36.64; H, 3.93; N, 6.55; F, 25.17; Gd, 12.26. Fnd: C, 34.49; H, 4.13; N, 6.48; F, 25.03; Gd, 12.11.

EXAMPLE 9 a) 2H,2H,4H,4H,5H,5H-3-Oxa-perfluorotridecanoic acid-N-(2,2-dimethyl-5-hydroxy-1,3-dioxepan-6-yl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 9.67 g (60 mmol) of 5-amino-2,2-dimethyl-1,3-dioxepan-6-ol and 6.07 g (60 mmol) of triethylamine, dissolved in 200 ml of dichloromethane. It is stirred for 3 hours at 0° C., then for 5 hours at room temperature. 300 ml of water is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=15:1).

Yield: 27.62 g (85% of theory).
Elementary analysis: Cld: C, 34.30; H, 3.03; N, 2.11; F, 48.54. Fnd: C, 34.15; H, 3.19; N, 2.04; F, 48.37.

b) N-(1-Hydroxymethyl-2,3-dihydroxypropyl)-N-(1H,1H, 2H,2H,4H,4H,5H,5H-3-oxa-perfluorotridecyl)-amine 27 g (40.58 mmol) of the title compound of Example 9a is dissolved in 300 ml of tetrahydrofuran, and 26 ml of 10 M boranedimethyl sulfide (in tetrahydrofuran) is added. It is refluxed for 20 hours. It is cooled to 0° C., and 300 ml of methanol is added in drops, then it is evaporated to the dry state in a vacuum. The residue is taken up in a mixture that consists of 300 ml of ethanol/100 ml of 10% aqueous hydrochloric acid, and it is stirred for 6 hours at 60° C. It is evaporated to the dry state in a vacuum, the residue is taken up in 400 ml of 5% aqueous sodium hydroxide solution, and it is extracted 5 times with 250 ml of chloroform each. The organic phases are dried on magnesium sulfate, evaporated to the dry state in a vacuum, and the residue is chromatographed on silica gel (mobile solvent: dichloromethane/methanol=6:1).

Yield: 20.09 g (81% of theory) of a colorless solid.
Elementary analysis: Cld: C, 31.44; H, 2.97; N, 2.29; F, 52.83. Fnd: C, 31.26; H, 3.11; N, 2.18; F, 52.67.

c) 1,4,7-Tris(carboxylatomethyl)-10-{(3-aza-4-oxo-hexan-5-ylic)-acid-[N-1-hydroxymethyl-2,3-dihydroxypropyl)-N-(1H,1H,2H,2H,4H,4H,5H,5H-3-oxa-perfluorotridecyl]-amide)-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.71 g (15.88 mmol) of the title compound of Example 9b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-18 (mobile solvent: gradient that consists of tetrahydrofuran/acetonitrile/water).

Yield: 13.40 g (69% of theory) of a colorless, amorphous powder.
Water content: 9.1%.
Elementary analysis (relative to anhydrous substance): Cld: C, 34.37; H, 3.79; N, 6.87; F, 24.41; Gd, 12.86. Fnd: C, 34.18; H, 3.95; N, 6.71; F, 24.25; Gd, 12.70.

EXAMPLE 10 a) Perfluorooctylsulfonic acid-N-[(2-benzyloxycarbonylamino)-ethyl]-amide 40 g (173.4 mmol) of 1-benzyloxycarbonylamino-2-aminoethane, hydrochloride, 87.1 g (173.4 mmol) of perfluorooctylsulfofluoride and 35.42 g (350 mmol) of triethylamine are heated for 10 hours to 80° C. It is cooled to room temperature and added directly to a silica gel column for chromatographic purification (mobile solvent: dichloromethane/acetone=20:1).

Yield: 42.22 g (36% of theory) of a colorless solid.
Elementary analysis: Cld: C, 31.97; H, 1.94; N, 4.14; F, 47.75; S, 4.74. Fnd: C, 31.83; H, 2.11; N, 4.03; F, 47.63 S4.63.

b) Perfluorooctylsulfonic acid-N-[(2-amino)-ethyl]-amide 30 g (44.36 mmol) of the title compound of Example 10a is dissolved in 300 ml of methanol, and 5 g of palladium catalyst (10% Pd/C) is added, and it is hydrogenated overnight at room temperature. Catalyst is filtered off, and the filtrate is evaporated to the dry state in a vacuum.

Yield: 24.05 g (quantitative) of a colorless solid.
Elementary analysis: Cld: C, 22.15; H, 1.30; N, 5.17; F, 59.57. Fnd: C, 22.04; H, 1.41; N, 5.05; F, 59.62.

c) 1,4,7-Tris(carboxylatomethyl)-10-{(3-aza-4-oxo-hexan-5-ylic)-acid-N-[(2-perfluorooctylsulfonylamino)-ethyl]-amide}-1,4,7,10-tetraazacyclododecane, gadolinium complex 10 g (15.88 mmol) of the gadolinium complex of 10-[1-carboxymethylcarboamoyl)-ethyl]-1,4,7,10-tetraazacyclododecane-1,4,7-triacetic acid and 1.35 g (31.76 mmol) of lithium chloride and 3.66 g (31.76 mmol) of N-hydroxysuccinimide are dissolved at 60° C. in 100 ml of dimethyl sulfoxide. It is cooled to 15° C., and 3.51 g (17 mmol) of N,N'-dicyclohexylcarbodiimide is added, and it is stirred for 5 hours at 15° C. To separate the urea, the solution is filtered. 8.61 g (15.88 mmol) of the title compound of Example 10b and 2.02 g (20 mmol) of triethylamine are added to the filtrate, and it is stirred for 12 hours at room temperature. The solution is poured into 1500 ml of diethyl ether/100 ml of acetone, and it is stirred for 30 minutes. The precipitated solid is filtered off and chromatographed on silica gel RP-18 (mobile solvent: gradient that consists of tetrahydrofuran/acetonitrile/water).

Yield: 15.76 g (86% of theory) of a colorless, amorphous powder.

Water content: 6.5%.

Elementary analysis (relative to anhydrous substance): Cld: C, 30.19; H, 3.06; N, 8.50; F, 27.99; Gd, 13.63; S, 2.78. Fnd: C, 30.03; H, 3.18; N, 8.41; F, 27.81; Gd, 13.50; S, 2.61.

EXAMPLE 11 a) 2H,2H,4H,4H,5H,5H-3-Oxa-perfluorotridecanoic acid-N-(2-benzyloxy-carboxylamino-ethyl]-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 13.84 g (60 mmol) of 1-benzyloxycarbonylamine-2-amino-ethane, hydrochloride and 12.14 g (120 mmol) of triethylamine, dissolved in 200 ml of dichloromethane. It is stirred for 3 hours at 0° C., then for 5 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

Yield: 33.30 g (83% of theory) of a colorless solid.

Elementary analysis: Cld: C, 37.84; H, 2.74; N, 4.01; F, 46.25. Fnd: C, 37.67; H, 2.89; N, 3.88; F, 46.11.

b) 2H,2H,4H,4H,5H,5H-3-Oxa-perfluorotridecanoic acid-N-[(2-amino)-ethyl]-amide 30 g (42.96 mmol) of the title compound of Example 11a is dissolved in 500 ml of methanol, and 5 g of palladium catalyst (10% Pd/C) is added, and it is hydrogenated overnight at room temperature. It is filtered off in the catalyst, and the filtrate is evaporated to the dry state in a vacuum.

Yield: 24.24 g (quantitative) of a colorless solid.

Elementary analysis: Cld: C, 29.80; H, 2.32; N, 4.96; F, 57.24. Fnd: C, 29.67; H, 2.41; N, 4.88; F, 57.15.

c) 1,4,7-Tris-carboxylatomethyl)-10-{(3-aza-4-oxo-hexan-5-ylic)-acid-N-[3-aza-6-oxa-4-oxo-($C_9$-$C_{16}$-heptadecafluoro)-hexadecyl]-amide}-1,4,7,10-tetraazacyclododecane-gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride and 3.66 g (31.76 mmol) of N-hydroxysuccinimide are dissolved at 60° C. in 100 ml of dimethyl sulfoxide. It is cooled to 15° C., 3.51 g (17 mmol) of N,N'-dicyclohexylcarbodiimide is added, and it is stirred for 5 hours at 15° C. To separate the urea, the solution is filtered. 8.96 g (15.88 mmol) of the title compound of Example 11b and 2.02 g (20 mmol) of triethylamine are added to the filtrate and stirred for 12 hours at room temperature. The solution is poured into 1500 ml of diethyl ether/100 ml of acetone, and it is stirred for 30 minutes. The precipitated solid is filtered off and chromatographed on silica gel RP-18 (mobile solvent: gradient that consists of tetrahydrofuran/acetonitrile/water).

Yield: 15.31 g (82% of theory) of a colorless, amorphous powder.

Water content: 6.3%.

Elementary analysis (relative to anhydrous substance): Cld: C, 33.71; H, 3.51; N, 8.34; F, 27.46; Gd, 13.37. Fnd: C, 33.61; H, 3.63; N, 8.17; F, 27.31; Gd, 13.20.

EXAMPLE 12 a) 2H,2H,4H,4H,5H,5H-3-Oxa-perfluoroundecanoic acid-N-[(2-hydroxy)-ethyl]-amide 8.90 g (70 mmol) of oxalyl chloride is added to 24.25 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 3.66 g (60 mmol) of ethanolamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

Yield: 24.86 g (93% of theory) of a colorless solid.

Elementary analysis: Cld: C, 30.98; H, 2.60; N, 3.01; F, 53.09. Fnd: C, 30.71; H, 2.81; N, 2.87; F, 52.82.

b) N-(2-Hydroxyethyl)-N-1H,1H,2H,2H,4H,4H,5H,5H-3-oxa-perfluoroundecyl)-amine 24 g (51.59 mmol) of the title compound of Example 12a is dissolved in 300 ml of tetrahydrofuran, and 31 ml of 10 M boranedimethyl sulfide (in tetrahydrofuran) is added. It is refluxed for 12 hours. It is cooled to 0° C., and 200 ml of methanol is added in drops, then it is evaporated to the dry state in a vacuum. The residue is taken up in a mixture that consists of 300 ml of ethanol/50 ml of 10% aqueous hydrochloric acid, and it is stirred for 8 hours at 40° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 20.95 g (90% of theory) of a colorless solid.

Elementary analysis: Cld: C, 31.94; H, 3.13; N, 3.10; F, 54.73. Fnd: C, 31.71; H, 3.31; N, 3.01; F, 54.58.

c) 1,4,7-Tris-(carboxylatomethyl)-10-{(3-aza-4-oxo-hexan-5-ylic)-acid-N-[(2-hydroxy)-ethyl-N-(1H,1H,2H,2H,4H,4H,5H,5H-3oxa)-perfluoroundecyl]-amide}-1,4,7,10-tetraazacyclododecane-gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 8.98 g (15.88 mmol) of the title compound of Example 12b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/ water, and it is chromatographed on silica gel RP-18 (mobile solvent: gradient that consists of tetrahydrofuran/acetonitrile/water).

Yield: 14.01 g (83% of theory) of a colorless, amorphous powder.

Elementary analysis: Cld: C, 35.03; H, 3.98; N, 7.91; F, 23.24; Gd, 14.79. Fnd: C, 34.85; H, 4.19; N, 7.75; F, 23.05; Gd, 14.58.

EXAMPLE 13 a) 2H,2H,4H,4H,5H,5H-3-Oxa-perfluoroundecanoic acid-N-(3,6,9,12-tetraoxa-tridecyl)-amide 8.90 g (70 mmol) of oxalyl chloride is added to 24.25 g (57.45 mmol) of 2H,2H,4H,4H,5H,5H-3-oxa-perfluoroundecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 12.44 g (60 mmol) of 3,6,9,12-tetraoxa-tridecylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane acetone=15:1).

Yield: 31.61 g (90% of theory) of a colorless solid.

Elementary analysis: Cld: C, 37.33; H, 4.29; N, 2.29; F, 40.40. Fnd: C, 37.15; H, 4.41; N, 2.12; F, 40.18.

b) N-(3,6,9,12-Tetraoxatridecyl)-N-1H,1H,2H,2H,4H,4H,5H,5H-3-oxa-perfluoroundecyl)-amine 31 g (50.7 mmol) of the title compound of Example 13a is dissolved in 300 ml of tetrahydrofuran, and 32 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 300 ml of ethanol 50 ml of 10% aqueous hydrochloric acid, and it is stirred for 8 hours at 40° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 28.17 g (93% of theory) of a colorless solid.

Elementary analysis (relative to anhydrous substance): Cld: C, 38.20; H, 4.72; N, 2.34; F, 41.34. Fnd: C, 38.05; H, 4.83; N, 2.40; F, 41.50.

c) 1,4,7-Tris-(carboxylatomethyl)-10-{(3-aza-4-oxo-hexan-5-ylic)-acid-N-[(3,6,9,12-tetraoxa)-tridecyl-N-(1H,1H,2H,2H,4H,4H,5H,5H-3oxa)-perfluoroundecyl]-amide}-1,4,7,10-tetraazacyclododecane-gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.49 g (15.88 mmol) of the title compound of Example 13b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-18 (mobile solvent: gradient that consists of tetrahydrofuran/acetonitrile/water).

Yield: 16.13 g (84% of theory).

Elementary analysis: Cld: C, 37.75; H, 4.67; N, 6.95; F, 20.43; Gd, 13.01. Fnd: C, 37.91; H, 4.81; N, 6.83; F, 20.60; Gd, 13.15.

EXAMPLE 14 a) 2-N-(1H,1H,2H,2H,4H,4H,5H,5H-3-Oxa-perfluorotridecyl)-amino-acetic acid-t-butyl ester 6.523 g (40 mmol) of bromoacetic acid-t-butyl ester is added in drops at 50° C. to 32.0 g (58.65 mmol) of the title compound of Example 5b and 24.89 g (180 mmol) of potassium carbonate in 300 ml of acetonitrile, and it is stirred for 3 hours at this temperature. 300 ml of dichloromethane is added, precipitated salts are filtered out, and the filtrate is evaporated to the dry state in a vacuum. The residue is chromatographed on silica gel (mobile solvent: dichloromethane/2-propanol=20:1).

Yield: 28.11 g (57% of theory) of a colorless solid.

Elementary analysis: Cld: C, 34.80; H, 3.24; N, 2.25; F, 51.98. Fnd: C, 34.98; H, 3.31; N, 2.20; F, 52.16.

b) 1,4,7-Tris-carboxylatomethyl)-10-{(3-aza-4-oxo-hexan-5-ylic)-acid-N-[(t.butyloxycarbonylmethyl)-N-(1H,1H,2H,2H,4H,4H,5H,5H-3oxa)-perfluorotridecyl]-amide)-1,4,7,10-tetraazacyclododecane-gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.87 g (15.88 mmol) of the title compound of Example 14a is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-18 (mobile solvent: gradient that consists of tetrahydrofuran/acetonitrile/water).

Yield: 16.64 g (85% of theory).

Elementary analysis: Cld: C, 36.04; H, 3.92; N, 6.82; F, 26.19; Gd, 12.72. Fnd: C, 35.92; H, 3.83; N, 6.91; F, 26.29; Gd, 12.84.

c) 1,4,7-Tris-(carboxylatomethyl)-10-{(3-aza-4-oxo-hexan-5-ylic)-acid-N-[(carboxymethyl)-N-(1H,1H,2H,2H,4H,4H,5H,5H-3oxa)-perfluorotridecyl]-amide)-1,4,7,10-tetraazacyclododecane-gadolinium complex 10 g (8.11 mmol) of the title compound of Example 14b is dissolved in 50 ml of trifluoroacetic acid, and it is stirred for 5 hours at room temperature. It is evaporated to the dry state in a vacuum, and the residue is chromatographed on silica gel RP-18 (mobile solvent: gradient that consists of tetrahydrofuran/acetonitrile/water). After the product-containing fractions are concentrated by evaporation, the residue is dissolved in water and set at pH, 7.2 with 5% aqueous sodium hydroxide solution. The solution is filtered, and the filtrate is freeze-dried.

Yield: 10.48 g (91% of theory).

Elementary analysis (relative to anhydrous substance): Cld: C, 33.06; H, 3.28; N, 7.01; F, 26.94; Gd, 13.12; Na, 1.92. Fnd: C, 33.19; H, 3.40; N, 7.20; F, 27.14; Gd, 13.25; Na, 2.00.

a) 2H,2H,4H,4H,5H,5H-3-Oxa-perfluorotridecanoic acid-N-(2-hydroxyethyl)-amide 2.96 g (74 mmol) of sodium hydride (that consists of 60% sodium hydride in paraffin oil) in 300 ml of tetrahydrofuran is added to 32 g (56.61 mmol) of the title compound of Example 4a, and it is stirred for 3 hours at room temperature under nitrogen. 7.67 g (74 mmol) of bromoacetic acid-t.butylester, dissolved in 20 ml of tetrahydrofuran, is added in drops, and it is stirred for 5 hours at 50° C. 50 ml of methanol is added, and it is evaporated to the dry state in a vacuum. The residue is chromatographed on silica gel (mobile solvent: dichloromethane(/2-propanol=20:1).

Yield: 23.46 g (61% of theory).

Elementary analysis: Cld: C, 35.36; H, 3.26; N, 2.06; F, 47.54. Fnd: C, 35.52; H, 3.40; N, 2.17; F, 47.40.

b) N-(1H,1H,2H,2H,4H,4H,5H,5H-3-Oxa-perfluorotridecyl)-N-[4-t.butyloxycarbonyl-3-oxa)-butyl]-amine 35.0 g (51.52 mmol) of the title compound of Example 15a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 300 ml of ethanol/50 ml of 10% aqueous hydrochloric acid, and it is stirred for 8 hours at 40° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 31.88 g (93% of theory).

Elementary analysis: Cld: C, 36.10; H, 3.64; N, 2.11; F, 48.54. Fnd: C, 35.90; H, 3.75; N, 2.20; F, 48.71.

c) 1,4,7-Tris-(carboxylatomethyl)-10-[(3-aza-4-oxo-hexan-5-yl ic)-acid-N-[(4-t.butyloxycarbonyl-3-oxa)-butyl)-N-(1H,1H,2H,2H,4H,4H,5H,5H-3oxa)-perfluorotridecyl]-amide}-1,4,7,10-tetraazacyclododecane, gadolinium complex 10 g (15.88 mmol) of the gadolinium complex of 10-[1-carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 10.57 g (15.88 mmol) of the title compound of Example 15b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-18 (mobile solvent: gradient that consists of tetrahydrofuran/acetonitrile/water).

Yield: 16.63 g (82% of theory).

Elementary analysis: Cld: C, 36.68; H, 4.10; N, 6.58; F, 25.29; Gd, 12.31. Fnd: C, 36.81; H, 4.20; N, 6.41; F, 25.40; Gd, 12.19.

d) 1,4,7-Tris-(carboxylatomethyl)-10-((3-aza-4-oxo-hexan-5-ylic)-acid-[N-(4-carboxy-3-oxa)-butyl)N-(1H,1H,2H,2H,4H,4H,5H,5H-3oxa)-perfluorotridecyl]-amide}-1,4,7,10-tetraazacyclododecane, gadolinium complex 12 g (9.40 mmol) of the title compound of Example 15c is dissolved in 50 ml of trifluoroacetic acid, and it is stirred for 5 hours at room temperature. It is evaporated to the dry state in a vacuum, and the residue is chromatographed on silica gel RP-18 (mobile solvent: gradient that consists of tetrahydrofuran/acetonitrile/water). After the product-containing fractions are concentrated by evaporation, the residue is dissolved in water and set at pH, 7.2 with 5% aqueous sodium hydroxide solution. The solution is filtered, and the filtrate is freeze-dried.

Yield: 11.41 g (92% of theory).

Water content: 5.8%.

Elementary analysis (relative to anhydrous substance): Cld: C, 33.82; H, 3.49; N, 6.76; F, 25.98; Gd, 12.65; Na, 1.85. Fnd: C, 33.95; H, 3.60; N, 6.88; F, 26.15; Gd, 12.49; Na, 1.93.

EXAMPLE 16 a) 2H,2H,4H,4H,5H,5H-3-Oxa-perfluorotridecanoic acid-N-(2H,2H,4H,4H,5H,5H-3-oxa-perfluorotridecyl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane, and it is added in drops at 0° C. to a solution that consists of 32.62 g (60 mmol) of the title compound of Example 5b and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=15:1).

Yield: 52.87g (91% of theory).

Elementary analysis: Cld: C, 28.50; H, 1.49; N, 1.38; F, 63.87. Fnd: C, 28.65; H, 1.61; N, 1.50; F, 64.01.

b) N-Bis-(1H,1H,2H,2H,4H,4H,5H,5H-3-oxa)-perfluorotridecyl)-amine 52 g (51.42 mmol) of the title compound of Example 16a is dissolved in 500 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 400 ml of ethanol/70 ml of 10% aqueous hydrochloric acid, and it is stirred for 8 hours at 40° C. It is evaporated to the dry state in a vacuum, the residue is taken up in 400 ml of 5% aqueous sodium hydroxide solution and extracted 3 times with 400 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 47.18 g (92% of theory) of a colorless solid.

Elementary analysis: Cld: C, 28.90; H, 1.72; N, 1.40; F, 64.77. Fnd: C, 30.03; H, 1.81; N, 1.55; F, 65.00.

c) 1,4,7-Tris(carboxylatomethyl)-10-[(3-aza-4-oxo-hexan-5-ylic)-acid-N-bis-(1H,1H,2H,2H,4H,4H,5H,5H-3-oxa-perfluorotridecyl)-amide]-1,4,7,10-tetraazacyclododecane, gadolinium complex 10 g (15.88 mmol) of the gadolinium complex of 10-[1-(carboxymethylcarboamoyl)-ethyl]-1,4,7,10-tetrazacyclododecane-1,4,7-triacetic acid and 1.35 g (31.76 mmol) of lithium chloride are dissolved at 60° C. in 100 ml of dimethyl sulfoxide. It is cooled to 15° C., and 15.84 g (15.88 mmol) of the title compound of Example 16b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-18 (mobile solvent: gradient that consists of tetrahydrofuran/acetonitrile/water).

Yield: 20.95 g (82% of theory).

Elementary analysis: Cld: C, 32.10; H, 2.82; N, 5.22; F, 40.14; Gd, 9.77. Fnd: C, 29.87; H, 2.91; N, 5.09; F, 40.28; Gd, 9.98.

EXAMPLE 17 a) 2H,2H,4H,4H,5H,5H-3-Oxa-perfluorotridecanoic acid-N-(5-hydroxy-3-oxa-pentyl)-amide 2.80 g (70 mmol) of sodium hydride (that consists of 60% sodium hydride in paraffin oil) in 300 ml of tetrahydrofuran is added to 32 g (52.52 mmol) of the title compound of Example 3a, and it is stirred for 3 hours at room temperature under nitrogen. 9.68 g (70 mmol) of bromoacetic acid-t.butyl ester, dissolved in 20 ml of tetrahydrofuran, is added in drops, and it is stirred for 5 hours at 50° C. 50 ml of methanol is added, and it is evaporated to the dry state in a vacuum. The residue is chromatographed on silica gel (mobile solvent: dichloromethane(/2-propanol=20:1).

Yield: 19.31 g (59% of theory).

Elementary analysis: Cld: C, 32.76; H, 2.91; N, 2.25; F, 51.82. Fnd: C, 32.98; H, 2.99; N, 2.36; F, 51.98.

b) N-3,6-Dioxa-heptyl)-N-(1H,1H,2H,2H,4H,4H,5H,5H-3-oxa-perfluorotridecyl)-amine 32 g (51.34 mmol) of the title compound of Example 17a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 300 ml of ethanol/50 ml of 10% aqueous hydrochloric acid, and it is stirred for 8 hours at 40° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol 20:1).

Yield: 28.47 g (91% of theory).

Elementary analysis: Cld: C, 33.51; H, 3.31; N, 2.30; F, 53.01. Fnd: C, 33.63; H, 3.41; N, 2.21; F, 52.87.

c) 1,4,7-Tris(carboxylatomethyl)-10-[(3-aza-4-oxo-hexan-5-ylic)-acid-N-(3,6-dioxa)-heptyl-N-(1H,1H,2H,2H,4H,4H,5H,5H-3-oxa-perfluorotridecyl)-amide]-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.68 g (15.88 mmol) of the title compound of Example 17b is added. It is stirred for 10 minutes and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-18 (mobile solvent: gradient that consists of tetrahydrofuran/acetonitrile/water).

Yield: 16.09 g (83% of theory).

Elementary analysis: Cld: C, 35.41; H, 3.96; N, 6.88; F, 26.45; Gd, 12.88. Fnd: C, 35.57; H, 4.11; N, 6.72; F, 26.58; Gd, 12.97.

a) 2H,2H,4H,4H,5H,5H-3-Oxa-perfluorotridecanoic acid-N-(hexyl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 6.07 g (60 mmol) of nhexylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

Yield: 30.95 g (89% of theory).

Elementary analysis: Cld: C, 35.72; H, 3.33; N, 2.31; F, 53.35. Fnd: C, 35.60; H, 3.45; N, 2.43; F, 53.63.

b) N-(Hexyl)-N-(1H,1H,2H,2H,4H,4H,5H,5H-3-oxa-perfluorotridecyl)-amine 31 g (51.21 mmol) of the title compound of Example 18a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 300 ml of ethanol/50 ml of 10% aqueous hydrochloric acid, and it is stirred for 8 hours at 40° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 28.16 g (93% of theory).

Elementary analysis: Cld: C, 36.56; H, 3.75; N, 2.37; F, 54.62. Fnd: C, 36.40; H, 3.82; N, 2.27; F, 54.81.

c) 1,4,7-Tris(carboxylatomethyl)-10-{(3-aza-4-oxo-hexan-5-ylic)-acid-[N-(hexyl)-N-(1H,1H,2H,2H,4H,4H,5H,5H-3-oxa-perfluorotridecyl]-amide}-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 10.98 g (15.88 mmol) of the title compound of Example 18b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-18 (mobile solvent: gradient that consists of tetrahydrofuran/acetonitrile/water).

Yield: 16.29 g (84% of theory).

Elementary analysis: Cld: C, 36.94; H, 4.19; N, 6.99; F, 26.85; Gd, 13.07. Fnd: C, 37.18; H, 4.31; N, 7.18; F, 26.67; Gd, 13.19.

EXAMPLE 19 a) 2H,2H,4H,4H,5H,5H-3-Oxa-perfluorotridecanoic acid-N-[(10-t.butyloxycarbonyl)-decyl]-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane, and it is added in drops at 0° C. to a solution that consists of 15.45 g (60 mmol) of 11-amino-undecanoic acid-t.butylester and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

Yield: 42.04 g (92% of theory).

Elementary analysis: Cld: C, 42.58; H, 4.76; N, 1.84; F, 42.41. Fnd: C, 42.74; H, 4.90; N, 1.73; F, 42.61.

b) N-(10-t.Butyloxycarbonyl-decyl)-N-(1H,1H,2H,2H,4H,4H,5H,5H-3-oxa-perfluorotridecyl)-amine 39 g (51.21 mmol) of the title compound of Example 19a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 400 ml of ethanol/70 ml of 10% aqueous hydrochloric acid, and it is stirred for 8 hours at 40° C. It is evaporated to the dry state in a vacuum, the residue is taken up in 350 ml of 5% aqueous sodium hydroxide solution, and it is extracted 3 times with 400 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 34.84 g (91% of theory).

Elementary analysis: Cld: C, 43.38; H, 5.12; N, 1.87; F, 43.20. Fnd: C, 43.22; H, 5.23; N, 1.96; F, 43.33.

c) 1,4,7-Tris(carboxylatomethyl)-10-{(3-aza-4-oxo-hexan-5-ylic)-acid-[N-(10-t.butyloxycarbonyl)-decyl-N-(1H,1H,2H,2H,4H,4H,5H,5H-3-oxa-perfluorotridecyl]-amide}-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 11.87 g (15.88 mmol) of the title compound of Example 19b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-18 (mobile solvent: gradient that consists of tetrahydrofuran/acetonitrile/water).

Yield: 17.92 g (83% of theory).

Elementary analysis: Cld: C, 40.65; H, 4.89; N, 6.18; F, 23.76; Gd, 11.57. Fnd: C, 40.81; H, 4.99; N, 6.32; F, 23.94; Gd, 11.73.

d) 1,4,7-Tris-(carboxylatomethyl)-10-{(3-aza-4-oxo-hexan-5-ylic)-acid-[N-(10-carboxy)-decyl-N-1H,1H,2H,2H,4H,4H,5H,5H-3oxa)-perfluorotridecyl]-amide}-1,4,7,10-tetraazacyclododecane, gadolinium complex, sodium salt 12 g (8.83 mmol) of the title compound of Example 19c is dissolved in 50 ml of trifluoroacetic acid, and it is stirred for 5 hours at room temperature. It is evaporated to the dry state in a vacuum, and the residue is chromatographed on silica gel RP-18 (mobile solvent: gradient that consists of tetrahydrofuran/acetonitrile/water). After the product-containing fractions are concentrated by evaporation, the residue is dissolved in water and set at pH, 7.2 with 5% aqueous sodium hydroxide solution. The solution is filtered, and the filtrate is freeze-dried.

Yield: 12.48 g (92% of theory).

Water content: 6.2%.

Elementary analysis (relative to anhydrous substance): Cld: C, 38.07; H, 4.34; N, 6.34; F, 24.37; Gd, 11.87; Na, 1.73. Fnd: C, 37.89; H, 4.44; N, 6.22; F, 24.51; Gd, 12.01; Na, 1.80.

EXAMPLE 20 a) 15-Benzyl-3,6,9,12,15-pentaoxa-hexadecylic acid-N-(1H,1H,2H,2H,4H,4H,5H,5H-3oxa)-perfluorotridecyl)-amide 8.90 g (70 mmol) of oxalyl chloride is added to 19.67 g (57.45 mmol) of 15-benzyl-3,6,9,12,15-pentaoxahexadecylic acid in 250 ml of dichloromethane, and it is stirred for 12 hours at room temperature. It is evaporated to the dry state in a vacuum. The residue is dissolved in 100 ml of dichloromethane and added in drops at 0° C. to a solution that consists of 32.62 g (60 mmol) of 1H,1H,2H,2H,4H,4H,5H,5H-3-oxa-perfluorotridecylamine, hydrochloride and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for IS minutes. The organic phase is separated, dried on magnesium sulfate and evaporated to the dry state in a vacuum. The residue is chromatographed on silica gel (mobile solvent: dichloromethane/acetone=20:1).

Yield: 44.91 g (94% of theory) of a colorless solid.

Elementary analysis: Cld: C, 41.89; H, 4.12; N, 1.68; F, 38.84. Fnd: C, 42.02; H, 4.25; N, 1.83; F, 39.07.

b) N-15-Benzyl-3,6,9,12,15-pentaoxa-hexadecyl)-N-1H,1H,2H,2H,4H,4H,5H,5H-3oxa)-perfluorotridecyl)-amine 43 g (51.72 mmol) of the title compound of Example 20a) is dissolved in 400 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 400 ml of ethanol/50 ml of 10% aqueous hydrochloric acid, and it is stirred for 8 hours at 40° C. It is evaporated to the dry state in a vacuum, the residue is taken up in 350 ml of 5% aqueous sodium hydroxide solution, and it is extracted 3 times with 400 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 39.32 g (93% of theory).

Elementary analysis: Cld: C, 42.60; H, 4.12; N, 1.68; F, 38.84. Fnd: C, 42.45; H, 4.23; N, 1.57; F, 38.99.

c) 1,4,7-Tris-(carboxylatomethyl)-10-{(3-aza-4-oxo-hexan-5-ylic)-acid-[N-(15-benzyl-3,6,9,12,15-pentaoxa)-hexadecyl-N-(1H,1H,2H,2H,4H,4H,5H,5H-3-oxa)-tridecyl]-amide}-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 12.98 g (15.88 mmol) of the title compound of Example 20b) is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water, and it is chromatographed on silica gel RP-18 (mobile solvent: gradient that consists of tetrahydrofuran/acetonitrile/water).

Yield: 18.84 g (83% of theory).

Elementary analysis: Cld: C, 40.34; H, 4.51; N, 5.88; F, 22.60; Gd, 11.00. Fnd: C, 40.50; H, 4.62; N, 5.76; F, 22.73; Gd, 11.16.

d) 1,4,7-Tris-(carboxylatomethyl)-10-{(3-aza-4-oxo-hexan-5-ylic)-acid-[N-14-hydroxy-3,6,9,12-tetraoxa)-tetradecyl-N-(1H,1H,2H,2H,4H,4H,5H,5H-3-oxa)-perfluorotridecyl]-amide}-1,4,7,10-tetraazacyclododecane, gadolinium complex 12 g (8.40 mmol) of the title compound of Example 20c is dissolved in 150 ml of methanol, and 1.0 g of palladium catalyst (10% Pd/C) is added, and it is hydrogenated overnight at room temperature. It is filtered off in the catalyst, and the filtrate is evaporated to the dry state in a vacuum.

Yield: 10.13 g (95% of theory).

Elementary analysis: Cld: C, 38.80; H, 4.61; N, 1.10; F, 25.45; Gd, 12.39. Fnd: C, 38.87; H, 4.73; N, 1.20; F, 25.58; Gd, 12.50.

EXAMPLE 21 a) 2-N-Trifluoroacetyl-6-N-benzyloxycarbonyl-L-lysine 100.0 g (356.7 mmol) of 6-N-benzyloxycarbonyl-L-lysine is dissolved in a mixture that consists of 1000 ml of trifluoroacetic acid ethyl ester and 500 ml of ethanol, and it is stirred for 24 hours at room temperature. It is evaporated to the dry state, and the residue is crystallized from diisopropyl ether.

Yield: 128.9 g (96% of theory) of a colorless, crystalline powder.

Melting point: 98.5° C.

Elementary analysis: Cld: C, 51.07; H, 5.09; N, 7.44; F, 15.14. Fnd: C, 51.25; H, 5.18; N, 7.58; F, 15.03.

b) 2-N-Trifluoroacetyl-6-N-benzyloxycarbonyl-L-lysine[1-(4-perfluorooctylsulfonyl)-piperazine]-amide 164.2 g (0.664 mmol) of EEDQ (2-ethoxy-1,2-dihydroquinoline-1-carboxylic acid ethyl ester) is added at 0° C. to 125.0 g (332.0 mmol) of the title compound of Example 21a) and 188.7 g (332.0 mmol) of 1-perfluorooctylsulfonylpiperazine (produced according to DE 19603033) in 750 ml of tetrahydrofuran, and it is stirred overnight at room temperature. It is evaporated to the dry state in a vacuum, and it is chromatographed on silica gel (mobile solvent: dichloromethane/methanol=20:1).

Yield: 286.0 g (93% of theory) of a colorless solid.

Melting point: 92° C.

Elementary analysis: Cld: C, 36.30; H, 2.83; N, 6.05; F, 41.01; S, 3.46. Fnd: C, 36.18; H, 2.94; N, 5.98; F, 40.87; S, 3.40.

c) 6-N-Benzyloxycarbonyl-L-lysine-[1-(4-perfluorooctylsulfonyl)-piperazine]-amide Ammonia gas is introduced at 0° C. for one hour into a solution that consists of 280.0 g (302.2 mol) of the title compound of Example 21b) in 2000 ml of ethanol. It then is stirred for 4 hours at 0° C. It is evaporated to the dry state, and the residue is absorptively precipitated from water. The solid is filtered off and dried in a vacuum at 50° C.

Yield: 243.5 g (97% of theory) of an amorphous solid.

Elementary analysis: Cld: C, 37.60; H, 3.28; N, 6.75; F, 38.89; S, 3.86. Fnd: C, 37.55; H, 3.33; N, 6.68; F, 38.78; S, 3.81.

d) 6-N-Benzyloxycarbonyl-2-N-[1-O-α-D-carbonylmethyl-(2,3,4,6-tetra-O-benzyl-mannopyranose]-L-lysine-[1-(4-perfluorooctylsulfonyl)-piperazine]-amide 41.27 g (200.0 mmol) of N,N-dicyclohexylcarbodiimide is added at 0° C. to a solution that consists of 100.0 g (120.4 mol) of the title compound of Example 21c), 72.1 g (120.4 mol) of 1-O-α-D-carboxymethyl-2,3,4,6-tetra-O-benzyl-mannopyranose and 13.86 g (120.4 mol) of N-hydroxysuccinimide, dissolved in 500 ml of dimethylformamide. It is stirred for 3 hours at 0° C. and then overnight at room temperature. Precipitated urea is filtered out, the filtrate is evaporated to the dry state in a vacuum and chromatographed on silica gel. (Mobile solvent: dichloromethane/ethanol=20:1).

Yield: 136.1 g (87% of theory) of a viscous oil.

Elementary analysis: Cld: C, 57.32; H, 4.89; N, 4.31; F, 24.86; S, 2.47. Fnd: C, 57.38; H, 5.07; N, 4.22; F, 24.78; S, 2.39.

e) 2-N-[1-O-α-D-Carbonylmethyl-mannopyranose]-L-lysine-1-[(4-perfluorooctylsulfonyl)-piperazine]-amide 130.0 g (100.0 mmol) of the title compound of Example 21d) is dissolved in 2000 ml of ethanol, and 10.0 g of palladium catalyst (10% Pd/C) is added. It is hydrogenated for 12 hours at room temperature. Catalyst is filtered out, and the filtrate is evaporated to the dry state in a vacuum.

Yield: 91.7 g (quantitative) of a colorless solid.

Elementary analysis: Cld: C, 34.07; H, 3.63; N, 6.11; S, 3.50; F, 35.24. Fnd: C, 33.91; H, 3.72; N, 6.04; S, 3.40; F, 35.31.

f) 6-N-[1,4,7-Tris(carboxylatomethyl)]-1,4,7,10-tetraazacyclododecane-10-N-(pentanoyl-3-aza-4-oxo-5-methyl-5-yl)]-2-N-[1-O-α-D-carbonylmethyl-mannopyranose]-L-lysine-[1-(4-perfluorooctylsulfonyl)-piperazine]-amide, Gd complex (metal complex XV)

50.0 g (54.55 mmol) of the title compound of Example 21e), 6.28 g (54.55 mmol) of N-hydroxysuccinimide, 4.62 g (109.0 mol) of lithium chloride and 34.35 g (54.55 mol) of 1,4,7-tris(carboxylatomethyl)-10-carboxy-3-aza-4-5-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added, and it is then stirred overnight at room temperature. The solution is poured into 3000 ml of acetone, and it is stirred for 10 minutes. The precipitated solid is filtered off and then purified by chromatography (LP-18 mobile solvent: gradient that consists of water/ethanol/acetonitrile).

Yield: 75.9 g (91.0% of theory) of a colorless solid.

Water content: 8.6%.

Elementary analysis (relative to anhydrous substance): Cld: C, 35.34; H, 4.09; N, 8.24; S, 2.10; F, 21.12; Gd, 10.28. Fnd: C, 35.28; H, 4.15; N, 8.19; S, 2.15; F, 21.03; Gd, 10.14.

EXAMPLE 22 a) 6-N-[1,4,7-Tris(carboxylatomethyl]-1,4,7,10-tetraazacyclododecane-10-N-(pentanoyl-3-aza-4-oxo-5-methyl-5-yl)]-2-N-[1-O-α-D-carbonylmethyl-mannopyranose]-L-lysine-[1-(4-perfluorooctylsulfonyl)-piperazine]-amide, Gd complex 50.0 g (54.55 mmol) of the title compound of Example 21e), 6.28 g (54.55 mmol) of N-hydroxysuccinimide, 4.62 g (109.0 mol) of lithium chloride and 34.35 g (54.55 mol) of 1,4,7-tris(carboxylatomethyl)-10-(carboxy-3-aza-4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mmol) of N,N-dicyclohexylcarbodiimide is added, and it then is stirred overnight at room temperature. The solution is poured into 3000 ml of acetone and stirred for 10 minutes. The precipitated solid is filtered off, and then it is purified by chromatography (RP-18 mobile solvent: gradient that consists of water/ethanol/acetonitrile).

Yield: 76.0 g (92.0% of theory) of a colorless solid.
Water content: 6.88%.
Elementary analysis (relative to anhydrous substance):
Cld: C, 34.90; H, 3.93; N, 8.32; S, 2.12; F, 21.33; Gd, 10.38.
Fnd: C, 34.81; H, 4.02; N, 8.27; S, 2.09; F, 21.22; Gd, 10.19.

EXAMPLE 23 a) 2-[4-3-Oxapropionic acid ethyl ester]-phenylacetic acid methyl ester 233.8 g (1400.0 mmol) of 2-bromoacetic acid ethyl ester is added to 200.0 g (1204.0 mmol) of 4-hydroxyphenylacetic acid methyl ester and 212.0 g (2000.0 mmol) of sodium carbonate in 2000 ml of acetone, and it is refluxed for 5 hours. The solid is filtered off and evaporated to the dry state in a vacuum. The residue is chromatographed on silica gel. (Mobile solvent: n-hexane/ethyl acetate=15:1).

Yield: 288.5 g (95.0% of theory) of a colorless oil.
Elementary analysis: Cld: C, 61.90; H, 6.39. Fnd: C, 61.75; H, 6.51.

b) 2-[4-3-Oxapropionic acid ethyl ester)]-phenyl-2-bromoacetic acid methyl ester 201.0 g (1130.0 mmol) of N-bromosuccinimide and 100.0 mg of dibenzoyl peroxide are added to 285.0 g (1130.0 mmol) of the title compound of Example 23a), dissolved in 2000 ml of carbon tetrachloride, and it is refluxed for eight hours. It is cooled in an ice bath, the precipitated succinimide is filtered off, and the filtrate is evaporated to the dry state in a vacuum. The residue is purified on silica gel (mobile solvent: n-hexane/acetone=15:1).

Yield: 359.2 g (96.0% of theory) of a colorless, viscous oil.
Elementary analysis: Cld: C, 47.28; H, 4.57; Br, 24.16. Fnd: C, 47.19; H, 4.71; Br, 24.05.

c) 2-[4-(3-Oxapropionic acid ethyl ester)]-phenyl-2-[1-(1,4,7,10-tetraazacyclododecan-1-yl]-acetic acid methyl ester 350.0 g (1057.0 mmol) of the title compound of Example 23b) is added to 603.0 g (3500.0 mmol) of 1,4,7,10-tetraazacyclododecane, in 6000 ml of chloroform, and it is stirred overnight at room temperature. It is extracted 3 times with 3000 ml of water in each case, the organic phase is dried on magnesium sulfate and evaporated to the dry state in a vacuum. The residue is used without further purification in the next reaction (Example 23d).

Yield: 448.0 g (quantitative) of a viscous oil.
Elementary analysis: Cld: C, 59.70; H, 8.11; N, 13.26. Fnd: C, 59.58; H, 8.20; N, 13.18.

d) 2-[4-3-Oxapropionic acid)]-phenyl-2-[1,4,7-tris(carboxymethyl)-1,4,7,10-tetraazacyclododecan-10-yl]-acetic acid 445.0 g (1053.0 mmol) of the title compound of Example 23c) and 496.0 g (5270.0 mmol) of chloroacetic acid are dissolved in 4000 ml of water. It is set at a pH of 10 with 30% aqueous sodium hydroxide solution, and it is stirred for 8 hours at 70° C. Then, the pH of the reaction solution is set at 13 by mixing with 30% aqueous sodium hydroxide solution, and it is refluxed for 30 minutes. The solution is cooled in an ice bath and set at a pH of 1 by adding concentrated hydrochloric acid. It is evaporated to the dry state in a vacuum. The residue is taken up in 4000 ml of methanol and absorptively precipitated for one hour at room temperature. Precipitated common salt is filtered out, the filtrate is evaporated to the dry state, and the residue is purified on RP-18 C (mobile solvent: gradient that consists of water/ethanol/acetonitrile).

Yield: 403.0 g (69.0% of theory) of a colorless solid.
Water content: 10.2%.
Elementary analysis (relative to anhydrous substance):
Cld: C, 51.98; H, 6.18; N, 10.10. Fnd: C, 51.80; H, 6.31; N, 10.01.

e) 2-[4-3-Oxapropionic acid)]-phenyl-2-[1,4,7-tris(carboxylatomethyl)-1,4,7,10-tetraazacyclododecan-10-yl]-acetic acid, Gd complex 130.73 g (360.65 mmol) of gadolinium oxide is added to 400 g (721.3 mmol) of the title compound of Example 23d) in 2000 ml of water, and it is stirred for 5 hours at 80° C. The solution is filtered, and the filtrate is freeze-dried.

Yield: 511 g (quantitative) of an amorphous solid.
Water content: 11.0%.
Elementary analysis (relative to anhydrous substance):
Cld: C, 40.67; H, 4.41; N, 7.98; Gd, 22.19. Fnd: C, 40.51; H, 4.52; N, 8.03; Gd, 22.05.

f) 6-N-[2-[4-(3-Oxapropionyl)-phenyl]-2-[1,4,7-tris(carboxylatomethyl)-1,4,7,10-tetraazacyclododecan-10-yl]-acetic acid)]-2-N-(1-O-α-D-carbonylmethyl-mannopyranose)-L-lysine-[1-(4-perfluorooctylsulfonyl)-piperazine]-amide, Gd complex, sodium salt 50.0 g (54.55 mmol) of the title compound of Example 21e), 6.28 g (54.55 mmol) of N-hydroxysuccinimide, 4.62 g (109.0 mmol) of lithium chloride and 38.66 g (54.55 mmol) of the title compound of Example 23e) are dissolved in 400 ml of dimethyl sulfoxide while being heated slightly. At 10° C., 16.88 g (81.8 mmol) of N,N-dicyclohexylcarbodiimide is added, and it is then stirred overnight at room temperature. The solution is poured into 3000 ml of acetone and stirred for 10 minutes. The precipitated solid is filtered off and then purified by chromatography (RP-18; mobile solvent: gradient that consists of water/ethanol/acetonitrile). The product that is obtained is dissolved in a little water, and the pH of the solution is set at 7.4 with aqueous sodium hydroxide solution. Then, the product solution is freeze-dried.

Yield: 79.1 g (89% of theory) of a colorless solid.
Water content: 10.3%.
Elementary analysis (relative to anhydrous substance):
Cld: C, 36.86; H, 3.77; N, 6.88; S, 1.97; F, 19.82; Gd, 9.65.
Fnd: C, 36.75; H, 3.8; N, 6.80; S, 2.03; F, 19.75; Gd, 9.57.

EXAMPLE 24 a) 6-N-[1,4,7-Tris(t butyloxycarbonylmethyl)-10-carboxymethyl-1,4,7,10-tetraazacyclododecane-10-carbonylmethyl]-2-N-(1-O-α-D-carbonylmethyl-mannopyranose)-L-lysine-[1-(4-perfluorooctylsulfonyl)-piperazine]-amide 15.0 g (26.19 mmol) of 1,4,7-tris(t-butyloxycarbonylmethyl)-10-carboxymethyl-1,4,7,10-tetraazacyclododecane, 24.0 g (26.19 mmol) of the title compound of Example 21e), and 3.01 g (26.19 mmol) of N-hydroxysuccinimide are dissolved in 150 ml of dimethylformamide, and 8.25 g (40.0 mmol) of N,N-dicyclohexylcarbodiimide is added at 0° C. It is stirred overnight at room temperature. The precipitated urea is filtered off, and the filtrate is evaporated to the dry state in a vacuum. The residue is chromatographed on silica gel. (Mobile solvent: dichloromethane/methanol=20:1).

Yield: 35.45 g (92.0% of theory) of a colorless solid.
Elementary analysis: Cld: C, 44.08; H, 5.69; N, 7.62; F, 21.95; S, 2.18. Fnd: C, 44.01; H, 5.81; N, 7.53; F, 21.87; S, 2.03.

b) 6-N-[1,4,7-Tris(carboxylatomethyl]-1,4,7,10-tetraazacyclododecane-10-carbonyl-methyl-]-2-N-[1-O-α-D-carbonylmethyl-mannopyranose]-L-lysine-[1-(4-perfluorooctylsulfonyl)-piperazine]-amide, Gd complex 30.0 g (20.39 mmol) of the title compound of Example 24a) is dissolved in 50 ml of chloroform, and 300 ml of trifluoroacetic acid is added. It is stirred for 10 minutes at room temperature. It is evaporated to the dry state in a vacuum, and the residue is dissolved in 300 ml of water. 3.69 g (10.19 mmol) of gadolinium oxide is added, and it is stirred for 5 hours at 80° C. The solution is evaporated to the dry state in a vacuum and purified on silica gel (RP-18; mobile solvent: gradient that consists of water/ethanol/acetonitrile).

Yield: 11.0 g (37.0% of theory) of a colorless and amorphous solid.

Water content: 11.3%.

Elementary analysis (relative to anhydrous substance):
Cld: C, 34.62; H, 3.87; N, 7.69; F, 22.16; S, 2.20; Gd, 10.97.
Fnd: C, 34.57; H, 3.95; N, 7.60; F, 22.05; S, 2.13; Gd, 10.90.

a) 6-N-[3,6,9-Tris(carboxymethyl)-3,6,9-triazaundecanedioic acid-1-carboxy-11-oyl]-2-N-[1-O-α-D-carbonylmethyl-mannopyranose]-L-lysine-[1-(4-perfluorooctylsulfonyl)-piperazine]-amide 12.10 g (30.0 mmol) of 3-N-(2,6-dioxomorpholinoethyl)-6-N-(ethoxycarbonylmethyl)-3,6-diazaoctanedioic acid is added to 24.0 g (26.19 mmol) of the title compound of Example 21e), dissolved in 100 ml of dimethylformamide/30 ml of pyridine, and it is stirred for 5 hours at 50° C. It is evaporated to the dry state in a vacuum. The residue is dissolved in 200 ml of water, and the pH of the resulting solution is set at 13 by adding 20% aqueous sodium hydroxide solution. It is stirred for 8 hours at 22° C. and a pH of 13. The solution is brought to a pH of 7.2 by adding concentrated hydrochloric acid, and then it is evaporated to the dry state in a vacuum. The residue is chromatographed on silica gel RP-18 (mobile solvent: gradient that consists of water/ethanol/acetonitrile).

Yield: 17.26 g (51.0% of theory) of a colorless solid.

Water content: 9.3%.

Elementary analysis (relative to anhydrous substance):
Cld: C, 37.19; H, 4.21; N, 7.59; F, 25.00; S, 2.48. Fnd: C, 37.10; H, 4.30; N, 7.48; F, 25.07; S, 2.42.

b) 6-N-[3,6,9-Tris(carboxylatomethyl)-3,6,9-triazaundecanedioic acid-1-carboxy-11-oyl]-2-N-[1-O-α-D-carbonylmethyl-mannopyranose]-L-lysine-[1-4-perfluorooctylsulfonyl)-piperazine]-amide, Gd complex, sodium salt 1.40 g (3.87 mmol) of gadolinium oxide is added to 10.0 g (7.74 mmol) of the title compound of Example 25a) in 100 ml of water, and it is stirred for 2 hours at 70° C. The solution is filtered. The filtrate is set at a pH of 7.4 with 2N sodium hydroxide solution, and it is freeze-dried.

Yield: 11.36 g (quantitative) of an amorphous solid.

Water content: 10.5%.

Elementary analysis (relative to anhydrous substance):
Cld: C, 32.72; H, 3.43; N, 6.68; S, 2.18; Gd, 10.71; Na, 1.57; F, 22.00. Fnd: C, 32.65; H, 3.51; N, 6.71; S, 2.08; Gd, 10.61; Na, 1.68; F, 21.87.

EXAMPLE 26 a) 6-N-Benzyloxycarbonyl-2-N-[1,4,7-tris(carboxylatomethyl)-1,4,7,10-tetraazacyclododecane]-10-(pentanoyl-3aza-4-oxo-5-methyl-5yl)]-L-lysine-[1-(4-perfluorooctylsulfonyl)-piperazine]-amide, Gd complex 50.0 g (60.20 mmol) of the title compound of Example 21c), 6.93 g (60.20 mmol) of N-hydroxysuccinimide, 5.09 g (120.0 mmol) of lithium chloride and 37.91 g (60.20 mmol) of 1,4,7-tris[carboxylatomethyl)-1,4,7,10-tetraazacyclododecane-10-(pentanoyl-3-aza-4-oxo-5-methyl-5-yl), Gd complex are dissolved in 400 ml of dimethyl sulfoxide while being heated slightly. At 10° C., 20.63 g (100.0 mmol) of N,N-dicyclohexylcarbodiimide is added, and it is then stirred overnight at room temperature. The solution is poured into 3000 ml of acetone, and it is stirred for 10 minutes. The precipitated solid is filtered off and then purified by chromatography (silica gel RP-18; mobile solvent: gradient that consists of water/ethanol/acetonitrile).

Yield: 75.53 g (87.0% of theory) of a colorless solid.

Water content: 10.1%.

Elementary analysis (relative to anhydrous substance):
Cld: C, 37.48; H, 3.84; N, 8.74; S, 2.22; F, 22.39; Gd, 10.90.
Fnd: C, 37.39; H, 4.02; N, 8.70; S, 2.16; F, 22.29; Gd, 10.75.

b) 2-N-[1,4,7-Tris(carboxylatomethyl]-1,4,7,10-tetraazacyclododecane-Gd complex, 10-(pentanoyl-3-aza-4-oxo-5-methyl-5-yl)-L-lysine-[1-(4-perfluorooctylsulfonyl)-piperazine]-amide 70.0 g (48.53 mmol) of the title compound of Example 21d) is dissolved in 500 ml of water/100 ml of ethanol, mixed with 5.0 g of palladium catalyst (10% Pd/C) and hydrogenated at room temperature under a hydrogen atmosphere (1 atm) until no more hydrogen absorption can be observed. Then, catalyst is suctioned out, it is thoroughly rewashed with ethanol (twice with 75 ml each) and evaporated to the dry state in a vacuum. The title compound is obtained as a strongly viscous and colorless oil.

Yield: 63.5 g (quantitative).

Water content: 9.8%.

Elementary analysis (relative to anhydrous substance):
Cld: C, 37.48; H, 3.84; N, 8.74; S, 2.22; F, 22.39; Gd, 10.90.
Fnd: C, 37.39; H, 4.03; N, 8.65; S, 2.20; F, 22.31; Gd, 10.78.

c) 6-N-(1-O-α-D-Carbonylmethyl-2,3,4,6-tetra-O-benzyl-mannopyranose)-2-N-[1,4,7-tris(carboxylatomethyl)-1,4,7,10-tetraazacyclododecane, Gd-complex-10-(pentanoyl-3-aza-4oxo-5-methyl-5yl)]-L-lysine-[1-(4-perfluorooctylsulfonyl)-piperazine]-amide 50.0 g (38.22 mmol) of the title compound of Example 26b), 4.40 g (38.22 mmol) of N-hydroxysuccinimide, 3.39 g (80.0 mmol) of lithium chloride and 22.88 g (38.22 mmol) of 1-O-α-D-carboxymethyl-2,3,4,6-tetra-O-benzyl-mannopyranose are dissolved in 400 ml of dimethyl sulfoxide while being heated slightly (30 to 40° C.). At 10° C., 10.32 g (50.0 mmol) of N,N-dicyclohexylcarbodiimide is added, and it is then stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 64.25 g (89.0% of theory) of a colorless solid.

Water content: 10.9%.

Elementary analysis (relative to anhydrous substance):
Cld: C, 46.42; H, 4.54; N, 6.67; S, 1.70; F, 17.10; Gd, 8.33.
Fnd: C, 46.36; H, 4.71; N, 6.60; S, 1.61; F, 17.19; Gd, 8.21.

d) 6-N-(1-O-α-D-Carbonylmethyl-2,3,4,6-tetra-O-benzyl-mannopyranose)-2-N-[1,4,7-tris(carboxylatomethyl)-1,4,8,10-tetraazacyclododecane-10-(pentanoyl-3-aza-4oxo-5-methyl-5yl)]-L-lysine-[1-(4-perfluorooctylsulfonyl)-piperazine]-amide, Gd complex 60.0 g (31.77 mmol) of the title compound of Example 26c) is dissolved in 500 ml of ethanol and mixed with 6.0 g of palladium catalyst (10% Pd/C). It is hydrogenated at room temperature under a hydrogen atmosphere (1 atm) until no more hydrogen absorption can be observed. Then, catalyst is suctioned out, it is rewashed thoroughly with ethanol (twice with 150 ml each) and evaporated to the dry-state in a vacuum.

Yield: 48.55 g (quantitative) of a colorless solid.
Water content: 3.9%.
Elementary analysis (relative to anhydrous substance):
Cld: C, 35.37; H, 4.02; N, 8.25; S, 2.10; F, 21.13; Gd, 10.29.
Fnd: C, 35.28; H, 4.13; N, 8.17; S, 2.03; F, 21.05; Gd, 10.20.

EXAMPLE 27 a) 1,7-Bis-(benzyloxycarbonyl)-4-[2-N-ethyl-N-perfluorooctylsulfonyl)-amino]-acetyl]-1,4,7,10-tetraazacyclododecane)

49.46 g (200.0 mmol) of EEDQ (2-ethoxy-1,2-dihydroquinoline-1-carboxylic acid ethyl ester) is added at 0° C. to 50.0 g (113.5 mmol) of 1,7-bis(benzyloxycarbonyl)-1,4,7,10-tetraazacyclododecane and 66.42 g (113.5 mmol) of 2-(N-ethyl-N-perfluorooctylsulfonyl)-aminoacetic acid (produced according to DE 196 03 033) in 300 ml of tetrahydrofuran, and it is stirred overnight at room temperature. It is evaporated to the dry state in a vacuum and chromatographed on silica gel (mobile solvent: dichloromethane/methanol=20:1).

Yield: 65.2 g (57% of theory) of a colorless solid.
Elementary analysis: Cld: C, 42.91; H, 3.80; N, 6.95; F, 32.05; S, 3.18. Fnd: C, 42.85; H, 3.90; N, 6.87; F, 31.98; S, 3.15.

b) 1,7-Bis-(benzyloxy)-4-[2-(N-ethyl-N-perfluorooctylsulfonyl)-amino]-acetyl-10-[1-O-α-D-carbonylmethyl-2,3,4,6-tetra-O-benzyl-mannopyranose]-1,4,7,10-tetraazacyclododecane 24.73 g (100 mmol of EEDQ (2-ethoxy-1,2-dihydroquinoline-1-carboxylic acid ethyl ester) is added at 0° C. to 60.0 g (59.53 mmol) of the title compound of Example 27a) and 35.64 g (59.53 mmol) of 1-O-α-D-carboxymethyl-2,3,4,6-tetra-O-benzyl-mannopyranose, produced according to DE 19728954, in 300 ml of tetrahydrofuran, and it is stirred overnight at room temperature. It is evaporated to the dry state in a vacuum and chromatographed on silica gel (mobile solvent: dichloromethane/methanol=20:1).

Yield: 76.6 g (81.0% of theory) of a colorless solid.
Elementary analysis: Cld: C, 54.44; H, 4.70; N, 4.41; F, 20.33; S, 2.02. Fnd: C, 54.37; H, 4.81; N, 4.35; F, 20.27; S, 1.96.

c) 1-[2-(N-Ethyl-N-perfluorooctylsulfonyl)-amino]-acetyl-7-(1-O-α-D-carbonylmethyl-mannopyranose)-1,4,7,10-tetraazacyclododecane 70 g (44.07 mmol) of the title compound of Example 27b is dissolved in 800 ml of ethanol, and 8 g of palladium catalyst (10% Pd/C) is added. It is hydrogenated at room temperature. Catalyst is filtered out, and the filtrate is evaporated to the dry state in a vacuum.

Yield: 42.3 g (quantitative) of a colorless solid.
Elementary analysis: Cld: C, 35.04; H, 3.99; N, 7.30; F, 33.65; S, 3.34. Fnd: C, 35.15; H, 4.13; N, 7.13; F, 33.48; S, 3.26.

d) 1,7-Bis-[1,4,7-tris(carboxylatomethyl)-1,4,7,10-tetraazacyclododecane-Gd-complex-10-(pentanoyl-3-aza-4-oxo-5-methyl-5yl)-4-[2-(N-ethyl-N-perfluorooctylsulfonyl)-amino]-acetyl-10-(1-O-α-D-carbonylmethyl-mannopyranose)-1,4,7,10-tetraazacyclododecane 20 g (20.84 mmol) of the title compound of Example 27c), 5.09 g (120 mmol) of lithium chloride and 37.78 g (60 mmol) of 1,4,7-tris(carboxylatomethyl)-10-pentanoyl-3-aza-4-oxo-5-methyl-5yl)-1,4,7,10-tetraazacyclododecane, Gd complex, are dissolved in 400 ml of dimethyl sulfoxide while being heated slightly. At 10° C., 29.67 g (120 mmol) of EEDQ is added, and it is then stirred overnight at room temperature. The solution is poured into 3000 ml of acetone, and it is stirred for 10 minutes. The precipitated solid is filtered off and then purified by chromatography (silica gel RP-18, mobile solvent: gradient that consists of water/ethanol/acetonitrile).

Yield: 13.2 g (29.0% of theory) of a colorless solid.
Water content: 11.8%.
Elementary analysis (relative to anhydrous substance):
Cld: C, 36.31; H, 4.34; N, 9.62; S, 1.47; F, 14.79; Gd, 14.41.
Fnd: C, 36.24; H, 4.27; N, 9.58; S, 1.51; F, 14.85; Gd, 14.25.

EXAMPLE 28 a) 1,7-Bis(benzyloxycarbonyl)-4-[2-(N-ethyl-N-perfluorooctylsulfonyl)-amino]-acetyl-10-[pentanoyl-3-aza-4-oxo-5-methyl-5yl-[1,4,7-tris(carboxylatomethyl)-Gd complex, 1,4,7,10-tetraazacyclododecan-10-yl]-1,4,7,10-tetraazacyclododecane.

50.0 g (49.61 mmol) of the title compound of Example 27a), 5.71 g (49.61 mmol) of N-hydroxysuccinimide, 4.24 g (100 mmol) of lithium chloride and 31.24 g (49.61 mmol) and 1,4,7-tris(carboxylatomethyl)-10-(pentanoyl-3-aza-oxo-5-methyl-5-yl)-1,4,7,10-tetraazacyclododecane, Gd-complex, are dissolved in 350 ml of dimethyl sulfoxide while being heated slightly. At 10° C., 15.47 g (75 mmol) of N,N-dicyclohexylcarbodiimide is added, and it is then stirred overnight at room temperature. The solution is poured into 2000 ml of acetone, and it is stirred for 10 minutes. The precipitated solid is filtered off and then purified by chromatography (silica gel RP-18, mobile solvent: gradient that consists of water/ethanol/acetonitrile).

Yield: 65.1 g (81.0% of theory) of a colorless solid.
Water content: 7.9%.
Elementary analysis (relative to anhydrous substance):
Cld: C, 40.79; H, 4.11; N, 8.65; S, 1.98; F, 19.94; Gd, 9.72.
Fnd: C, 40.71; H, 4.20; N, 8.58; S, 2.03; F, 19.87; Gd, 9.68.

b) 1-[2-(N-Ethyl-N-perfluorooctylsulfonyl)-amino]-acetyl-7{(-pentanoyl-3-aza-4-oxo-5-methyl-5yl)-10-[1,4,7-tris(carboxylatomethyl)-1,4,7,10-tetraazacyclododecane, Gd-complex]}-1,4,7,10-tetraazacyclododecane.

60.0 g (37.05 mmol) of the title compound of Example 28a) is dissolved in 600 ml of ethanol, and 6.0 g of palladium catalyst (10% Pd/C) is added. It is hydrogenated at room temperature. Catalyst is filtered out, and the filtrate is evaporated to the dry state in a vacuum.

Yield: 50.06 g (quantitative) of a colorless solid.
Water content: 3.9%.
Elementary analysis (relative to anhydrous substance):
Cld: C, 34.67; H, 4.03; N, 10.37; S, 2.37; F, 23.90; Gd, 11.64. Fnd: C, 34.58; H, 4.15; N, 10.28; S, 2.30; F, 23.84; Gd, 11.57.

c) 1-[2-(N-Ethyl-N-perfluorooctylsulfonyl)-amino]-acetyl-4,10-bis[1-O-α-D-carbonylmethyl-2,3,4,6-tetra-O-benzyl-mannopyranose]-7-{(pentanoyl-3-aza-4-oxo-5-methyl-5-yl)-[1,4,7-tris(carboxylatomethyl)-1,4,7,10-tetraazacyclododecan-10-yl]-Gd-complex}-1,4,7,10-tetraazacyclododecane 40.0 g (29.60 mmol) of the title compound of Example 28b), 2.54 g (60.0 mmol) of lithium chloride and 44.9 g (75.0 mmol) of 1-O-α-D-carboxymethyl-2,3,4,6-tetra-O-benzyl-mannopyranose are dissolved in 300 ml of dimethyl sulfoxide while being heated slightly. At 10° C., 24.73 g (100.0 mmol) of EEDQ is added, and it is then stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 31.98 g (43.0% of theory) of a colorless solid.
Water content: 3.5%.

Elementary analysis (relative to anhydrous substance):
Cld: C, 53.06; H, 5.05; N, 5.57; S, 1.28; F, 12.85; Gd, 6.26.
Fnd: C, 52.95; H, 5.19; N, 5.48; S, 1.23; F, 12.77; Gd, 6.14.

d) 1-[2-(N-Ethyl-N-perfluorooctylsulfonyl)-amino]-acetyl-4,10-bis[1-O-α-D-carbonylmethyl-2,3,4,6-tetra-O-benzyl-mannopyranose]-7-((pentanoyl-3-aza-4-oxo-5-methyl-5-yl)-[1,4,7-tris(carboxylatomethyl)-1,4,7,10-tetraazacyclododecan-10-yl]-Gd-complex}-1,4,7,10-tetraazacyclododecane 30.0 g (11.94 mmol) of the title compound of Example 28c) is dissolved in 300 ml of ethanol/30 ml of water, and 4.0 g of palladium catalyst (10% Pd/C) is added. It is hydrogenated at room temperature, catalyst is filtered out, and the filtrate is evaporated to the dry state in a vacuum.

Yield: 21.39 g (quantitative) of a colorless solid.
Water content: 3.4%.

Elementary analysis (relative to anhydrous substance):
Cld: C, 36.87; H, 4.39; N, 7.82; S, 1.79; F, 18.03; Gd, 8.78.
Fnd: C, 36.80; H, 4.50; N, 7.85; S, 1.68; F, 17.91; Gd, 8.70.

EXAMPLE 29 a) 6-N-[3,6-Bis(carboxymethyl)-octane-1,8-dicarboxylic acid-1-carboxy-8-oyl]-2-N-(1-O-α-D-carboxymethyl-mannopyranose)-lysine-[1-(4perfluorooctylsulfonyl)-piperazine]-amide 25.62 g (100.0 mmol) of ethylenediamine-N,N,N',N'-tetraacetic acid dianhydride is added to 27.5 g (30.0 mmol) of the title compound of Example 21e), dissolved in 300 ml of dimethylformamide/100 ml of pyridine, and it is stirred for 5 hours at 50° C. It is evaporated to the dry state in a vacuum. The residue is dissolved in 300 ml of water, set at a pH of 10 by adding 20% aqueous sodium hydroxide solution, and then the basic product solution is brought to a pH of 3 by adding concentrated hydrochloric acid, and it is evaporated to the dry state in a vacuum. The residue is chromatographed on silica gel RP-18 (mobile solvent: gradient that consists of water/ethanol/acetonitrile).

Yield: 18.22 g(51.0% of theory) of a colorless solid.
Water content: 7.9%.

Elementary analysis (relative to anhydrous substance):
Cld: C, 36.31; H, 3.98; N, 7.06; F, 27.12; S, 2.69. Fnd: C, 36.23; H, 4.07; N, 6.98; F, 27.05; S, 2.62.

b) 6-N-[3,6-Bis(carboxylatomethyl)-octane-1,8-dicarboxylic acid-]-carboxylato-8-oyl-]-2-N-(1-O-α-D-carboxymethyl-mannopyranose)-L-lysine-[1-(4-perfluorooctylsulfonyl)-piperazine]-amide, Mn complex, sodium salt 10 g (8.397 mmol) of the title compound of Example 29a) is dissolved in 200 ml of water. 965 mg (8.397 mmol) of manganese(II) carbonate is added, and it is stirred for 3 hours to 60° C. The solution is set at a pH of 7.4 with 5% aqueous sodium hydroxide solution, filtered, and then freeze-dried.

Yield: 10.52 g (99.0% of theory) of a colorless solid.
Water content: 7.8%.

Elementary analysis (relative to anhydrous substance):
Cld: C, 34.16; H, 3.50; N, 6.64; S, 2.53; F, 25.52 Mn 4.34; Na, 1.82. Fnd: C, 34.06; H, 3.61; N, 6.58; S, 2.47; F, 25.47 Mn 4.30; Na, 1.97.

EXAMPLE 30 a) 1,2,3,4,6-Penta-O-acetyl-α,β-D-mannopyranose

Analogously, as described in the literature [M. L. Wolfrom and A. Thompson in Methods in Carbohydrate Chemistry (R. L. Whistler, M. L. Wolfrom and J. N. BeMiller, Eds.), Academic Press, New York, Vol. II, 53, pp. 211–215, (1963)], the reaction of 150 g (832.5 mmol) of α,β-D-mannopyranose with a mixture that consists of 1500 ml of absolute pyridine and 1500 ml of acetic acid anhydride after working-up yields 315 g (96.7%) of the above-mentioned title compound as crude product in the form of a viscous and colorless oil. By $^1$H-NMR-spectroscopic study of the thus obtained title compound, it was possible to determine the α to β ratio of both anomers at 4:1. A separation of the α,β-anomers of the above-mentioned title compound can thus be eliminated in performing the subsequent reaction steps.

Elementary analysis: Cld: C, 49.21; H, 5.68. Fnd: C, 49.12; H, 5.78.

b) 1-O-α-D-(5-Ethoxycarbonyl)-pentyl-2,3,4,6-tetra-O-acetyl-mannopyranose

Analogously, as described in the literature for the synthesis of aryl glycopyranosides [J. Conchie and G. A. Levvy in Methods in Carbohydrate Chemistry (R. L. Whistler, M. L. Wolfrom and J. N. BeMiller, Eds.), Academic Press, New York, Vol. II, 90, pp. 345–347, (1963)], the reaction of 156.2 g (400 mmol) of the title compound of Example 21a) as an α,β-anomer mixture with 67 ml (400 mmol) of 6-hydroxy-hexanoic acid ethyl ester and 60.8 ml (520 mmol) of tin(IV) chloride results in a total of 600 ml of 1,2-dichloroethane after purification by column chromatography (eluant: hexane/ethyl acetate 2:1) for the formation of 100.05 g (51% of theory) of the above-mentioned title compound as a colorless and viscous oil. By $^1$H-NMR-spectroscopic study of the thus obtained title compound, it was possible to show that the above-mentioned title compound is exclusively the pure α-anomer.

Elementary analysis: Cld: C, 52.94; H, 6.77. Fnd: C, 52.80; H, 6.78.

c) 1-O-α-D-(5-Carboxy)-pentyl-2,3,4,6-tetra-O-benzyl-mannopyranose

A stirred suspension of 141.0 g (289 mmol) of the title compound of Example 30b) in 200 ml of dioxane is mixed at room temperature and with simultaneous vigorous stirring in portions with a total of 238.5 g (4.26 mmol) of fine-powder potassium hydroxide powder. To make it easier to stir, the reaction mixture is mixed with another 200 ml of dioxane, and the thus obtained suspension is subsequently heated to boiling and mixed drop by drop at this temperature with a total of 372 ml (3.128 mol) of benzyl bromide over a period of two hours. After a reaction time of 4 hours at 110° C. followed by 12 hours at room temperature, the reaction mixture is slowly poured into a total of 2.5 liters of ice water for the purpose of working-up, and the aqueous phase is subsequently completely extracted with diethyl ether. After the thus obtained ether phase is washed and after the subsequent drying of the same on sodium sulfate, salt is suctioned out, and the diethyl ether is removed in a vacuum. Excess benzyl bromide is then distilled off from the reaction mixture in an oil pump vacuum quantitatively at an oil bath temperature of 180° C. The thus obtained, resinous-oily residue is purified on silica gel with use of ethyl acetate/hexane (1:10) as an eluant.

Yield: 172.2 g (91.0% of theory) of the above-mentioned title compound in the form of a colorless and extremely viscous oil.

Elementary analysis: Cld: C, 75.68; H, 7.16. Fnd: C, 75.79; H, 7.04.

d) 6-N-Benzyloxycarbonyl-2-N-[1-O-α-D-(5-carbonyl)-pentyl-2,3,4,6-tetra-O-benzyl-mannopyranose]-L-lysine-[1-(4-perfluorooctylsulfonyl)-piperazine]-amide 100.0 g (134.0 mmol) of the carboxylic acid that is produced under Example 30c) and 32.4 g (281.4 mmol) of N-hydroxysuccinimide are dissolved in 500 ml of dimethylformamide and mixed in portions at 0° C. with a total of 58.0 g (281.4 mmol) of N,N'-dicyclohexylcarbodiimide, and it is stirred for 3 more hours at this temperature. A solution of 111.3 g (134.0 mmol) of the title compound of Example 21c) that is cooled to 0° C. and dissolved in 300 ml of dimethylformamide is added drop by drop to the thus produced active ester solution, and it is stirred for 2 hours at 0° C. and for 12 hours at room temperature. For working-up, precipitated dicyclohexylurea is filtered out, and the solution is drawn off until a dry state is reached. The thus obtained residue is then chromatographed on silica gel (mobile solvent: dichloromethane/ethanol 20:1; the chromatography is carried out with use of a solvent gradient with continuous increase of the proportion of ethanol).

Yield: 132.5 g (67.4% of theory) of the title compound in the form of a colorless and strongly viscous oil.

Elementary analysis: Cld: C, 54.02; H, 4.88; N, 3.82; F, 22.01; S, 2.19. Fnd; C, 53.87; H, 4.85; N, 4.02; F, 22.55; S, 2.06.

e) 2-N-[1-O-α-D-(5-Carbonyl)pentyl-mannopyranose]-L-lysine-[1-(4-perfluorooctylsulfonyl)-piperazine]-amide 120.0 g (81.77 mmol) of the compound that is produced under 30d) is dissolved in 800 ml of ethanol, mixed with 4.5 g of Pearlman's catalyst (Pd 20%, C) and hydrogenated at room temperature under a hydrogen atmosphere (1 atm) until no more hydrogen absorption can be observed (about 8 hours). Catalyst is suctioned out, it is thoroughly rewashed with ethanol (about 200 ml) and evaporated to the dry state in a vacuum. The title compound is obtained as a strongly viscous and colorless oil.

Yield: 78.5 g (98.7% of theory).

Elementary analysis: Cld: C, 37.04; H, 4.25; N, 5.76; F, 33.20; S, 3.30. Fnd: C, 36.96; H, 4.85; N, 5.41; F, 34.13; S, 3.22.

f) 2-N-[1-O-α-D-(5-Carbonyl)pentyl-mannopyranose]-6-N-[1,4,7-tris-(carboxylatomethyl)-10-(-3-aza-4-oxo-5-methyl-5-yl-pentanoyl)-1,4,7,10-tetraazacyclododecane]-L-lysine-[1-(4-perfluorooctylsulfonyl)-piperazine]-amide, Gd complex 99.8 g (158.4 mmol; 2.2 molar equivalents relative to the amine components of Example 30e) that are used) of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 6.7 g of anhydrous lithium chloride (158.4 mmol) are dissolved at 40° C. in 800 ml of absolute dimethyl sulfoxide while being stirred. At this temperature, it is subsequently mixed with a total of 18.2 g (158.4 mmol) of N-hydroxysuccinimide and 70.0 g (71.96 mmol) of the title compound of Example 30e), dissolved in 250 ml of absolute dimethyl sulfoxide. After cooling to room temperature, the reaction solution is mixed with 32.7 g (158.4 mmol) of N,N'-dicyclohexylcarbodiimide and stirred for 12 hours at room temperature. The suspension that is obtained is then mixed with sufficient acetone until the above-mentioned title compound is completely precipitated, the precipitate is suctioned off, dried, taken up in water, insoluble dicyclohexylurea is filtered off, and the filtrate is desalinated with an AMICON® YM-3 ultrafiltration membrane (cut-off: 3,000 Da), and low-molecular components are removed. The retentate is then freeze-dried.

Yield: 93.0 g (81.6% of theory) as a colorless lyophilizate.

H$_2$O content (Karl-Fischer): 9.53%.

Elementary analysis (relative to anhydrous substance): Cld: C, 37.15; H, 4.39; N, 7.96; F, 20.38; S, 2.02; Gd, 9.92. Fnd: C, 36.92; H, 4.50; N, 7.68; F, 19.77; S, 1.91; Gd, 10.08.

EXAMPLE 31 a) 2-N-[1-O-α-D-(5-Carbonyl)pentyl-mannopyranose]-6-N-{2-[4-(3-oxapropionyl)-phenyl]-2-[1,4,7-tris (carboxylatomethyl)-1,4,7,10-tetraazacyclododecan-10-yl]-acetic acid}-L-lysine-[1-(4-perfluorooctylsulfonyl)-piperazine]-amide, Gd complex, sodium salt A stirred suspension of 5.0 g (9.06 mmol) of the title compound of Example 23e) in 15 ml of absolute dimethyl sulfoxide is mixed at 70° C. with 0.68 g (15.9 mmol) of lithium chloride. After 30 minutes of stirring at 70° C., the now clear reaction solution is mixed in portions with a total of 1.83 g (15.9 mmol) of N-hydroxysuccinimide, and the reaction mixture is kept at this temperature for 1 more hour. After cooling to 0° C., it is mixed with 4.52 g (23.85 mmol) of dicyclohexylcarbodiimide, and the reaction solution is stirred for 1 more hour at 0° C., followed by 12 hours at 22° C. The thus obtained reaction solution of the N-hydroxysuccinimide ester of the title compound of Example 3e) is now mixed at 22° C. drop by drop with a solution of 4.0 g (4.12 mmol) of the title compound of Example 10Ae) in 15 ml of absolute dimethyl sulfoxide, and it is stirred for another 12 hours at room temperature. For working-up, the reaction solution is added in drops at 22° C. into 900 ml of acetone, whereby the title compound precipitates as a colorless precipitate. The precipitate is suctioned off, dissolved in 200 ml of distilled water, and then the pH of this solution is set precisely at 7.2 with 1 molar sodium hydroxide solution. The thus obtained aqueous product solution is ultrafiltered three times with a YM3-ultrafiltration membrane (AMICON®: cut-off: 3,000 Da) for the purposes of desalination and separation of low-molecular components. The thus obtained retentate is then freeze-dried.

Yield: 6.33 g (92.4% of theory, relative to the amine component used) as a colorless lyophilizate with a water content of 7.38%.

Elementary analysis (relative to anhydrous substance): Cld: C, 38.48; H, 4.13; N, 6.65; F, 19.16; S, 1.90; Gd, 9.33; Na, 1.36. Fnd: C, 39.52; H, 4.12; N, 6.67; F, 19.70; S, 1.89; Gd, 9.30; Na, 1.41.

EXAMPLE 32 a) 3,5-Bis-benzyloxycarbonylamino-benzoic acid-N-(3-oxa-1H,1H,2H,2H,4H,4H,5H,5H-perfluorotridecyl)-amide 20 g (47.5 mmol) of 3,5-bisbenzyloxycarbonylamino-benzoic acid (synthesis according to the subsequent bibliographic reference: Skulnick, Harvey I.; Johnson, Paul D.; Aristoff, Paul A.; Morris, Jeanette K.; Lovasz, Kristine D.; et al.; J. Med. Chem.; 40; 7; 1997; 1149–1164) and 4.78 g (47.5 mmol) of triethylamine are dissolved in a solvent mixture that consists of 125 ml of dry tetrahydrofuran and 125 ml of dry dioxane. After cooling to −15° C., a solution of 6.56 g (48 mmol) of isobutyl chloroformate in 30 ml of dry tetrahydrofuran is slowly added in drops while being stirred, whereby the internal temperature is to be kept below −10° C. After a reaction time of 15 minutes at −15° C., a solution of 58.6 g (47.5 mmol) of 1-amino-1H,1H,2H,2H,4H,4H,5H,5H-3-oxo-perfluorotridecane and 4.78 g (47.5 mmol) of triethylamine in 100 ml of dry tetrahydrofuran is added in drops at −20° C. After a reaction time of one hour at −15° C. and two hours at room temperature, the reaction solution is evaporated to the dry state in a vacuum. The remaining residue is taken up in 300 ml of ethyl acetate and washed twice with 200 ml each of saturated sodium bicarbonate solution and once with 300 ml of water. After the organic phase is dried on sodium sulfate, salt is suctioned out, and the ethyl acetate is removed in a vacuum. The remaining oily residue is purified on silica gel with use of dichloromethane/hexane/2-propanol (10:5:1) as an eluant.

Yield: 36.2 g (82.5% of theory) of the title compound as a colorless oil.

Elementary analysis: Cld: C, 46.82; H, 3.27; N, 4.55; F, 34.97. Fnd: C, 47.21; H, 3.31; N, 4.61; F, 34.48.

b) 3,5-Di-amino-benzoic acid-N-(3-oxa-1H,1H,2H,2H,4H,4H,5H,5H-perfluorotridecyl)]-amide 30.0 g (32.4 mmol) of the amide that is produced under 32a) is dissolved in 300 ml of ethanol and mixed with 1.2 g of Pearlman's catalyst (Pd 20%, C). It is hydrogenated at room temperature under a hydrogen atmosphere (1 atm) until no more hydrogen absorption can be observed. Catalyst is suctioned out, it is thoroughly rewashed with ethanol (about 300 ml), and it is evaporated to the dry state in a vacuum. The title compound is obtained as a strongly viscous, yellowish oil.

Yield: 20.12 g (94.8% of theory).

Elementary analysis: Cld: C, 36.66; H, 2.77; N, 6.41; F, 49.28. Fnd: C, 36.07; H, 2.87; N, 6.23; F, 49.43.

c) 3-N-[-(1-O-α-D-Carbonylmethyl-2,3,4,6-tetra-O-benzyl-mannopyranose)-5-amino-benzoic acid-N-3-oxa-1H,1H,2H,2H,4H,4H,5H,5H-perfluorotridecyl)amide 10.95 g (18.30 mmol) of 1-carboxymethyloxy-2,3,4-tetra-O-benzyl-α-D-mannopyranoside [Production as described in Patent DE 197 28 954 C1] is dissolved in 150 ml of dimethylformamide and mixed with a total of 2.09 g (18.3 mmol) of N-hydroxysuccinimide. It is cooled to 0° C., and 3.78 g (18.3 mmol) of dicyclohexylcarbodiimide is added. It is stirred for one hour at 0° C. and then for 4 hours at room temperature. It is cooled to 0° C., and a solution that consists of 24.0 g (36.6 mmol, 2 molar equivalents relative to the carboxylic acid used) of the diamino compound that is described under Example 32b), dissolved in 350 ml of dimethylformamide, is slowly added in drops within 3 hours. Then, it is stirred for one more hour at 0° C., then overnight at room temperature. It is evaporated to the dry state in a vacuum, and the residue is taken up in 300 ml of ethyl acetate. Precipitated urea is filtered out, and the filtrate is washed twice with 100 ml each of 5% aqueous soda solution. The organic phase is dried on magnesium sulfate and evaporated to the dry state in a vacuum. The residue is chromatographed on silica gel (mobile solvent: n-hexane/isopropanol 13:1). 16.8 g (74.3% of theory, relative to the carboxylic acid used) of the title compound is obtained in the form of a colorless oil. By increasing the polarity of the eluant composition in n-hexane/isopropanol to 5:1, a total of 10.15 g of unreacted diamino compound 32b) is recovered in the subsequent chromatography fractions, which can be reacted again according to the above-mentioned reaction instructions.

Elementary analysis: Cld: C, 54.42; H, 4.40; N, 3.40; F, 26.13. Fnd: C, 54.32; H, 4.49; N, 3.48; F, 25.94.

d) 3-N-[-(1-O-α-D-Carbonylmethyl-mannopyranose)]-5-amino-benzoic acid-N-(3-oxa-1H,1H,2H,2H,4H,4H,5H,5H-perfluorotridecyl)-amide Similar to what is described for the synthesis of the title compound of Example 32b), the hydrogenolysis of 12.0 g (9.70 mmol) of the title compound of Example 32c), with use of 0.5 g of Pearlman's catalyst (Pd 20%, C) in an ethanol/water (9:1) mixture after working-up yields 8.08 g (96.7% of theory) of the above-mentioned title compound in the form of a yellowish-colored and viscous oil.

Elementary analysis: Cld: C, 37.64; H, 3.28; N, 4.88; F, 37.49. Fnd: C, 37.32; H, 3.17; N, 4.97; F, 37.55.

e) 3-N-(1-O-α-D-Carbonylmethyl-mannopyranose)-5-N-{2-[4-(3-oxapropionyl)-phenyl]-2-[1,4,7-tris-(carboxylatomethyl)-1,4,7,10-tetraazacyclododecan-10-yl]-acetic acid}-benzoic acid-N-(3-oxa-1H,1H,2H,2H,4H,4H,5H,5H-perfluorotridecyl)-amide, Gd complex, sodium salt 13.6 g (19.2 mmol; 2.2 molar equivalents relative to the amine component of Example 32d) that is used) of the Gd complex that is described under Example 23Ae) and 0.81 g of anhydrous lithium chloride (19.2 mmol) are dissolved at 40° C. in 100 ml of absolute dimethyl sulfoxide while being stirred and mixed at this temperature with a total of 2.2 g (19.2 mmol) of N-hydroxysuccinimide and 7.5 g (8.7 mmol) of the title compound of Example 32d), dissolved in 50 ml of absolute dimethyl sulfoxide. After cooling to room temperature, the reaction solution is mixed with 3.96 g (19.2 mmol) of N,N'-dicyclohexylcarbodiimide and stirred for 12 hours at room temperature. The suspension that is obtained is then mixed with sufficient acetone until the above-mentioned title compound is completely precipitated, the precipitate is suctioned off, dried, taken up in water, insoluble dicyclohexylurea is filtered off, and the filtrate is desalinated with an AMICON® YM-3 ultrafiltration membrane (cut-off: 3,000 Da), and low-molecular components are removed. The retentate is then freeze-dried.

Yield: 11.51 g (84.5% of theory) as a colorless lyophilizate.

H, 20 content (Karl-Fischer): 6.77%.

Elementary analysis (relative to anhydrous substance): Cld: C, 40.05; H, 3.94; N, 6.29; F, 20.71; Gd, 10.08; Na, 1.47. Fnd: C, 39.98; H, 4.00; N, 6.31; F, 20.73; Gd, 10.11; Na, 1.42.

EXAMPLE 33 a) 3,5-Bis-(benzyloxycarbonylamino)-1-{N-[1-(4-perfluorooctylsulfonyl)-piperazine]}-benzamide 10 g (23.75 mmol) of 3,5-bis-benzyloxycarbonylamino-benzoic acid (synthesis according to the subsequent bibliographic reference: Skulnick, Harvey I.; Johnson, Paul D.; Aristoff, Paul A.; Morris, Jeanette K.; Lovasz, Kristine D.; et al.; J. Med. Chem.; 40; 7; 1997; 1149–1164) and 2.39 g (23.75 mmol) of triethylamine are dissolved in a solvent mixture that consists of 60 ml of dry tetrahydrofuran and 70 ml of dry dioxane. After cooling to −15° C., a solution of 3.28 g (24 mmol) of isobutyl chloroformate in 20 ml of dry tetrahydrofuran is slowly added in drops while being stirred, whereby the internal temperature does not exceed −10° C. After a reaction time of 15 minutes at −15° C, a solution of 23.0 g (23.75 mmol) of perfluorooctylsulfonyl-piperazine and 2.39 g (23.75 mmol) of triethylamine in 50 ml of dry tetrahydrofuran is added in drops at −20° C. After a reaction time of one hour at −15° C. and two hours at room temperature, the reaction solution is evaporated to the dry state in a vacuum. The remaining residue is taken up in 200 ml of ethyl acetate and washed twice with 100 ml each of saturated sodium bicarbonate solution and once with 300 ml of water. After the organic phase is dried on sodium sulfate, salt is suctioned out, and the ethyl acetate is removed in a vacuum. The remaining oily residue is purified on silica gel with use of dichloromethane/hexane/2-propanol (15:5:1) as an eluant.

Yield: 18.35 g (79.6% of theory) of the title compound as a colorless oil.

Elementary analysis: Cld: C, 43.31; H, 2.80; N, 5.77; F, 33.27; S, 3.30. Fnd: C, 43.21; H, 2.75; N, 5.61; F, 33.38; S, 3.22.

b) 3,5-Di-amino-1-{N-[1-(4-perfluorooctylsulfonyl)-piperazine]}-benzamide 9.70 g (10.0 mmol) of the amide that is produced under 33a) is dissolved in 100 ml of ethanol and mixed with 0.4 g of Pearlman's catalyst (Pd 20%, C). It is hydrogenated at room temperature under a hydrogen atmosphere (1 atm) until no more hydrogen absorption can be observed. Catalyst is suctioned out, it is thoroughly rewashed with ethanol (about 150 ml) and evaporated to the dry state in a vacuum. The title compound is obtained as a strongly viscous, yellowish oil.

Yield: 6.9 g (98.2% of theory).

Elementary analysis: Cld: C, 32.49; H, 2.15; N, 7.98; F, 45.98; S, 4.56. Fnd: C, 32.56; H, 2.17; N, 8.09; F, 45.63; S, 4.61.

c) 5-Amino-3-N-(1-O-α-D-carbonylmethyl-2,3,4,6-tetra-O-benzyl-mannopyranose)-benzoic acid-N-[1-(4-perfluorooctylsulfonyl)-piperazine]-amide 5.48 g (9.15 mmol) of 1-carboxymethyloxy-2,3,4,-tetra-O-benzyl-α-D-mannopyranoside [production as described in Patent DE 197 28 954 C1] is dissolved in 100 ml of dimethylformamide and mixed with a total of 1.04 g (9.15 mmol) of N-hydroxysuccinimide. It is cooled to 0° C., and 1.89 g (9.15 mmol) of dicyclohexylcarbodiimide is added. It is stirred for one hour at 0° C. and then for 4 hours at room temperature. After renewed cooling to 0° C., a solution that consists of 12.85 g (18.30 mmol, 2 molar equivalents relative to the carboxylic acid used) of the diamino compound that is described under Example 33b) and that is dissolved in 250 ml of dimethylformamide is slowly added in drops within 3 hours. Then, it is stirred for one more hour at 0° C., and then overnight at room temperature. It is evaporated to the dry state in a vacuum, and the residue is taken up in 100 ml of ethyl acetate. Precipitated urea is filtered out, and the filtrate is washed twice with 100 ml each of 5% aqueous soda solution. The organic phase is dried on magnesium sulfate and evaporated to the dry state in a vacuum. The residue is chromatographed on silica gel (mobile solvent: n-hexane/isopropanol 13:1). 8.14 g (69.4% of theory, relative to the carboxylic acid used) of the title compound is obtained in the form of a colorless oil. By increasing the polarity of the eluant composition during the chromatography to 6:1 (n-hexane/isopropanol), a total of 4.36 g of unreacted diamino compound 33b) is recovered in the subsequent chromatography fractions, and the compound can be reacted again according to above-mentioned reaction instructions.

Elementary analysis: Cld: C, 51.49; H, 4.01; N, 4.37; F, 25.17; S, 2.50. Fnd: C, 51.60; H, 4.19; N, 4.28; F, 25.14; S, 2.44.

d) 5-Amino-3-N-(1-O-α-D-carbonylmethyl-mannopyranose)-benzoic acid-N-[1-(4-perfluorooctylsulfonyl)-piperazine]-amide Similar to what is described for the synthesis of the title compound of Example 33b), the hydrogenolysis of 6.4 g (5.0 mmol) of the title compound of Example 33c), with use of 0.3 g of Pearlman's catalyst (Pd 20%, C), in an ethanol/water (8:1) mixture after working-up yields 4.43 g (96.2% of theory) of the above-mentioned title compound in the form of a yellowish-colored and viscous oil.

Elementary analysis: Cld: C, 35.15; H, 2.95; N, 6.07; F, 35.01; S, 3.48. Fnd: C, 35.32; H, 3.02; N, 5.89; F, 35.05; S, 3.58.

e) 3-N-(1-O-α-D-Carbonylmethyl-mannopyranose)-5-N-[1,4,7-tris(carboxylatomethyl)-10-(3-aza-4-oxo-5-methyl-5-yl-pentanoyl)-1,4,7,10-tetraazacyclododecane]-benzoic acid-N-[1-(4-perfluorooctylsulfonyl)-piperazine]-amide, Gd complex 5.54 g (8.8 mmol; 2.2 molar equivalents relative to the amine components of Example 33d) that are used) of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 0.37 g of anhydrous lithium chloride (8.8 mmol) are dissolved at 40° C. in 60 ml of absolute dimethyl sulfoxide while being stirred and mixed at this temperature with a total of 1.01 g (8.8 mmol) of N-hydroxysuccinimide and 3.7 g (4.0 mmol) of the title compound of Example 13Ad), dissolved in 40 ml of absolute dimethyl sulfoxide. After cooling to room temperature, the reaction solution is mixed with 1.82 g (8.8 mmol) of N,N'-dicyclohexylcarbodiimide, and it is stirred for 12 hours at room temperature. The suspension that is obtained is then mixed with sufficient acetone until the above-mentioned title compound is completely precipitated, the precipitate is suctioned off, dried, taken up in water, insoluble dicyclohexylurea is filtered out, and the filtrate is desalinated with an AMICON® YM-3 ultrafiltration membrane (cut-off, 3,000 Da), and low-molecular components are removed. The retentate is then freeze-dried.

Yield: 5.36 g (87.4% of theory) as a colorless lyophilizate.
$H_2O$-content (Karl-Fischer): 6.77%.

Elementary analysis (relative to anhydrous substance): Cld: C, 36.01; H, 3.61; N, 8.22; F, 21.05; Gd, 10.25; S, 2.09. Fnd: C, 35.87; H, 3.70; N, 8.22; F, 20.91; Gd, 10.18; S, 2.16.

EXAMPLE 34 a) 1,4,7-Triazaheptane-1,7-bis-(2-N-trifluoroacetyl-6-N-benzyloxycarbonyl-L-lysine)-diamide 100 g (107.9 mmol) of the carboxylic acid that is produced under Example 21a) and 26.1 g (226.59 mmol) of N-hydroxysuccinimide are dissolved in 500 ml of dimethylformamide and mixed in portions at 0° C. with a total of 46.7 g (226.59 mmol) of N,N'-dicyclohexylcarbodiimide, and it is stirred for 3 more hours at this temperature. A solution of 5.57 g (53.95 mmol) of diethylenetriamine that is cooled to 0° C. and dissolved in 60 ml of dimethylformamide is added drop by drop to the thus produced active ester solution, and it is stirred for 2 hours at 0° C. and for 12 hours at room temperature. For working-up, precipitated dicyclohexylurea is filtered out, and the solvent is drawn off until a dry state is reached. The thus obtained residue is then chromatographed on silica gel (mobile solvent: dichloromethane/ethanol 15:1; chromatography is carried out with use of a solvent gradient with continuous increase of the proportion of ethanol).

Yield: 26.0 g (58.8% of theory, relative to the amine component that is used) of the title compound in the form of a colorless and strongly viscous oil.

Elementary analysis: Cld: C, 52.74; H, 5.78; N, 11.96; F, 13.90. Fnd: C, 52.66; H, 5.89, N, 11.88; F, 14.02.

b) 1,4,7-Triazaheptane-1,7-bis-(2-N-trifluoroacetyl-6-N-benzyloxycarbonyl-L-lysine)-diamide-4-[2-(N-ethyl-N-perfluorooctylsulfonyl)-amino]-acetyl 16.18 g (27.0 mmol) of 2-[N-ethyl-N-perfluorooctylsulfonyl)-aminoacetic acid (production according to: DE 196 03 033), dissolved in 50 ml of tetrahydrofuran, is added at 0° C. and under nitrogen atmosphere to a solution that consists of 20 g (24.4 mmol) of the diamide that is produced under 34a) and that is dissolved in a mixture that consists of 150 ml of tetrahydrofuran and 15 ml of chloroform. Then, a total of 18.0 g (36.6 mmol) of EEDQ [2-ethoxy-1-ethoxycarbonyl-1,2-dihydroquinoline] is added in portions at 0° C. and allowed to stir overnight at room temperature, and it is then concentrated by evaporation in a vacuum. The remaining oil is chromatographed on silica gel (mobile solvent: n-hexane/isopropanol 15:1). 24.74 g (72.4% of theory, relative to the sec-amine that is used) of the title compound is obtained in the form of a colorless oil.

Elementary analysis: Cld: C, 42.01; H, 3.96; F, 31.19; N, 8.00; S, 2.29. Fnd: C, 41.92; H, 4.07; F, 31.22; N, 7.87; S, 2.34.

c) 1,7-Bis-(6-N-benzyloxycarbonyl-L-lysine)-diamide-4-[2-(N-ethyl-N-perfluorooctylsulfonyl)-amino]-acetyl-1,4,7-triazaheptane 22.0 g (15.7 mmol) of the title compound that is produced under Example 34b) is dissolved in 100 ml of ethanol, and ammonia gas is introduced at 0° C. in this solution for 40 minutes. Then, it is stirred for another 4 hours at 0° C. and for 3 hours at room temperature, and it is evaporated to the dry state in a vacuum at a bath temperature of 40° C. The remaining oily residue is purified on silica gel with use of dichloromethane/hexane/2-propanol (20:10:1) as an eluant.

Yield: 12.92 g (98.4% of theory) of the above-mentioned title compound as a colorless and strongly viscous oil.

Elementary analysis: Cld: C, 44.22; H, 4.64; N, 9.38; S, 2.68; F, 27.03. Fnd: C, 44.31; H, 4.72; N, 9.30; S, 2.74; F, 26.99.

d) 1,7-Bis-[6-N-benzyloxycarbonyl-2-N-(1-O-α-D-carbonylmethyl-2,3,4,6-tetra-O-benzyl-mannopyranose)-L-lysine]-diamide-4-[2-(N-ethyl-N-perfluorooctylsulfonyl)-amino]-acetyl-1,4,7-triazaheptane 5.47 g (9.15 mmol) of 1-carboxymethyloxy-2,3,4,-tetra-O-benzyl-α-D-mannopyranoside [production as described in Patent DE 197 28 954 C1] is dissolved in 80 ml of dimethylformamide and mixed with a total of 1.05 g (9.15 mmol) of N-hydroxysuccinimide. It is cooled to 0° C., and 1.9 g (9.15 mmol) of dicyclohexylcarbodiimide is added. It is stirred for one hour at 0° C. and then for 4 hours at room temperature. It is cooled to 0° C., and a solution that consists of 7.65 g (9.15 mmol) of the amino compound that is described under Example 34e) and that is dissolved in 50 ml of dimethylformamide is slowly added in drops within 3 hours. Then, it is stirred for one more hour at 0° C., then overnight at room temperature. It is evaporated to the dry state in a vacuum, and the residue is taken up in 100 ml of ethyl acetate. Precipitated urea is filtered out, and the filtrate is washed twice with 50 ml each of 5% aqueous soda solution. The organic phase is dried on magnesium sulfate and evaporated to the dry state in a vacuum. The residue is chromatographed on silica gel (mobile solvent: n-hexane/isopropanol 20:1). 17.01 g (78.9% of theory, relative to the carboxylic acid used) of the title compound is obtained in the form of a colorless oil.

Elementary analysis: Cld: C, 59.13; H, 5.43; N, 4.76; F, 13.71; S, 1.36. Fnd: C, 59.22; H, 5.39; N, 4.85; F, 13.70; S, 1.40.

e) 1,7-Bis-[2-N-(1-O-α-D-carbonylmethyl-mannopyranose)-L-lysine]-diamide-4-[2-(N-ethyl-N-perfluorooctylsulfonyl)-amino]-acetyl-1,4,7-triazaheptane 15.0 g (6.36 mmol) of the amide that is produced under 34d) is dissolved in 150 ml of ethanol and mixed with 0.5 g of Pearlman's catalyst (Pd 20%, C). It is hydrogenated at room temperature under a hydrogen atmosphere (1 atm) until no more hydrogen absorption can be observed. Catalyst is suctioned out, it is thoroughly rewashed with ethanol (about 100 ml) and evaporated to the dry state in a vacuum. The title compound is obtained as a strongly viscous, yellowish oil.

Yield: 8.54 g (97.2% of theory).

Elementary analysis: Cld: C, 39.13; H, 5.04; N, 8.11; F, 23.38; S, 2.32. Fnd: C, 39.07; H, 4.98; N, 8.18; F, 23.40; S, 2.30.

f) 1,7-Bis-[2-N-(1-O-α-D-carbonylmethyl-mannopyranose)-6-N-[1,4,7-tris(carboxylatomethyl)-10-(3-aza-4-oxo-5-methyl-5-yl-pentanoyl)-1,4,7,10-tetraazacyclododecane]-L-lysine]-diamide-4-[2-(N-ethyl-N-perfluorooctylsulfonyl)-amino]-acetyl-1,4,7-triazaheptane, digadolinium complex A stirred suspension of 5.7 g (9.06 mmol) of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid in 75 ml of absolute dimethyl sulfoxide is mixed at 70° C. with 0.68 g (15.9 mmol) of lithium chloride. After 30 minutes of stirring at 70° C., the now clear reaction solution is mixed in portions with a total of 1.83 g (15.9 mmol) of N-hydroxysuccinimide, and the reaction mixture is kept at this temperature for 1 more hour. After cooling to 0° C., it is mixed with 4.52 g (23.85 mmol) of dicyclohexylcarbodiimide, and the reaction solution is stirred for another hour at 0° C., followed by 12 hours at 22° C. The thus obtained reaction solution of N-hydroxysuccinimide ester of the Gd complex of 10-(4-carboxy-1-methyl-2-oxo-3-azabutyl)-1,4,7,10-tetraazacyclododecane-1,4,7-triacetic acid is now mixed at 22° C. drop by drop with a solution of 2.84 g (2.06 mmol) of the title compound of Example 34e) in 15 ml of absolute dimethyl sulfoxide, and it is stirred for another 12 hours at room temperature. For working-up, the reaction solution is added in drops at 22° C. into 500 ml of acetone, whereby the title compound precipitates as a colorless precipitate. The precipitate is suctioned off, dissolved in 200 ml of distilled water and ultrafiltered three times with a YM3-ultrafiltration membrane (AMICON®: cut-off: 3,000 Da) for the purpose of desalination and separation of low-molecular components. The thus obtained retentate is then freeze-dried.

Yield: 4.80 g (89.6% of theory, relative to the amine component that is used) as a colorless lyophilizate with a water content of 8.98%.

Elementary analysis (relative to anhydrous substance): Cld: C, 38.28; H, 4.84; N, 9.68; F, 12.40; S, 1.23; Gd, 12.07. Fnd: C, 38.20; H, 4.91; N, 9.77; F, 12.45; S, 1.19; Gd, 12.10.

EXAMPLE 35 a) 1,7-Bis(benzyloxycarbonyl)-4-{3-oxa-pentane-1,5-dicarboxylic acid-1-oyl-5-[1-(4-perfluorooctylsulfonyl)-piperazine]-amide}-1,4,7,10-tetraazacyclododecane 16.56 g (24.4 mmol) of the title compound of Example 35e), dissolved in 150 ml of tetrahydrofuran, is added at 0° C. and under nitrogen atmosphere to a solution of 10.75 g (24.4 mmol) of 1,7-bis-[benzyloxycarbonyl]-1,4,7,10-tetraazacyclododecane, dissolved in a mixture that consists of 150 ml of tetrahydrofuran and 15 ml of chloroform. Then, a total of 18.0 g (36.6 mmol) of EEDQ [2-ethoxy-1-ethoxycarbonyl-1,2-dihydroquinoline] is added in portions at 0° C., and it is allowed to stir overnight at room temperature and then concentrated by evaporation in a vacuum. The remaining oil is chromatographed on silica gel (mobile solvent: n-hexane/isopropanol 12:1). 17.22 g (64.3% of theory relative to the sec-amine that is used) of the monoamide and 3.8 g (8.8% of theory) of the diamide are obtained as a by-product. The title compound is isolated in the form of a colorless oil.

Elementary analysis: Cld: C, 43.41; H, 3.92; F, 29.18; N, 7.59; S, 2.60. Fnd: C, 43.52; H, 4.07; F, 29.24; N, 7.67; S, 2.55.

b) 1,7-Bis(benzyloxycarbonyl)-4-{3-oxa-pentane-1,5-dicarboxylic acid-1-oyl-5-[1-(4-perfluorooctylsulfonyl)-piperazine]-amide}-10-[1-O-α-D-(5-arbonyl)-pentyl-2,3,4,6-tetra-O-benzyl-mannopyranose]-1,4,7,10-tetraazacyclododecane 10.0 g (13.4 mmol) of the carboxylic acid that is produced under Example 30c) and 3.24 g (28.1 mmol) of N-hydroxysuccinimide are dissolved in 100 ml of dimethylformamide and mixed in portions at 0° C. with a total of 5.8 g (28.1 mmol) of N,N'-dicyclohexylcarbodiimide, and it is stirred for 3 more hours at this temperature. A solution of 14.83 g (13.4 mmol) of the title compound of Example 35a) that is cooled to 0° C. and that is dissolved in 100 ml of dimethylformamide is added drop by drop to the thus produced active ester solution, and it is stirred for 2 hours at 0° C. and for 12 hours at room temperature. For working-up, precipitated dicyclohexylurea is filtered out, and the solvent is then drawn off until a dry state is reached. The thus obtained residue is then chromatographed on silica gel (mobile solvent: dichloromethane/ethyl acetate 20:1; chromatography was carried out with use of a solvent gradient with continuous increase of the proportion of ethyl acetate).

Yield: 18.3 g (78.2% of theory) of the title compound in the form of a colorless and strongly viscous oil.

Elementary analysis: Cld: C, 55.11; H, 5.03; N, 4.82; F, 18.52; S, 1.84. Fnd: C, 54.87; H, 4.85; N, 4.92; F, 18.55; S, 1.86.

c) 1-{3-Oxa-pentane-1,5-dicarboxylic acid-1-oyl-5-[1-(4-perfluorooctylsulfonyl)-piperazine]-amide}-7-[1-O-α-D-(5-carbonyl)-pentyl-mannopyranose]-1,4,7,10-tetraazacyclododecane 17.0 g (9.75 mmol) of the compound that is produced under 34b) is dissolved in 150 ml of ethanol, mixed with 1.0 g of Pearlman's catalyst (Pd 20%, C) and hydrogenated at room temperature under a hydrogen atmosphere (1 atm) until no more hydrogen absorption can be observed. Catalyst is suctioned out, it is thoroughly rewashed with ethanol (twice with 75 ml each) and evaporated to the dry state in a vacuum. The title compound is obtained as a strongly viscous and colorless oil.

Yield: 10.76 g (99.0% of theory).

Elementary analysis: Cld: C, 38.78; H, 4.61; N, 7.54; F, 8.97; S, 2.88. Fnd: C, 38.86; H, 4.65; N, 7.41; F, 29.02; S, 2.92.

d) 1,7-Bis-[1,4,7-tris(carboxylatomethyl)-1,4,7,10-tetraazacyclododecane-Gd-complex-10-(pentanoyl-3-aza-4-oxo-5-methyl-5yl)-4-[2-(N-ethyl-N-perfluorooctylsulfonyl]-amino]-acetyl-2-oxa-acetyl]-10-[1-O-α-D-6-carbonylpentyl-mannopyranose]-1,4,7,10-tetraazacyclododecane 24.86 g (39.46 mmol; 4.4 molar equivalents relative to the amine component 35c) that is used) of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 1.67 g of anhydrous lithium chloride (39.46 mmol) are dissolved at 40° C. in 200 ml of absolute dimethyl sulfoxide while being stirred and mixed at this temperature with a total of 4.53 g (39.46 mmol) of N-hydroxysuccinimide and 10.0 g (8.97 mmol) of the title compound of Example 34c), dissolved in 100 ml of absolute dimethyl sulfoxide. After cooling to room temperature, the reaction solution is mixed with 8.14 g (39.46 mmol) of N,N'-dicyclohexylcarbodiimide and stirred for 12 hours at room temperature. The suspension that is obtained is then mixed with sufficient acetone until the above-mentioned title compound is completely precipitated, the precipitate is suctioned off, dried, taken up in water, insoluble dicyclohexylurea is filtered out, and the filtrate is desalinated with an AMICON® YM-3 ultrafiltration membrane (cut-off; 3,000 Da), and low-molecular components are removed. The retentate is then freeze-dried.

Yield: 16.37 g (79.3% of theory) as a colorless lyophilizate.

$H_2O$ content (Karl-Fischer): 7.65%.

Elementary analysis (relative to anhydrous substance): Cld: C, 38.01; H, 4.61; N, 9.58; F, 13.81; S, 1.37; Gd, 13.45. Fnd: C, 37.92; H, 4.55; N, 9.58; F, 13.77; S, 1.31; Gd, 13.48.

e) 3-Oxa-pentane-1,5-dicarboxylic acid-mono-[1-(4-perfluorooctylsulfonyl)-piperazine]-amide 25 g (44.0 mmol) of 1-perfluorooctylsulfonylpiperazine is dissolved in 150 ml of tetrahydrofuran and mixed at room temperature with a total of 5.1 g (44.0 mmol) of diglycolic acid anhydride, and the thus obtained reaction solution is refluxed for 12 hours. After cooling to room temperature, it is evaporated to the dry state, and the remaining oily residue is purified on silica gel with use of dichloromethane/2-propanol (16:1) as an eluant.

Yield: 27.94 g (92.8% of theory) of the above-mentioned title compound in the form of a colorless and viscous oil.

Elementary analysis: Cld: C, 58.52; H, 4.27; N, 1.98; S, 2.26; F, 22.80. Fnd: C, 58.42; H, 4.41; N, 1.80; S, 2.28; F, 23.02.

EXAMPLE 36 a) 1,7-Bis(benzyloxycarbonyl)-4-{3-(oxa-pentane-1,5-dicarboxylic acid-1-oyl-5-[1-(4-perfluorooctylsulfonyl)-piperazine]-amide}-10-[1-O-β-D-6-carbonylpentyl-2,3,4,6-tetra-O-benzyl-glucopyranose]-1,4,7,10-tetraazacyclododecane)

68.5 g (91.79 mmol) of 1-carboxymethyloxy-2,3,4,-tetra-O-benzyl-α-D-mannopyranoside [production as described in Patent DE 197 28 954 C1] is dissolved in 750 ml of dry tetrahydrofuran, and then 9.25 g (91.79 mmol) of triethylamine is added. After the reaction solution is cooled to −15° C. to −20° C., a solution of 12.64 g (92.5 mmol) of isobutyl chloroformate in 150 ml of dry tetrahydrofuran is slowly added in drops at this temperature while being stirred, whereby the rate of addition by drops can be selected so that an internal temperature of −10° C. is not exceeded. After a reaction time of 15 minutes at −15° C., a solution of 101.6 g (91.79 mmol) of the title compound of Example 35a) and 9.25 g (91.79 mmol) of triethylamine are then slowly added in drops as a solution in 500 ml of dry tetrahydrofuran at −20° C. After a reaction time of one hour at −15° C. and two hours at room temperature, the reaction solution is evaporated to the dry state in a vacuum. The remaining residue is taken up in 450 ml of ethyl acetate and washed twice with 300 ml each of saturated sodium bicarbonate solution and once with 400 ml of water. After the organic phase is dried on sodium sulfate, salt is suctioned out, and the ethyl acetate is drawn off in a vacuum. The remaining oily residue is purified on silica gel with use of dichloromethane/hexane/2-propanol (10:20:1) as an eluant.

Yield: 130.6 g (81.6% of theory) of the above-mentioned title compound as a colorless and strongly viscous oil.

Elementary analysis: Cld: C, 55.11; H, 5.03; N, 4.82; F, 18.52; S, 1.84. Fnd: C, 55.20; H, 5.09; N, 4.91; F, 18.48; S, 1.80.

b) 1-{3-Oxa-pentane-1,5-dicarboxylic acid-1-oyl-5-[1-(4-perfluorooctylsulfonyl)-piperazine]-amide}-7-[1-O-α-D-(5-carbonyl)-pentyl-mannopyranose]-1,4,7,10-tetraazacyclododecane 110.0 g (63.08 mmol) of the compound that is produced under 36a) is dissolved in 1000 ml of ethanol, mixed with 5.0 g of Pearlman's catalyst (Pd 20%, C) and hydrogenated until quantitative hydrogen uptake is reached. Catalyst is suctioned out, it is rewashed with ethanol and evaporated to the dry state in a vacuum. The title compound is obtained as a viscous and colorless oil.

Yield: 92.61 g (99.5% of theory).

Elementary analysis: Cld: C, 52.10; H, 5.12; N, 5.70; F, 21.89; S, 2.17. Fnd: C, 52.20; H, 5.09; N, 5.71; F, 21.87; S, 2.20.

c) 1,7-Bis-[1,4,7-tris(carboxylatomethyl)-10-(3-aza-4-oxo-5-methyl-5-yl-pentanoyl)-4-{3-oxa-pentane-1,5-dicarboxylic acid-1-oyl-5-[1-(4-perfluorooctylsulfonyl)-piperazine]-amide}-10-[1-O-α-D-(5-carbonyl)-pentyl-mannopyranose]-1,4,7,10-tetraazacyclododecane, digadolinium complex 55.4 g [88.0 mmol; 4.4 molar equivalents relative to the diamine component of Example 33d) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 3.7 g of anhydrous lithium chloride (88.0 mmol) are dissolved at 40° C. in 500 ml of absolute dimethyl sulfoxide while being stirred and mixed at this temperature with a total of 10.1 g (88.0 mmol) of N-hydroxysuccinimide and 29.5 g (20.0 mmol) of the title compound of Example 36b), dissolved in 200 ml of absolute dimethyl sulfoxide. After cooling to room temperature, the reaction solution is mixed with 18.2 g (88.0 mmol) of N,N'-dicyclohexylcarbodiimide and stirred for 12 hours at room temperature. The suspension that is obtained is then mixed with sufficient acetone until the above-mentioned title compound is completely precipitated, the precipitate is suctioned off, dried, taken up in water, insoluble dicyclohexylurea is filtered out, and the filtrate is desalinated with an AMICON® YM-3 ultrafiltration membrane (cut-off 3,000 Da), and low-molecular components are removed. The retentate is then freeze-dried.

Yield: 35.96 g (76.9% of theory) as a colorless lyophilizate.

$H_2O$ content (Karl-Fischer): 5.98%.

Elementary analysis (relative to anhydrous substance): Cld: C, 38.01; H, 4.61; N, 8.22; F, 13.81; Gd, 13.45; S, 1.37. Fnd: C, 37.87; H, 4.70; N, 8.22; F, 13.90; Gd, 13.48; S, 1.36.

EXAMPLE 37 a) 5-(Ethoxycarbonyl)pentyl-2,3,4,6-tetra-O-acetyl-α-D-mannopyranoside

Similar to what is described in the literature for the synthesis of arylglycopyranosides [J. Conchie and G. A. Levvy in Methods in Carbohydrate Chemistry (R. L. Whistler, M. L. Wolfrom and J. N. BeMiller, Eds.), Academic Press, New York, Vol. II, 90, pp. 345–347, (1963)], the reaction of 156.2 g (400 mmol) of D-mannose pentaacetate as an α,β-(α,β-ratio=4:1)-anomer mixture [for synthesis of 1,2,3,4,6-penta-O-acetyl-α,β-D-mannopyranose cf.: M. L. Wolfrom and A. Thompson in Methods in Carbohydrate Chemistry (R. L. Whistler, M. L. Wolfrom and J. N. BeMiller, Eds.), Academic Press, New York, Vol. II, 53, pp. 211–215, (1963)] with 67 ml (400 mmol) of 6-hydroxyhexanoic acid ethyl ester and 60.8 ml (520 mmol) of tin(IV) chloride results in a total of 600 ml of 1,2-dichloroethane after purification by column chromatography (eluant: hexane/ethyl acetate 2:1) for the formation of 100.05 g (51% of theory) of the above-mentioned title compound as a colorless and viscous oil. By $^1$H-NMR-spectroscopic study of the thus obtained title compound, it was possible to show that the above-mentioned title compound is only the pure α-anomer.

Elementary analysis: Cld: C, 52.94; H, 6.77. Fnd: C, 52.80; H, 6.78.

b) 5-(Carboxy)pentyl-2,3,4,6-tetra-O-benzyl-α-D-mannopyranoside

A stirred suspension of 141.0 g (289 mmol) of the title compound of Example 37a) in 200 ml of dioxane is mixed in portions at room temperature and with simultaneous vigorous stirring with a total of 238.5 g (4.26 mol) of fine-powder potassium hydroxide powder. To make it easier to stir, the reaction mixture is mixed with another 200 ml of dioxane, and the thus obtained suspension is subsequently heated to boiling heat and mixed drop by drop at this temperature with a total of 372 ml (3.128 mol) of benzyl bromide over a period of two hours. After a reaction time of 4 hours at 110° C., followed by 12 hours at room temperature, the reaction mixture is slowly poured into a total of 2.5 liters of ice water for the purpose of working-up, and the aqueous phase is subsequently completely extracted with diethyl ether. After the thus obtained ether phase is washed and the ether phase is subsequently dried on sodium sulfate, salt is suctioned out, and the diethyl ether is drawn off in a vacuum. Excess benzyl bromide is then distilled off quantitatively in an oil pump vacuum at an oil bath temperature of 180° C. from the reaction mixture. The thus obtained, resinous-oily residue is purified on silica gel with use of ethyl acetate/hexane (1:10) as an eluant.

Yield: 172.2 g (91.0% of theory) of the above-mentioned title compound in the form of a colorless and extremely viscous oil.

Elementary analysis: Cld: C, 75.68; H, 7.16. Fnd: C, 75.79; H, 7.04.

c) 5-[(Carboxy)-pentyl-2,3,4,6-tetra-O-benzyl-α-D-mannopyranoside-]N-hydroxysuccinimide ester 60.0 g (91.5 mmol) of the title compound of Example 37b) is dissolved in 750 ml of dimethylformamide and mixed with a total of 10.4 g (91.5 mmol) of N-hydroxysuccinimide. It is cooled to 0° C., and 18.9 g (91.5 mmol) of dicyclohexylcarbodiimide is added. It is stirred for one hour at 0° C. and then for 4 hours at room temperature. The solvent is drawn off in a vacuum, and the remaining residue is mixed with 100 ml of ethyl acetate and cooled to 0° C. Precipitated urea is filtered out, and the filtrate that is obtained is evaporated to the dry state in a vacuum. The thus obtained, resinous-oily residue is purified on silica gel with use of ethyl acetate/hexane (1:20) as an eluant.

Yield: 61.23 g (89.0% of theory) of the above-mentioned title compound in the form of a colorless and viscous oil.

Elementary analysis: Cld: C, 70.29; H, 6.57; N, 1.86. Fnd: C, 70.39; H, 5.64; N, 1.91.

d) 2,6-Bis-{6-$N_\epsilon$-2-$N_\alpha$-[-[1-O-α-D-6-carbonyl-pentyl-(2,3,4,6-tetra-O-benzyl)-mannopyranose}-L-lysine}-methyl ester A solution of 27.51 g (36.6 mmol) of the title compound of Example 37c) in 150 ml of dimethylformamide is added in drops to a solution, cooled to 0° C., that consists of 4.26 g (18.30 mmol; 0.5 molar equivalent relative to the carboxylic acid that is used) of L-lysine methyl ester-dihydrochloride (commercially available from the Bachem Company) and 4.05 g (40.26 mmol) of triethylamine in 100 ml of dimethylformamide. After the addition is completed, it is stirred for one more hour at 0° C. and then overnight at room temperature. It is evaporated to the dry state in a vacuum, and the residue is taken up in 300 ml of ethyl acetate. Precipitated urea is filtered out, and the filtrate is washed twice with 100 ml each of 5% aqueous soda solution. The organic phase is dried on magnesium sulfate and evaporated to the dry state in a vacuum. The residue is chromatographed on silica gel (mobile solvent: n-hexane/isopropanol 25:1). 39.56 g (75.4% of theory) of the title compound is obtained in the form of a colorless oil.

Elementary analysis: Cld: C, 72.88; H, 7.31; N, 1.95. Fnd: C, 72.90; H, 7.29; N, 2.02.

e) 2,6-Bis-[6-$N_\epsilon$-2-$N_\alpha$-[1-O-α-D-6-carbonyl-pentyl-(2,3,4,6-tetra-O-benzyl)-mannopyranose]]-L-lysine 30.0 g (20.92 mmol) of the compound that is produced under Example 37d) is dissolved in 150 ml of ethanol. The solution of 4 g (100.0 mmol) of sodium hydroxide in 10 ml of distilled water is then added to it, and it is stirred for 3 hours at 50° C. According to the thin-layer chromatogram, saponification is quantitative. It is evaporated to the dry state in a vacuum, the remaining residue is taken up in 300 ml of ethyl acetate, and the organic phase is extracted twice with 100 ml each of dilute, aqueous citric acid solution. After drying on sodium sulfate, it is filtered, and evaporated to the dry state in a vacuum. The residue is chromatographed on silica gel (mobile solvent: n-hexane/isopropanol 13:1). 25.56 g (88.5% of theory) of the title compound is obtained in the form of a colorless oil.

Elementary analysis: Cld: C, 72.88; H, 7.31; N, 1.95. Fnd: C, 72.78; H, 7.33; N, 1.96.

f) 2,6-Bis-[6-$N_\epsilon$-2-$N_\alpha$-[1-O-α-D-6-carbonyl-pentyl-(2,3,4, 6-tetra-O-benzyl)-mannopyranose]-L-lysine]-N-hydroxysuccinimide ester 14.0 g (9.15 mmol) of the title compound of Example 37e) is dissolved in 100 ml of dimethylformamide and mixed with a total of 1.04 g (9.15 mmol) of N-hydroxysuccinimide. It is cooled to 0° C., and 1.89 g (9.15 mmol) of dicyclohexylcarbodiimide is added. It is stirred for one hour at 0° C. and then for 4 hours at room temperature. The solvent is then drawn off in a vacuum, and the remaining residue is mixed with 100 ml of ethyl acetate and cooled to 0° C. Precipitated urea is filtered out, and the filtrate that is obtained is evaporated to the dry state in a vacuum. The thus obtained, resinous-oily residue is purified on silica gel with use of ethyl acetate/n-hexane (1:20) as an eluant.

Yield: 12.94 g (92.4% of theory) of the above-mentioned title compound in the form of a colorless and viscous oil.

Elementary analysis: Cld: C, 71.40; H, 7.05; N, 2.74. Fnd: C, 71.39; H, 7.14; N, 2.81.

g) 2,6-N,N'-Bis[1-O-α-D-(6-carbonyl)-pentyl-2,3,4,6-tetra-O-benzyl-mannopyranose]-L-lysine-1,7-(1,4,7-triazaheptane)-diamide A solution that consists of 14.0 g (9.15 mmol; 2 molar equivalents relative to the amine that is used) of the title compound of Example 37f) in 100 ml of dimethylformamide is slowly added in drops to a solution, cooled to 0° C., of 0.47 g (4.57 mmol) of diethylenetriamine in 25 ml of dimethylformamide. After the addition is completed, it is stirred for one more hour at 0° C. and then overnight at room temperature. It is evaporated to the dry state in a vacuum, and the residue is taken up in 200 ml of ethyl acetate. Precipitated urea is filtered out, and the filtrate is washed twice with 50 ml each of 5% aqueous soda solution. The organic phase is dried on magnesium sulfate and evaporated to the dry state in a vacuum. The residue is chromatographed on silica gel (mobile solvent: n-hexane/isopropanol 25:1). 9.53 g (71.4% of theory) of the title compound is obtained in the form of a colorless oil.

Elementary analysis: Cld: C, 72.79; H, 7.42; N, 3.36. Fnd: C, 72.90; H, 7.39; N, 3.32.

h) 2-N-[2-(N-Ethyl-N-perfluorooctylsulfonyl)-amino]-acetyl-6-N-benzyloxycarbonyl)-L-lysine-methyl ester 20.8 g (35.6 mmol) of the 2-[N-ethyl-N-perfluorooctylsulfonyl)-aminoacetic acid and 3.60 g (35.6 mmol) of triethylamine are dissolved in 200 ml of dimethylformamide, and 4.09 g (35.6 mol) of N-hydroxysuccinimide is added. It is cooled to 0° C., and 7.34 g (35.6 mmol) of dicyclohexylcarbodiimide is added. It is stirred for one hour at 0° C. and then for 4 hours at room temperature. It is cooled to 0° C., and a solution that consists of 11.77 g (35.6 mmol) of 6-N-benzyloxycarbonyl-L-lysine-methyl ester-hydrochloride and 4.0 g (40.0 mmol) of triethylamine in 100 ml of dimethylformamide is added in drops within 10 minutes. It is stirred for one hour at 0° C., then overnight at room temperature. It is evaporated to the dry state in a vacuum, and the residue is taken up in 100 ml of ethyl acetate. Precipitated urea is filtered out, and the filtrate is washed twice with 100 ml each of 5% aqueous soda solution. The organic phase is dried on magnesium sulfate and evaporated to the dry state in a vacuum. The residue is chromatographed on silica gel (mobile solvent: n-hexane/ethyl acetate 20:1). 27.43 g (88.0% of theory) of a colorless oil is obtained.

Elementary analysis: Cld: C, 38.41; H, 3.45; N, 4.80; F, 36.89; S, 3.66. Fnd: C, 38.45; H, 3.38; N, 4.88; F, 37.02; S, 3.71.

i) 2-Nα-{[2-(N-Ethyl-N-perfluorooctylsulfonyl]-aminoacetyl}-6-$N_\epsilon$-(benzyloxycarbonyl)-L-lysine 25.0 g (28.55 mmol) of the compound that is produced under Example 37h) is dissolved in 150 ml of ethanol. The solution of 4 g (100.0 mmol) of sodium hydroxide in 10 ml of distilled water is then added to it, and it is stirred for 3 hours at 50° C. According to the thin-layer chromatogram, saponification is quantitative. It is evaporated to the dry state in a vacuum, and the remaining residue is taken up in 300 ml of ethyl acetate, and the organic phase is extracted twice with 100 ml each of dilute, aqueous citric acid solution. After drying on sodium sulfate, it is filtered and evaporated to the dry state in a vacuum. The residue is chromatographed on silica gel (mobile solvent: n-hexane/isopropanol 10:1). 22.73 g (92.4% of theory) of the title compound is obtained in the form of a colorless oil.

Elementary analysis: Cld: C, 37.64; H, 3.28; N, 4.88; F, 37.49; S, 3.72. Fnd: C, 37.65; H, 3.38; N, 4.88; F, 37.52; S, 3.73.

j) 1,4,7-Triazaheptane-4-{2-N-[2-(N-ethyl-N-perfluorooctylsulfonyl)-amino]-acetyl-6-N-benzyloxycarbonyl}-L-lysine-amide-1,7-bis{2,6-N,N'-bis[1-O-α-D-(5-carbonyl)-pentyl-2,3,4,6-tetra-O-benzylmannopyranose]-L-lysine-diamide}

15.33 g (17.8 mmol) of the title compound of Example 37i) and 1.80 g (17.8 mmol) of triethylamine are dissolved in 250 ml of dry tetrahydrofuran. After the reaction solution is cooled to −15° C. to −20° C., a solution of 4.92 g (35.6 mmol) of isobutyl chloroformate, dissolved in 50 ml of dry tetrahydrofuran, is slowly added in drops at this temperature while being stirred, whereby the rate of addition by drops can be selected so that an internal temperature of −10° C. is not exceeded. After a reaction time of 15 minutes at −15° C., a solution of 52.0 g (17.8 mmol) of the title compound of Example 37g) and 1.80 g (17.8 mmol) of triethylamine in 300 ml of dry tetrahydrofuran is then slowly added in drops at −20° C. After a reaction time of one hour at −15° C. and two hours at room temperature, the reaction solution is evaporated to the dry state in a vacuum. The remaining residue is taken up in 500 ml of ethyl acetate and washed twice with 200 ml each of saturated sodium bicarbonate solution and once with 200 ml of water. After the organic phase is dried on sodium sulfate, salt is suctioned out, and the ethyl acetate is drawn off in a vacuum. The remaining oily residue is purified on silica gel with use of ethyl acetate/n-hexane (1:20) as an eluant.

Yield: 54.6 g (81.6% of theory) of the above-mentioned title compound as a colorless and strongly viscous oil.

Elementary analysis: Cld: C, 65.09; H, 6.45; N, 3.72; F, 8.58; S, 0.85. Fnd: C, 65.13; H, 4.41; N, 3.69; F, 8.52; S, 0.90.

k) 1,4,7-Triazaheptane-4-{2-N-[2-(N-ethyl-N-perfluorooctylsulfonyl)-amino]-acetyl}-L-lysine-amide-1, 7-bis{2,6-N,N'-bis[1-O-α-D-(5-carbonyl)-pentyl-mannopyranose]-L-lysine-diamide}

50.0 g (13.28 mmol) of the compound that is produced under 37j) is dissolved in 500 ml of ethanol, mixed with 4.0 g of Pearlman's catalyst (Pd 20%, C) and hydrogenated at room temperature under a hydrogen atmosphere (1 atm) until no more-hydrogen absorption can be observed. Catalyst is suctioned out, it is thoroughly rewashed with ethanol (about 400 ml) and evaporated to the dry state in a vacuum. The title compound is obtained as a strongly viscous and colorless oil.

Yield: 26.85 g (93.0% of theory). Elementary analysis: Cld: C, 45.85; H, 6.35; N, 6.44; F, 14.86; S, 1.47. Fnd: C, 45.76; H, 6.35; N, 6.41; F, 14.92; S, 1.39.

l) 1,4,7-Triazaheptane-4-{2-N-[2-(N-ethyl-N-perfluorooctylsulfonyl)-amino]-acetyl-6-N-[1,4,7-tris(carboxylatomethyl)-10-(3-aza-4-oxo-5-methyl-5-yl-pentanoyl)-1,4,7,10-tetraazacyclododecane}-L-lysine-amide-1,7-bis{2,6-N,N'-bis[1-O-α-D-(5-carbonyl)-pentyl-mannopyranose]-L-lysine-diamide}, gadolinium complex 5.54 g (8.8 mmol; 2.2 molar equivalents relative to the amine component of Example 37k) that is used) of the Gd complex, described in Patent Application DE 197 28 954 C1 under Example 31h), of 10-(4-carboxy-1-methyl-2-oxo-3-aza-butyl)-1,4,7,10-tetraazacyclododecane-1,4,7-triacetic acid and 0.37 g of anhydrous lithium chloride (8.8 mmol) are dissolved at 40° C. in 60 ml of absolute dimethyl sulfoxide while being stirred and mixed at this temperature with a total of 1.01 g (8.8 mmol) of N-hydroxysuccinimide and 1.84 g (4.0 mmol) of the title compound of Example 37k), dissolved in 40 ml of absolute dimethyl sulfoxide. After cooling to room temperature, the reaction solution is mixed with 1.82 g (8.8 mmol) of N,N'-dicyclohexylcarbodiimide and stirred for 12 hours at room temperature. The suspension that is obtained is then mixed with sufficient acetone until the above-mentioned title compound is completely precipitated, the precipitate is suctioned off, dried, taken up in water, insoluble dicyclohexylurea is filtered out, and the filtrate is desalinated with an AMICON® YM-3 ultrafiltration membrane (cut-off 3,000 Da), and low-molecular components are removed. The retentate is then freeze-dried.

Yield: 8.77 g (78.7% of theory) as a colorless lyophilizate.

H$_2$O content (Karl-Fischer): 4.43%.

Elementary analysis (relative to anhydrous substance): Cld: C, 43.98; H, 5.97; N, 7.54; F, 11.59; Gd, 5.64; S, 1.15. Fnd: C, 43.97; H, 6.02; N, 7.62; F, 11.61; Gd, 10.18; S, 1.15.

EXAMPLE 38 a) 2-Nα-6-Nε-Bis-[1-O-α-D-carbonylmethyl-2,3,4,6-tetra-O-benzyl-mannopyranose]-L-lysine]-methyl ester 10.95 g (18.30 mmol) of 1-carboxymethyloxy-2,3,4,-tetra-O-benzyl-α-D-mannopyranoside [production as described in Patent DE 197 28 954 C1] is dissolved in 150 ml of dimethylformamide and mixed with a total of 2.09 g (18.3 mmol) of N-hydroxysuccinimide. It is cooled to 0° C., and 3.78 g (18.3 mmol) of dicyclohexyl-carbodiimide is added. It is stirred for one hour at 0° C. and then for 4 hours at room temperature. It is cooled to 0° C., and a solution that consists of 2.13 g (9.15 mmol; 0.5 molar equivalent relative to the carboxylic acid that is used) of L-lysine methyl ester-dihydrochloride (commercially available from the Bachem Company) and 2.02 g (20.13 mmol) of triethylamine in 70 ml of dimethylformamide is added in drops within one hour. After the addition is completed, it is stirred for one more hour at 0° C. and then overnight at room temperature. It is-evaporated to the dry state in a vacuum, and the residue is taken up in 300 ml of ethyl acetate. Precipitated urea is filtered out, and the filtrate is washed twice with 100 ml each of 5% aqueous soda solution. The organic phase is dried on magnesium sulfate and evaporated to the dry state in a vacuum. The residue is chromatographed on silica gel (mobile solvent: n-hexane/isopropanol 25:1). 10.05 g (82.3% of theory) of the title compound is obtained in the form of a colorless oil.

Elementary analysis: Cld: C, 71.94; H, 6.79; N, 2.10. Fnd: C, 71.90; H, 6.79; N, 2.09.

b) 2-Nα-6-Nε-Bis-[1-O-α-D-carbonylmethyl-2,3,4,6-tetra-O-benzyl-mannopyranose]-L-lysine Similar to what is described in Example 37e) for the synthesis of the title compound that is relevant there, the methyl ester saponification of 15 g (11.23 mmol) of the title compound of Example 38a) results in the formation of 13.89 g (93.6% of theory) of the above-mentioned title compound in the form of a colorless and viscous oil.

Elementary analysis: Cld: C, 71.80; H, 6.71; N, 2.12. Fnd: C, 71.84; H, 6.69; N, 2.15.

c) 2-Nα-6-Nε-Bis-[1-O-α-D-carbonylmethyl-2,3,4,6-tetra-O-benzyl-mannopyranose]-L-lysine-N-hydroxysuccinimide ester 12.09 g (9.15 mmol) of the title compound of Example 38b) is dissolved in 100 ml of dimethylformamide and mixed with a total of 1.04 g (9.15 mmol) of N-hydroxysuccinimide. It is cooled to 0° C., and 1.89 g (9.15 mmol) of dicyclohexylcarbodiimide is added. It is stirred for one hour at 0° C. and then for 4 hours at room temperature. The solvent is then drawn off in a vacuum, and the remaining residue is mixed with 100 ml of ethyl acetate and cooled to 0° C. Precipitated urea is filtered out, and the filtrate that is obtained is evaporated to the dry state in a vacuum. The thus obtained, resinous-oily filtrate is purified on silica gel with use of ethyl acetate/n-hexane (1:20) as an eluant.

Yield: 12.24 g (94.4% of theory) of the above-mentioned title compound in the form of a colorless and viscous oil.

Elementary analysis: Cld: C, 70.27; H, 6.47; N, 2.96. Fnd: C, 70.31; H, 6.44; N, 3.01.

d) 6-N-Benzyloxycarbonyl-2-N-{[2,6-N,N'-bis(1-O-α-D-carbonylmethyl-2,3,4,6-tetra-O-benzyl-mannopyranose)]-L-lysyl-}-L-lysine-[1-(4-perfluorooctylsulfonyl)-piperazine]-amide 19.0 g (13.4 mmol) of the carboxylic acid-N-hydroxysuccinimide ester that is produced under Example 38c) is dissolved in 75 ml of dimethylformamide and mixed drop by drop at 0° C. with a solution, cooled to 0° C., of 11.13 g (13.4 mmol) of the title compound of Example 21c), dissolved in 50.0 ml of dimethylformamide. The resulting reaction solution is stirred for 2 more hours at 0° C. and for 12 hours at room temperature. For working-up, precipitated dicyclohexylurea is filtered out, and the solvent is then drawn off until a dry state is reached in a vacuum. The thus obtained residue is chromatographed on silica gel [mobile solvent: dichloromethane/ethanol 28:1; and chromatography is performed here with use of a solvent gradient with a proportion of the polar eluant component that is used (here: ethanol) that rises continuously in the course of the chromatography].

Yield: 25.28 g (88.4% of theory) of the title compound in the form of a colorless and strongly viscous oil.

Elementary analysis: Cld: C, 59.10; H, 5.34; N, 3.94; F, 15.13; S, 1.50. Fnd: C, 59.18; H, 5.35; N, 4.02; F, 15.15; S, 1.56.

e) 2-N-{[2,6-N,N'-Bis(1-O-α-D-carbonylmethyl-mannopyranose)]-L-lysyl-L-lysine-[1-(4-perfluorooctylsulfonyl)-piperazine]-amide 20.0 g (9.37 mmol) of the compound that is produced under 38d) is dissolved in 200 ml of ethanol, mixed with 1.5 g of Pearlman's catalyst (Pd 20%, C) and hydrogenated at room temperature under a hydrogen atmosphere (1 atm) until no more hydrogen absorption can be observed. Catalyst is suctioned out, it is thoroughly rewashed with ethanol (twice with about 100 ml each) and evaporated to the dry state in a vacuum. The title compound is obtained as a strongly viscous and colorless oil.

Yield: 11.62 g (97.0% of theory).

Elementary analysis: Cld: C, 38.50; H, 4.65; N, 6.57; F, 25.25; S, 2.51. Fnd: C, 38.46; H, 4.65; N, 6.51; F, 25.23; S, 2.52.

f) 6-N-[1,4,7-Tris(carboxylatomethyl)-10-(3-aza-4-oxo-5-methyl-5-yl-pentanoyl)-1,4,7,10-tetraazacyclododecane)-2-N-{[2,6-N,N'-bis(1-O-α-D-carbonylmethyl-mannopyranose)]-L-lysyl}-L-lysine-[1-(4-perfluorooctylsulfonyl)-piperazine]-amide, Gd complex 9.98 g (15.84 mmol; 2.2 molar equivalents relative to the amine component of Example 38e) that is used) of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 0.67 g of anhydrous lithium chloride (15.84 mmol) are dissolved at 40° C. in 100 ml of absolute dimethyl sulfoxide while being stirred and mixed at this temperature with a total of 1.82 g (15.84 mmol) of N-hydroxysuccinimide and 9.19 g (7.19 mmol) of the title compound of Example 38e), dissolved in 50 ml of absolute dimethyl sulfoxide. After cooling to room temperature, the reaction solution is mixed with 3.27 g (15.84 mmol) of N,N'-dicyclohexylcarbodiimide and stirred for 12 hours at room temperature. The suspension that is obtained is then mixed with sufficient acetone until the above-mentioned title compound is completely precipitated, the precipitate is suctioned off, dried, taken up in water, insoluble dicyclohexylurea is filtered off, and the filtrate is desalinated with an AMICON® YM-3 ultrafiltration membrane (cut-off 3,000 Da), and in this case possible, still present low-molecular components are simultaneously removed. The retentate is then freeze-dried.

Yield: 11.85 g (87.2% of theory) as a colorless lyophilizate.

$H_2O$ content (Karl-Fischer): 5.54%.

Elementary analysis (relative to anhydrous substance): Cld: C, 38.12; H, 4.64; N, 8.15; F, 20.38; S, 1.70; Gd, 8.32. Fnd: C, 38.16; H, 4.59; N, 8.18; F, 20.37; S, 1.68; Gd, 8.28.

EXAMPLE 39 a) 1,7-Bis(benzyloxycarbonyl)-4-(3-oxa-2H,2H,4H,4H,5H,5H-perfluorotridecanoyl)-1,4,7,10-tetraazacyclododecane At 0° C. and under nitrogen atmosphere, 12.74 g (24.4 mmol) of the title compound of Example 39g), dissolved in 150 ml of tetrahydrofuran, is added to a solution of 10.75 g (24.4 mmol) of 1,7-bis-[benzyloxycarbonyl]-1,4,7,10-tetraazacyclododecane, dissolved in a mixture that consists of 150 ml of tetrahydrofuran and 15 ml of chloroform. Then, a total of 18.0 g (36.6 mmol) of EEDQ [2-ethoxy-1-ethoxycarbonyl-1,2-dihydroquinoline] is added in portions at 0° C., allowed to stir overnight at room temperature, and then concentrated by evaporation in a vacuum. The remaining oil is chromatographed on silica gel (mobile solvent: n-hexane/isopropanol 16:1). 15.89 g (69.0% of theory, relative to the sec-amine that is used) of the monoamide and 3.8 g (8.8% of theory) of the diamide are obtained as by-products. The title compound is isolated in the form of a colorless oil.

Elementary analysis: Cld: C, 45.77; H, 3.95; F, 34.19; N, 5.93. Fnd: C, 45.72; H, 4.01; F, 34.22; N, 5.88.

b) 1,7-Bis(benzyloxycarbonyl)-4-(3-oxa-2H,2H,4H,4H,5H,5H-perfluorotridecanoyl)-10-[1-S-α-D-(2-carbonyl)-ethyl-2,3,4,6-tetra-O-acetyl-mannopyranose]-1,4,7,10-tetraazacyclododecane 7.09 g (13.4 mmol) of 3-(2,3,4,6-tetra-O-acetyl-1-thio-α-D-mannopyranosyl)-propionic acid-N-hydroxysuccinimide ester (production according to: J. Haensler et al., Bioconjugate Chem. 4, 85, (1993); Chipowsky, S., and Lee, Y. C. (1973), Synthesis of 1-Thio-Aldosides; Carbohydrate Research 31, 339–346) is dissolved in 100 ml of dimethylformamide and mixed drop by drop at 0° C. with a solution, precooled to 0° C., of 12.65 g (13.4 mmol) of the title compound of Example 39a), dissolved in 100 ml of dimethylformamide. It is stirred for 2 hours at 0° C. and for 12 hours at room temperature. For working-up, the solvent is drawn off in a vacuum until a dry state is reached, and the thus obtained residue is then chromatographed on silica gel (mobile solvent: dichloromethane/ethyl acetate 20:1; the chromatography was performed with use of a solvent gradient with continuous increase of the proportion of ethyl acetate).

Yield: 16.23 g (88.9% of theory) of the title compound in the form of a colorless and strongly viscous oil.

Elementary analysis: Cld: C, 46.70; H, 4.36; N, 4.11; F, 23.69; S, 2.35. Fnd: C, 46.66; H, 4.35; N, 4.12; F, 23.65; S, 2.30.

c) 1-(3-Oxa-2H,2H,4H,4H,5H,5H-perfluorotridecanoyl)-7-[1-S-α-D-(2-carbonyl)-ethyl-2,3,4,6-tetra-O-acetyl-mannopyranose]-1,4,7,10-tetraazacyclododecane 15.0 g (11.0 mmol) of the compound that is produced under 39b) is dissolved in 150 ml of ethanol, mixed with 1.0 g of Pearlman's catalyst (Pd 20%, C) and hydrogenated at room temperature under a hydrogen atmosphere (1 atm) until no more hydrogen absorption can be observed. Catalyst is suctioned out, it is thoroughly rewashed with ethanol (twice with 75 ml each) and evaporated to the dry state in a vacuum. The title compound is obtained as a strongly viscous and colorless oil.

Yield: 11.56 g (96.0% of theory).

Elementary analysis: Cld: C, 40.59; H, 4.33; N, 5.12; F, 29.50; S, 2.93. Fnd: C, 40.63; H, 4.35; N, 5.11; F, 29.52; S, 2.92.

d) 1-(3-Oxa-2H,2H,4H,4H,5H,5H-perfluorotridecanoyl)-7-[1-S-α-D-(2-carbonyl)-ethyl-mannopyranose]-1,4,7,10-tetraazacyclododecane 10.0 g (9.13 mmol) of the title compound of Example 39c) is suspended in 100 ml of absolute methanol and mixed at 5° C. with a catalytic amount of sodium methanolate. After a reaction time of 3 hours at room temperature, even thin-layer chromatographic checking (eluant: chloroform/methanol 4:1) of the course of the reaction indicates a quantitative reaction. For the purpose of working-up, the now clear reaction solution is neutralized by mixing with Amberlite IR 120 ($H^+$ form)-cation-exchange resin, exchanger is suctioned out, rewashed with methanol, and the thus obtained methanolic filtrate is drawn off in a vacuum until a dry state is reached. The oily residue that is obtained is purified by column chromatography on silica gel (mobile solvent: dichloromethane/n-hexane/ethyl acetate 15:20:1; and chromatography is performed with use of a solvent gradient with continuous increase of the proportion of ethyl acetate). After $^1$H-NMR spectroscopic study of the title compound, the presence of the α-configuration at the anomeric center of the D-mannopyranose was definitively established based on the size of the coupling constant of $J_{1,2}$=0.9 Hz. This α-configuration is the existing configuration that is exclusive to the anomeric center, i.e., the amount of the β-configured anomer of the title compound that can possibly be formed thus lies below the $^1$H-NMR-spectroscopic detection limit. The above-mentioned title compound was accordingly shown only in the form of the pure α-configured anomer.

Yield: 8.28 g (98.0% of theory) of the title compound in the form of a colorless and strongly viscous oil.

Elementary analysis: Cld: C, 37.59; H, 4.24; N, 6.05; F, 34.85; S, 3.46. Fnd: C, 37.57; H, 4.28; N, 6.02; F, 34.85; S, 3.44.

e) 1-(3-Oxa-2H,2H,4H,4H,5H,5H-perfluorotridecanoyl)-7-[1-S-α-D-(2-carbonyl)-ethyl-mannopyranose]-4,10-bis[1,4,7-tris(carboxylatomethyl)-10-(3-aza-4-oxo-5-methyl-5-yl-pentanoyl)]-1,4,7,10-tetraazacyclododecane, digadolinium complex Amide conjugate of the 1,4,7,10-tetraazacyclododecane with [1,7-bis-[gadolinium complex of 10-(4-carboxy-1-methyl-2-oxo-3-azabutyl)-1,4,7,10-tetraazacyclododecane-1,4,7-triacetic acid]; 3-(2,3,4,6-tetra-O-acetyl-1-thio-α-D-mannopyranosyl)-propionic acid.

2.48 g [(3.94 mmol); 4.4 molar equivalents relative to the diamine component 39d) that is
of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 167 mg of anhydrous lithium chloride (3.94 mmol) are dissolved at 40° C. in 40 ml of absolute dimethyl sulfoxide while being stirred and mixed at this temperature with a total of 453 mg (3.94 mmol) of N-hydroxysuccinimide and 980 mg (0.895 mmol) of the title compound of Example 19Ad), dissolved in 10 ml of absolute dimethyl sulfoxide. After cooling to room temperature, the reaction solution is mixed with 814 mg (3.946 mmol) of N,N'-dicyclohexylcarbodiimide and stirred for 12 hours at room temperature. The suspension that is obtained is then mixed with sufficient acetone until the above-mentioned title compound is completely precipitated, the precipitate is suctioned off, dried, taken up in water, insoluble dicyclohexylurea is filtered out, and the filtrate is desalinated with an AMICON® YM-3 ultrafiltration membrane (cut-off 3,000 Da), and low-molecular components are removed. The retentate is then freeze-dried.

Yield: 1.32 g (69.1% of theory) as a colorless lyophilizate. H$_2$O content (Karl-Fischer): 7.65%.

Elementary analysis (relative to anhydrous substance): Cld: C, 37.43; H, 4.45; N, 9.12; F, 15.02; S, 1.49; Gd, 14.63. Fnd: C, 37.42; H, 4.50; N, 9.18; F, 15.07; S, 1.51; Gd, 14.58.

f) 3-Oxa-2H,2H,4H,4H,5H,5H-perfluorotridecanoic acid-t-butyl ester 25.0 g (53.8 mmol) of 1H,1H,2H,2H-perfluoro-1-decanol [commercially available from the Lancaster Company] is dissolved in 250 ml of absolute toluene and mixed at room temperature with a catalytic amount (about 0.75 g) of tetra-n-butyl-ammonium hydrogen sulfate. Then, a total of 7.55 g (134.6 mmol; 2.5 equivalents relative to the alcohol component that is used) of fine-powder potassium hydroxide powder is added at 0° C., followed by 15.73 g (80.7 mmol; 1.5 equivalents relative to the alcohol component that is used) of bromoacetic acid-tert-butylester, and it is allowed to stir for 2 more hours at 0° C. The thus obtained reaction solution is stirred for 12 hours at room temperature, and for the purpose of working-up, it is mixed with a total of 500 ml of ethyl acetate and 250 ml of water. The organic phase is separated and washed twice with water. After the organic phase is dried on sodium sulfate, salt is suctioned out, and the solvent is drawn off in a vacuum. The remaining oily residue is purified on silica gel with use of ethyl acetate/hexane (1:10) as an eluant.

Yield: 26.3 g (84.6% of theory) of the above-mentioned title compound as a colorless and strongly viscous oil.

Elementary analysis: Cld: C, 33.23; H, 2.61; F, 55.85. Fnd: C, 33.29; H, 2.61; F, 55.90.

g) 3-Oxa-2H,2H,4H,4H,5H,5H-perfluorotridecanecarboxylic acid 20.0 g (34.58 mmol) of the title compound of Example 39f) is suspended in 200 ml of a mixture that consists of methanol and 0.5 molar sodium hydroxide solution at a ratio of 2:1 while being stirred at room temperature, and then it is heated to 60° C. After a reaction time of 12 hours at 60° C., the now clear reaction mixture is neutralized for working-up by mixing with Amberlite IR 120 (H$^+$ form)-cation-exchange resin, exchanger is suctioned out, and the thus obtained methanolic-aqueous filtrate is drawn off in a vacuum until a dry state is reached. The amorphous-oily residue that is obtained is purified on silica gel with use of ethyl acetate/n-hexane (1:3) as an eluant.

Yield: 16.0 g (88.6% of theory) of the above-mentioned title compound as a colorless and strongly viscous oil.

Elementary analysis: Cld: C, 27.60; H, 1.35; F, 61.85. Fnd: C, 27.58; H, 1.36; F, 61.90.

EXAMPLE 40 a) 6-Benzyloxycarbonyl-2-[2-(N-ethyl-N-perfluorooctylsulfonyl)-amino]-acetyl-L-lysine-methyl ester 16.18 g (27.0 mmol) of 2-[N-ethyl-N-perfluorooctylsulfonyl)-aminoacetic acid (production according to: DE 196 03 033), dissolved in 50 ml of tetrahydrofuran, is added drop by drop at 0° C. and under nitrogen atmosphere to 8.0 g (24.4 mmol) of ε-carbonyloxybenzyl-L-lysinemethyl ester hydrochloride (commercially available from the Bachem Company), dissolved in a mixture that consists of 150 ml of tetrahydrofuran, 15 ml of chloroform and 2.62 g (26.0 mmol) of triethylamine. Then, a total of 18.0 g (36.6 mmol) of EEDQ [2-ethoxy-1-ethoxycarbonyl-1,2-dihydroquinoline] is added in portions at 0° C. and allowed to stir overnight at room temperature. It is then concentrated by evaporation in a vacuum, and the remaining oil is chromatographed on silica gel (mobile solvent: n-hexane/isopropanol 15:1). 17.0 g (79.6% of theory, relative to the primary amine used) of the title compound is obtained in the form of a colorless oil.

Elementary analysis: Cld: C, 38.41; H, 3.45; F, 36.89; N, 4.80; S, 3.66. Fnd: C, 38.42; H, 3.47; F, 36.92; N, 4.87; S, 3.64.

b) 2-[2-(N-Ethyl-N-perfluorooctylsulfonyl)-amino]-acetyl-L-lysine-methyl ester 15.0 g (20.23 mmol) of the compound that is produced under Example 40a) is dissolved in 200 ml of ethanol, mixed with 800 mg of Pearlman's catalyst (Pd 20% on activated carbon) and hydrogenated until the calculated amount of hydrogen is taken up. Catalyst is suctioned out, thoroughly rewashed with ethanol and evaporated to the dry state in a vacuum. The title compound is obtained as a colorless oil.

Yield: 14.68 g (97.9% of theory).

Elementary analysis: Cld: C, 32.40; H, 3.26; F, 43.56; N, 5.67; S, 4.32. Fnd: C, 32.42; H, 3.27; F, 43.60; N, 5.67; S, 4.34.

c) 6-(1-O-α-D-Carbonylmethyl-2,3,4,6-tetra-O-benzyl-mannopyranose) 2-[2-(N-ethyl-N-perfluorooctylsulfonyl)-amino]-acetyl-L-lysine-methyl ester 21.31 g (35.6 mmol) of 1-carboxymethyloxy-2,3,4,-tetra-O-benzyl-α-D-mannopyranoside [production as described in Patent DE 197 28 954 C1] and 3.60 g (35.6 mmol) of triethylamine are dissolved in 500 ml of dry tetrahydrofuran. After the reaction solution is cooled to –15° C. to –20° C., a solution of 4.92 g (35.6 mmol) of isobutyl chloroformate in 75 ml of dry tetrahydrofuran is slowly added at this temperature while being stirred, whereby the rate of addition by drops can be selected so that an internal temperature of –10° C. is not exceeded. After a reaction time of 15 minutes at −15° C., a solution of 26.39 g (35.6 mmol) of the title compound of Example 40b) and 3.60 g (35.6 mmol) of triethylamine in 100 ml of dry tetrahydrofuran is then slowly added in drops at −20° C. After a reaction time of one hour at −15° C. and two hours at room temperature, the reaction solution is evaporated to the dry state in a vacuum. The remaining residue is taken up in 250 ml of ethyl acetate and washed twice with 100 ml each of saturated sodium bicarbonate solution and once with 200 ml of water. After the organic phase is dried on sodium sulfate, salt is suctioned out, and the ethyl acetate is drawn off in a vacuum. The remaining oily residue is purified on silica gel with use of ethyl acetate/n-hexane (1:10) as an eluant.

Yield: 38.12 g (81.0% of theory) of the above-mentioned title compound as a colorless and strongly viscous oil.

Elementary analysis: Cld: C, 49.92; H, 3.92; N, 2.53; F, 29.18; S, 2.90. Fnd: C, 49.99; H, 4.11; N, 2.69; F, 29.22; S, 3.01.

d) 6-(1-O-α-D-Carbonylmethyl-2,3,4,6-tetra-O-benzyl-mannopyranose) 2-[2-(N-ethyl-N-perfluorooctylsulfonyl)-amino]-acetyl-L-lysine 27.65 g (20.92 mmol) of the compound that is produced under Example 40c) is dissolved in 250 ml of methanol. The solution of 4.0 g (100.0 mmol) of sodium hydroxide in 10 ml of distilled water is then added, and it is stirred for 3 hours at 50° C. After the course of the reaction is checked by means of thin-layer chromatography, methyl ester saponification has already taken place quantitatively. It is evaporated to the dry state in a vacuum, the remaining residue is taken up in 300 ml of ethyl acetate, and the organic phase is extracted twice with 100 ml each of dilute, aqueous citric acid solution. After drying on sodium sulfate, it is filtered and evaporated to the dry state in a vacuum. The residue that is obtained is chromatographed on silica gel (mobile solvent: n-hexane/chloroform/isopropanol 15:10:1). 24.31 g (88.9% of theory) of the title compound is obtained in the form of a colorless and viscous oil.

Elementary analysis: Cld: C, 51.46; H, 4.70; N, 3.21; F, 24.71; S, 2.45. Fnd: C, 51.49; H, 4.71; N, 3.19; F, 24.72; S, 2.41.

e) 6-(1-O-α-D-Carbonylmethyl-mannopyranose) 2-[2-(N-ethyl-N-perfluorooctylsulfonyl)-amino]-acetyl-L-lysine 20.0 g (15.30 mmol) of the title compound of Example 40d) is dissolved in a mixture that consists of 250 ml of 2-propanol and 25 ml of water, and it is mixed with 1.0 g of palladium catalyst (10% Pd on activated carbon). It is hydrogenated for 12 hours at room temperature and a hydrogen pressure of one atmosphere. Catalyst is filtered out, and the filtrate is evaporated to the dry state in a vacuum. The residue is dissolved in 200 ml of methanol, and the reaction product is precipitated by mixing with a total of 800 ml of diethyl ether. After the thus obtained solid is suctioned off, the latter is dried in a vacuum at 50° C.

Yield: 14.32 g (99.0% of theory) of an amorphous solid.

Elementary analysis: Cld: C, 35.56; H, 3.84; N, 4.44; S, 3.39; F, 34.15. Fnd: C, 35.58; H, 3.81; N, 4.45; S, 3.40; F, 34.17.

f) 6-(1-O-α-D-Carbonylmethyl-mannopyranose) 2-[2-(N-ethyl-N-perfluorooctylsulfonyl)-amino]-acetyl-L-lysine-N-{2-hydroxyprop-3-yl-[1,4,7-tris(carboxylatomethyl)-1,4,7,10-tetraazacyclododecan-10-yl]}-amide, Gd complex 7.48 g (7.91 mmol) of the title compound of Example 40e) is dissolved in 50 ml of dimethyl sulfoxide at 40° C., and 1.00 g (8.70 mol) of N-hydroxysuccinimide is added. It is cooled to 20° C., and 1.795 g (8.7 mmol) of dicyclohexyl-carbodiimide is added. It is stirred for one hour at 20° C. and then for 4 hours at 40° C. Then, a solution that consists of 4.53 g (7.91 mmol) of the gadolinium complex of 10-(2-hydroxy-3-aminopropyl)-4,7,10-tris(carboxymethyl)-1,4,7,10-tetraazacyclododecanine [for production, cf.: WO 97/02051] in 20 ml of dimethyl sulfoxide is added in drops at this temperature within 10 minutes. It is stirred for one hour at 40° C., then overnight at room temperature. The thus obtained suspension is then mixed with sufficient acetone until the above-mentioned title compound is completely precipitated, the precipitate is suctioned off, dried, taken up in water, insoluble dicyclohexylurea is filtered out, and the filtrate is desalinated with an AMICON® YM-3 ultrafiltration membrane (cut-off 3,000 Da), and low-molecular components are removed. The retentate is then freeze-dried.

Yield: 9.71 g (81.7% of theory) as a colorless lyophilizate.

$H_2O$ content (Karl-Fischer): 3.97%.

Elementary analysis (relative to anhydrous substance): Cld: C, 35.16; H, 4.16; N, 7.45; F, 21.48; Gd, 10.46; S, 2.13. Fnd: C, 35.17; H, 4.20; N, 7.42; F, 21.49; Gd, 10.48; S, 2.09.

EXAMPLE 41 a) 6-N-[1-O-α-D-(5-Carbonyl)-pentyl-2,3,4,6-tetra-O-benzyl-mannopyranose]-2N-[2-(N-ethyl-N-perfluorooctylsulfonyl)-amino]-acetyl-L-lysine-methyl ester 5.23 g (8.0 mmol) of the 5-(carboxy)pentyl-2,3,4,6-tetra-O-benzyl-α-D-mannopyranoside described in Example 30c), 1.3 g (8.0 mmol) of 1-hydroxybenzotriazole and 2.6 g (3.0 mmol) of 2-(1H-benzotriazol-1-yl)-1,1,3,3-tetramethyluronium tetrafluoroborate (TBTU; Peboc Limited, UK) are dissolved in 75 ml of DMF and stirred for 15 minutes. This solution is then mixed with 5.16 ml (30 mmol) of N-ethyldiisopropylamine and with 5.93 g (8.0 mmol) of the amine that is described under Example 40b), and it is stirred for 1.5 days at room temperature. For working-up, the solvent is drawn off in a vacuum until a dry state is reached, and the thus obtained residue is then chromatographed on silica gel (mobile solvent: dichloromethane/ethyl acetate 30:1; chromatography was carried out with use of a solvent gradient with a proportion of ethyl acetate that rises continuously).

Yield: 9.70 g (88.0% of theory) of the title compound in the form of a colorless and strongly viscous oil.

Elementary analysis: Cld: C, 52.29; H, 4.97; N, 3.05; F, 23.43; S, 2.33. Fnd: C, 52.33; H, 4.95; N, 3.12; F, 23.50; S, 2.30.

b) 6-N-[1-O-α-D-(5-Carbonyl)-pentyl-2,3,4,6-tetra-O-benzyl-mannopyranose]-2N-[2-(N-ethyl-N-perfluorooctylsulfonyl)-amino]-acetyl-L-lysine 9.0 g (12.40 mmol) of the compound that is produced under Example 41a) is dissolved in 150 ml of methanol. The solution of 2.48 g (62.0 mmol) of sodium hydroxide in 15 ml of distilled water is then added to it, and it is stirred for 3 hours at 50° C. After the course of the reaction is checked by means of thin-layer chromatography, methyl ester saponification has already taken place quantitatively according to the above-mentioned reaction time. It is evaporated to the dry state in a vacuum, and the remaining residue is taken up in 300 ml of ethyl acetate, and the organic phase is extracted twice with 100 ml each of dilute, aqueous citric acid solution. After drying on sodium sulfate, it is filtered and evaporated to the dry state in a vacuum. The residue that is obtained is chromatographed on silica gel (mobile solvent: n-hexane/chloroform/isopropanol 25:10:1). 15.88 g (93.9% of theory) of the title compound is obtained in the form of a colorless and strongly viscous oil.

Elementary analysis: Cld: C, 51.95; H, 4.88; N, 3.08; F, 23.67; S, 2.35. Fnd: C, 51.99; H, 4.91; N, 3.09; F, 23.70; S, 2.33.

c) 6-N-[1-O-α-D-(5-Carbonyl)-pentyl-mannopyranose]-2N-[2-N-ethyl-N-perfluorooctylsulfonyl)-amino]-acetyl-L-lysine 13.0 g (9.52 mmol) of the title compound of Example 41b) is dissolved in a mixture that consists of 150 ml of 2-propanol and 25 ml of water, and 1.0 g of the palladium catalyst (10% Pd on activated carbon) is added. It is hydrogenated for 12 hours at 1 atmosphere of hydrogen pressure and room temperature. Catalyst is filtered out, and the filtrate is evaporated to the dry state in a vacuum. The residue that is obtained is chromatographed on silica gel (mobile solvent: n-hexane/chloroform/isopropanol 15:10:1). 9.09 g (95.1% of theory) of the title compound is obtained in the form of a colorless and strongly viscous oil.

Elementary analysis: Cld: C, 37.10; H, 4.22; N, 4.19; F, 32.18; S, 3.10. Fnd: C, 37.09; H, 4.21; N, 4.19; F, 32.20; S, 3.13.

d) 6-N-[1-O-α-D-(5-Carbonyl)-pentyl-mannopyranose]-2N-[2-(N-ethyl-N-perfluorooctylsulfonyl)-amino]-acetyl-L-lysine-N-{2-hydroxy-prop-3-yl-[1,4,7-tris(carboxylatomethyl)-1,4,7,10-tetraazacyclododecan-10-yl]}-amide, Gd complex 7.93 g (7.91 mmol) of the title compound of Example 41c) is dissolved at 40° C. in 75 ml of dimethyl sulfoxide, and it is mixed with 1.00 g (8.70 mol) of N-hydroxysuccinimide. It is cooled to room temperature, and a total of 1.795 g (8.7 mmol) of dicyclohexylcarbodiimide is added. It is stirred for one hour at 20° C. and then for 4 hours at 40° C. Then, a solution that consists of 4.53 g (7.91 mmol) of the gadolinium complex of 10-(2-hydroxy-3-aminopropyl)-4,7,10-tris(carboxymethyl)-1,4,7,10-tetraazacyclododecanine [for production, cf.: WO 97/02051] in 20 ml of dimethyl sulfoxide is added in drops at 40° C. within 10 minutes to this solution of the active ester of the title compound of Example 41c). It is stirred for one hour at 40° C., then overnight at room temperature. The thus obtained suspension is then mixed with a sufficient amount of a mixture that consists of acetone/2-propanol (2:1) until the above-mentioned title compound is completely precipitated, the precipitate is suctioned off, rewashed with ethyl acetate, dried, taken up in water, insoluble dicyclohexylurea is filtered out, and the filtrate is desalinated with an AMICON® YM-3 ultrafiltration membrane (cut-off 3,000 Da), and low-molecular components are removed. The retentate is then freeze-dried.

Yield: 9.71 g (78.8% of theory) as a colorless lyophilizate.

$H_2O$ content (Karl-Fischer): 6.65%.

Elementary analysis (relative to anhydrous substance): Cld: C, 36.97; H, 4.52; N, 7.19; F, 20.71; Gd, 10.08; S, 2.06. Fnd: C, 37.02; H, 4.50; N, 7.22; F, 20.69; Gd, 10.08; S, 2.09.

EXAMPLE 42 a) 6-N-{4-[2,3-Bis-(N,N-bis(t-butyloxycarbonylmethyl)-amino)-propyl]-phenyl}-3-oxa-propionyl-2-N-(1-α-D-carbonylmethyl-mannopyranose) L-lysine-[1-(4-perfluorooctylsulfonyl)-piperazine]-amide 5.25 g (7.72 mmol) of the tetra-t.bu-ester of "Tyr-EDTA-carboxylic acid" and 781 mg (7.72 mmol) of triethylamine are dissolved in 50 ml of methylene chloride. At −15° C., a solution that consists of 1.16 g (8.5 mmol) of isobutyl chloroformate in 10 ml of methylene chloride is added in drops within 5 minutes, and it is stirred for another 20 minutes at −15° C. Then, the solution is cooled to −25° C., and a solution that consists of 7.07 g (7.72 mmol) of the title compound of Example 30e) and 2.12 g (21.0 mmol) of triethylamine, in 70 ml of tetrahydrofuran, is added in drops within 30 minutes, and subsequently stirred for 30 more minutes at −15° C., and then stirring is continued overnight at room temperature. For working-up, the solvent is drawn off in a vacuum, and the remaining oily residue is taken up in 250 ml of chloroform. The chloroform phase is extracted twice with 100 ml each of a 10% aqueous ammonium chloride solution, the organic phase is dried on magnesium sulfate and evaporated to the dry state in a vacuum. The residue is chromatographed on silica gel (mobile solvent: methylene chloride/ethanol=20:1).

Yield: 9.60 g (79.0% of theory) of a colorless and very viscous oil.

Elementary analysis: Cld: C, 46.39; H, 5.55; N, 5.32; F, 20.45; S, 2.03. Fnd: C, 46.42; H, 5.51; N, 5.29; F, 20.49; S, 2.09.

b) 6-N-{4-[2,3-Bis-(N,N-bis(carboxymethyl)-amino)-propyl]-phenyl}-3-oxa-propionyl-2-N-(1-α-D-carbonylmethyl-mannopyranose) L-lysine-[1-(4-perfluorooctylsulfonyl)-piperazine]-amide 9.0 g (5.70 mmol) of the compound produced under Example 42a) is dissolved in 150 ml of methanol. The solution of 4.0 g (100.0 mmol) of sodium hydroxide in 25 ml of distilled water is then added to it, and it is stirred for 6 hours at 60° C. After the course of the reaction is checked by means of thin-layer chromatography, saponification of the tetra-t-butyl ester has already taken place quantitatively according to the above-mentioned reaction time. It is evaporated to the dry state in a vacuum, and the remaining residue is taken up in 50 ml of dimethyl sulfoxide in the heat, and then it is mixed with a sufficient amount of a mixture that consists of acetone/ethyl acetate (1:1) until the above-mentioned title compound is completely precipitated, the thus obtained precipitate is suctioned off, thoroughly rewashed with ethyl acetate, dried, taken up in water, the pH of the product solution is set at 3.5 with 1 molar hydrochloric acid, possibly present insoluble components are filtered out, and the filtrate is desalinated with an AMICON® YM-3 ultrafiltration membrane (cut-off 3,000 Da), and low-molecular components are removed. The retentate is then freeze-dried.

Yield: 6.76 g (87.6% of theory) as a colorless lyophilizate.

$H_2O$ content (Karl-Fischer): 3.30%.

Elementary analysis (relative to anhydrous substance): Cld: C, 39.89; H, 4.09; N, 6.20; F, 23.84; S, 2.37. Fnd: C, 39.92; H, 4.15; N, 6.22; F, 23.92; S, 2.29.

c) 6-N-{4-[2,3-Bis-(N,N-bis(carboxylatomethyl)-amino)-propyl]-phenyl}-3-oxa-propionyl-2-N-(1-α-D-carbonylmethyl-mannopyranose) L-lysine-[1-(4-perfluorooctylsulfonyl)-piperazine]-amide, Mn complex, disodium salt 3.0 g (2.22 mmol) of the title compound of Example 42b) is dissolved in 150 ml of a water/ethanol (3:1) mixture at boiling heat, and it is mixed in portions with 0.25 g (2.22 mmol) of manganese(II) carbonate at 80° C. Then, the thus obtained reaction solution is refluxed for 5 hours. After cooling to room temperature, the solvent mixture is completely drawn off in a vacuum, and the remaining residue is dissolved in a mixture that consists of 200 ml of distilled water/n-butanol (1:1). A pH of 7.2 is set by mixing with 1N sodium hydroxide solution while being stirred vigorously. After the n-butanol is completely drawn off in a vacuum, the remaining aqueous phase is desalinated with an AMICON® YM-3 ultrafiltration membrane (cut-off 3,000 Da), and low-molecular components are removed. The retentate is then freeze-dried.

Yield: 3.19 g (99.0% of theory) as a colorless lyophilizate.

$H_2O$ content (Karl-Fischer): 5.08%.

Elementary analysis (relative to anhydrous substance): Cld: C, 37.23; H, 3.54; F, 22.25 Mn 3.78; N, 5.79; Na, 3.17; S, 2.21. Fnd: C, 37.30; H, 3.49; F, 22.29 Mn 3.81; N, 5.76; Na, 3.19; S, 2.18.

EXAMPLE 43 a) 3-Benzyloxycarbonylamino-glutaric acid-[1-(4-perfluorooctylsulfonyl)-piperazine]-monoamide A stirred solution of 25.0 g (94.96 mmol) of 3-N-(benzyloxycarbonyl)-glutaric acid-anhydride [synthesis according to: Hatanaka, Minoru; Yamamoto, Yu-ichi; Nitta, Hajime; Ishimaru, Toshiyasu; TELEAY; Tetrahedron Lett.: EN; 22; 39; 1981; 3883–3886;] in 150 ml of absolute tetrahydrofuran is mixed drop by drop while being stirred with a solution of 53.97 g (95.0 mmol) of 1-perfluorooctylsulfonylpiperazine in 150 ml of tetrahydrofuran, and the thus obtained reaction solution is refluxed for 12 hours. After cooling to room temperature, it is concentrated by evaporation to the dry state, and the remaining oily residue is purified on silica gel with use of dichloromethane/2-propanol (20:1) as an eluant.

Yield: 75.80 g (96.0% of theory) of the above-mentioned title compound in the form of a colorless and viscous oil.

Elementary analysis: Cld: C, 36.11; H, 2.67; N, 5.05; S, 3.86; F, 38.84. Fnd: C, 36.12; H, 2.61; N, 5.08; S, 3.88; F, 38.82.

b) 3-Amino-glutaric acid-[1-4-perfluorooctylsulfonyl)-piperazine]-monoamide 31.50 g (37.88 mmol) of the compound that is produced under 43b) is dissolved in 300 ml of ethanol, it is mixed with 2.5 g of Pearlman's catalyst (Pd 20%, C) and hydrogenated until quantitative hydrogen uptake is reached at 1 atmosphere of hydrogen pressure. Catalyst is suctioned out, it is rewashed with ethanol and evaporated to the dry state in a vacuum. The title compound is obtained as a whitish-yellow, viscous oil.

Yield: 25.22 g (95.5% of theory).

Elementary analysis: Cld: C, 29.28; H, 2.31; N, 6.03; S, 4.06; F, 46.31. Fnd: C, 29.32; H, 2.29; N, 6.08; S, 4.08; F, 46.28.

c) 3-N-(1-α-D-Carbonylmethyl-2,3,4,6-tetra-O-benzyl-mannopyranose)-glutaric acid-[1-(4-perfluorooctylsulfonyl)-piperazine]-monoamide 21.52 g (18.96 mmol) of 1-carboxymethyloxy-2,3,4,-tetra-O-benzyl-α-D-mannopyranoside [production as described in Patent DE 197 28 954 C1] is dissolved at room temperature in 100 ml of absolute dimethylformamide, and it is mixed at 0° C. with 2.56 g (22.2 mmol) of N-hydroxysuccinimide, followed by 4.55 g (22.2 mmol) of dicyclohexylcarbodiimide. After a reaction time of 60 minutes at 0° C. and 3 hours at 22° C., insoluble dicyclohexylurea is filtered out, and the thus obtained clear active ester solution of the above-mentioned title compound is slowly added in drops at 0° C. to a stirred solution of 13.22 g (18.96 mmol) of the compound of Example 43b), dissolved in 100 ml of dimethylformamide. After a reaction time of 12 hours at room temperature, the solvent is drawn off in a vacuum, and the remaining residue is taken up in 300 ml of ethyl acetate, urea is filtered out, and the organic filtrate is washed twice with 100 ml each of saturated sodium bicarbonate solution and once with 100 ml of 10% aqueous citric acid solution and once with 200 ml of water. After the organic phase is dried on sodium sulfate, salt is suctioned out, and the ethyl acetate is drawn off in a vacuum. The remaining oily residue is purified on silica gel with use of ethyl acetate/n-hexane (1:15) as an eluant.

Yield: 21.39 g (88.3% of theory) of the above-mentioned title compound as a colorless and strongly viscous oil.

Elementary analysis: Cld: C, 49.81; H, 4.10; N, 3.29; F, 25.27; S, 2.51. Fnd: C, 49.89; H, 4.11; N, 3.32; F, 25.22; S, 2.51.

d) 3-N-(1-α-D-Carbonylmethyl-mannopyranose)-glutaric acid-[1-(4-perfluorooctylsulfonyl)-piperazine]-monoamide 19.55 g (15.30 mmol) of the title compound of Example 43c) is dissolved in a mixture that consists of 250 ml of 2-propanol and 25 ml of water and mixed with 1.5 g of palladium catalyst (10% Pd on activated carbon). It is hydrogenated for 12 hours at room temperature and a hydrogen pressure of one atmosphere. Catalyst is filtered out, and the filtrate is evaporated to the dry state in a vacuum. The residue is dissolved in 200 ml of methanol, and the reaction product is precipitated by mixing with a total of 800 ml of diethyl ether. After the thus obtained solid is suctioned off, the latter is dried in a vacuum at 40° C.

Yield: 17.49 g (97.5% of theory) of an amorphous solid.

Elementary analysis: Cld: C, 32.73; H, 3.08; N, 4.58; S, 3.49; F, 35.20. Fnd: C, 32.68; H, 3.15; N, 4.55; S, 3.50; F, 35.17.

e) 3-N-(1-α-D-Carbonylmethyl-mannopyranose)-glutaric acid-[1-(4-perfluorooctylsulfonyl)-piperazine]-amide-5-N-(2-hydroxy-prop-3-yl-[1,4,7-tris(carboxylatomethyl)-1,4,7,10-tetraazacyclododecan-10-yl]}-amide, Gd complex 14.43 g (15.84 mmol) of the title compound of Example 43d) and 0.67 g of anhydrous lithium chloride (15.84 mmol) are dissolved at 40° C. in 100 ml of absolute dimethyl sulfoxide while being stirred, and it is mixed at this temperature with a total of 1.82 g (15.84 mmol) of N-hydroxysuccinimide and a solution of 9.08 g (15.84 mmol) of the gadolinium complex of 10-(2-hydroxy-3-aminopropyl)-4,7,10-tris(carboxymethyl)-1,4,7,10-tetraazacyclododecanine [for production, cf.: WO 97/02051], in 50 ml of dimethyl sulfoxide. After cooling to room temperature, the reaction solution is mixed with 3.27 g (15.84 mmol) of N,N'-dicyclohexylcarbodiimide, and it is stirred for 12 hours at room temperature. The suspension that is obtained is then mixed with sufficient acetone until the above-mentioned title compound is completely precipitated, the precipitate is suctioned off, dried, taken up in water, insoluble dicyclohexylurea is filtered out, and the filtrate is desalinated with an AMICON® YM-3 ultrafiltration membrane (cut-off 3,000 Da) and in this case possible, still present low-molecular components are simultaneously removed. The retentate is then freeze-dried.

Yield: 18.71 g (80.2% of theory) as a colorless lyophilizate.

$H_2O$ content (Karl-Fischer): 4.87%.

Elementary analysis (relative to anhydrous substance): Cld: C, 34.24; H, 3.83; N, 7.61; F, 21.92; S, 2.18; Gd, 10.67. Fnd: C, 34.26; H, 3.79; N, 7.58; F, 21.87; S, 2.18; Gd, 10.68.

EXAMPLE 44 a) 1,7-Bis(benzyloxycarbonyl)-4-{3-oxa-pentane-1,5-dicarboxylic acid-1-oyl-5-[1-(4-perfluorooctylsulfonyl)-piperazine]-amide}-10-(2,6-N,N'-bis(1-O-α-D-carbonylmethyl-2,3,4,6-tetra-O-benzyl-mannopyranose)]-L-lysyl-1,4,7,10-tetraazacyclododecane 33.04 g (25.0 mmol) of the title compound of Example 18c), dissolved in 250 ml of tetrahydrofuran, is added at 0° C. and under nitrogen atmosphere to a solution that consists of 27.0 g (24.4 mmol) of the sec-amine that is produced under Example 35a), in a mixture that consists of 150 ml of tetrahydrofuran and 15 ml of chloroform. Then, a total of 18.0 g (36.6 mmol) of EEDQ [2-ethoxy-1-ethoxycarbonyl-1,2-dihydroquinoline] is added in portions at 0° C. and allowed to stir overnight at room temperature. It is then evaporated to the dry state in a vacuum, and the remaining oil is chromatographed on silica gel (mobile solvent: n-hexane/isopropanol 25:1). 45.87 g (78.0% of theory, relative to the sec-amine that is used) of the title compound is obtained in the form of a colorless oil.

Elementary analysis: Cld: C, 59.30; H, 5.39; F, 13.40; N, 4.65; S, 1.33. Fnd: C, 59.32; H, 5.37; F, 13.37; N, 4.70; S, 1.34.

b) 1-{3-Oxa-pentane-1,5-dicarboxylic acid-1-oyl-5-[1-(4-perfluorooctylsulfonyl)-piperazine]-amide}-7-[2,6-N,N'-bis(1-O-α-D-carbonylmethyl-mannopyranose)]-L-lysyl-1,4,7,10-tetraazacyclododecane 24.1 g (10.0 mmol) of the title compound that is produced under Example 44a) is dissolved in 250 ml of ethanol, and it is mixed with 1.4 g of Pearlman's catalyst (Pd 20%, C). It is hydrogenated until quantitative hydrogen uptake is reached, then catalyst is suctioned out, it is thoroughly rewashed with ethanol and evaporated to the dry state in a vacuum. The product is yellowish in color, and extremely viscous oil is obtained.

Yield: 12.80 g (90.1% of theory).

Elementary analysis: Cld: C, 39.72; H, 4.89; F, 22.73; N, 7.88; S, 2.26. Fnd: C, 39.72; H, 4.87; F, 22.77; N, 7.90; S, 2.24.

c) 1-{3-Oxa-pentane-1,5-dicarboxylic acid-1-oyl-5-[1-(4-perfluorooctylsulfonyl)-piperazine]-amide}-7-[2,6-N,N'-bis(1-O-α-D-carbonylmethyl-mannopyranose)]-L-lysyl-4,10-bis[1,4,7-tris(carboxylatomethyl)-10-(3-aza-4-oxo-5-methyl-5-yl-pentanoyl)]-1,4,7,10-tetraazacyclododecane, digadolinium complex 5.54 g [8.8 mmol; 2.2 molar equivalents relative to the amine component of Example 44b) that is used] of the Gd-complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and anhydrous lithium chloride (0.37 g, 8.8 mmol) is dissolved at 40° C. in 60 ml of absolute dimethyl sulfoxide while being stirred, and a total of 1.01 g (8.8 mmol) of N-hydroxysuccinimide and 5.68 g (4.0 mmol) of the title compound of Example 44b), dissolved in 40 ml of absolute dimethyl sulfoxide, is mixed at this temperature. After cooling to room temperature, the reaction solution is mixed with 1.82 g (8.8 mmol) of N,N'-dicyclohexylcarbodiimide and stirred for 12 hours at room temperature. The suspension that is obtained is then mixed with sufficient acetone until the above-mentioned title compound is completely precipitated, the precipitate is suctioned off, dried, taken up in water, insoluble dicyclohexylurea is filtered out, and the filtrate is desalinated with an AMICON® YM-3 ultrafiltration membrane (cut-off 3,000 Da), and low-molecular components are removed. The retentate is then freeze-dried.

Yield: 8.52 g (80.6% of theory; relative to the diamine component that is used) as a colorless lyophilizate.

H$_2$O content (Karl-Fischer): 6.09%.

Elementary analysis (relative to anhydrous substance):
Cld: C, 38.61; H, 4.76; N, 9.53; F, 12.21; Gd, 11.89; S, 1.12.
Fnd: C, 38.57; H, 4.82; N, 9.52; F, 12.21; Gd, 11.93; S, 1.15.

EXAMPLE 45 a) 1,7-Bis(benzyloxycarbonyl)-4-{3-oxa-pentane-1,5dicarboxylic acid-1-oyl-5-[1-(4-perfluorooctylsulfonyl)-piperazine]-amide}-10-{2,6-N,N'-bis(1-O-α-D(5-carbonyl)-pentyl-2,3,4,6-tetra-O-benzyl-mannopyranose)}-L-lysyl-1,4,7,10-tetraazacyclododecane 35.80 g (25.0 mmol) of the title compound of Example 37e), dissolved in 250 ml of tetrahydrofuran, is added at 0° C. and under nitrogen atmosphere to a solution that consists of 27.0 g (24.4 mmol) of the sec-amine that is produced under Example 35a), in a mixture that consists of 150 ml of tetrahydrofuran and 15 ml of chloroform. Then, a total of 18.0 g (36.6 mmol) of EEDQ [2-ethoxy-1-ethoxycarbonyl-1,2-dihydroquinoline] is added in portions at 0° C., and it is allowed to stir overnight at room temperature. It is then evaporated to the dry state in a vacuum, and the remaining oil is chromatographed on silica gel (mobile solvent: n-hexane/isopropanol 20:1). 49.48 g (80.4% of theory, relative to the sec-amine that is used) of the title compound is obtained in the form of a colorless oil.

Elementary analysis: Cld: C, 60.47; H, 5.79; F, 12.80; N, 4.44; S, 1.27. Fnd: C, 60.52; H, 5.77; F, 12.77; N, 4.50; S, 1.30.

b) 1-{3-Oxa-pentane-1,5-dicarboxylic acid-1-oyl-5-[1-(4-perfluorooctylsulfonyl)-piperazine]-amide}-7-[2,6-N,N'-bis(1-O-α-D-(5-carbonyl)-pentyl-mannopyranose)]-L-lysyl-1,4,7,10-tetraazacyclododecane 25.2 g (10.0 mmol) of the title compound that is produced under Example 45a) is dissolved in 250 ml of ethanol and mixed with 1.8 g of Pearlman's catalyst (Pd 20%, C). It is hydrogenated until quantitative hydrogen uptake is reached, then catalyst is suctioned out, it is thoroughly rewashed with ethanol and evaporated to the dry state in a vacuum. The product is yellowish in color, and extremely viscous oil is obtained.

Yield: 14.11 g (92.5% of theory).

Elementary analysis: Cld: C, 49.60; H, 7.20; F, 21.17; N, 7.34; S, 2.10. Fnd: C, 49.62; H, 7.17; F, 21.20; N, 7.30; S, 2.14.

c) 1-{3-Oxa-pentane-1,5-dicarboxylic acid-1-oyl-5-[1-(4-perfluorooctylsulfonyl)-piperazine]-amide}-7-[2,6-N,N'-bis(1-O-α-D-(5-carbonyl)-pentyl-mannopyranose)]-L-lysyl-4,10-bis[1,4,7-tris(carboxylatomethyl)-10-(3-aza-4-oxo-5-methyl-5-yl-pentanoyl)]-1,4,7,10-tetraazacyclododecane, digadolinium complex 5.54 g [8.8 mmol; 2.2 molar equivalents relative to the amine component of Example 45b) that is used] of the Gd, complex, described in Patent Application DE 197 28 954 C1 under Example 31h), of the 10-(4-carboxy-1-methyl-2-oxo-3-azabutyl)-1,4,7,10-tetraazacyclododecane-1,4,7-triacetic acid and anhydrous lithium chloride (0.37 g, 8.8 mmol) are dissolved at 40° C. in 60 ml of absolute dimethyl sulfoxide while being stirred, and it is mixed at this temperature with a total of 1.01 g (8.8 mmol) of N-hydroxysuccinimide and 6.10 g (4.0 mmol) of the title compound of Example 45b), dissolved in 40 ml of absolute dimethyl sulfoxide. After cooling to room temperature, the reaction solution is mixed with 1.82 g (8.8 mmol) of N,N'-dicyclohexylcarbodiimide, and it is stirred for 12 hours at room temperature. The suspension that is obtained is then mixed with sufficient acetone until the above-mentioned title compound is completely precipitated, the precipitate is suctioned off, dried, taken up in water, insoluble dicyclohexylurea is filtered out, and the filtrate is desalinated with an AMICON® YM-3 ultrafiltration membrane (cut-off 3,000 Da), and low-molecular components are removed. The retentate is then freeze-dried.

Yield: 9.26 g (84.0% of theory; relative to the diamine component that is used) as a colorless lyophilizate.

H$_2$O content (Karl-Fischer): 5.89%.

Elementary analysis (relative to anhydrous substance):
Cld: C, 40.52; H, 5.16; N, 9.15; F, 11.72; Gd, 11.41; S, 1.16.
Fnd: C, 40.57; H, 5.20; N, 9.12; F, 11.69; Gd, 11.43; S, 1.18.

EXAMPLE 46 a) 6-N-t-Butyloxycarbonyl-2-N-benzyloxycarbonyl-L-lysine-[1-(4-perfluorooctylsulfonyl)-piperazine]-amide 19.02 g (50.0 mmol) of α-N-(benzyloxycarbonyl)-α-N'-tert-butyloxycarbonyl-L-lysine (commercially available from the Bachem Company) is dissolved in 150 ml of absolute tetrahydrofuran. 8.31 g (50.0 mmol) of carbonyl diimidazole and 5.03 g (50.0 mmol) of triethylamine, dissolved in 75 ml of dry tetrahydrofuran, are added drop by drop at 0° C., and stirring is allowed to continue for 10 minutes at this temperature. Then, a solution of 48.42 g (50.0 mmol) of perfluorooctylsulfonyl-piperazine and 5.03 g (50.0 mmol) of triethylamine in 250 ml of dry tetrahydrofuran is added in drops at 0° C. After stirring overnight, the tetrahydrofuran is drawn off in a vacuum, and the remaining oil is chromatographed on silica gel (mobile solvent: n-hexane/isopropanol 15:1). 49.48 g (80.4% of theory, relative to the sec-amine that is used) of the title compound is obtained in the form of a colorless oil.

Elementary analysis (relative to anhydrous substance): Cld: C, 40.01; H, 3.79; N, 6.02; F, 34.70; S, 3.45. Fnd: C, 40.07; H, 3.82; N, 6.02; F, 34.67; S, 3.48.

b) 6-N-t-Butyloxycarbonyl-L-lysine-[1-(4-perfluorooctylsulfonyl)-piperazine]-amide 30.0 g (32.2 mmol) of the title compound of Example 46a) is dissolved in 300 ml of isopropanol and mixed with 1.5 g of Pearlman's catalyst (20% palladium hydroxide on carbon). It is hydrogenated for 10 hours at room temperature, whereby after the course of the reaction is checked by means of thin-layer chromatography, hydrogenolytic cleavage of the benzyloxycarbonyl protective group has already taken place quantitatively according to the above-mentioned reaction time. Catalyst is filtered out, and the filtrate is evaporated to the dry state in a vacuum. The remaining residue is chromatographed on silica gel (mobile solvent: n-hexane/isopropanol 25:1). 25.13 g (98.0% of theory) of the title compound is obtained in the form of a colorless oil.

Elementary analysis: Cld: C, 34.68; H, 3.67; F, 40.55; N, 7.03; S, 4.03. Fnd: C, 34.72; H, 3.70; F, 40.60; N, 7.01; S, 3.98.

c) 6-N-t-Butyloxycarbonyl-2-N-[1-S-α-D-(2-carbonyl)-ethyl-2,3,4,6-tetra-O-acetyl-mannopyranose]-L-lysine-[1-(4-perfluorooctylsulfonyl)-piperazine]-amide 15.53 g (35.60 mmol) of 3-(2,3,4,6-tetra-O-acetyl-1-thio-α-D-mannopyranosyl)-propionic acid (production according to: J. Haensler et al., Bioconjugate Chem. 4, 85, (1993); Chipowsky, S. and Lee, Y. C. (1973), Synthesis of 1-Thio-aldosides; Carbohydrate Research 31, 339–346) and 3.60 g (35.60 mmol) of triethylamine are dissolved in 300 ml of dry tetrahydrofuran. After the reaction solution is cooled to −15° C. to −20° C., a solution of 4.92 g (35.60 mmol) of isobutyl chloroformate in 75 ml of dry tetrahydrofuran is slowly added in drops at this temperature while being stirred, whereby the rate of addition by drops can be selected in such a way that an internal temperature of −10° C. is not exceeded. After a reaction time of 15 minutes at −15° C., a solution of 28.35 g (35.60 mmol) of the title compound of Example 42b) and 3.60 g (35.60 mmol) of triethylamine is then slowly added in drops to 200 ml of dry tetrahydrofuran at 20° C. After a reaction time of one hour at −15° C. and two hours at room temperature, the reaction solution is evaporated to the dry state in a vacuum. The remaining residue is taken up in 250 ml of ethyl acetate and washed twice with 100 ml each of saturated sodium bicarbonate solution and once with 200 ml of water. After the organic phase is dried on sodium sulfate, salt is suctioned out, and the ethyl acetate is drawn off in a vacuum. The remaining oily residue is purified on silica gel with use of ethyl acetate/n-hexane (1:25) as an eluant.

Yield: 34.21 g (79.1% of theory) of the above-mentioned title compound as a colorless and strongly viscous oil.

Elementary analysis: Cld: C, 39.54; H, 4.23; N, 4.61; F, 26.58; S, 5.28. Fnd: C, 39.49; H, 4.21; N, 4.59; F, 26.52; S, 5.31.

d) 6-N-t-Butyloxycarbonyl-2-N-[1-S-α-D-(2-carbonyl)-ethyl-mannopyranose]-L-lysine-[1-(4-perfluorooctylsulfonyl)-piperazine]-amide 29.93 g (24.64 mmol) of the title compound of Example 46c) is suspended in 400 ml of absolute methanol, and it is mixed at 5° C. with a catalytic amount of sodium methanolate. After a reaction time of 3 hours at room temperature, even thin-layer chromatographic checking (eluant: chloroform/methanol=9:1) of the course of the reaction indicates a quantitative reaction. For the purpose of working-up, the now clear reaction solution is neutralized by mixing with Amberlite® IR 120 (H$^+$-form)-cation-exchange resin, exchanger is suctioned out, and the thus obtained methanolic filtrate is evaporated to the dry state in a vacuum. The amorphous residue that is obtained is purified by chromatography on silica gel with use of 2-propanol/ethyl acetate/n-hexane (1:1:15) as an eluant.

Yield: 23.42 g (90.8% of theory) of a colorless and viscous oil.

Elementary analysis: Cld: C, 36.72; H, 4.14; N, 5.35; F, 30.85; S, 6.13. Fnd: C, 36.69; H, 4.11; N, 5.35; F, 30.82; S, 6.11.

e) 2-N-[1-S-α-D-(2-Carbonyl)-ethyl-mannopyranose]-L-lysine-[1-(4-perfluorooctylsulfonyl)-piperazine]-amide 20.93 g (20.0 mmol) of the title compound of Example 46d) is dissolved in a mixture that consists of 50 ml of trifluoroacetic acid and 100 ml of dichloromethane at 0° C. while being stirred vigorously, and it is stirred for 10 minutes at this temperature. Then, it is evaporated to the dry state in a vacuum, and the residue is taken up in 150 ml of water. The pH of this aqueous product solution is set at 9.5 by adding 2 molar aqueous sodium hydroxide solution drop by drop. The aqueous product solution is desalinated with an AMICON® YM-3 ultrafiltration membrane (cut-off: 3,000 Da), and in this case, possible, still present, low-molecular components are simultaneously removed. The retentate is then freeze-dried.

Yield: 17.79 g (94.2% of theory) of the free amine as a colorless lyophilizate.

$H_2O$ content (Karl-Fischer): 3.09%.

Elementary analysis (relative to anhydrous substance): Cld: C, 34.26; H, 3.73; N, 5.92; F, 34.12; S, 6.77. Fnd: C, 34.26; H, 3.79; N, 5.88; F, 34.07; S, 6.80.

f) 2-N-[1-S-α-D-(2-Carbonyl)-ethyl-mannopyranose]-6-N-[1,4,7-tris(carboxylatomethyl)-10-(3-aza4-oxo-5-methyl-5-yl-pentanoyl)-1,4,7,10-tetraazacyclododecane]-L-lysine-[1-(4-perfluorooctylsulfonyl)-piperazine]-amide, gadolinium complex 5.54 g [(8.8 mmol, 2.2 molar equivalents relative to the amine component of Example 46e) that is used] of the Gd complex, described in Patent Application DE 197 28 954 C1 under Example 31h), of the 10-(4-carboxy-1-methyl-2-oxo-3-azabutyl)-1,4,7,10-tetraazacyclododecane-1,4,7-triacetic acid and 0.37 g of anhydrous lithium chloride (8.8 mmol) are dissolved at 40° C. in 60 ml of absolute dimethyl sulfoxide while being stirred, and it is mixed at this temperature with a total of 1.01 g (8.8 mmol) of N-hydroxysuccinimide and 3.78 g (4.0 mmol) of the title compound of Example 46e), dissolved in 40 ml of absolute dimethyl sulfoxide. After cooling to room temperature, the reaction solution is mixed with 1.82 g (8.8 mmol) of N,N'-dicyclohexylcarbodiimide, and it is stirred for 12 hours at room temperature. The suspension that is obtained is then mixed with sufficient acetone until the above-mentioned title compound is completely precipitated, the precipitate is suctioned off, taken up in water, insoluble dicyclohexylurea is filtered out, and the filtrate is desalinated with an AMICON® YM-3 ultrafiltration membrane (cut-off 3,000 Da), and low-molecular components are removed. The retentate is then freeze-dried.

Yield: 5.17 g (83.0% of theory) as a colorless lyophilizate.

$H_2O$ content (Karl-Fischer): 4.43%.

Elementary analysis (relative to anhydrous substance): Cld: C, 35.45; H, 4.07; N, 8.09; F, 20.72; Gd, 10.09; S, 4.11. Fnd: C, 35.50; H, 4.01; N, 8.12; F, 20.6; Gd, 10.13; S, 4.14.

EXAMPLE 47 a) 6-N-Benzyloxycarbonyl-2-N-(1-O-β-D-carbonylmethyl-2,3,4,6-tetra-O-benzylglucopyranose)-L-lysine-[1-(4-perfluorooctylsulfonyl)-piperazine]-amide 8.02 g (13.4 mmol) of the title compound [1-carboxymethyloxy-2,3,4,6-tetra-O-benzyl-β-D-gluocopyranoside], described in Patent Application DE 197 28 954 C1 under Example 46a), and 3.24 g (28.14 mmol) of N-hydroxysuccinimide are dissolved in 100 ml of dimethylformamide and mixed in portions at 0° C. with a total of 5.80 g (28.14 mmol) of N,N'-dicyclohexylcarbodiimide It is stirred for 3 more hours at this temperature. A solution, cooled to 0° C., of 11.13 g (13.4 mmol) of the title compound of Example 21c), dissolved in 50 ml of dimethylformamide, is added drop by drop to the thus produced active ester solution, and it is stirred for 2 hours at 0° C. and for 12 hours at room temperature. For working-up, precipitated dicyclohexylurea is filtered out, and the solvent is then drawn off until a dry state is reached. The thus obtained residue is then chromatographed on silica gel (mobile solvent: dichloromethane/ethanol, 20:1; chromatography was carried out with use of a solvent gradient with continuous increase of the ethanol content).

Yield: 12.67 g (67.0% of theory) of the title compound in the form of a colorless and strongly viscous oil.

Elementary analysis: Cld: C, 52.77; H, 4.50; N, 3.97; F, 22.89; S, 2.27. Fnd: C, 52.75; H, 4.61; N, 3.98; F, 22.94; S, 2.26.

b) 2-N-(1-O-β-D-Carbonylmethyl-glucopyranose)-L-lysine-[1-(4-perfluorooctylsulsulfonyl)-piperazine]-amide 11.52 g (8.17 mmol) of the compound that is produced under 47a) is dissolved in 100 ml of ethanol, mixed with 0.5 g of Pearlman's catalyst (Pd 20%, C), and hydrogenated at room temperature under a hydrogen atmosphere (1 atm) until no more hydrogen absorption can be observed. Catalyst is suctioned out, it is thoroughly rewashed with ethanol (three times with about 40 ml in each case), and evaporated to the dry state in a vacuum. The title compound is obtained as a strongly viscous and colorless oil.

Yield: 7.36 g (98.4% of theory).

Elementary analysis: Cld: C, 34.07; H, 3.63; N, 6.11; F, 35.24; S, 3.50. Fnd: C, 34.11; H, 3.59; N, 6.08; F, 35.23; S, 3.52.

c) 2-N-(1-O-β-D-Carbonylmethyl-glucopyranose)-6-N-[1,4,7-tris(carboxylatomethyl)-10-(aza-4-oxo-5-methyl-5-yl-pentanoyl)-1,4,7,10-tetraazacyclododecane]-L-lysine-[1-(4-perfluorooctylsulfonyl)-piperazine]-amide, Gd complex 9.98 g [(15.84 mmol; 2.2 molar equivalents relative to the amine component of Example 47b) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 0.67 g (15.84 mmol) of anhydrous lithium chloride are dissolved at 40° C. in 80 ml of absolute dimethyl sulfoxide while being stirred, and it is mixed at this temperature with a total of 1.82 g (15.84 mmol) of N-hydroxysuccinimide and 7.25 g (7.19 mmol) of the title compound of Example 47b), dissolved in 30 ml of absolute dimethyl sulfoxide. After cooling to room temperature, the reaction solution is mixed with 3.27 g (15.84 mmol) of N,N'-dicyclohexylcarbodiimide, and it is stirred for 12 hours at room temperature. The suspension that is obtained is then mixed with sufficient acetone until the above-mentioned title compound is completely precipitated, the precipitate is suctioned off, taken up in water, insoluble dicyclohexylurea is filtered out, and the filtrate is desalinated with an AMICON® YM-3 ultrafiltration membrane (cut-off 3,000 Da), and low-molecular components are removed. The retentate is then freeze-dried.

Yield: 9.11 g (83.0% of theory) as a colorless lyophilizate. $H_2O$ content (according to Karl-Fischer): 4.02%.

Elementary analysis (relative to anhydrous substance): Cld: C, 35.37; H, 4.02; N, 8.25; F, 21.13; S, 2.10; Gd, 10.29. Fnd: C, 35.42; H, 4.07; N, 8.18; F, 21.09; S, 2.06; Gd, 10.34.

EXAMPLE 48 a) 2-N-Trifluoroacetyl-L-lysine-[1-(4-perfluorooctylsulfonyl)-piperazine]-amide 10.0 g (11.46 mmol) of the compound, produced under 21b), is dissolved in 100 ml of ethanol, mixed with 1.0 g of Pearlman's catalyst (Pd 20%/C) and hydrogenated until quantitative hydrogen uptake is reached. Catalyst is suctioned out, it is rewashed with ethanol and evaporated to the dry state in a vacuum. The title compound is obtained as a viscous and colorless oil.

Yield: 8.85 g (97.5% of theory).

Elementary analysis: Cld: C, 30.31; H, 2.54; N, 7.07; F, 47.95; S, 4.05. Fnd: C, 30.36; H, 2.50; N, 7.11; F, 47.99; S, 4.00.

b) 2-N-Trifluoroacetyl-6-N-[1-O-α-D-(5-carbonyl)-pentyl-2,3,4,6-tetra-O-benzyl-mannopyranose]-L-lysine-[1-(4-perfluorooctylsulfonyl)-piperazine]-amide A solution of 27.51 g (36.6 mmol) of the title compound of Example 37c) in 150 ml of dimethylformamide is added in drops to a solution, cooled to 0° C., that consists of 29.0 g (36.6 mmol) of the title compound of Example 48a) and 4.05 g (40.26 mmol) of triethylamine in 100 ml of dimethylformamide. After addition is completed, it is stirred for one more hour at 0° C. and then overnight at room temperature. It is evaporated to the dry state in a vacuum, and the residue is taken up in 300 ml of ethyl acetate. Insoluble components are filtered out, and the filtrate is washed twice with 100 ml each of 5% aqueous soda solution. The organic phase is dried on magnesium sulfate and evaporated to the dry state in a vacuum. The residue is chromatographed on silica gel (mobile solvent: n-hexane/isopropanol 25:1). 42.05 g (80.4% of theory) of the title compound is obtained in the form of a colorless oil.

Elementary analysis: Cld: C, 50.42; H, 4.51; N, 7.96; F, 26.59; S, 2.24. Fnd: C, 50.38; H, 4.50; N, 7.91; F, 26.62; S, 2.20.

c) 6-N-[1-O-α-D-(5-Carbonyl)-pentyl-2,3,4,6-tetra-O-benzyl-mannopyranose]-L-lysine-[1-(4-perfluorooctylsulfonyl)-piperazine]-amide 20.0 g (14.0 mmol) of the compound that is produced under Example 48b) is dissolved in 150 ml of ethanol. The solution of 2.8 g (70.0 mmol) of sodium hydroxide in 25 ml of distilled water is then added to it, and it is stirred for 0.5 hour at 50° C. According to the thin-layer chromatogram, the protective group cleavage is already carried out quantitatively at this time. It is evaporated to the dry state in a vacuum, and traces of water are removed by repeated co-distillation with ethanol. The residue is chromatographed on silica gel (mobile solvent: n-hexane/isopropanol 20:1). 16.66 g (89.3% of theory) of the title compound is obtained in the form of a colorless oil.

Elementary analysis: Cld: C, 52.25; H, 4.91; N, 4.20; F, 24.22; S, 2.41. Fnd: C, 52.30; H, 4.90; N, 4.18; F, 24.22; S, 2.38.

d) 6-N-[1-O-α-D-5-Carbonyl)-pentyl-mannopyranose]-L-lysine-[1-(4-perfluorooctylsulfonyl)-piperazine]-amide 15.0 g (11.25 mmol) of the compound that is produced under 48c) is dissolved in 150 ml of a 10:1 mixture that consists of ethanol and water, and it is mixed with 1.0 g of Pearlman's catalyst (Pd 20%/C). Then, it is hydrogenated until quantitative hydrogen uptake is reached at room temperature and under one atmosphere of hydrogen pressure. Catalyst is suctioned out, it is rewashed with ethanol/water (10:1) and evaporated to the dry state in a vacuum. The title compound is obtained as a viscous and colorless oil.

Yield: 10.77 g (98.4% of theory).

Elementary analysis: Cld: C, 37.04; H, 4.25; N, 5.76; F, 33.20; S, 3.30. Fnd: C, 37.06; H, 4.20; N, 5.81; F, 33.19; S, 3.30.

e) 6-N-[1-O-α-D-(5-Carbonyl)-pentyl-mannopyranose]-2-N-[1,4,7-tris(carboxylatomethyl)-10-(3-aza-4-oxo-5-methyl-5-yl-pentanoyl)-1,4,7,10-tetraazacyclododecane]-L-lysine-[1-(4-perfluorooctylsulfonyl)-piperazine]-amide, Gd complex 5.54 g [(8.8 mmol; 2.2 molar equivalents relative to the amine component of Example 48d) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 0.37 g (8.8 mmol) of anhydrous lithium chloride are dissolved at 40° C. in 60 ml of absolute dimethyl sulfoxide while being stirred and mixed at this temperature with a total of 1.01 g (8.8 mmol) of N-hydroxysuccinimide and 3.89 g (4.0 mmol) of the title compound of Example 48d), dissolved in 60 ml of absolute dimethyl sulfoxide. After cooling to room temperature, the reaction solution is mixed with 1.82 g (8.8 mmol) of N,N'-dicyclohexylcarbodiimide and stirred for 12 hours at room temperature. The suspension that is obtained is then mixed with sufficient acetone until the above-mentioned title compound is completely precipitated, the precipitate is suctioned off, taken up in water, insoluble dicyclohexylurea is filtered out, and the filtrate is desalinated with an AMICON® YM-3 ultrafiltration membrane (cut-off: 3,000 Da), and low-molecular components are removed. The retentate is then freeze-dried.

Yield: 4.81 g (75.9% of theory) as a colorless lyophilizate.

$H_2O$ content (Karl-Fischer): 8.98%.

Elementary analysis (relative to anhydrous substance): Cld: C, 37.15; H, 4.39; N, 7.96; F, 20.38; Gd, 9.92; S, 2.02. Fnd: C, 37.27; H, 4.40; N, 8.02; F, 20.31; Gd, 10.00; S, 1.98.

EXAMPLE 49 a) 1,7-Bis(benzyloxycarbonyl)4-(1-O-β-D-carbonylmethyl-2,3,4,6-tetra-O-benzyl-galactopyranose)-10-{3-oxa-pentane-1,5-dicarboxylic acid-1-oyl-5-[1-(4-perfluorooctylsulfonyl)-piperazine]-amide]-1,4,7,10-tetraazacyclododecane 35.80 g (25.0 mmol) of the title compound of Example 37e), dissolved in 250 ml of tetrahydrofuran, is added at 0° C. and under nitrogen atmosphere to a solution that consists of 27.0 g (24.4 mmol) of the sec-amine that is produced under Example 35a), in a mixture that consists of 150 ml of tetrahydrofuran and 15 ml of chloroform. Then, a total of 18.0 g (36.6 mmol) of EEDQ [2-ethoxy-1-ethoxycarbonyl-1,2-dihydroquinoline] is added in portions at 0° C., and it is allowed to stir overnight at room temperature. It is then evaporated to the dry state in a vacuum, and the remaining oil is chromatographed on silica gel (mobile solvent: n-hexane/isopropanol 20:1). 32.11 g (78.0% of theory, relative to the sec-amine that is used) of the title compound is obtained in the form of a colorless oil.

Elementary analysis: Cld: C, 54.09; H, 4.72; F, 19.14; N, 4.98; S, 1.90. Fnd: C, 54.12; H, 4.77; F, 19.17; N, 5.03; S, 1.90.

b) 1-(1-O-β-D-Carbonylmethyl-galactopyranose)-7-{3-oxa-pentane-1,5-dicarboxylic acid-1-oyl-5-[1-(4-perfluorooctylsulfonyl)-piperazine]-amide}-1,4,7,10-tetraazacyclododecane In 250 ml of ethanol, 30.0 g (17.77 mmol) of the title compound that is produced under Example 49a) is dissolved, and it is mixed with 3.0 g of Pearlman's catalyst (Pd 20%,/C). It is hydrogenated until quantitative hydrogen uptake is reached, catalyst is then suctioned out, it is thoroughly rewashed with ethanol and evaporated to the dry state in a vacuum. The product is yellowish in color, and extremely viscous oil is obtained.

Yield: 17.89 g (95.1% of theory).

Elementary analysis: Cld: C, 36.30; H, 4.09; F, 30.50; N, 7.94; S, 3.03. Fnd: C, 36.26; H, 4.12; F, 30.46; N, 7.90; S, 3.04.

c) 1-(1-O-β-D-Carbonylmethyl-galactopyranose)-7-{3-oxa-pentane-1,5-dicarboxylic acid-1-oyl-5-[1-(4-perfluorooctylsulfonyl)-piperazine]-amide}-4,10-bis[1,4,7-tris(carboxylatomethyl)-10-(3-aza-4-oxo-5-methyl-5-yl-pentanoyl)-1,4,7,10-tetraazacyclododecane]-1,4,7,10-tetraazacyclododecane, di-gadolinium complex 5.54 g [8.8 mmol; 4.4 molar equivalents relative to the amine component of Example 49b) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 0.37 g (8.8 mmol) of anhydrous lithium chloride are dissolved at 40° C. in 60 ml of absolute dimethyl sulfoxide while being stirred and mixed at this temperature with a total of 1.01 g (8.8 mmol) of N-hydroxysuccinimide and 2.11 g (2.0 mmol) of the title compound of Example 49b), dissolved in 25 ml of absolute dimethyl sulfoxide. After cooling to room temperature, the reaction solution is mixed with 1.82 g (8.8 mmol) of N,N'-dicyclohexylcarbodiimide and stirred for 12 hours at room temperature. The suspension that is obtained is then mixed with sufficient acetone until the above-mentioned title compound is completely precipitated, the precipitate is suctioned off, dried, taken up in water, insoluble dicyclohexylurea is filtered out, and the filtrate is desalinated with an AMICON® YM-3 ultrafiltration membrane (cut-off 3,000 Da), and low-molecular components are removed. The retentate is then freeze-dried.

Yield: 3.29 g (72.2% of theory; relative to the amine component that is used) as a colorless lyophilizate.

$H_2O$ content (Karl-Fischer): 5.99%.

Elementary analysis (relative to anhydrous substance): Cld: C, 36.84; H, 4.37; N, 9.82; F, 14.15; Gd, 19.63; S, 1.40. Fnd: C, 36.87; H, 4.40; N, 9.82; F, 14.09; Gd, 19.59; S, 1.38.

EXAMPLE 50 a) 3-(1-O-α-D-2,3,4,6-Tetra-O-benzyl-mannopyranose)-2-N-benzyloxycarbonyl-L-serine-methyl ester 21.42 g (39.61 mmol) of 2,3,4,6-tetra-O-benzyl-α-D-mannopyranose (production according to: F. Kong et al., J. Carbohydr. Chem.; 16; 6; 1997; 877–890) is dissolved in 500 ml of dry acetonitrile. After the reaction solution is cooled to 5° C., a solution of 13.23 g (59.52 mmol) of trifluoromethanesulfonic acid trimethyl silyl ester in 30 ml of acetonitrile, followed by a solution that consists of 20.06 g (79.21 mmol) of N-benzyloxycarbonyl-L-serine methyl ester (commercially available from the Bachem Company) in 50 ml of acetonitrile, are slowly added in drops at this temperature while being stirred, whereby the rate of addition by drops can be selected in such a way that an internal temperature of 10° C. is not exceeded. After a reaction time of 15 hours at room temperature, the reaction solution is evaporated to the dry state in a vacuum. The remaining residue is taken up in 250 ml of ethyl acetate and washed twice with 100 ml each of saturated sodium bicarbonate solution and once with 200 ml of water. After the organic phase is dried on sodium sulfate, salt is suctioned out, and the ethyl acetate is drawn off in a vacuum. The remaining oily residue is purified on silica gel with use of ethyl acetate/n-hexane (1:5) as an eluant.

Yield: 23.60 g (76.8% of theory) of the above-mentioned title compound as a colorless oil.

Elementary analysis: Cld: C, 71.21; H, 6.37; N, 1.81. Fnd: C, 71.19; H, 6.41; N, 1.79.

b) 3-(1-O-α-D-2,3,4,6-Tetra-O-benzyl-mannopyranose)-2-N-benzyloxycarbonyl-L-serine 10.0 g (12.90 mmol) of the compound that is produced under Example 50a) is dissolved in a mixture that consists of 20 ml of methanol, 20 ml of water and 50 ml of tetrahydrofuran. 0.47 g (19.35 mmol) of lithium hydroxide, dissolved in 25 ml of distilled water, is then added at room temperature, and it is then stirred for 6 hours at 60° C. After the course of the reaction is checked by means of thin-layer chromatography (eluant: methylene chloride/methanol 10:1), saponification of the methyl ester of Example 30a) has already taken place quantitatively according to the above-mentioned reaction time. For the purpose of working-up, the product solution is evaporated to the dry state in a vacuum, and the remaining residue is taken up in 250 ml of ethyl acetate in heat (about 60° C.). Then, the thus obtained ethyl acetate phase is washed twice with 50 ml each of a 15% aqueous hydrochloric acid, and once with 100 ml of distilled water. The organic phase is dried on magnesium sulfate, filtered and evaporated to the dry state in a vacuum. The residue is chromatographed on silica gel (mobile solvent: n-hexane/ethyl acetate 5:1). 8.40 g (85.7% of theory) of the title compound is obtained in the form of a colorless oil.

Elementary analysis: Cld: C, 70.94; H, 6.22; N, 1.84. Fnd: C, 70.97; H, 6.30; N, 1.78.

c) 3-(1-O-α-D-2,3,4,6-Tetra-O-benzyl-mannopyranose-2-N-benzyloxycarbonyl-L-serine-[1-(4-perfluorooctylsulfonyl)piperazine]-amide 20.57 g (27.0 mmol) of the carboxylic acid, produced according to Example 50b) and dissolved in 50 ml of tetrahydrofuran, is added drop by drop at 0° C. and under nitrogen atmosphere to 13.86 g (24.40 mmol) of 1-perfluorooctylsulfonyl-piperazine (produced according to DE 19603033), dissolved in a mixture that consists of 150 ml of tetrahydrofuran and 15 ml of chloroform. Then, a total of 18.0 g (36.60 mmol) of EEDQ [2-ethoxy-1-ethoxycarbonyl-1,2-dihydroquinoline] is added in portions at 0° C., and it is allowed to stir overnight at room temperature. For the purpose of working-up, the reaction solution is concentrated by evaporation in a vacuum, and the remaining, extremely viscous oil is chromatographed on silica gel with use of an n-hexane/isopropanol (15:1) mixture as an eluant system. 17.0 g (79.6% of theory, relative to the primary amine that is used) of the title compound is obtained in the form of a colorless and viscous oil.

Elementary analysis: Cld: C, 51.53; H, 4.23; N, 3.15; F, 25.65; S, 2.41. Fnd: C, 51.48; H, 4.27; N, 3.10; F, 25.71; S, 2.35.

d) 3-(1-O-α-D-Mannopyranose)-L-serine-[1-(4-perfluorooctylsulfonyl)piperazine]-amide 15.0 g (11.41 mmol) of the compound that is produced according to Example 50c) is dissolved in 200 ml of ethanol, and it is mixed with 1.5 g of Pearlman's catalyst (Pd 20%, C). Then, the reaction solution is hydrogenated at room temperature under a hydrogen atmosphere (1 atm) until no more hydrogen absorption can be observed (about 8 hours). For the purpose of working-up, catalyst is suctioned out, it is thoroughly rewashed with ethanol (twice with about 100 ml each), and the product-containing ethanolic filtrate is evaporated to the dry state in a vacuum. The title compound is obtained as a strongly viscous and colorless oil.

Yield: 8.79 g (94.0% of theory).

Elementary analysis: Cld: C, 30.78; H, 3.20; N, 5.13; F, 39.41; S, 3.91. Fnd: C, 30.87; H, 3.14; N, 5.19; F, 39.50; S, 3.88.

e) 3-(1-O-α-D-Mannopyranose)-2-N-[1,4,7-tris (carboxylatomethyl)-10-(3-aza-4-oxo-5-methyl-5-yl-pentanoyl)-1,4,7,10-tetraazacyclododecane]-L-serine-[1-(4-perfluorooctylsulfonyl)-piperazine]-amide, Gd complex A stirred suspension of 5.7 g [9.06 mmol; corresponding to 1.5 molar equivalents relative to the title compound (primary amine) of Example 50d) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid in 75 ml of absolute dimethyl sulfoxide is mixed at 70° C. with 0.68 g (15.9 mmol) of lithium chloride. After 30 minutes of stirring at 70° C., the now clear reaction solution is mixed in portions with a total of 1.83 g (15.9 mmol) of N-hydroxysuccinimide, and the reaction mixture is kept for 1 more hour at 70° C. After the reaction solution is cooled to 10° C., it is mixed with 4.52 g (23.85 mmol) of dicyclohexylcarbodiimide, and the reaction solution is stirred for another hour at 0° C., followed by 12 hours at 22° C. The thus obtained solution of N-hydroxysuccinimide ester of the Gd complex of 10-(4-carboxy-1-methyl-2-oxo-3-azabutyl)-1,4,7,10-tetraazacyclododecane-1,4,7-triacetic acid is now mixed at 22° C. drop by drop with a solution of 4.94 g (6.03 mmol) of the title compound of Example 30d), in 15 ml of absolute dimethyl sulfoxide, and it is stirred for another 12 hours at room temperature. For working-up, the reaction solution is slowly added in drops at 22° C. in a solvent mixture that consists of 250 ml of acetone and 250 ml of 2-propanol, whereby the title compound has settled completely as a light yellowish-colored oil after 12 hours at 10° C. Supernatant eluant mixture is carefully decanted out, and the oily product is taken up in 200 ml of distilled water, whereby the latter goes completely into solution in such a way that a light yellowish-colored aqueous solution of the above-mentioned title compound is obtained. Subsequently, the aqueous product solution is first filtered with a membrane filter and then, for the purpose of desalination and separation of low-molecular components, it is ultrafiltered three times with a YM3-ultrafiltration membrane (AMICON®: cut-off: 3,000 Da). The thus obtained retentate is then freeze-dried.

Yield: 8.63 g (80.2% of theory, relative to the title compound of Example 30d) that is used) as a colorless lyophilizate with a water content of 7.65%.

Elementary analysis (relative to anhydrous substance): Cld: C, 33.57; H, 3.80; N, 7.83; F, 22.57; Gd, 10.99; S, 2.24. Fnd: C, 33.57; H, 3.76; N, 7.82; F, 22.63; Gd, 11.06; S, 2.18.

EXAMPLE 51 a) 6-N-Benzyloxycarbonyl-2-N-[O-β-D-galactopyranosyl (1→4)-gluconosyl]-L-lysine-[1-(4-perfluorooctylsulfonyl)-piperazine]-amide A solution of 13.3 g (37.2 mmol) of O-β-D-galactopyranosyl-(1→4)-D-glucono-1,5-lactone [lactobionolactone; production according to: (a) Williams, T. J.; Plessas, N. R.; Goldstein, I. J. Carbohydr. Res. 1978, 67, Cl. (b) Kobayashi, K.; Sumitomo, H.; Ina, Y. Polym. J. 1985, 17, 567, (c) Hiromi Kitano, Katsuko Sohda, and Ayako Kosaka, Bioconjugate Chem. 1995, 6 131–134] in 40 ml of absolute dimethyl sulfoxide is added drop by drop at room temperature to a stirred solution of 4.98 g (6.0 mmol) of the title compound of Example 21c) in 40 ml of absolute dimethyl sulfoxide. The thus obtained reaction solution is then stirred for 14 hours at 40° C. For working-up, it is mixed at room temperature with 500 ml of absolute 2-propanol, and the resulting colorless precipitate is suctioned off by means of a G4 frit and thoroughly rewashed with a total of 250 ml of absolute 2-propanol. The thus obtained solid is now dissolved in 300 ml of distilled water and ultrafiltered a total of three times with a YM3-ultrafiltration membrane (AMICON®: cut-off: 3,000 Da). By the third time of the ultrafiltration process, both the excess lactobionolactone and also possibly still present low-molecular components are separated from the desired product. The residue that remains in the ultrafiltration membrane is subsequently dissolved completely in 300 ml of distilled water and freeze-dried.

Yield: 6.51 g (92.7% of theory) as a colorless lyophilizate. Water content: 10.03%.

Elementary analysis (relative to anhydrous substance): Cld: C, 38.98; H, 4.05; N, 4.79; F, 27.58; S, 2.74. Fnd: C, 39.04; H, 4.09; N, 4.82; F, 27.61; S, 2.71.

b) 2-N-[O-β-D-Galactopyranosyl (1→4)-gluoconosyl]-L-lysine-[1-(4-perfluorooctylsulfonyl)-piperazine]-amide 5.0 g (4.27 mmol) of the compound that is produced under 51a) is dissolved in 100 ml of ethanol, mixed with 0.5 g of Pearlman's catalyst (Pd 20%, C) and hydrogenated until quantitative hydrogen uptake is reached at 1 atmosphere of hydrogen pressure. Catalyst is suctioned out, rewashed with ethanol and evaporated to the dry state in a vacuum. The title compound is obtained as a colorless and viscous oil.

Yield: 4.36 g (98.5% of theory).

Elementary analysis: Cld: C, 34.76; H, 3.99; N, 5.40; F, 31.51; S, 3.09. Fnd: C, 34.78; H, 4.04; N, 5.34; F, 31.51; S, 3.15.

c) 2-N-[O-β-D-Galactopyranosyl(1→4)-gluoconosyl]-6-N-[1,4,7-tris(carboxylatomethyl)-10-(3-aza-4-oxo-5-methyl-5-yl-pentanoyl)-1,4,7,10-tetraazacyclododecane]-L-lysine-[1-(4-perfluorooctylsulfonyl)-piperazine]-amide, Gd complex 5.54 g [(8.8 mmol; 2.2 molar equivalents relative to the amine component of Example 51b) that is used] of the Gd complex, described in Patent Application DE 197 28 954 C1 under Example 31h), of 10-(4-carboxy-1-methyl-2-oxo-3-azabutyl)-1,4,7,10-tetraazacyclododecane-1,4,7-triacetic acid and 0.37 g (8.8 mmol) of anhydrous lithium chloride are dissolved at 40° C. in 60 ml of absolute dimethyl sulfoxide while being stirred and mixed at this temperature with a total of 1.01 g (8.8 mmol) of N-hydroxysuccinimide and 3.85 g (4.0 mmol) of the title compound of Example 31 Ab), dissolved in 60 ml of absolute dimethyl sulfoxide. After cooling to room temperature, the reaction solution is mixed with 1.82 g (8.8 mmol) of N,N'-dicyclohexylcarbodiimide and stirred for 12 hours at room temperature. The suspension that is obtained is then mixed with sufficient acetone/2-propanol (1:1) until the above-mentioned title compound is completely precipitated, and the precipitate is suctioned off. The thus obtained precipitate is subsequently taken up in 300 ml of water, and insoluble dicyclohexylurea is filtered out. The filtrate is ultrafiltered three times with an AMICON® YM-3 ultrafiltration membrane (cut-off: 3,000 Da). By the third time that the ultrafiltration process is performed, both the excess Gd complex and possibly still present, low-molecular components are separated from the desired product. The residue that remains in the ultrafiltration membrane is subsequently completely dissolved in 500 ml of distilled water and freeze-dried.

Yield: 4.64 g (70.4% of theory) as a colorless lyophilizate.
H₂O content (Karl-Fischer): 10.08%.

Elementary analysis (relative to anhydrous substance): Cld: C, 35.70; H, 4.22; N, 7.65; F, 19.59; Gd, 9.54; S, 1.95. Fnd: C, 35.77; H, 4.17; N, 7.71; F, 19.61; Gd, 9.60; S, 1.99.

EXAMPLE 52 a) 2-N-Trifluoroacetyl-6-N-benzyloxycarbonyl-lysine 100 g (356.7 mmol) of 6-N-benzyloxycarbonyl-lysine is dissolved in a mixture that consists of 1000 ml of trifluoroacetic acid ethyl ester/500 ml of ethanol, and it is stirred for 24 hours at room temperature. It is evaporated to the dry state, and the residue is crystallized from diisopropyl ether.

Yield: 128.9 g (96% of theory) of a colorless, crystalline powder.

Elementary analysis: Cld: C, 51.07; H, 5.09; F, 15.14; N, 7.44. Fnd: C, 51.25; H, 5.18; F, 15.03; N, 7.58.

b) 2-N-Trifluoroacetyl-6-N-benzyloxycarbonyl-lysine-[1-(4-perfluorooctylsulfonyl)-piperazine]-amide 164.2 g (0.664 mmol) of EEDQ (2-ethoxy-1,2-dihydroquinoline-1-carboxylic acid ethyl ester) is added at 0° C. to 125 g (332 mmol) of the title compound of Example 52a) and 188.7 g (332 mmol) of 1-perfluorooctylsulfonyl-piperazine (produced according to DE 19603033) in 800 ml of tetrahydrofuran, and it is stirred overnight at room temperature. It is evaporated to the dry state in a vacuum and chromatographed on silica gel (mobile solvent: dichloromethane/methanol=20:1).

Yield: 286 g (93% of theory) of a colorless solid.

Elementary analysis: Cld: C, 36.30; H, 2.83; F, 41.01; N, 6.05; S, 3.46. Fnd: C, 36.18; H, 2.94; F, 40.87; N, 5.98; S, 3.40.

c) 6-N-Benzyloxycarbonyl-lysine-[1-(4-perfluorooctylsulfonyl)-piperazine]-amide

Ammonia gas is introduced at 0° C. for one hour into a solution that consists of 280 g (302.2 mmol) of the title compound of Example 52b) in 2000 ml of ethanol. It is then stirred for 4 hours at 0° C. It is evaporated to the dry state, and the residue is absorptively precipitated from water. The solid is filtered off and dried in a vacuum (50° C.).

Yield: 243.5 g (97% of theory) of an amorphous solid.

Elementary analysis: Cld: C, 37.60; H, 3.28; F, 38.89; N, 6.75; S, 3.86. Fnd: C, 37.15; H, 3.33; F, 38.78; N, 6.68; S, 3.81.

d) 6-N-Benzyloxycarbonyl-2-N-(3,6,9,12,15-pentaoxahexadecanoyl)-lysine [1-(4-perfluorooctylsulfonyl)-piperazine]-amide A solution that consists of 19.93 g (70 mmol) of 3,6,9,12,15 pentaoxahexadecanoic acid chloride [produced according to Liebigs Ann. Chem. (1980), (6), 852–62] in 50 ml of dichloromethane is added in drops at 0° C. to 50 g (60.20 mmol) of the title compound of Example 52c) and 7.10 g (70 mmol) of triethylamine, dissolved in 350 ml of dichloromethane, and it is stirred for 3 hours at 0° C. 200 ml of 5% aqueous hydrochloric acid is added, and it is stirred for 5 minutes at room temperature. The organic phase is separated, dried on magnesium sulfate and evaporated to the dry state in a vacuum. The residue is chromatographed on silica gel (mobile solvent: dichloromethane/acetone=15:1).

Yield: 53.7 g (93% of theory) of a colorless, viscous oil.

Elementary analysis: Cld: C, 33.83; H, 4.94; F, 3.34; N, 5.84; S, 33.69. Fnd: C, 33.75; H, 5.05; F, 3.29; N, 5.78; S, 33.75.

e) 2-N-(3,6,9,12,15-Pentaoxahexadecanoyl)-lysine[1-(4-perfluorooctylsulfonyl)-piperazine]-amide 50 g (52.15 mmol) of the title compound of Example 52d) is dissolved in 500 ml of ethanol, and 6 g of palladium catalyst (10% Pd/C) is added. It is hydrogenated at room temperature. Catalyst is filtered out, and the filtrate is evaporated to the dry state in a vacuum.

Yield: 43.0 g (quantitative) of a colorless solid.

Elementary analysis: Cld: C, 27.68; H, 5.01; F, 39.17; N, 6.79; S, 3.89. Fnd: C, 27.60; H, 5.13; F, 39.09; N, 6.68; S, 3.81.

f) 6-N-[1,4,7-Tris(carboxylatomethyl)-1,4,7,10-tetraazacyclododecane-10-(pentanoyl-3-aza 4-oxo-5-methyl-5-yl)]-2-N-(3,6,9,12,15-pentaoxahexadecanoyl)-lysine [1-(4-perfluorooctylsulfonyl)-piperazine]-amide, Gd complex 20 g (24.25 mmol) of the title compound of Example 52e), 2.79 g (24.25 mmol) of N-hydroxysuccinimide, 2.12 g (50 mmol) of lithium chloride and 15.27 g (24.25 mmol) of 1,4,7-tris(carboxylatomethyl)-10-[(3-aza-4-oxo-5-methyl-5-yl)]-pentanoic acid]-1,4,7,10-tetraazacyclododecane, Gd complex are dissolved in 200 ml of dimethyl sulfoxide while being heated slightly. At 10° C., 8.25 g (40 mmol) of N,N-dicyclohexylcarbodiimide is added, and it is then stirred overnight at room temperature. The solution is poured into 3000 ml of acetone, and it is stirred for 10 minutes. The precipitated solid is filtered off and then purified by chromatography (silica gel RP-18, mobile solvent: gradient that consists of water/ethanol/acetonitrile).

Yield: 28.21 g (81% of theory) of a colorless solid.

Water content: 11.0%.

Elementary analysis (relative to anhydrous substance): Cld: C, 31.78; H, 4.84; F, 22.49; N, 8.78; S, 2.23; Gd, 10.95. Fnd: C, 31.74; H, 4.98; F, 22.39; N, 8.69; S, 2.15; Gd, 10.87.

EXAMPLE 53 a) 6-N-[3,9-Bis(t-butyloxycarbonylmethyl)-3,6,9-triazaundecane-1,11-dicarboxylic acid bis (t butylester)-6-carbonylmethyl]-2-N-[3,6,9,12,15-pentaoxahexadecanoyl)-lysine-[1-(4-perfluorooctylsulfonyl)-piperazine]-amide 8.25 g (40 mmol) of N,N-dicyclohexylcarbodiimide is added at 0° C. to a solution that consists of 20 g (24.08 mmol) of the title compound of Example 52e), 14.88 g (24.08 mmol) of 3,9-bis(t butyloxycarbonylmethyl-3,6,9-triazaundecane-1,11-dicarboxylic acid-bis(t butylester) and 2.77 g (24.08 mmol) of N-hydroxysuccinimide, dissolved in 150 ml of dimethylformamide. It is stirred for 3 hours at 0° C., then overnight at room temperature. Precipitated urea is filtered out, the filtrate is evaporated to the dry state in a vacuum and chromatographed on silica gel (mobile solvent:=dichloromethane/ethanol=20:1).

Yield: 31.61 g (91% of theory) of a viscous oil.

Elementary analysis: Cld: C, 40.80; H, 6.71; F, 22.39; N, 6.80; S, 2.22. Fnd: C, 40.72; H, 6.82; F, 22.30; N, 6.75; S, 2.14.

b) 6-N-[6-Carbonylmethyl-3,9-bis(carboxylatomethyl)-3,6,9-triazaundecanedicarboxylic acid-1-carboxy-11-carboxylato-]-2-N-(3,6,9,12,15-pentaoxahexadecanoyl)-lysine-[1-(4-perfluorooctylsulfonyl)-piperazine]-amide, Gd complex, sodium salt 30 g (20.8 mmol) of the title compound of Example 53a) is dissolved in 300 ml of trifluoroacetic acid, and it is stirred for 5 hours at room temperature. It is evaporated to the dry state, the residue is taken up in 300 ml of water, and it is set at a pH of 2.5 with 10% aqueous NaOH. Then, 3.77 g (10.4 mmol) of gadolinium oxide is added, and it is stirred for 3 hours at 60° C. It is allowed to reach room temperature, and it is set at a pH of 7.4 with sodium hydroxide solution. It is evaporated to the dry state, and the residue is purified on silica gel RP-18 (mobile solvent: gradient that consists of water/acetonitrile).

Yield: 19.18 g (67% of theory) of a colorless, amorphous solid.

Water content: 9.8%.

Elementary analysis (relative to anhydrous substance): Cld: C, 28.80; H, 4.25; F, 23.47; N, 7.12; S, 2.33; Gd, 11.48; Na, 1.67. Fnd: C, 28.67; H, 4.34; F, 23.38; N, 7.03; S, 2.27; Gd, 11.37; Na, 1.74.

EXAMPLE 54 a) Lysine-[1-(4-perfluorooctylsulfonyl-piperazine]-amide 20 g (24.08 mmol) of the tide compound of Example 52c) is dissolved in 300 ml of ethanol, and 4 g of palladium catalyst (10% Pd/C) is added. It is hydrogenated at room temperature. Catalyst is filtered out, and the filtrate is evaporated to the dry state in a vacuum.

Yield: 16.77 g (quantitative) of a colorless solid.

Elementary analysis: Cld: C, 31.04; H, 3.04; F, 46.38; N, 8.04; S, 4.60. Fnd: C, 30.97; H, 3.15; F, 46.31; N, 7.98; S, 4.51.

b) 2,6-N,N'-Bis[1,4,7-tris(carboxylatomethyl)-1,4,7,10-tetraazacyclododecane-10-(pentanoyl-3-aza-4-oxo-5-methyl-5-yl)]-lysine-[1-(4-perfluorooctylsulfonyl-piperazine]-amide, Gd complex (metal complex XVI)

10 g (14.36 mmol) of the title compound of Example 54a), 3.34 g (29 mmol) of N-hydroxysuccinimide, 2.54 g (mmol) of lithium chloride and 18.26 g (29 mmol) of 1,4,7-tris(carboxylatomethyl)-10(3-aza-4-oxo-5-methyl-5yl) 1,4,7,10-tetraazacyclododecane-Gd complex are dissolved in 200 ml of dimethyl sulfoxide while being heated slightly. At 10° C, 12.38 g (60 mmol) of N,N-dicyclohexylcarbodiimide is added, and it is then stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 19.02 g (69% of theory) of a colorless solid.

Water content: 11.3%.

Elementary analysis (relative to anhydrous substance): Cld: C, 35.03; H, 4.04; F, 16.82; N, 10.21; S, 1.67; Gd, 16.38. Fnd: C, 34.96; H, 4.13; F, 16.74; N, 10.16; S, 1.61; Gd, 16.33.

EXAMPLE 55 a) 2-[4-(3-Oxapropionic acid ethyl ester)]-phenylacetic acid methyl ester 233.8 g (1.4 mol) of 2-bromoacetic acid-ethyl ester is added to 200 g (1.204 mol) of 4-hydroxyphenylacetic acid methyl ester, 212 g (2 mol) of sodium carbonate in 2000 ml of acetone, and it is refluxed for 5 hours. The solid is filtered off, and it is evaporated to the dry state in a vacuum. The residue is chromatographed on silica gel (mobile solvent: -n-hexane/ethyl acetate=15:1).

Yield: 288.5 g (95% of theory) of a colorless oil.

Elementary analysis: Cld: C, 61.90; H, 6.39. Fnd: C, 61.75; H, 6.51.

b) 2-[4-(3-Oxapropionic acid ethyl ester)]-phenyl-2-bromoacetic acid methyl ester 201 g (1.13 mol) of N-bromosuccinimide and 100 mg of dibenzylperoxide are added to 285 g (1.13 mol) of the title compound of Example 55a), dissolved, in 2000 ml of carbon tetrachloride, and it is refluxed for 8 hours. It is cooled in an ice bath, the precipitated succinimide is filtered off, and the filtrate is evaporated to the dry state in a vacuum. The residue is purified on silica gel (mobile solvent: n-hexane/acetone=15:1).

Yield: 359.2 g (96% of theory) of a colorless, viscous oil.

Elementary analysis: Cld: C, 47.28; H, 4.57; Br, 24.16. Fnd: C, 47.19; H, 4.71; Br, 24.05.

c) 2-[4-(3-Oxapropionic acid ethyl ester)]-phenyl-2-[1-(1,4,7,10-tetraazacyclododecan-7-yl]-acetic acid methyl ester 350 g (1.057 mol) of the title compound of Example 55b) is added to 603 g (3.5 mol) of 1,4,7,10-tetraazacyclododecane in 6000 ml of chloroform, and it is stirred overnight at room temperature. It is extracted 3 times with 3000 ml of water, the organic phase is dried on magnesium sulfate and evaporated to the dry state in a vacuum. The residue is used without further purification in the next reaction (3d).

Yield: 448 g (quantitative) of a viscous oil.

Elementary analysis: Cld: C, 59.70; H, 8.11; N, 13.26. Fnd: C, 59.58; H, 8.20; N, 13.18.

d) 2-[4-(3-Oxapropionic acid)]-phenyl-2-[1,4,7-tris(carboxymethyl)-1,4,7,10-tetraazacyclododecan-10-yl]-acetic acid 445 g (1.053 mol) of the title compound of Example 55c) and 496 g (5.27 mol) of chloroacetic acid are dissolved in 4000 ml of water. It is set with 30% aqueous sodium hydroxide solution to a pH of 10. It is heated to 70° C., and the pH is kept at 10 by adding 30% aqueous sodium hydroxide solution. It is stirred for 8 hours at 70° C. It is then set at a pH of 13 and refluxed for 30 minutes. The solution is cooled in an ice bath and set at a pH of 1 by adding concentrated hydrochloric acid. It is evaporated to the dry state in a vacuum. The residue is taken up in 4000 ml of methanol and absorptively precipitated for one hour at room temperature. Precipitated common salt is filtered out, the filtrate is evaporated to the dry state, and the residue is purified on silica gel. RP-18 (mobile solvent: gradient that consists of water/ethanol/acetonitrile).

Yield: 403 g (69% of theory) of a colorless solid.

Water content: 10.2%.

Elementary analysis (relative to anhydrous substance): Cld: C, 51.98; H, 6.18; N, 10.10. Fnd: C, 51.80; H, 6.31; N, 10.01.

e) 2-[4-(3-Oxapropionic acid)]-phenyl-2-[1,4,7-tris(carboxymethyl)-1,4,7,10-tetraazacyclododecan-10-yl]-acetic acid, Gd complex 130.73 g (360.65 mmol) of gadolinium oxide is added to 400 g (721.3 mmol) of the title compound of Example 55d) in 2000 ml of water, and it is stirred for 5 hours at 80° C. The solution is filtered, and the filtrate is freeze-dried.

Yield: 511 g (quantitative) of an amorphous solid.

Water content: 11.0%.

Elementary analysis (relative to anhydrous substance): Cld: C, 40.67; H, 4.41; Gd, 22.19; N, 7.98. Fnd: C, 40.51; H, 4.52; Gd, 22.05; N, 8.03.

f) 2,6-N,N'-Bis{2-[4-(3-oxapropionyl)-phenyl]-2-[1,4,7-tris(carboxylatomethyl)-1,4,7,10-tetraazacyclododecan-10-yl]-acetic acid]-lysine-[4-perfluorooctylsulfonyl)-piperazine]-amide, digadolinium complex, disodium salt 10 g (14.36 mmol) of the title compound of Example 54a), 3.45 g (30 mmol) of N-hydroxysuccinimide, 2.54 g (60 mmol) of lithium chloride and 21.26 g (30 mmol) of the title compound of Example 4Be are dissolved in 250 ml of dimethyl sulfoxide while being heated slightly. At 10° C., 16.51 g (80 mmol) of N,N-dicyclohexylcarbodiimide is added, and it is then stirred overnight at room temperature. The solution is poured into 2000 ml of acetone and stirred for 10 minutes. The precipitated solid is filtered off and then purified by chromatography (silica gel RP-18, mobile solvent: gradient that consists of water/ethanol/-acetonitrile). It is dissolved in a little water, set at a pH of 7.4 with sodium hydroxide solution and freeze-dried.

Yield: 21.02 g (69% of theory) of a colorless solid.

Water content: 11.2%.

Elementary analysis (relative to anhydrous substance): Cld: C, 37.36; H, 3.66; F, 15.22; Gd, 14.82; N, 7.92; Na, 2.71; S, 1.51. Fnd: C, 37.28; H, 3.74; F, 15.14; Gd, 14.75; N, 8.03; Na, 2.23; S, 1.46.

EXAMPLE 56 a) 2,6-N,N'-Bis[6-carbonylmethyl-3,9-bis(t butyloxycarbonylmethyl)3,6,9-triazaundecane-1,11-dicarboxylic acid-bis(t butylester)]-lysine-[1-(4-perfluorooctylsulfonyl)-piperazine]-amide 10.32 g (50 mmol) of N,N-dicyclohexylcarbodiimide is added at 0° C. to a solution that consists of 10 g (14.36 mmol) of the title compound of Example 54a), 18.53 g (30 mmol) of 3,9-bis(t butyloxycarbonylmethyl)-6-carboxymethyl-3,6,9-triazaundecane-1,11-dicarboxylic acid-bis(t butylester), and 3.45 g (30 mol) of N-hydroxysuccinimide, dissolved in 150 ml of dimethylformamide. It is stirred for 3 hours at 0° C., then overnight at room temperature. Precipitated urea is filtered out, the filtrate is evaporated to the dry state in a vacuum and chromatographed on silica gel (mobile solvent: dichloromethane/ethanol=20:1).

Yield: 19.60 g (72% of theory) of a viscous oil.

Elementary analysis: Cld: C, 49.41; H, 6.75; F, 17.03; N, 7.39; S, 1.69. Fnd: C, 49.35; H, 6.82; F, 16.92; N, 7.32; S, 1.62.

b) 2,6-N,N-Bis[6-carbonylmethyl-3,9-bis(carboxylatomethyl)-3,9,9-triazaundecanedicarboxylic acid-1-carboxy-11-carboxylato-lysine-[1-(4-perfluorooctylsulfonyl)-piperazine]-amide, Gd complex, sodium salt]

15 g (7.91 mol) of the title compound of Example 56a) is dissolved in 50 ml of chloroform, and 200 ml of trifluoroacetic acid is added. It is stirred for 10 minutes at room temperature. It is evaporated to the dry state in a vacuum, and the residue is dissolved in 150 ml of water. 2.87 g (7.91 mmol) of gadolinium oxide is added, and it is stirred for 5 hours at 80° C. It is allowed to cool to room temperature and set at pH 7.4 with 2N, sodium hydroxide solution. The solution is evaporated to the dry state in a vacuum and purified on RP-18 (mobile solvent: gradient that consists of water/ethanol/acetonitrile).

Yield: 8.11 g (57% of theory) of a colorless, amorphous solid.

Water content: 9.6%.

Elementary analysis (relative to anhydrous substance): Cld: C, 30.70; H, 3.08; Gd, 17.48; N, 7.78; Na, 2.56; S, 1.78. Fnd: C, 30.58; H, 3.19; Gd, 17.42; N, 7.71; Na, 2.68; S, 1.72.

EXAMPLE 57 a) 6-N-Benzyloxycarbonyl-2-N-[6-carboxymethyl-3,9-bis(t-butyloxycarbonylmethyl)-3,6,9-triazaundecane-1,11-dicarboxylic acid-bis(t butylester)]-lysine-[1(4-perfluorooctylsulfonyl)-piperazine]-amide 8.25 g (40 mol) of N,N-dicyclohexylcarbodiimide is added at 0° C. to a solution that consists of 20 g (24.08 mmol) of the title compound of Example 52c), 14.88 g (24.08 mmol) of 3,9-bis(t butyloxycarbonylmethyl)-6-carboxymethyl-3,6,9-triazaun-decane-1,11-dicarboxylic acid-bis(t butylester) and 2.88 g (25 mol) of N-hydroxysuccinimide, dissolved in 100 ml of dimethylformamide. It is stirred for 3 hours at 0° C., then overnight at room temperature. Precipitated urea is filtered out, the filtrate is evaporated to the dry state in a vacuum and chromatographed on silica gel (mobile solvent: dichloromethane/ethanol=20:1).

Yield: 27.21 g (79% of theory) of a viscous oil.

Elementary analysis: Cld: C, 47.03; H, 5.64; F, 22.58; N, 6.85; S, 2.24. Fnd: C, 46.94; H, 5.58; F, 22.65; N, 6.84; S, 2.31.

b) 2-N-[Carbonylmethyl-3,9-bis(t butyloxycarbonylmethyl)-3,6,9-triazaundecane-1,11-dicarboxylic acid-bis(t butylester)]-lysine-[1-(4-perfluorooctylsulfonyl)-piperazine]-amide 25 g (17.48 mmol) of the title compound of Example 57a) is dissolved in 350 ml of ethanol, and 5 g of palladium catalyst (10% Pd/C) is added. It is hydrogenated at room temperature. Catalyst is filtered out, and the filtrate is evaporated to the dry state in a vacuum.

Yield: 22.66 g (quantitative) of a colorless solid.

Elementary analysis: Cld: C, 44.48; H, 5.75; F, 24.92; N, 7.56; S, 2.47. Fnd: C, 44.59; H, 5.81; F, 25.03; N, 7.46; S, 2.52.

c) 6N-[1,4,7-Tris(carboxylatomethyl)-1,4,7,10-tetraazacyclododecane-10-(pentanoyl-3-aza 4oxo-5-methyl-5yl)]-2-N-[6-carbonylmethyl-3,9-bis(t butyloxycarbonylmethyl) 3,6,9-triazaundecane-1,11-dicarboxylic acid bis (t butylester)]-lysine-[1-(4-perfluorooctylsulfonyl)-piperazine-]-amide, Gd complex 20 g (15.43 mmol) of the title compound of Example 57b), 1.78 g (15.43 mmol) of N-hydroxysuccinimide, 1.48 g (35 mmol) of lithium chloride and 9.72 g (15.43 mmol) of 1,4,7-tris(carboxylatomethyl)-10-(3-aza-4oxo-5methyl-5yl)-pentanoic acid-1,4,7,10-tetraazacyclododecane, Gd complex, are dissolved in 150 ml of dimethyl sulfoxide while being heated slightly. At 10° C., 5.16 g (25 mmol) of N,N-dicyclohexylcarbodiimide is added, and then it is stirred overnight at room temperature. The solution is poured into 2500 ml of acetone and stirred for 10 minutes. The precipitated solid is filtered off and then purified by chromatography (silica gel RP-18, mobile solvent: gradient that consists of water/ethanol/acetonitrile).

Yield: 22.94 g (78% of theory) of a colorless solid.
Water content: 7.9%.
Elementary analysis (relative to anhydrous substance):
Cld: C, 42.22; H, 5.29; F, 16.95; Gd, 8.25; N, 8.82; S, 1.68.
Fnd: C, 42.15; H, 5.41; F, 16.87; Gd, 8.13; N, 8.70; S, 1.60.

d) 6-N-[1,4,7-Tris(carboxylatomethyl)-1,4,7,10-tetraazacyclododecane-10-(3-aza-4-oxo-5-methyl-5-yl-pentanoyl)]-2-N-[6-carbonylmethyl-3,9-bis(carboxylatomethyl) 3,6,9-triazaundecanedicarboxylic acid-carboxy-11-carboxylato-z]-lysine-[1-(4-perfluorooctylsulfonyl)-piperazine]-amide, digadolinium complex, sodium salt 20 g (10.49 mmol) of the title compound of Example 57c) is dissolved in 200 ml of trifluoroacetic acid. It is stirred for 60 minutes at room temperature. It is evaporated to the dry state in a vacuum, and the residue is dissolved in 150 ml of water. 1.90 g (5.25 mmol) of gadolinium oxide is added, and it is stirred for 5 hours at 80° C. It is allowed to cool to room temperature and set at a pH of 7.4 with sodium hydroxide solution. The solution is evaporated to the dry state in a vacuum and purified on silica gel RP-18 (mobile solvent: gradient that consists of water/ethanol/acetonitrile).

Yield: 11.89 g (61% of theory) of a colorless, amorphous solid.
Water content: 10.2%.
Elementary analysis (relative to anhydrous substance):
Cld: C, 32.97; H, 3.47; F, 17.39; Gd, 16.93; N, 9.05; Na, 1.24; S, 1.73. Fnd: C, 32.90; H, 3.53; F, 17.31; Gd, 16.87; N, 8.92; Na, 1.33; S, 1.67.

EXAMPLE 58 a) 5,6-Bis(benzyloxy)-3oxa-hexanoic acid-t butylester 100 g (376.2 mmol) of 1,2-di-O-benzyl-glycerol [produced according to Chem. Phys. Lipids (1987), 43(2), 113–277] and 5 g of tetrabutylammonium hydrogen sulfate are dissolved in a mixture that consists of 400 ml of toluene and 200 ml of 50% aqueous sodium hydroxide solution. At 0° C., 78 g (400 mmol) of 2-bromoacetic acid-t butyl ester is added in drops over 30 minutes, and then it is stirred for 3 hours at 0° C. The organic phase is separated, dried on magnesium sulfate and evaporated to the dry state in a vacuum. The residue is chromatographed on silica gel (mobile solvent: n-hexane/acetone=20:1).

Yield: 133.4 g (94% of theory) of a colorless oil.
Elementary analysis: Cld: C, 71.48; H, 7.82. Fnd: C, 71.61; H, 7.92.

b) 5,6-Bis(benzyloxy)3-oxa-hexanoic acid 130 g (336.4 mmol) of the title compound of Example 58a) is dissolved in 200 ml of dichloromethane, and 100 ml of trifluoroacetic acid is added at 0° C. It is stirred for 4 hours at room temperature, and then it is evaporated to the dry state. The residue is crystallized from pentane/diethyl ether.

Yield: 102.2 g (92% of theory) of a waxy solid.
Elementary analysis: Cld: C, 69.07; H, 6.71. Fnd: C, 69.19; H, 6.82.

c) 6-N-Benzyloxycarbonyl-2-N-[1,4,7-tris(carboxylatomethyl) 1,4,7,10-tetraazacyclo-dodecane-10-(pentanoyl-3-aza-4-oxo-5-methyl-5-yl)]-lysine-[1-(4-perfluorooctylsulfonyl)-piperazine]-amide, Gd complex 50 g (60.20 mmol) of the title compound of Example 52c), 6.93 g (60.20 mmol) of N-hydroxysuccinimide, 5.09 g (120 mmol) of lithium chloride, and 37.91 g (60.20 mmol) of 1,4,7-tris(carboxylatomethyl)-1,4,7,10-tetraazacyclododecane-10-pentanoyl-3-aza4-oxo-5-methyl-5yl), Gd complex, are dissolved in 400 ml of dimethyl sulfoxide while being heated slightly. At 10° C., 20.63 g (100 mmol) of N,N-dicyclohexylcarbodiimide is added, and then it is stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 75.53 g (87% of theory) of a colorless solid.
Water content: 10.1%.
Elementary analysis (relative to anhydrous substance):
Cld: C, 37.48; H, 3.84; F, 22.39; Gd, 10.90; N, 8.74; S, 2.22.
Fnd: C, 37.39; H, 4.02; F, 22.29; Gd, 10.75; N, 8.70; S, 2.22.

d) 2-N-[1,4,7-Tris(carboxylatomethyl)-1,4,7,10-tetraazacyclododecane-10-(pentanoyl-3aza-4-oxo-5methyl-5yl]-lysine-[1-(4-perfluorooctylsulfonyl)-piperazine]-amide, Gd complex 70 g (48.53 mmol) of the title compound of Example 58c) is dissolved in 500 ml of water/100 ml of ethanol, and 5 g of palladium catalyst (10% Pd/C) is added. It is hydrogenated at room temperature. Catalyst is filtered out, and the filtrate is evaporated to the dry state in a vacuum.

Yield: 63.5 g (quantitative) of a colorless solid.
Water content: 9.8%.
Elementary analysis (relative to anhydrous substance):
Cld: C, 37.48; H, 3.84; F, 22.39; Gd, 10.90; N, 8.74; S, 2.22.
Fnd: C, 37.39; H, 4.03; F, 22.31; Gd, 10.78; N, 8.65; S, 2.20.

e) 6-N-[5,6-Bis(benzyloxy)-3-oxahexanoyl]-2-N-[1,4,7-tris(carboxylatomethyl)-1,4,7,10-tetraazacyclododecane-10-(pentanoyl-3aza-4-oxo-5-methyl-5yl)]-lysine-[1-(4-perfluorooctylsulfonyl)-piperazine]-amide, Gd complex 10 g (7.64 mmol) of the title compound of Example 58d), 3.30 g (10 mmol) of the title compound of Example 7b, 0.85 g (20 mmol) of lithium chloride and 1.15 g (10 mmol) of N-hydroxysuccinimide are dissolved in 150 ml of dimethyl sulfoxide while being heated slightly. At 10° C., 3.10 g (15 mmol) of N,N'-dicyclohexylcarbodiimide is added, and it is stirred for 8 hours at room temperature. The reaction solution is poured into 2000 ml of acetone, and the deposited precipitate is isolated. The title compound is purified on silica gel RP-18 (mobile solvent: gradient that consists of water/ethanol/acetonitrile).

Yield: 11.14 g (90% of theory) of a colorless, amorphous solid.
Water content: 4.3%.
Elementary analysis (relative to anhydrous substance):
Cld: C, 41.51; H, 4.29; F, 19.93; N, 7.78; Gd, 9.70; S, 1.98.
Fnd: C, 41.45; H, 4.38; F, 19.84; N, 7.70; Gd, 9.58; S, 1.90.

f) 6-N-(5,6,-Dihydroxy-3-oxahexanoyl)-2-N-[1,4,7-tris carboxylatomethyl)-1,4,7,10-tetraazacyclododecane-10-pentanoyl-3-aza-4-oxo-5-methyl-5-yl)]-lysine [1-(4-perfluorooctylsulfonyl)-piperazine]-amide, Gd complex 10 g (6.17 mmol) of the title compound of Example 58e) is dissolved in 200 ml of ethanol, and 3 g of palladium catalyst (10% Pd/C) is added. It is hydrogenated at room temperature. Catalyst is filtered out, and the filtrate is evaporated to the dry state in a vacuum.

Yield: 8.89 g (quantitative) of a colorless solid.
Water content: 3.1%.
Elementary analysis (relative to anhydrous substance): Cld: C, 35.03; H, 3.99; F, 22.42; Gd, 10.92; N, 8.75; S, 2.23. Fnd: C, 34.95; H, 4.12; F, 22.30; Gd, 10.78; N, 8.71; S, 2.18.

EXAMPLE 59 a) 6-N-Benzyloxycarbonyl-2-N[-5,6-bis(benzyloxy)-3-oxa-hexanoyl]-lysine-[1-(4-perfluorooctylsulfonyl)-piperazine]-amide 9.28 g (45 mmol) of N,N-dicyclohexylcarbodiimide is added at 0° C. to a solution that consists of 20 g (24.08 mmol) of the title compound of Example 52c), 9.91 g (30 mmol) of the title compound of Example 7b and 3.45 g (30 mmol) of N-hydroxysuccinimide, dissolved in 100 ml of dimethylformamide. It is stirred for 3 hours at 0° C. and then overnight at room temperature. Precipitated urea is filtered out, the filtrate is evaporated to the dry state in a vacuum and chromatographed on silica gel (mobile solvent: dichloromethane/ethanol=20:1).

Yield: 24.50 g (89% of theory) of a viscous oil.
Elementary analysis: Cld: C, 47.29; H, 4.14; F, 28.26; N, 4.90; S, 2.81. Fnd: C, 47.14; H, 4.26; F, 28.17; N, 4.91; S, 2.69.

b) 2-N-(5,6-Dihydroxy-3-oxahexanoyl)-lysine-[1-(4-perfluorooctylsulfonyl)-piperazine]-amide 20 g (17.5 mmol) of the title compound of Example 52d) is dissolved in 300 ml of ethanol, and 5 g of palladium catalyst (10% Pd/C) is added. It is hydrogenated at room temperature. Catalyst is filtered out, and the filtrate is evaporated to the dry state in a vacuum.

Yield: 17.65 g (quantitative) of a colorless solid.
Elementary analysis: Cld: C, 44.05; H, 4.10; F, 32.02; N, 5.55; S, 3.18. Fnd: C, 43.96; H, 4.21; F, 31.94; N, 5.48; S, 3.24.

c) 6-N-[1,4,7-Tris(carboxylatomethyl-1,4,7,10-tetraazacyclododecane-10-(pentanoyl-3-aza-4-oxo-5-methyl-5yl)]-lysine-[1-(4-perfluorooctylsulfonyl)-piperazine]-amide, Gd complex 15 g (14.87 mmol) of the title compound of Example 59b), 1.73 g (15 mmol) of N-hydroxysuccinimide, 1.27 g (30 mmol) of lithium chloride and 9.48 g (15 mmol) of 1,4,7-tris(carboxylatomethyl)-10-(3-aza-4-oxo-5-methyl-5-yl)-pentanoic acid-1,4,7,10-tetraazacyclododecane, Gd complex, are dissolved in 100 ml of dimethyl sulfoxide while being heated slightly. At 10° C., 5.16 g (25 mol) of N,N-dicyclohexylcarbodiimide is added, and then it is stirred overnight at room temperature. The solution is poured into 1500 ml of acetone and stirred for 10 minutes. The precipitated solid is filtered off and then purified by chromatography (silica gel RP-18 mobile solvent: gradient that consists of water/ethanol/acetonitrile).

Yield: 19.28 g (80% of theory) of a colorless solid.
Water content: 10.3%.
Elementary analysis (relative to anhydrous substance): Cld: C, 41.51; H, 4.29; F, 19.93; Gd, 9.70; N, 7.78; S, 1.98. Fnd: C, 41.37; H, 4.40; F, 19.88; Gd, 9.58; N, 7.67; S, 1.85.

EXAMPLE 60 a) 6-N-Benzyloxycarbonyl-2-N-[2,6-N,N'-bis(benzyloxycarbonyl)-lysyl]-lysine-[1-(4-perfluorooctylsulfonyl)-piperazine]-amide 20 g (24.08 mmol) of the title compound of Example 52c) and 2.53 g (25 mmol) of triethylamine are dissolved in 200 ml of tetrahydrofuran (THF), and 14.46 g (27 mmol) of di-N,N'-Z-lysine paranitrophenylester is added. It is stirred for 5 hours at 50° C. It is evaporated to the dry state in a vacuum, and the residue is chromatographed on silica gel. Mobile solvent: dichloromethane/methanol=20:1).

Yield: 28.07 g (95% of theory) of a colorless solid.
Elementary analysis: Cld: C, 46.99; H, 4.19; F, 26.32; N, 6.85; S, 2.61. Fnd: C, 47.08; H, 4.32; F, 26.21; N, 6.75; S, 2.54.

b) 2-N-(Lysyl)-lysine-[1-(4-perfluorooctylsulfonyl)-piperazine]-amide, trihydrobromide 100 ml of hydrobromic acid in glacial acetic acid (48%) is added to 25 g (20.37 mmol) of the title compound of Example 60a) and stirred for 2 hours at 40° C. It is cooled to 0° C., 1500 ml of diethyl ester is added in drops, and the precipitated solid is filtered off. After drying in a vacuum (60° C.), 21.52 g (99% of theory) of a slightly yellow-colored, crystalline solid is obtained.

Elementary analysis: Cld: C, 27.01; H, 3.40; Br, 22.46; F, 30.26; N, 7.87; S, 3.00. Fnd: C, 26.92; H, 3.53; Br, 22.15; F, 30.14; N, 7.69; S, 2.87.

c) 6-N-[1,4,7-Tris(carboxylatomethyl 1,4,7,10-tetraazacyclododecane-10-(pentanoyl-3-aza-4-oxo-5-methyl-5yl)]-2-N-]2,6-N,N'-bis[1,4,7-tris carboxylatomethyl)-1,4,7,10-tetraazacyclododecane-10-(pentanoyl-3-aza-4-oxo-5-methyl-5yl)]-lysyl]-lysine-[1-(4-perfluorooctylsulfonyl)-piperazine]-amide, trigadolinium complex 31.49 g (50 mmol) of 1,4,7-tris(carboxylatomethyl)-10-(3-aza4-oxo-5-methyl-)-5-yl)-pentanoic acid, Gd complex 6.91 g (60 mmol) of N-hydroxysuccinimide and 4.24 g (100 mmol) of lithium chloride are dissolved in 350 ml of dimethyl sulfoxide while being heated slightly. At 10° C., 16.51 g (80 mmol) of N,N-dicyclohexylcarbodiimide is added, and it is stirred for 5 hours at 10° C. 10 g (9.37 mmol) of the title compound of Example 60b) and 3.03 g (30 mmol) of triethylamine are added to this mixture, and it is stirred for 12 hours at 60° C. It is allowed to cool to room temperature, and the mixture is poured into 3000 ml of acetone. The deposited precipitate is filtered off and purified on silica gel RP-18 (mobile solvent: gradient that consists of water/ethanol/acetonitrile).

Yield: 16.7 g (67% of theory) of a colorless solid.
Water content: 7.9%.
Elementary analysis (relative to anhydrous substance): Cld: C, 36.58; H, 4.43; F, 12.14; Gd, 17.74; N, 11.06; S, 1.14. Fnd: C, 36.47; H, 4.54; F, 12.03; Gd, 17.65; N, 10.95; S, 1.21.

EXAMPLE 61 a) 1,7-Bis(benzyloxycarbonyl)4-(3,6,9,12,15-pentaoxahexadecanoyl)-1,4,7,10-tetraazacyclododecane 24.73 g (100 mmol) of EEDQ (2-ethoxy-1,2-dihydroquinoline-1-carboxylic acid ethyl ester) is added at 0° C. to 18.13 g (68.1 mmol) of 3,6,9,12,15-pentaoxahexadecanoic acid and 30 g (68.1 mmol) of 1,7 di-Z-cyclene, produced according to Z. Kovacs and A. D. Sherry, J. Chem. Soc. Chem. Commun. (1995), 2, 185, in 300 ml of tetrahydrofuran, and it is stirred overnight at room temperature. It is evaporated to the dry state in a vacuum and chromatographed on silica gel (mobile solvent: dichloromethane/methanol=20:1).

Yield: 19.13 g (42% of theory) of a colorless solid.
Elementary analysis: Cld: C, 61.03; H, 7.61; N, 8.13. Fnd: C, 60.92; H, 7.75; N, 8.04.

b) 1,7-Bis(benzyloxycarbonyl)-4-(3,6,9,12,15-pentaoxahexadecanoyl)-10-(2H,2H,4H,5H-3-oxa-perfluorotridecanoyl)-1,4,7,10-tetraazacyclododecane 12.36 g (50 mmol) of EEDQ (2-ethoxy-1,2-dihydroquinoline-1-carboxylic acid ethyl ester) is added at 0° C. to 18 g (26.91 mmol) of the title compound of Example 61 a) and 14.05 g (26.91 mmol) of 2H,2H,4H,4H,5H,5H-3-oxa-perfluorotridecanoic acid, produced according to DE 19603033, in 300 ml of tetrahydrofuran, and it is stirred overnight at room temperature. It is evaporated to the dry state in a vacuum and chromatographed on silica gel (mobile solvent: dichloromethane/methanol=20:1).

Yield: 21.51 g (67% of theory) of a colorless solid.

Elementary analysis: Cld: C, 47.32; H, 4.82; F, 27.07; N, 4.70. Fnd: C, 47.26; H, 5.01; F, 26.94; N, 4.59.

c) 1-(3,6,9,12,15-Pentaoxahexadecanoyl)-7-(2H,2H,4H,4H,5H,5H-3-oxaperfluorotridecanoyl)-1,4,7,10-tetraazacyclododecane 20 g (16.77 mmol) of the title compound of Example 52d) is dissolved in 200 ml of ethanol, and 2.5 g of palladium catalyst (10% Pd/C) is added. It is hydrogenated at room temperature. Catalyst is filtered out, and the filtrate is evaporated to the dry state in a vacuum.

Yield: 15.5 g (quantitative) of a colorless solid.

Elementary analysis: Cld: C, 40.27; H, 4.90; F, 34.93; N, 6.06. Fnd: C, 40.15; H, 4.99; F, 34.87; N, 5.94.

d) 1,7-Bis(1,4,7-tris(carboxylatomethyl)-1,4,7,10-tetraazacyclododecane-10-(pentanoyl-3-aza-4-oxo-5-methyl-5-yl)]-4-(3,6,9,12,15-pentaoxahexadecanoyl)-10-(2H,2H,4H,4H,5H,5H,-3-oxaperfluorotridecanoyl)-1,4,7,10-tetraazacyclododecane, Gd complex 15 g (16.22 mmol) of the title compound of Example 61c), 4.60 g (40 mmol) of N-hydroxysuccinimide, 3.39 g (80 mmol) of lithium chloride and 25.19 g (40 mmol) of 1,4,7-tris(carboxylatomethyl)-10-(3-aza4-oxo-5-methyl-5-yl)-pentanoic acid, Gd complex, are dissolved in 300 ml of dimethyl sulfoxide while being heated slightly. At 10° C., 24.73 g (100 mmol) of EEDQ is added, and then it is stirred overnight at room temperature. The solution is poured into 3000 ml of acetone and stirred for 10 minutes.

The precipitated solid is filtered off and then purified by chromatography (silica gel RP-18, mobile solvent: gradient that consists of water/ethanol/acetonitrile).

Yield: 19.86 g (57% of theory) of a colorless solid.

Water content: 11.3%.

Elementary analysis (relative to anhydrous substance): Cld: C, 38.58; H, 4.74; F, 15.04; Gd, 14.64; N, 9.13. Fnd: C, 38.47; H, 4.91; F, 14.95; Gd, 14.57; N, 9.04.

EXAMPLE 62 a) 3,5-Dinitrobenzoic acid-1-[(4-perfluorooctylsulfonyl)-piperazine]-amide

A solution that consists of 8.76 g (38 mmol) of 3,5-dinitrobenzoyl chloride in 55 ml of dichloromethane is added in drops at 0° C. to 20 g (35.2 mmol) and 8.1 g (80 mmol) of triethylamine, dissolved in 200 ml of dichloromethane, and it is stirred for 3 hours at 0° C. 200 ml of 5% aqueous hydrochloric acid is added, and it is stirred for 5 minutes at room temperature. The organic phase is separated, dried on magnesium sulfate and evaporated to the dry state in a vacuum. The residue is chromatographed on silica gel (mobile solvent: dichloromethane/acetone=15:1).

Yield: 24.96 g (93% of theory) of a colorless solid.

Elementary analysis: Cld: C, 29.35; H, 1.45; F, 42.37; N, 7.35; S, 4.21. Fnd: C, 29.28; H, 1.61; F, 42.15; N, 7.25; S, 4.15.

b) 3,5 Diaminobenzoic acid-[1-(4-perfluorooctylsulfonyl)-piperazine]-amide 20 g (26.23 mmol) of the title compound of Example 62a) is dissolved in 400 ml of ethanol, and 6 g of palladium catalyst (10% Pd/C) is added. It is hydrogenated at room temperature. Catalyst is filtered out, and the filtrate is evaporated to the dry state in a vacuum.

Yield: 18.43 g (quantitative) of a cream-colored solid.

Elementary analysis: Cld: C, 32.49; H, 2.15; F, 45.98; N, 7.98; S, 4.57. Fnd: C, 32.29; H, 2.35; F, 45.69; N, 7.81; S, 4.40.

c) 3,5-N,N'-Bis[1,4,7-tris(carboxylatomethyl)-1,4,7,10-tetraazacyclododecane-10-(pentanoyl-3-aza-4-oxo-5-methyl-5-yl-)]-benzoic acid-[1-(4-perfluorooctyl-sulfonyl)-piperazine]-amide, Gd complex 10 g (14.24 mmol) of the title compound of Example 62b), 3.45 g (30 mmol) of N-hydroxysuccinimide, 2.54 g (60 mol) of lithium chloride and 18.89 g (30 mmol) of 1,4,7-tris(carboxylatomethyl)-10-(3-aza-4-oxo-5-methyl-5yl)-pentanoic acid, Gd complex, are dissolved in 200 ml of dimethyl sulfoxide while being heated slightly. At 10° C., 10.32 g (50 mmol) of N,N-dicyclohexylcarbodiimide is added, and then it is stirred overnight at room temperature. The solution is poured into 2000 ml of acetone, and it is stirred for 10 minutes. The precipitated solid is filtered off and then purified by chromatography (silica gel RP-18, mobile solvent: gradient that consists of water/ethanol/acetonitrile).

Yield: 19.74 g (72% of theory) of a colorless solid.

Water content: 11.8%.

Elementary analysis (relative to anhydrous substance): Cld: C, 35.55; H, 3.72; F, 16.77; Gd, 16.33; N, 10.18; S, 1.67. Fnd: C, 35.48; H, 3.84; F, 16.58; Gd, 16.24; N, 10.07; S, 1.58.

EXAMPLE 63 a) 3-Oxa-2H,2H,4H,4H,5H,5H-perfluorotridecanecarboxylic acid-t-butylester 25.0 g (53.8 mmol) of 1H,1H,2H,2H-perfluoro-1-decanol [commercially available from the Lancaster Company] is dissolved in 250 ml of absolute toluene and mixed at room temperature with a catalytic amount (about 0.75 g) of tetra-n-butyl-ammonium hydrogen sulfate. Then, a total of 7.55 g (134.6 mmol; 2.5 equivalents relative to the alcohol component that is used) of fine-powder potassium hydroxide powder is added at 0° C., followed by 15.73 g (80.7 mmol; 1.5 equivalents relative to the alcohol component that is used) of bromoacetic acid-tert-butylester, and it is allowed to stir for 2 more hours at 0° C. The thus obtained reaction solution is stirred for 12 more hours at room temperature, and for the purpose of working-up, it is mixed with a total of 500 ml of ethyl acetate and 250 ml of water. The organic phase is separated and washed twice with water. After the organic phase is dried on sodium sulfate, salt is suctioned out, and the solvent is drawn off in a vacuum. The remaining oily residue is purified on silica gel with use of ethyl acetate/hexane (1:10) as an eluant.

Yield: 26.3 g (84.6% of theory) of the above-mentioned title compound as a colorless and strongly viscous oil.

Elementary analysis: Cld: C, 33.23; H, 2.61; F, 55.85. Fnd: C, 33.29; H, 2.61; F, 55.90.

b) 3-Oxa-2H,2H,4H,4H,5H,5H-perfluorotridecanecarboxylic acid 20.0 g (34.58 mmol) of the title compound of Example 63a) is suspended in 200 ml of a mixture that consists of methanol and 0.5 molar sodium hydroxide solution at a ratio of 2:1 while being stirred at room temperature, and then it is heated to 60° C. After a reaction time of 12 hours at 60° C., the now clear reaction mixture is neutralized for working-up by mixing with Amberlite® IR 120 (H+ form)-cation-exchange resin, exchanger is suctioned out, and the thus obtained methanolic-aqueous filtrate is drawn off in a vacuum until a dry state is reached. The amorphous-oily residue that is obtained is purified on silica gel with use of ethyl acetate/n-hexane (1:3) as an eluant.

Yield: 16.0 g (88.6% of theory) of the above-mentioned title compound as a colorless and strongly viscous oil.

Elementary analysis: Cld: C, 27.60; H, 1.35; F, 61.85. Fnd: C, 27.58; H, 1.36; F, 61.90.

c) 1,7-Bis{[1,4,7-tris(carboxylatomethyl)-10-(3-aza-4-oxo-5-methyl-5-yl-pentanoyl)]-1,4,7,10-tetraazacyclododecane}-diethylenetriamine, digadolinium complex 2.48 g [(3.94 mmol); 2.05 molar equivalents relative to the diethylenetriamine that is used] of the Gd complex, described in Patent Application DE 197 28 954 C1 under Example 31 h), of 10-(4-carboxy-1-methyl-2-oxo-3-azabutyl)-1,4,7,10-tetraazacyclododecane-1,4,7-triacetic acid and 167 mg of anhydrous lithium chloride (3.94 mmol) are dissolved at 40° C. in 40 ml of absolute dimethyl sulfoxide while being stirred and mixed at this temperature with a total of 453 mg (3.94 mmol) of N-hydroxysuccinimide. After cooling to room temperature, the thus obtained reaction solution is mixed with 814 mg (3.946 mmol) of N,N'-dicyclohexylcarbodiimide and stirred for 2 hours at room temperature. The suspension of active ester that is obtained is then mixed with 198.3 mg (1.92 mmol) of diethylenetriamine, dissolved in 5 ml of absolute dimethyl sulfoxide, and it is stirred for 12 hours at room temperature. For the purpose of working-up, the reaction mixture is mixed with sufficient acetone until the above-mentioned title compound is completely precipitated, the precipitate is suctioned off, dried, taken up in water, insoluble dicyclohexylurea is filtered out, and the filtrate is desalinated with an AMICON® YM-3 ultrafiltration membrane (cut-off 3,000 Da), and low-molecular components are removed. The retentate is then freeze-dried.

Yield: 1.85 g (72.7% of theory) as a colorless lyophilizate.

H₂O content (Karl-Fischer): 3.89%.

Elementary analysis (relative to anhydrous substance): Cld: C, 38.03; H, 5.24; N, 13.73; Gd, 23.71. Fnd: C, 37.98; H, 5.20; N, 13.69; Gd, 23.78.

d) 1,7-Bis{[1,4,7-tris(carboxylatomethyl)-10-(3-aza4-oxo-5-methyl-5-yl-pentanoyl)]-1,4,7,10-tetraazacyclododecane}-4-(3-oxa-2H,2H,4H,4H,5H,5H-perfluorotridecanoyl) diethylenetriamine, digadolinium complex 1.27 g (2.44 mmol) of the title compound of Example 63b), dissolved in a mixture that consists of 15 ml of tetrahydrofuran and 15 ml of dimethyl sulfoxide, is added drop by drop at 50° C. and under nitrogen atmosphere to a solution of 3.23 g (2.44 mmol) of the title compound of Example 63c), in a mixture that consists of 30 ml of dimethyl sulfoxide and 3 ml of tetrahydrofuran. Then, a total of 1.80 g (3.66 mmol) of EEDQ [2-ethoxy-1-ethoxycarbonyl-1,2-dihydroquinoline] is added in portions at 0° C. and allowed to stir overnight at room temperature. The reaction solution that is obtained is then mixed with sufficient acetone until the above-mentioned title compound is completely precipitated, the precipitate is suctioned off, dried, taken up in water, insoluble components are filtered out, and the filtrate is ultrafiltered with an AMICON® YM-3 ultrafiltration membrane (cut-off 3,000 Da), which is used both for complete desalination and for removing low-molecular components from the title compound. The retentate is then freeze-dried.

Yield: 3.54 g (79.4% of theory) as a colorless lyophilizate.

H₂O content (Karl-Fischer): 5.87%.

Elementary analysis (relative to anhydrous substance): Cld: C, 35.43; H, 4.07; N, 9.95; F, 17.64; Gd, 17.18. Fnd: C, 35.42; H, 4.01; N, 9.89; F, 17.67; Gd, 17.18.

EXAMPLE 64 a) 2-N-Trifluoroacetyl-6-N-benzyloxycarbonyl-L-lysine 100.0 g (356.7 mmol) of 6-N-benzyloxycarbonyl-L-lysine is dissolved in a mixture that consists of 1000 ml of trifluoroacetic acid ethyl ester and 500 ml of ethanol, and it is stirred for 24 hours at room temperature. It is evaporated to the dry state, and the residue is crystallized from diisopropyl ether.

Yield: 128.9 g (96% of theory) of a colorless crystalline powder.

Melting point: 98.5° C.

Elementary analysis: Cld: C, 51.07; H, 5.09; N, 7.44; F, 15.14. Fnd: C, 51.25; H, 5.18; N, 7.58; F, 15.03.

b) 2-N-Trifluoroacetyl6-N-benzyloxycarbonyl-L-lysine [1-(4-perfluorooctylsulfonyl)-piperazine]-amide 164.2 g (0.664 mmol) of EEDQ (2-ethoxy-1,2-dihydroquinoline-1-carboxylic acid ethyl ester) is added at 0° C. to 125.0 g (332.0 mmol) of the title compound of Example 52a) and 188.7 g (332.0 mmol) of 1-perfluorooctylsulfonylpiperazine (produced according to DE 19603033) in 750 ml of tetrahydrofuran, and it is stirred overnight at room temperature. It is evaporated to the dry state in a vacuum and chromatographed on silica gel (mobile solvent: dichloromethane/methanol=20:1).

Yield: 286.0 g (93% of theory) of a colorless solid.

Melting point: 92° C.

Elementary analysis: Cld: C, 36.30; H, 2.83; N, 6.05; F, 41.01; S, 3.46. Fnd: C, 36.18; H, 2.94; N, 5.98; F, 40.87; S, 3.40.

c) 6-N-Benzyloxycarbonyl-L-lysine-[1-(4-perfluorooctylsulfonyl)-piperazine]-amide Ammonia gas is introduced at 0° C. for one hour into a solution that consists of 280.0 g (302.2 mol) of the title compound of Example 52b) in 2000 ml of ethanol. It is then stirred for 4 hours at 0° C., It is evaporated to the dry state, and the residue is absorptively precipitated from water. The solid is filtered off and dried in a vacuum at 50° C.

Yield: 243.5 g (97.0% of theory) of an amorphous solid.

Elementary analysis: Cld: C, 37.60; H, 3.28; N, 6.75; F, 38.89; S, 3.86. Fnd: C, 37.55; H, 3.33; N, 6.68; F, 38.78; S, 3.81.

d) L-Lysine-[1-(4-perfluorooctylsulfonyl)-piperazine]-amide 200.0 g (240.8 mmol) of the compound that is produced under 64c) is dissolved in 1000 ml of ethanol, mixed with 5.0 g of Pearlman's catalyst (Pd 20%, C) and hydrogenated at room temperature under a hydrogen atmosphere (1 atm) until no more hydrogen absorption can be observed. Catalyst is suctioned out, it is thoroughly rewashed with ethanol (three times with about 100 ml each) and evaporated to the dry state in a vacuum. The title compound is obtained as a strongly viscous and yellowish-colored oil.

Yield: 162.5 g (96.9% of theory).

Elementary analysis: Cld: C, 31.04; H, 3.04; N, 8.05; F, 46.38; S, 4.60. Fnd: C, 31.11; H, 3.09; N, 8.08; F, 46.33; S, 4.62.

e) 6N-2N-Bis-{4-[2,3-bis-(N,N-bis(t-butyloxycarbonylmethyl)-amino)-propyl]-phenyl}-3-oxa-propionyl-L-lysine-[1-(4-perfluorooctylsulfonyl)-piperazine]-amide 5.25 g (7.72 mmol) of the 4-[2,3-bis-(N,N-bis(t-butyloxycarbonylmethyl)-amino)-propyl]-phenyl}-3-oxa-propionic acid and 781.0 mg (7.72 mmol) of triethylamine are dissolved in 50 ml of methylene chloride. At −15° C., a solution that consists of 1.16 g (8.5 mmol) of isobutyl chloroformate in 10 ml of methylene chloride is added in drops within 5 minutes, and it is stirred for another 20 minutes at −15° C. Then, the solution is cooled to −25° C., and a solution, consisting of 2.68 g (3.86 mmol) of the title compound of Example 64d) and 2.12 g (21.0 mmol) of triethylamine, in 70 ml of tetrahydrofuran is added in drops within 30 minutes and subsequently stirred for another 30 minutes at −15° C., and then stirring is continued overnight at room temperature. For working-up, the solvent is drawn off in a vacuum, and the remaining oily residue is taken up in 250 ml of chloroform. The chloroform phase is extracted twice with 100 ml each of a 10% aqueous ammonium chloride solution, the organic phase is dried on magnesium sulfate and evaporated to the dry state in a vacuum. The residue is chromatographed on silica gel (mobile solvent: methylene chloride/ethanol=20:1).

Yield: 5.37 g (68.8% of theory) of a colorless and very viscous oil.

Elementary analysis: Cld: C, 52.27; H, 6.43; N, 5.54; F, 15.97; S, 1.59. Fnd: C, 52.22; H, 6.51; N, 5.49; F, 15.99; S, 1.63.

f) 6N-2N-Bis-{4-[2,3-bis-(N,N-bis(carboxylatomethyl)-amino)-propyl]-phenyl}-3-oxa-propionyl-L-lysine-[1-(4-perfluorooctylsulfonyl)-piperazine]-amide, octa-sodium salt 5.0 g (2.47 mmol) of the title compound of Example 64e) is dissolved in 60 ml of absolute dichloromethane. Then, it is mixed drop by drop at 0° C. with a total of 75 ml of trifluoroacetic acid. After a reaction time of 12 hours at room temperature, it is evaporated to the dry state in a vacuum. The remaining residue is mixed with 100 ml of water and drawn off again in a vacuum until a dry state is reached. The thus obtained residue is dissolved in 200 ml of distilled water, and the aqueous product solution of the above-mentioned title compound is extracted twice with 60 ml of diethyl ether in each case. The resulting aqueous product solution is made up to a total volume of 300 ml by mixing with water, insoluble components are filtered out, and the filtrate is ultrafiltered with an AMICON® YM-3 ultrafiltration membrane (cut-off 3,000 Da), which is used both for complete desalination and for removing low-molecular components from the title compound. The retentate is made up to a total volume of 200 ml by mixing with water, and the pH of this solution is then set at 10.0 with 15% sodium hydroxide solution. The basic, aqueous product solution is subsequently freeze-dried.

4.0 g (92.8% of theory) of the title compound is obtained in the form of the octa-sodium salt as an amorphous lyophilizate.

Water content: 5.37%.

Elementary analysis (relative to anhydrous substance): Cld: C, 38.46; H, 3.28; N, 6.41; F, 18.47; S, 1.83; Na, 10.52. Fnd: C, 38.42; H, 3.31; N, 6.39; F, 18.51; S, 1.87; Na, 10.38.

g) 6N-2N-Bis-{4-[2,3-bis-(N,N-bis(carboxymethyl)-amino)-propyl]-phenyl }-3-oxa-propionyl-L-lysine-[1-(4-perfluorooctylsulfonyl)-piperazine]-amide, di-manganese complex, tetra-sodium salt 1.94 g (1.11 mmol) of the title compound of Example 64f) is dissolved in 100 ml of distilled water, and the resulting solution is brought to a pH of 4.0 by mixing with 1 molar aqueous hydrochloric acid. At 80° C., it is now mixed in portions with 0.25 g (2.22 mmol) of manganese(II) carbonate. Then, the thus obtained reaction solution is refluxed for 5 hours. After cooling to room temperature, the pH of the aqueous product solution is set at 7.2 by mixing with 1N sodium hydroxide solution while being stirred vigorously, and it is desalinated with an AMICON® YM-3 ultrafiltration membrane (cut-off 3,000 Da), and low-molecular components are removed. The retentate is then freeze-dried.

Yield: 1.80 g (92.0% of theory) of the title compound as a colorless lyophilizate.

$H_2O$ content (Karl-Fischer): 7.28%.

Elementary analysis (relative to anhydrous substance): Cld: C, 38.07; H, 3.25; F, 18.28; Mn, 6.22; N, 6.34; Na, 5.20; S, 1.81. Fnd: C, 38.01; H, 3.29; F, 18.29; Mn, 6.21; N, 6.36; Na, 5.28; S, 1.78.

EXAMPLE 65 a) 6-N-(Benzyloxycarbonyl)-2-N-[(N-pteroyl)-L-glutaminyl]-lysine-[1-(4-perfluorooctylsulfonyl)-piperazine]-amide 20 g (45.31 mmol) of folic acid is dissolved in 300 ml of dimethyl sulfoxide, and 9.49 g (46 mmol) of N,N-dicyclohexylcarbodiimide is added at 10° C. It is stirred overnight at room temperature. 29.1 g (35 mmol) of the title compound of Example 52c) and 20 ml of pyridine are added to this mixture, and it is stirred for 3 hours at 50° C. It is cooled to room temperature, and a mixture that consists of 1500 ml of diethyl ether/1500 ml of acetone is added. The deposited precipitate is filtered off and purified on (RP-18) (mobile solvent gradient that consists of water/ethanol/tetrahydrofuran).

Yield: 21.59 g (38% of theory) of a yellow solid.

Water content: 2.1%.

Elementary analysis (relative to anhydrous substance): Cld: C, 43.10; H, 3.54; F, 25.76; N, 11.29; S, 2.56. Fnd: C, 43.02; H, 3.62; F, 25.68; N, 11.21; S, 2.48.

b) 2-N-[(N-Pteroyl)-L-glutaminyl]-lysine-[1-(4-perfluorooctylsulfonyl)-piperazine]-amide 200 ml of hydrobromic acid in glacial acetic acid (48%) is added to 20 g (15.95 mmol) of the title compound of Example 65a), and it is stirred for 2 hours at 40° C. It is cooled to 0° C., 2000 ml of diethyl ether is added in drops, and the precipitated solid is filtered off. After drying in a vacuum (60° C.), 18.96 g (99% of theory) of a yellow-colored, crystalline solid is obtained.

Elementary analysis: Cld: C, 37.01; H, 3.27; Br, 6.65; F, 26.90; N, 12.83; S, 2.67. Fnd: C, 36.91; H, 3.42; Br, 6.31; F, 29.75; N, 12.72; S, 2.56.

c) 6-N-[1,4,7-Tris(carboxylatomethyl)-1,4,7,10-tetraazacyclododecane-10-(pentanoyl-3-aza-4oxo-5-methyl-5yl]-2-N-[(N-pteroyl)-L-glutaminyl]-lysine-[1-(4-perfluorooctylsulfonyl)-piperazine]-amide, Gd complex 0.92 g (8 mmol) of N-hydroxysuccinimide, 0.68 g (16 mol) of lithium chloride and 5.04 g (8 mmol) of 1,4,7-tris (carboxylatomethyl-10-(3-aza-4-oxo-5-methyl-5yl)-1,4,7-10-tetraazacyclododecane, Gd complex, are dissolved in 80 ml of dimethyl sulfoxide while being heated slightly. At 10° C., 2.06 g (10 mol) of N,N-dicyclohexylcarbodiimide is added, and then it is stirred for 3 hours at room temperature. 5 g (4.16 mmol) of the title compound of Example 65b) and 10 ml of pyridine are added to this reaction solution. It is stirred overnight at room temperature. The solution is poured into 1000 ml of acetone and stirred for 10 minutes. The precipitated solid is filtered off and then purified by chromatography (silica gel RP-18, mobile solvent: gradient that consists of water/ethanol/acetonitrile). It is dissolved in some water, the pH is set at 7.4 with sodium hydroxide solution, and it is freeze-dried.

Yield: 3.87 g (53% of theory) of a yellow solid.

Water content: 5.8%.

Elementary analysis (relative to anhydrous substance): Cld: C, 38.36; H, 3.74; F, 18.42; Gd, 8.97; N, 12.78; Na, 1.31; S, 1.83. Fnd: C, 38.28; H, 3.85; F, 18.33; Gd, 8.85; N, 12.69; Na, 1.42; S, 1.75.

EXAMPLE 66 a) 2H,2H,4H,4H,5H,5H-3-Oxa)-perfluorotridecanoic acid-N-(2,3-dihydroxypropyl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane, and at 0° C., it is added in drops to a solution that consists of 5.47 g (60 mmol) of 2,3-dihydroxypropylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent; dichloromethane/ethanol=15:1).

Yield: 29.70 g (87% of theory) of a colorless solid.

Elementary analysis: Cld: C, 30.32; H, 2.20; N, 2.36; F, 54.35. Fnd: C, 30.12; H, 2.41; N, 2.18; F, 54.15.

b) N-(2,3-Dihydroxypropyl)-N-(1H,1H,2H,2H,4H,4H,5H,5H-3-oxa-perfluorotridecyl)-amine 30 g (48.8 mmol) of the title compound of Example 66a is dissolved in 300 ml of tetrahydrofuran, and 50 ml of 10 M boranedimethyl sulfide (in tetrahydrofuran) is added. It is refluxed for 16 hours. It is cooled to 0° C., and 300 ml of methanol is added in drops, then it is evaporated to the dry state in a vacuum. The residue is taken up in a mixture that consists of 300 ml of ethanol/50 ml of 10% aqueous hydrochloric acid, and it is stirred for 8 hours at 60° C. It is evaporated to the dry state in a vacuum, the residue is taken up in 300 ml of 5% aqueous sodium hydroxide solution, and it is extracted 3 times with 300 ml each of dichloromethane. The organic phases are dried on magnesium sulfate, evaporated to the dry state in a vacuum, and the residue is chromatographed on silica gel (mobile solvent: dichloromethane/methanol=15:1).

Yield: 24.07 g (85% of theory) of a colorless solid.

Elementary analysis: Cld: C, 31.05; H, 2.61; N, 2.41; F, 55.66. Fnd: C, 31.91; H, 2.78; N, 2.33; F, 55.47.

c) 1,4,7-Tris(carboxylatomethyl)-10-[(1(3-aza-4-oxo-hexan-5-ylic)-acid-N-(2,3-dihydroxypropyl)-N-(1H,1H,2H,2H,4H,4H,5H,5H-3-oxa)-perfluorotridecyl)-amide]-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.21 g (15.88 mmol) of the title compound of Example 66b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water and chromatographed on silica gel RP-18 (mobile solvent: gradient that consists of tetrahydrofuran/acetonitrile/water).

Yield: 16.09 g (85% of theory) of a colorless, amorphous powder

Water content: 6.3%.

Elementary analysis (relative to anhydrous substance): Cld: C, 34.26; H, 3.64; N, 7.05; F, 27.10; Gd, 13.19. Fnd: C, 34.12; H, 3.83; N, 6.91; F, 26.88; Gd, 12.93.

EXAMPLE 67

1,4,7-Tris(carboxylatomethyl)-10-[(3-aza-4-oxo-hexan-5-ylic)-acid-N-(1H,1H,2H,2H,4H,4H,5H,5H-3-oxa-perfluorotridecyl)-amide]-1,4,7,10-tetraazacyclododecan gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride and 3.66 g (31.76 mmol) of N-hydroxysuccinimide are dissolved at 60° C. in 100 ml of dimethyl sulfoxide. It is cooled to 15° C., 3.51 g (17 mmol) of N,N'-dicyclohexylcarbodiimide is added, and it is stirred for 5 hours at 15° C. To separate the urea, the solution is filtered. 8.63 g (15.88 mmol) of the title compound of Example 68b and 5.06 g (50 mmol) of triethylamine are added to the filtrate, and it is stirred for 12 hours at room temperature. The solution is poured into 1500 ml of diethyl ether/100 ml of acetone, and it is stirred for 30 minutes. The precipitated solid is filtered off and chromatographed on silica gel RP-18 (mobile solvent: gradient that consists of tetrahydrofuran/acetonitrile/water).

Yield: 13.86 g (78% of theory) of a colorless, amorphous powder

Water content: 9.3%

Elementary analysis (relative to anhydrous substance): Cld: C, 33.28; H, 3.42; N, 7.51; F, 28.87; Gd, 14.05. Fnd: C, 33.12; H, 3.61; N, 7.37; F, 28.69; Gd, 13.89.

EXAMPLE 68 a) 2H,2H,4H,4H,5H,5H-3-Oxa-perfluorotridecanoic acid amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 200 ml of dichloromethane. Ammonia gas is then directed into the solution for about 2 hours at 0° C. It is stirred for 4 more hours at 0° C., then for 2 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

Yield: 27.85 g (93% of theory).

Elementary analysis: Cld: C, 27.66; H, 1.55; N, 2.69; F, 61.97. Fnd: C, 27.49; H, 1.72; N, 2.54; F, 61.81.

b) 1H,1H,2H,2H,4H,4H,5H,5H-3-Oxa-perfluorotridecylamine, hydrochloride 27 g (51.8 mmol) of the title compound of Example 68a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 400 ml of ethanol/100 ml of 100% aqueous hydrochloric acid, and it is stirred for 8 hours at 60° C. It is evaporated to the dry state in a vacuum, and the residue is crystallized from a little ethanol/diethyl ether.

Yield. 26.75 g (95% of theory) of a colorless, crystalline solid.

Elementary analysis: Cld: C, 26.51; H, 2.04; N, 2.58; F, 59.41; Cl, 16.52. Fnd: C, 26.37; H, 2.21; N, 2.46; F, 59.25; Cl, 6.38.

c) 3,6,9,12,15-Pentaoxahexadecanoic acid-N-(1H,1H,2H,2H,4H,4H,5H,5H-3-oxa)-perfluorotridecyl)-amide 14.24 g (50 mmol) of 3,6,9,12,15-pentaoxahexadecanoic acid chloride is added at 0° C. to 26.5 g (48.74 mmol) of the title compound of Example 68b, and 14.8 g (146.2 mmol) of triethylamine, dissolved in 300 ml of dichloromethane, is added in drops, and it is stirred for 3 hours at 0° C. 300 ml of 5% aqueous hydrochloric acid is added, and it is thoroughly stirred for 30 minutes. The organic phase is separated, dried on magnesium sulfate and evaporated to the dry state in a vacuum. The residue is chromatographed on silica gel (mobile solvent: dichloromethane/acetone: 20:1).

Yield: 32.03 g (87% of theory) of a colorless oil.

Elementary analysis: Cld: C, 36.57; H, 4.00; N, 1.85; F, 42.75. Fnd: C, 36.46; H, 4.12; N, 1.76; F, 42.53.

d) N-(3,6,9,12,15-Pentaoxahexadecyl)-N-(1H,1H,2H,2H,4H,4H-3-oxa)-perfluorotridecyl)-amide 31 g (41.03 mmol) of the title compound of Example 68c is dissolved in 300 ml of tetrahydrofuran, and 25 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 300 ml of ethanol/50 ml of 10% aqueous hydrochloric acid, and it is stirred for 8 hours at 40° C. It is evaporated to the dry state in a vacuum, the residue is taken up in 300 ml of 5% aqueous sodium hydroxide solution, and it is extracted 3 times with 300 ml each of dichloromethane. The organic phases are dried on magnesium sulfate, evaporated to the dry state in a vacuum, and the residue is chromatographed on silica gel (mobile solvent: dichloromethane/2-propanol=15:1).

Yield: 27.68 g (91% of theory).

Elementary analysis: Cld: C, 37.26; H, 4.35; N, 1.89; F, 43.56. Fnd: C, 37.11; H, 4.51; N, 1.73; F, 43.41.

e) 1,4,7-Tris(carboxylatomethyl)-10-{(3-aza4-oxo-hexan-5-ylic)-acid-[N-3,6,9,12,15-pentaoxa)-hexadexyl)-N-(1H,1H,2H,2H,4H,4H,5H,5H-3-oxa)-perfluorotridecyl]-amide}-1,4,7,10-tetraazacyclododecane, gadolinium complex 10 g (15.88 mmol) of the gadolinium complex of 10-[1-(carboxymethylcarboamoyl)-ethyl]-1, 4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 11.77 g (15.88 mmol) of the title compound of Example 68d is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water and chromatographed on silica gel RP-18 (mobile solvent: gradient that consists of tetrahydrofuran/acetonitrile/water).

Yield: 18.05 g (84% of theory) of a colorless, amorphous powder.

Water content: 6.2%.

Elementary analysis (relative to anhydrous substance): Cld: C, 37.28; H, 4.47; N, 6.21; F, 23.87; Gd, 11.62. Fnd: C, 37.11; H, 4.61; N, 6.03; F, 23.64; Gd, 11.42.

EXAMPLE 69 a) 2H,2H,4H,4H,5H,5H-3-Oxa-perfluorotridecanoic acid-N-(5-hydroxy-3-oxa-pentyl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 6.25 g (60 mmol) of 5-hydroxy-3-oxa-pentylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=15:1).

Yield: 32.20 g (92% of theory) of a colorless solid.

Elementary analysis: Cld: C, 31.54; H, 2.65; N, 2.30; F, 53.01. Fnd: C, 31.61; H, 2.84; N, 2.14; F, 52.85.

b) N-(5-Hydroxy-3-oxa-pentyl)-N-(1H,1H,2H,2H,4H,4H,5H,5H-3-oxa-perfluorotridecyl)-amine 30 g (49.24 mmol) of the title compound of Example 69a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 300 ml of ethanol/10 ml of 10% aqueous hydrochloric acid, and it is stirred for 10 hours at 50° C. It is evaporated to the dry state in a vacuum, the residue is taken up in 300 ml of 5% aqueous sodium hydroxide solution, and it is extracted 3 times with 300 ml each of dichloromethane. The organic phases are dried on magnesium sulfate, evaporated to the dry state in a vacuum, and the residue is chromatographed on silica gel (mobile solvent: dichloromethane/2-propanol=20:1).

Yield: 26.09 g (89% of theory) of a colorless solid.

Elementary analysis: Cld: C, 32.28; H, 3.05; N, 2.35; F, 54.25. Fnd: C, 32.12; H, 3.21; N, 2.18; F, 54.09.

c) 1,4,7-Tris(carboxylatomethyl)-10-[(3-aza-oxo-hexan-5-ylic)-acid-N-(5-hydroxy-3-oxa-pentyl)-N-(1H,1H,2H,2H,4H,4H,5H,5H-3-oxa)-perfluorotridecyl)-amide]-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.45 g (15.88 mmol) of the title compound of Example 69b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, it is dissolved in a mixture that consists of a little ethanol/water and chromatographed on silica gel RP-18 (mobile solvent: gradient that consists of tetrahydrofuran/acetonitrile/water).

Yield: 16.10 g (84% of theory) of a colorless, amorphous powder.

Water content: 5.7%.

Elementary analysis (relative to anhydrous substance): Cld: C, 34.83; H, 3.84; N, 6.96; F, 26.76; Gd, 13.03. Fnd: C, 34.65; H, 3.96; N, 6.84; F, 26.62; Gd, 12.91.

EXAMPLE 70 a) 1,2,3,4,6-Penta-O-acetyl-α,β-D-mannopyranose

Analogously to what is described in the literature [M. L. Wolfrom and A. Thompson in Methods in Carbohydrate Chemistry (R. L. Whistler, M. L. Wolfrom and J. N. BeMiller, Eds.), Academic Press, New York, Vol. II, 53, pp. 211–215, (1963)], the reaction of 150 g (832.5 mmol) of α,β-D-mannopyranose with a mixture that consists of 1500 ml of absolute pyridine and 1500 ml of acetic acid anhydride yields, after working-up, 315 g (96.7%) of the above-mentioned title compound as a crude product in the form of a viscous and colorless oil. By ¹H-NMR spectroscopic study of the thus obtained title compound, it was possible to determine the α to β ratio of both anomers at 4:1. Separation of the α,β-anomers of the above-mentioned title compound can be eliminated to carry out the reaction steps below.

Elementary analysis: Cld: C, 49.21; H, 5.68. Fnd: C, 49.12; H, 5.78.

b) 6-[1-O-α-(2,3,4,6-Tetra-O-acetyl-D-mannopyranosyl)-hexanoic acid ethyl ester]

Analogously to what is described in the literature for the synthesis of aryl glycopyranosides [J. Conchie and G. A. Levvy in Methods in Carbohydrate Chemistry (R. L. Whistler, M. L. Wolfrom and J. N. BeMiller, Eds.), Academic Press, New York, Vol. II, 90, pp. 345–347, (1963)], the reaction of 156.2 g (400 mmol) of the title compound of Example 70a as an α,β-anomer mixture with 67 ml (400 mmol) of 6-hydroxy-hexanoic acid ethyl ester and 60.8 ml (520 mmol) of tin(IV) chloride in a total of 600 ml of 1,2-dichloroethane after column -chromatographic purification (eluant: hexane/ethyl acetate 2:1) results in the formation of 100.05 g (51% of theory) of the above-mentioned title compound as a colorless and viscous oil. By ¹H-NMR-spectroscopic study of the thus obtained title compound, it was possible to show that the above-mentioned title compound is only the pure α-anomer.

Elementary analysis: Cld: C, 52.94; H, 6.77. Fnd: C, 52.80; H, 6.78.

c) 6-[1-O-α-(2,3,4,6-Tetra-O-benzyl-D-mannopyranosyl)-hexanoic acid

A stirred suspension of 141.0 g (289 mmol) of the title compound of Example 70b in 200 ml of dioxane is mixed in portions with a total of 238.5 g (4.26 mol) of fine-powder potassium hydroxide powder at room temperature and with simultaneous vigorous stirring. To make it easier to stir, the reaction mixture is mixed with another 200 ml of dioxane, and the thus obtained suspension is subsequently heated to boiling and mixed at this temperature drop by drop with a total of 372 ml (3.128 mol) of benzyl bromide over a period of two hours. After a reaction time of 4 hours at 110° C. followed by 12 hours at room temperature, the reaction mixture is slowly poured into a total of 2.5 liters of ice water for the purpose of working-up, and the aqueous phase is subsequently completely extracted with diethyl ether. After the thus obtained ether phase is washed, and after the subsequent drying of the same with sodium sulfate, salt is suctioned out, and the diethyl ether is drawn off in a vacuum. Excess benzyl bromide is then quantitatively distilled off from the reaction mixture in an oil pump vacuum at an oil bath temperature of 180° C. The thus obtained, resinous-oily residue is purified on silica gel with use of ethyl acetate/hexane (1:10) as an eluant.

Yield: 172.2 g (91.0% of theory) of the above-mentioned title compound in the form of a colorless and extremely viscous oil.

Elementary analysis: Cld: C, 75.68; H, 7.16. Fnd: C, 75.79; H, 7.04.

d) 6-[1-O-α-(2,3,4,6-Tetra-O-benzyl-D-mannopyranosyl)-hexanoic acid-N-(3-oxa-1H,1H,2H,2H,4H,4H,5H,5H-perfluorotridecyl)-amide 100 g (134 mmol) of the acid that is described in Example 70c and 13.5 g (134 mmol) of triethylamine are dissolved in 1200 ml of dry tetrahydrofuran. After cooling to −15° C., a solution of 18.45 g (135 mmol) of isobutyl chloroformate in 200 ml of dry tetrahydrofuran is slowly added in drops while being stirred, whereby the internal temperature does not exceed −10° C. After a reaction time of 15 minutes at −15° C., a solution of 165.5 g (134 mmol) of 1-amino-1H,1H,2H,2H-perfluorodecane and 13.5 g (134 mmol) of triethylamine in 250 ml of dry tetrahydrofuran is added in drops at −20° C. After a reaction time of one hour at −15° C. and two hours at room temperature, the reaction solution is evaporated to the dry state in a vacuum. The remaining residue is taken up in 300 ml of ethyl acetate and washed twice with 400 ml each of saturated sodium bicarbonate solution and once with 500 ml of water. After the organic phase is dried on sodium sulfate, salt is suctioned out, and the ethyl acetate is drawn off in a vacuum. The remaining oily residue is purified on silica gel with use of dichloromethane/hexane/2-propanol (10:5:1) as an eluant.

Yield: 143.8 g (86.9% of theory).

Elementary analysis: Cld: C, 57.38; H, 4.98; N, 1.13; F, 26.15. Fnd: C, 57.30; H, 5.44; N, 1.01; F, 26.25.

e) 6-[1-O-α-D-Mannopyranosyl)-hexanoic acid N-(3-oxa-1H,1H,2H,2H,4H,4H,5H, 5H-perfluorotridecyl)-amide 40.0 g (32.38 mmol) of the title compound of Example 70d is dissolved in 750 ml of 2-propanol and mixed with 2.0 g of palladium catalyst (10% Pd/C). The reaction solution is hydrogenated for 12 hours at 22° C. and 1 atmosphere of hydrogen pressure. Then, catalyst is filtered out, and the filtrate is evaporated to the dry state. The remaining residue is taken up in 300 ml of dimethyl sulfoxide, and 21.52 g (88.0% of theory) of the above-mentioned title compound is obtained as a colorless and crystalline powder with the decomposition melting point of 88.5° C. from the thus obtained product solution by mixing with a total of 1000 ml of diethyl ether after the precipitated solid is suctioned off.

Elementary analysis: Cld: C, 36.01; H, 5.92; N, 1.75; F, 40.34. Fnd: C, 36.07; H, 6.08; N, 1.76; F, 40.66.

f) Production of a formulation that consists of metal complex I and 6-[1-O-α-D-mannopyranosyl)-hexanoic acid N-(3-oxa-1H,1H,2H,2H,4H,4H,5H,5H-perfluorotridecyl)-amide 3.17 g (4.2 mmol) of the title compound of Example 70e is added to 35 ml of a solution of metal complex 1(280 mmol/L), dissolved in 0.45% aqueous common salt solution (pH 7.4; 0.25 mg/L of CaNa₃DTPA), and it is made up with a 0.9% aqueous common salt solution to a total of 98 ml. It is heated for 2 hours at 60° C. in an ultrasound bath. The solution is cooled to room temperature and set at pH 7.4 with aqueous 2N, sodium hydroxide solution. It is filtered with a 0.2 μm filter, and the filtrate is decanted into vials. A solution that is produced in such a way can be used directly for biological experiments. (The concentration is 100 mmol of Gd/L.)

EXAMPLE 71 a) 1-O-α-D-[(1-Perfluorooctylsulfonylpiperazine-4-carbonyl)-pentyl-5]-2,3,4,6-tetra-O-benzyl-mannopyranose 74.59 g (100 mmol) of the acid that is described in Example 71c and 10.11 g (100 mmol) of triethylamine are dissolved in 800 ml of a mixture that consists of tetrahydrofuran/acetonitrile (mixing ratio 7:3). Then, it is mixed drop by drop at room temperature with 500 ml of a tetrahydrofuran solution of 58.0 g (102.0 mmol) of 1-perfluorooctylsulfonylpiperazine, 10.11 g (100 mmol) of triethylamine and 16.84 g (110 mmol) of 1-hydroxybenzotriazole. The thus obtained reaction solution is mixed at −5° C. with a solution of 22.7 g (110 mmol) of dicyclohexylcarbodiimide, dissolved in 100 ml of tetrahydrofuran, and then it is stirred at −5° C. for another two hours. After the reaction solution has thawed, it is stirred at room temperature for another 12 hours, precipitated dicyclohexylurea is filtered out, and the filtrate that is obtained is evaporated to the dry state in a vacuum. The remaining residue is taken up in 600 ml of ethyl acetate and washed twice with 300 ml each of saturated sodium bicarbonate solution and twice with 300 ml each of water. After the organic phase is dried on sodium sulfate, salt is suctioned out, and the ethyl acetate is drawn off in a vacuum. The remaining oily residue is purified on silica gel with use of dichloromethane/acetone/2-propanol (1 6:2:1) as an eluant.

Yield: 113.01 g (79.8% of theory) of a colorless and viscous oil.

Elementary analysis: Cld: C, 58.52; H, 4.27; N, 1.98; S, 2.26; F, 22.80. Fnd: C, 58.42; H, 4.41; N, 1.80; S, 2.28; F, 23.02.

b) 1-O-α-D-[(1-Perfluorooctylsulfonyl-piperazine4-carbonyl)-pentyl-5]-mannopyranose 50 g (35.30 mmol) of the title compound of Example 71a is dissolved in a mixture that consists of 500 ml of 2-propanol and 50 ml of water, and 2 g of palladium catalyst (10% Pd on activated carbon) is added. It is hydrogenated for 12 hours at room temperature. Catalyst is filtered out, and the filtrate is evaporated to the dry state in a vacuum. The residue is dissolved in 200 ml of methanol, and the reaction product is precipitated by mixing with a total of 800 ml of diethyl ether. After the thus obtained solid is suctioned off, the latter is dried in a vacuum at 50° C.

Yield: 29.51 g (99% of theory) of an amorphous solid.

Elementary analysis: Cld: C, 34.13; H, 3.46; N, 3.32; S, 3.80; F, 38.23. Fnd: C, 34.28; H, 3.81; N, 3.25; S, 3.80; F, 38.01.

c) Production of a formulation that consists of metal complex II and 1-O-α-D-[(1-perfluorooctylsulfonyl-piperazine4-carbonyl)-pentyl-5]-mannopyranose 9.92 g (11.75 mmol) of the title compound of Example 71b is added to 47 ml of a solution of metal complex II (250 mmol/L), dissolved in 0.45% aqueous sodium chloride solution, and it is heated for 10 minutes in the microwave. The solution is cooled to room temperature, filtered with a 0.2 μm filter, and the filtrate is decanted into vials. A thus produced solution can be used directly for biological experiments. (The concentration is 250 mmol of Gd/L.)

EXAMPLE 72 a) 2-Acetamido-2-deoxy-1,3,4,6-(tetra-O-benzyl)-α,β-D-glucopyranose

A total of 24.0 g (108.5 mmol) of 2-acetamido-2-deoxy-α,β-D-glucopyranose, dissolved in 500 ml of absolute dimethyl sulfoxide, is added drop by drop at room temperature to a stirred suspension of 20.16 g (700 mmol; 80% in mineral oil) of sodium hydride in 150 ml of dimethyl sulfoxide. Then, it is allowed to stir f6r another 120 minutes at room temperature, and then 159.5 g (1.26 mol) of benzyl chloride is added in drops. The thus obtained reaction solution is subsequently stirred for another 12 hours at room temperature. For working-up, the reaction solution is slowly poured into 1.5 liters of ice water and then exhaustively extracted with diethyl ether. The combined diethyl ether phases are subsequently washed twice with 600 ml each of saturated sodium bicarbonate solution and twice with 800 ml each of water. After the organic phase is dried on sodium sulfate, salt is suctioned out, and the solvent is drawn off in a vacuum. The remaining oily residue is purified on silica gel with use of ethyl acetate/hexane (1:5) as an eluant.

Yield: 48.68 g (73.6% of theory) of the above-mentioned title compound in the form of a viscous and colorless oil.

Elementary analysis: Cld: C, 70.92; H, 6.45; N, 6.89. Fnd: C, 71.43; H, 6.44; N, 7.02.

b) 1-O-Benzyl-3,4,6-tri-O-benzyl-2-amino-2-deoxy-α,β-D-glucopyranose 30.0 g (49.2 mmol) of the title compound of Example 72a is suspended in a mixture that consists of 750 ml of methanol and 215 ml of water, and it is mixed drop by drop at room temperature with a total of 440 ml (49.2 mmol) of a 0.112 molar aqueous perchloric acid solution. After the addition has been completed, the reaction solution is stirred for 10 more minutes at room temperature, and the thus obtained, now homogenous reaction solution is subsequently evaporated to the dry state in a vacuum. By mixing the remaining oily residue with a mixture that consists of equal parts of hexane and dichloromethane, the latter is brought to crystallization. The crystalline reaction product is suctioned off, washed with hexane and dried in a vacuum at room temperature.

Yield: 27.08 g (86% of theory) of the above-mentioned title compound in the form of its perchlorate, which is present as a colorless, crystalline compound.

Melting point: 180.5–181.5° C.

Elementary analysis: Cld: C, 63.68; H, 5.98; N, 2.19; Cl, 5.54. Fnd: C, 63.43; H, 6.04; N, 2.02; Cl, 5.71.

c) 1,3,4,6-Tetra-O-benzyl-2-deoxy-2-[acetyl-(2-amino-N-ethyl-N-perfluorooctylsulfonyl)-amino]-1-α,β-D-glucopyranose 20.8 g (35.6 mmol) of the 2-[N-ethyl-N-perfluorooctylsulfonyl)-aminoacetic acid and 3.60 g (35.6 mmol) of triethylamine are dissolved in 350 ml of dry tetrahydrofuran. After the reaction solution is cooled to −5° C. to −20° C., a solution of 4.92 g (35.6 mmol) of isobutyl chloroformate in 75 ml of dry tetrahydrofuran is slowly added in drops at this temperature while being stirred, whereby the rate of addition by drops can be selected in such a way that an internal temperature of −10° C. is not exceeded. After a reaction time of 15 minutes at −15° C., a solution of 22.78 g (35.6 mmol) of the perchlorate (title compound of Example 72b) and 3.60 g (35.6 mmol) of triethylamine, in 100 ml of dry tetrahydrofuran at −20° C. is then slowly added in drops. After a reaction time of one hour at −15° C. and two hours at room temperature, the reaction solution is evaporated to the dry state in a vacuum. The remaining residue is taken up in 250 ml of ethyl acetate and washed twice with 100 ml each of saturated sodium bicarbonate solution and once with 200 ml of water. After the organic phase is dried on sodium sulfate, salt is suctioned out, and the ethyl acetate is drawn off in a vacuum. The remaining oily residue is purified on silica gel with use of ethyl acetate/hexane (1:5) as an eluant.

Yield: 33.3 g (84.6% of theory) of the above-mentioned title compound as a colorless and strongly viscous oil.

Elementary analysis: Cld: C, 49.92; H, 3.92; N, 2.53; F, 29.18; S, 2.90. Fnd: C, 49.99; H, 4.11; N, 2.69; F, 29.22; S, 3.01.

d) 2-Deoxy-2-[acetyl-(2-amino-N-ethyl-N-perfluorooctylsulfonyl)-amino]-1-α,β-D-glucopyranose 20.0 g (18.06 mmol) of the title compound of Example 72c is dissolved in 250 ml of 2-propanol and mixed with 1.5 g of palladium catalyst (10% Pd/C). The reaction solution is hydrogenated for 12 hours at 22° C. and 1 atmosphere of hydrogen pressure. Then, catalyst is filtered out, and the filtrate is evaporated to the dry state. The remaining residue is taken up in 300 ml of dimethyl sulfoxide, and 12.65 g (93.8% of theory) of the above-mentioned title compound is obtained as a colorless and crystalline powder from the thus obtained product solution by mixing with 750 ml of a mixture that consists of equal parts of diethyl ether and ethyl acetate after the precipitated solid is suctioned off. The above-mentioned title compound is present as an α/β-anomer mixture, whereby the ratio relative to the two possible anomers was determined at about 1:1.2 by $^1$H-NMR-spectroscopic studies. The title compound is accordingly an almost approximately evenly distributed α/β-anomer mixture.

Melting point: 132.5–133° C.

Elementary analysis: Cld: C, 28.97; N, 2.57; N, 3.75; F, 43.27; S, 4.30. Fnd: C, 29.09; N, 2.56; N, 3.84; F, 43.36; S, 4.42.

e) Production of a formulation that consists of metal complex XIV and 2-deoxy-2-[acetyl-(2-amino-N-ethyl-N-perfluorooctylsulfonyl)-amino]-1-β,β-D-glucopyranose A solution that consists of 4.90 g (6.57 mmol) of the title compound of Example 3d, dissolved in 200 ml of ethanol, is added to 51 ml of a solution of metal complex XIV (300 mmol/L), dissolved in 0.45% sodium chloride solution (pH 7.4/0.25 mg(L of CaNa$_3$DTPA), and it is stirred for 2 hours at 50° C. The solution is evaporated to the dry state in a vacuum, and the residue is made up with distilled water to a total of 153 ml. It is stirred for 10 minutes at 40° C. and filtered with a 0.2 μm filter. The filtrate is decanted into vials. A thus produced solution can be used directly for biological experiments. (The concentration is 100 mmol of Gd/L.)

EXAMPLE 73 a) 1,2,3,4,6-Penta-O-acetyl-α-D-glucopyranose

Analogously to what is described for the synthesis of title compound 70a, the reaction of 100 g (555.0 mmol) of α-D-glucopyranose with a mixture that consists of 1000 ml of absolute pyridine and 1000 ml of acetic acid anhydride after working-up and recrystallization from 95% aqueous ethanol yields 190.6 g (88.0%) of the above-mentioned title compound as a colorless and crystalline compound. By $^1$H-NMR-spectroscopic study of the thus obtained title compound, it was possible to determine the a to β ratio of two possible anomers at ≧98:2. The title compound accordingly is the exclusively α-configured anomer.

Melting point: 110.5° C.

Elementary analysis: Cld: C, 49.21; H, 5.68. Fnd: C, 49.24; H, 5.68.

b) 5-(Ethoxycarbonyl)pentyl-2,3,4,6-tetra-O-acetyl-α-D-glucopyranoside

Analogously to what is described in the synthesis of the title compound of Example 70b, the reaction of 130.0 g (332.8 mmol) of the title compound of Example 4a) with 55.8 ml (332.8 mmol) of 6-hydroxy-hexanoic acid ethyl ester and 50.6 ml (520 mmol) of tin(IV) chloride in 500 ml of 1,2-dichloroethane after column-chromatographic purification (eluant: hexane/ethyl acetate 2:1) yields 101.85 g (62.4% of theory) of the above-mentioned title compound as a colorless and viscous oil. After $^1$H-NMR-spectroscopic study of the title compound, the presence of the β-configuration at the anomeric center was definitively established based on the size of the coupling constant of $J_{1,2}$=8.8 Hz; moreover, said configuration represents the sole existing configuration at the anomeric center. The above-mentioned title compound thus could be shown only in the form of the β-configured anomer.

Elementary analysis: Cld: C, 52.94; H, 6.77. Fnd: C, 52.77; H, 6.70.

c) 5-(Carboxy)pentyl-2,3,4,6-tetra-O-benzyl-α-D-glucopyranoside

A stirred suspension of 100.0 g (204.96 mmol) of the title compound of Example 73b in 150 ml of dioxane is mixed in portions at room temperature and with simultaneous, vigorous stirring with a total of 169.14 g (3.02 mol) of fine-powder potassium hydroxide powder. To make it easier to stir, the reaction mixture is mixed with another 150 ml of dioxane, and the thus obtained suspension is subsequently heated to boiling and mixed drop by drop at this temperature with a total of 264 ml (2.218 mol) of benzyl bromide over a period of two hours. After a reaction time of 4 hours at 110° C. followed by 12 hours at room temperature, the reaction mixture is slowly poured into a total of 2.0 liters of ice water for the purpose of working-up, and the aqueous phase is subsequently completely extracted with diethyl ether. After the thus obtained ether phase is washed and after the subsequent drying of the organic phase on sodium sulfate, salt is suctioned out, and the diethyl ether is drawn off in a vacuum. Excess benzyl bromide is then quantitatively distilled off from the reaction mixture in an oil pump vacuum at an oil bath temperature of 180° C. The thus obtained, remaining oily residue is purified on silica gel with use of ethyl acetate/hexane (1:10) as an eluant.

Yield: 128.8 g (84.3% of theory) of the above-mentioned title compound in the form of a colorless and extremely viscous oil.

Elementary analysis: Cld: C, 75.68; H, 7.16. Fnd: C, 75.66; H, 7.23.

d) 2,3,4,6-Tetra-O-benzyl-1-O-β-D-[6-hexanoic acid-N-(3-oxa-1H,1H,2H,2H,4H,4H,5H,5H-perfluorotridecyl)-amide]-glucopyranose 68.5 g (91.79 mmol) of the acid that is described in Example 73c and 9.25 g (91.79 mmol) of triethylamine are dissolved in 825 ml of dry tetrahydrofuran. After the reaction solution is cooled to −15° C. to −20° C., a solution of 12.64 g (92.5 mmol) of isobutyl chloroformate in 150 ml of dry tetrahydrofuran is slowly added in drops at this temperature while being stirred, whereby the rate of addition by drops can be selected in such a way that an internal temperature of −10° C. is not exceeded. After a reaction time of 15 minutes at −15° C., a solution of 46.40 g (91.79 mmol) of 1H,1H,2H,2H-heptadecafluoro-1-(2-aminoethoxy)-decane and 9.25 g (91.79 mmol) of triethylamine is then slowly added in drops as a solution to 200 ml of dry tetrahydrofuran at −20° C. After a reaction time of one hour at −15° C. and two hours at room temperature, the reaction solution is evaporated to the dry state in a vacuum, The remaining residue is taken up in 250 ml of ethyl acetate and washed twice with 300 ml each of saturated sodium bicarbonate solution and once with 400 ml of water. After the organic phase is dried on sodium sulfate, salt is suctioned out, and the ethyl acetate is drawn off in a vacuum. The remaining oily residue is purified on silica gel with use of dichloromethane/hexane/2-propanol (10:5:1) as an eluant.

Yield: 104.7 g (92.4% of theory) of the above-mentioned title compound as a colorless and strongly viscous oil.

Elementary analysis: Cld: C, 57.38; H, 4.98; N, 1.13; F, 26.15. Fnd: C, 57.27; H, 5.09; N, 1.11; F, 26.08.

e) 1-O-β-D-[6-Hexanoic acid-N-(3-oxa-1H,1H,2H,2H,4H, 4H,5H,5H-perfluorotridecy)-amide]-glucopyranose 40.0 g (32.38 mmol) of the title compound of Example 73d is dissolved in 750 ml of 2-propanol and mixed with 2.0 g of palladium catalyst (10% Pd/C). The reaction solution is hydrogenated for 12 hours at 22° C. and 1 atmosphere of hydrogen pressure. Then, catalyst is filtered out, and the filtrate is evaporated to the dry state. The remaining residue is taken up in 300 ml of dimethyl sulfoxide, and 22.05 g (90.2% of theory) of the title compound is obtained as a colorless and crystalline powder with a decomposition melting point of 122–124° C. from the thus obtained product solution by mixing with a total of 1000 ml of diethyl ether and subsequent suctioning-off of the precipitated solid.

Elementary analysis: Cld: C, 36.01; H, 5.92; N, 1.75; F, 40.34. Fnd: C, 36.07; H, 6.08; N, 1.76; F, 40.66.

f) Production of a formulation that consists of the title compound of Example 12 from WO 99/01161 (1,4,7-tris {1,4,7-tris(N-carboxylatomethyl)-10-(N-1-methyl-3-aza-2, 5-dioxo-pentane-1,5-diyl]-1,4,7,10-tetraazacyclododecane, Gd complex}-10-[2-(N-ethyl-N-perfluorooctylsulfonyl)-amino]-acetyl-1,4,7,10-tetraazacyclododecane) and 1-O-β-D-[6-hexanoic acid-N-(3-oxa-1H,1H,2H,2H,4H,4H,5H,5H-perfluorotridecyl)-amide]-glucopyranose 20.29 g (25.9 mmol) of the title compound of Example 73e is added to 37 ml of a solution of 1,4,7-tris {1,4,7-tris (N-carboxylatomethyl)-10-(N-1-methyl-3-aza-2,5-dioxo-pentane-1,5-diyl]-1,4,7,10-tetraazacyclododecane, Gd complex}-10-[2-(N-ethyl-N-perfluorooctylsulfonyl)-amino]-acetyl-1,4,7,10-tetraazacyclododecane (300 mmol), dissolved in 0.45% aqueous common salt solution (pH 7.4; 0.25 mg/L of CaNa₃DTPA), and it is made up with a 0.9% aqueous common salt solution to a total of 111 ml. It is heated for 2 hours at 60° C. in an ultrasound bath. The solution is cooled to room temperature and set at pH 7.4 with aqueous 2N, sodium hydroxide solution. It is filtered with a 0.2 μm filter, and the filtrate is decanted into vials. A thus produced solution can be used directly for biological experiments. (The concentration is 100 mmol of Gd/L.)

EXAMPLE 74 a) 1-O-(1H,1H,2H,2H-Perfluorodecyl)-(2,3,4,6-tetra-O-acetyl)-α-D-mannopyranose

The reaction of 50 g (128.09 mmol) of the title compound of Example 70a, which is used as a 4:1 mixture relative to the α,β-anomers, with a solution of 75.84 g (128.1 mmol) of 1-hydroxy-1H,1H,2H,2H-perfluorodecane in 150 ml of 1,2-dichloroethane and a total of 19.47 g (166.53 mmol) of tin(IV) chloride, analogously to what is described for the syntheses of the title compounds of Examples 1b) and 4b), results, after working-up and column-chromatographic purification (eluant: hexane/ethyl acetate, 2:1), in the formation of 74.2 g (63.4% of theory) of the above-mentioned title compound in the form of a viscous and colorless oil. After ¹H-NMR-spectroscopic study of the title compound, the presence of the α-configuration at the anomeric center was definitively established based on the size of the coupling constant of $J_{1,2}=1.3$ Hz; moreover, said configuration represents the sole existing configuration at the anomeric center, so that the above-mentioned title compound accordingly could be represented only in the form of the pure α-configured anomer.

Elementary analysis: Cld: C, 44.65; H, 2.53; F, 35.32. Fnd: C, 44.77; H, 2.61; F, 35.09.

b) 1-(1H,1H,2H,2H-Perfluorodecyl)-α-D-mannopyranose 25 g (27.33 mmol) of the title compound of Example 74a is suspended in 400 ml of absolute methanol and mixed at 5° C. with a catalytic amount of sodium methanolate. After a reaction time of 3 hours at room temperature, even thin-layer chromatographic checking (eluant: chloroform/methanol 9:1) of the course of the reaction indicates quantitative reaction. For the purpose of working-up, the now clear reaction solution is neutralized by mixing with Amberlite IR 120 (H⁺ form)-cation-exchange resin, exchanger is suctioned out, and the thus obtained methanolic filtrate is drawn off in a vacuum until a dry state is reached. The crystalline residue that is obtained is purified by twice-repeated recrystallization of ethanol. After ¹H-NMR-spectroscopic study of the title compound, the presence of the α-configuration at the anomeric center was definitively established based on the size of the coupling constant of $J_{1,2}=1.0$ Hz. The existing α-configuration is the sole existing configuration at the anomeric center, i.e., the amount of β-configured anomer of the title compound that can possibly be formed lies below the ¹H-NMR-spectroscopic detection limit. The above-mentioned title compound was accordingly represented only in the form of the pure α-configured anomer, Yield: 16.2 g (94.6% of theory) of a colorless and crystalline solid.

Melting point: 172–174° C. while decomposing.

Elementary analysis: Cld: C, 30.69; H, 2.41; F, 51.57. Fnd: C, 30.57; H, 2.48; F, 51.65.

c) Production of a formulation that consists of metal complex II and 1-O-(1H,1H,2H,2H-perfluorodecyl)α-D-mannopyranose A solution that consists of 2.01 g (3.21 mmol) of the title compound of Example 74b, dissolved in 200 ml of ethanol, is added to 50 ml of a solution of metal complex II (150 mmol/L), dissolved in 0.45% sodium chloride solution (pH 7.4/0.25 mg/L of CaNa₃DTPA), and it is stirred for 2 hours at 50° C. The solution is evaporated to the dry state in a vacuum, and the residue is made up with distilled water to a total of 75 ml. It is stirred for 10 minutes at 40° C. and filtered with a 0.2 μm filter. The filtrate is decanted into vials. A thus produced solution can be used directly for biological experiments. (The concentration is 100 mmol of Gd/L.)

EXAMPLE 75 a) 1-O-(1H,1H,2H,2H-Perfluorododecyl)-2,3,4,6-tetra-O-acetyl-α-D-mannopyranose

The reaction of 35 g (89.66 mmol) of the title compound of Example 70a, which is used as a 4:1 mixture relative to the α,β-anomers, with a solution of 50.60 g (89.7 mmol) of I-hydroxy-1H,1H,2H,2H-perfluorododecane in 100 ml of 1,2-dichloroethane and a total of 13.63 g (16.61 mmol) of tin(IV) chloride, analogously to what is described for the syntheses of the title compounds of Examples 1b), 4b) and 5b), results, after working-up and column-chromatographic purification (eluant: hexane/ethyl acetate=2:1), in the formation of 62.49 g (68.7% of theory) of the above-mentioned title compound in the form of a viscous and colorless oil. After ¹H-NMR-spectroscopic study of the title compound, the presence of the α-configuration at the anomeric center was definitively established based on the size of the coupling constant of $J_{1,2}=1.4$ Hz; moreover, said α-configuration represents the sole existing configuration at the anomeric center, so that accordingly the above-mentioned title compound can be represented only in the form of the pure α-configured anomer.

Elementary analysis: Cld: C, 42.62; H, 2.28; F, 39.32. Fnd: C, 42.55; H, 2.38; F, 39.40.

b) 1-O-(1H,1H,2H,2H-Perfluorododecyl)-α-D-mannopyranose 25 g (24.64 mmol) of the title compound of Example 75a is suspended in 400 ml of absolute methanol and mixed at 5° C. with a catalytic amount of sodium methanolate. After a reaction time of 3 hours at room temperature, even thin-layer chromatographic checking (eluant: chloroform/methanol=9:1) of the course of the reaction indicates quantitative reaction. For the purpose of working-up, the now clear reaction solution is neutralized by mixing with Amberlite IR 120 (H⁺ form)-cation-exchange resin, exchanger is suctioned out, and the thus obtained methanolic filtrate is drawn off in a vacuum until a dry state is reached. The crystallization residue that is obtained is purified by twice-repeated recrystallization of a mixture that consists of 2-propanol/ethanol (1:1). After ¹H-NMR-spectroscopic study of the title compound, the presence of the α-configuration at the anomeric center was definitively established based on the size of the coupling constant of $J_{1,2}=0.9$ Hz. The existing α-configuration is the sole existing configuration at the anomeric center, i.e., the amount of β-configured anomer of the title compound that can possibly be formed lies below the ¹H-NMR-spectroscopic detection limit. The above-mentioned title compound was accordingly represented only in the form of the pure α-configured anomer.

Yield: 16.96 g (90.8% of theory) of a colorless and crystalline solid.

Melting point: 187–188° C. while decomposing.

Elementary analysis: Cld: C, 29.77; H, 2.08; F, 54.93. Fnd: C, 29.70; H, 2.28; F, 54.83.

c) Production of a formulation that consists of metal complex VI and 1-O-(1H,1H,2H,2H-perfluorodecyl)-α-D-mannopyranose 1.70 g (2.34 mmol) of the title compound of Example 75b is added to 52 ml of a solution of metal complex VI (180 mmol/L), dissolved in 0.45% aqueous sodium chloride solution, and it is heated for 10 minutes in the microwave. The solution is cooled to room temperature, filtered with a 0.2 μm filter, and the filtrate is decanted into vials. A thus produced solution can be used directly for biological experiments. (The concentration is 180 mmol of Gd/L.)

EXAMPLE 76 a) 2,3,4,6-Tetra-O-acetyl)1-O-α-D-[3,6,9-trioxa-($C_{12}$–$C_{19}$-heptadecafluoro)-nonadecyl]-mannopyranose The reaction of 20 g (51.23 mmol) of the title compound of Example 70a, which is used as a 4:1 mixture relative to the α,β-anomers, with a solution of 30.54 g (51.23 mmol) of 1-hydroxy-tris-(1H,1H,2H,2H-O)-1H,1H,2H,2H-perfluorodecane in 100 ml of 1,2-dichloroethane and a total of 5.98 g (51.23 mmol) of tin(IV) chloride, analogously to what is described for the syntheses of the title compounds of Examples 1b), 4b) and 5b), results, after working-up and column-chromatographic purification (eluant: hexane/ethyl acetate=1:1), in the formation of 34.22 g (72.1% of theory) of the above-mentioned title compound in the form of a viscous and colorless oil. After $^1$H-NMR-spectroscopic study of the title compound, the presence of the α-configuration at the anomeric center was definitively established based on the size of the coupling constant of $J_{1,2}$=1.1 Hz; moreover, said α-configuration represents the sole existing configuration at the anomeric center, so that accordingly the above-mentioned title compound can be represented only in the form of the pure α-configured anomer.

Elementary analysis: Cld: C, 38.89; H, 3.81; F, 34.86. Fnd: C, 39.02; H, 3.77; F, 34.90.

b) 1-O-α-D-[3,6,9-Trioxa-($C_{12}$–$C_{19}$-heptadecafluoro)-nonadecyl]-mannopyranose 20 g (21.58 mmol) of the title compound of Example 76a is suspended in 350 ml of absolute methanol and mixed at 5° C. with a catalytic amount of sodium methanolate. After a reaction time of 3 hours at room temperature, even thin-layer chromatographic checking (eluant: chloroform/methanol=6:1) of the course of the reaction indicates quantitative reaction. For working-up, the now clear reaction solution is neutralized by mixing with Amberlite IR 120 (H$^+$ form)-cation-exchange resin, exchanger is suctioned out, and the thus obtained methanolic filtrate is drawn off in a vacuum until a dry state is reached. The crystalline residue that is obtained is purified by twice-repeated recrystallization from a mixture that consists of ethyl acetate/2-propanol/ethanol (1:0.5:1). After $^1$H-NMR-spectroscopic study of the tide compound, the presence of the α-configuration at the anomeric center was definitively established based on the size of the coupling constant of $J_{1,2}$=1.0 Hz. The existing α-configuration is the sole existing configuration at the anomeric center, i.e., the amount of β-configured anomer of the title compound that can possibly be formed lies below the $^1$H-NMR-spectroscopic detection limit. The above-mentioned title compound was accordingly represented only in the form of the pure α-configured anomer.

Yield: 15.20 g (92.9% of theory) of a colorless, crystalline solid.

Melting point: 141° C.

Elementary analysis: Cld: C, 34.84; H, 3.59; F, 42.58. Fnd: C, 34.72; H, 3.66; F, 42.67.

c) Production of a formulation that consists of the title compound of Example 68 and 1-O-α-D-[3,6,9-trioxa-($C_{12}$–$C_{19}$-heptadecafluoro)-nonadecyl]-mannopyranose 3.71 g (4.89 mmol) of the title compound of Example 76b is added to 38 ml of a solution of the title compound of Example 68 (300 mmol/L), dissolved in 0.45% aqueous common salt solution (pH 7.4; 0.25 mg/L of CaNa$_3$DTPA), and it is made up with a 0.9% aqueous common salt solution to a total of 114 ml. It is heated for 2 hours at 60° C. in an ultrasound bath. The solution is cooled to room temperature and set at pH 7.4 with aqueous 2N, sodium hydroxide solution. It is filtered with a 0.2 μm filter, and the filtrate is decanted into vials. A thus produced solution can be used directly for biological experiments. (The concentration is 100 mmol of Gd/L.)

EXAMPLE 77 a) 2,3,4,6-Tetra-O-acetyl-1-α-D-[3-thiopropionic acid-N-(3-oxa-1H,1H,2H,2H,4H,4H,5H,5H-perfluorotridecyl)-amide]-mannopyranose 25.0 g (57.28 mmol) [production according to: Ponpipom, Mitree M.; Bugianesi, Robert L.; Robbins, James C.; Doebber, T. W.; Shen, T. Y.; J. Med. Chem.; 24; 12; 1981; 1388–1395] of 3-(tetra-O-acetyl-α-D-mannopyranosylmercapto)-propionic acid and 5.77 g (57.28 mmol) of triethylamine are dissolved in 500 ml of dry tetrahydrofuran. After the reaction solution is cooled to −15° C. to −20° C., a solution of 7.82 g (57.28 mmol) of isobutyl chloroformate in 100 ml of dry tetrahydrofuran is slowly added in drops at this temperature while being stirred, whereby the rate of addition by drops can be selected in such a way that an internal temperature of −10° C. is not exceeded. After a reaction time of 15 minutes at −15° C., a solution of 29.05 g (57.28 mmol) of 1H,1H,2H,2H-heptadecafluoro-1-(2-aminoethyoxy)-decane and 5.77 g (57.28 mmol) of triethylamine is subsequently slowly added in drops as a solution to 200 ml of dry tetrahydrofuran at −20° C. After a reaction time of one hour at −15° C. and two hours at room temperature, the reaction solution is evaporated to the dry state in a vacuum. The remaining residue is taken up in 250 ml of ethyl acetate, and it is washed twice with 200 ml each of saturated sodium bicarbonate solution and once with 300 ml of water. After the organic phase is dried on sodium sulfate, salt is suctioned out, and the ethyl acetate is drawn off in a vacuum. The remaining oily residue is purified on silica gel with use of dichloromethane/hexane/2-propanol (8:5:1) as an eluant.

Yield: 44.90 g (84.7% of theory) of the above-mentioned title compound as a colorless and strongly viscous oil.

Elementary analysis: Cld: C, 37.63; H, 3.48; N, 1.51; S, 3.46; F, 34.89. Fnd: C, 37.77; H, 3.37; N, 1.61; S, 3.57; F, 35.21.

b) 1-α-D-[3-Thiopropionic acid-N-(3-oxa-1H,1H,2H,2H,4H,4H,5H,5H-perfluorotridecyl)-amide]-mannopyranose 30 g (32.41 mmol) of the title compound of Example 77a is suspended in 400 ml of absolute methanol and mixed at 5° C. with a catalytic amount of sodium methanolate. After a reaction time of 3 hours at room temperature, even thin-layer chromatographic checking (eluant: chloroform/methanol=9:1) of the course of the reaction indicates quantitative reaction. For working-up, the now clear reaction solution is neutralized by mixing with Amberlite IR 120 (H$^+$ form)-cation-exchange resin, exchanger is suctioned out, and the thus obtained methanolic filtrate is drawn off in a vacuum until a dry state is reached. The crystalline residue that is obtained is purified by recrystallization from a mixture that consists of ethyl acetate/methanol (0.5:1). After $^1$H-NMR-spectroscopic study of the title compound, the presence of the α-configuration at the anomeric center was definitively established based on the size of the coupling constant of $J_{1,2}$=1.1 Hz. The existing α-configuration is the sole existing configuration at the anomeric center, i.e., the amount of β-configured anomer of the title compound that can possibly be formed lies below the $^1$H-NMR-spectroscopic detection limit. The above-mentioned title compound was accordingly represented only in the form of the pure α-configured anomer.

Yield: 23.76 g (96.8% of theory) of a colorless and crystalline solid.

Melting point: 113–114.5° C.

Elementary analysis: Cld: C, 33.30; H, 3.19; N, 1.85; S, 4.23; F, 42.64. Fnd: C, 33.21; H, 3.26; N, 1.96; S, 4.08; F, 42.77.

c) Production of a formulation that consists of the title compound of Example 66 and 1-α-D-[3-thiopropionic acid-N-(3-oxa-1H,1H,2H,2H,4H,4H,5H,5H-perfluorotridecyl)-amide]-mannopyranose A solution that consists of 27.41 g (36.19 mmol) of the title compound of Example 77b, dissolved in 200 ml of ethanol, is added to 47 ml of a solution of the title compound of Example 66 (330 mmol/L), dissolved in 0.45% sodium chloride solution (pH 7.4/0.25 mg/L of CaNa$_3$DTPA), and it is stirred for 2 hours at 50° C. The solution is evaporated to the dry state in a vacuum, and the residue is made up with distilled water to a total of 155 ml. It is stirred for 10 minutes at 40° C. and filtered with a 0.2 µm filter. The filtrate is decanted into vials. A thus produced solution can be used directly for biological experiments. (The concentration is 100 mmol of Gd/L.)

EXAMPLE 78 a) 2,3,4,6-Tetra-O-acetyl-1-β-D-[3,6,9-trioxa-$C_{12}$–$C_{19}$-heptadecafluoro)-nonadecyl]-glucopyranosyluronic acid 20.2 g (50.85 mmol) of methyl (1-bromo-2,3,4-tri-O-acety-α-D-glucopyranoside)uronate [production according to: Pelzer; Hoppe-Seyler's Z. Physiol. Chem; 314; 1949; 234,237 and Goebel; Babers; J. Biol. Chem.; 111; 1935; 347, 350 and Bollenback et al.; J. Amer. Chem. Soc.; 77; 1955; 3310, 3313] and 60.64 g (101.7 mmol) of 3,6,9-trioxa-($C_{12}$–$C_{19}$-heptadecafluoro)-nonadecan-1-ol are dissolved in 250 ml of anhydrous acetonitrile and mixed at room temperature with 13.0 g of freshly precipitated silver oxide. After a reaction time of 12 hours at room temperature, insoluble silver salts are filtered out, the salts are thoroughly rewashed with dichloromethane, and the thus obtained filtrate is drawn off in a vacuum until a dry state is reached. The remaining residue is purified by column chromatography (eluant: hexane/ethyl acetate=3:1).

Yield: 22.99 g (53.3% of theory) of the above-mentioned title compound as a colorless, highly viscous oil.

Elementary analysis: Cld: C, 41.05; H, 3.92; F, 38.06. Fnd: C, 41.20; H, 3.76; F, 38.22.

b) 1-O-β-D-[3,6,9-Trioxa-($C_{12}$–$C_{19}$-heptadecafluoro)-nonadecyl]-glucopyranosyluronic acid 10.0 g (11.78 mmol) of the title compound of Example 78a is suspended in 200 ml of a mixture that consists of methanol and 0.5 molar sodium hydroxide solution at a ratio of 2:1 while being stirred at room temperature. After a reaction time of 12 hours at room temperature, the now clear reaction mixture is neutralized for working-up by mixing with Amberlite IR 120 (H$^+$ form)-cation-exchange resin, exchanger is suctioned out, and the thus obtained methanolic-aqueous filtrate is drawn off in a vacuum until a dry state is reached. The crystalline residue that is obtained is purified by recrystallization from a mixture that consists of ethyl acetate methanol (0.25:1). After $^1$H-NMR-spectroscopic study of the title compound, the presence of the β-configuration at the anomeric center was definitively established based on the size of the coupling constant of $J_{1,2}$=9.2 Hz. The existing β-configuration is the sole existing configuration at the anomeric center, i.e., the amount of P-configured anomer of the title compound that can possibly be formed lies below the $^1$H-NMR-spectroscopic detection limit. The above-mentioned title compound was accordingly represented only in the form of the pure β-configured anomer.

Melting point: 78.5° C.

Elementary analysis: Cld: C, 34.21; H, 3.26; F, 41.81. Fnd: C, 34.38; H, 3.26; F, 41.90.

c) Production of a formulation that consists of metal complex I and I-O-β-D-[3,6,9-trioxa-($C_{12}$–$C_{19}$-heptadecafluoro)-nonadecyl]-glucopyranosyluronic acid 19.18 g (24.83 mmol) of the title compound of Example 78b is added to 38 ml of a solution of metal complex I (280 mmol/L), dissolved in 0.45% aqueous common salt solution (pH 7.4; 0.25 mg/L of CaNa$_3$DTPA), and it is made up with a 0.9% aqueous common salt solution to a total of 53.2 ml. It is heated for 2 hours at 60° C. in an ultrasound bath. The solution is cooled to room temperature and set at pH 7.4 with aqueous 2N, sodium hydroxide solution. It is filtered with a 0.2 µm filter, and the filtrate is decanted into vials. A thus produced solution can be used directly for biological experiments. (The concentration is 200 mmol of Gd/L.)

EXAMPLE 79 a) 6(2-Oxa-1H,1H,3H,3H,4H,4H-perfluorodecyl)-O$^1$,O$^2$,O$^3$,O$^4$-diisopropylidene-α-D-galactopyranose A total of 12.15 g (46.66 mmol) of O$^1$,O$^2$,O$^3$,O$^4$-diisopropylidene-α-galactopyranose [production according to: Levene; Meyer; J. Biol. Chem.; 64; 1925; 473 and McCreath; Smith; J. Chem. Soc.; 1939; 387, 389 and Freudenberg; Hixon; Chem. Ber.; 56; 1923; 2119, 2122], dissolved in 200 ml of absolute dimethylformamide, is added drop by drop at room temperature to a stirred suspension of 2.01 g (70.0 mmol; 80% in mineral oil) of sodium hydride in 25 ml of dimethylformamide. It is then allowed to stir for 120 more minutes at room temperature, and subsequently a total of 30.09 g (48.0 mmol) of 1-bromo-1H,1H,2H,2H-perfluorododecane, dissolved in 150 ml of absolute dimethylformamide, is slowly added in drops. The thus obtained reaction solution is subsequently stirred for another 12 hours at room temperature. For working-up, the reaction solution is slowly poured into I liter of ice water and then exhaustively extracted with diethyl ether. The combined organic phases are subsequently washed twice with 200 ml each of saturated sodium bicarbonate solution and twice with 200 ml each of water. After the organic phase is dried on sodium sulfate, salt is suctioned out, and the solvent is drawn off in a vacuum. The remaining oily residue is purified on silica gel with use of ethyl acetate/hexane (1:10) as an eluant.

Yield: 29.8 g (79.3% of theory) of the above-mentioned title compound in the form of a viscous, colorless oil.

Elementary analysis: Cld: C, 35.75; H, 2.87; F, 49.47. Fnd: C, 35.64; H, 2.98; F, 49.54.

b) 6-(2-Oxa-1H,1H,3H,3H,4H,4H-perfluorodecyl)-α-D-galactopyranose 20 g (24.8 mmol) of the title compound of Example 79a is mixed with 300 ml of a 1% aqueous sulfuric acid solution and stirred for 3 hours at 80° C. After cooling to room temperature, it is neutralized by mixing with aqueous barium hydroxide solution, precipitated barium sulfate is subsequently filtered out, and the thus obtained clear aqueous product solution is freeze-dried. By $^1$H-NMR-spectroscopic study of the title compound, it was possible to show clearly the presence of two possible configurations at the anomeric center, whereby the existing α/β-configuration ratio according to $^1$H-NMR-spectroscopic study was determined with 1:1.4 (α:β) at the anomeric center. The above-mentioned title compound was accordingly isolated only in the form of 1:1.4 (α:β)-anomer mixture, i.e., an anomeric separation was eliminated.

Yield: 15.28 g (98.4% of theory) of the above-mentioned title compound as a colorless lyophilizate Elementary analysis (relative to anhydrous substance): Cld: C, 35.75; H, 2.87; F, 49.47. Fnd: C, 35.64; H, 2.98; F, 49.54.

c) Production of a formulation that consists of the title compound of Example 67 and 6-(2-oxa-1; H, 1 H,3H,3H, 4H,4H-perfluorodecyl)-α-D-galactopyranose A solution that consists of 1.68 g (2.69 mmol) of the title compound of Example 79b, dissolved in 200 ml of ethanol, is added to 43 ml of a solution of the title compound of Example 67 (250 mmol/L), dissolved in 0.45% sodium chloride solution (pH 7.4/0.25 mg/L of CaNa$_3$DTPA), and it is stirred for 2 hours at 50° C. The solution is evaporated to the dry state in a vacuum, and the residue is made up with distilled water to a total of 107.5 ml. It is stirred for 10 minutes at 40° C. and filtered with a 0.2 μm filter. The filtrate is decanted into vials. A thus produced solution can be used directly for biological experiments. (The concentration is 100 mmol of Gd/L.)

EXAMPLE 80 a) 1-O-α-D-[(1-Perfluorooctylsulfonylpiperazine-4-carbonyl-)-methyl]-mannopyranose 30 g (52.8 mmol) of 1-perfluorooctylsulfonylpiperazine (production described in DE 196 03 033) and 31.73 g (53 mmol) of 2,3,4,6-tetra-O-benzyl-α-D-carboxymethyl-mannopyranose (production described in DE 19728 954) are dissolved in 300 ml of tetrahydrofuran. At 0° C., 24.73 g (100 mmol) of EEDQ (=1,2-dihydro-2-ethoxyquinoline-1-carboxylic acid ethyl ester) is added, and it is stirred for 3 hours at 0° C., then for 6 hours at room temperature. The solution is evaporated to the dry state in a vacuum, and the residue is purified by flash chromatography on silica gel (mobile solvent: hexane/ethyl acetate=10:1). The product-containing fractions are evaporated to the dry state, the residue is dissolved in a mixture that consists of 200 ml of methanol/150 ml of dichloromethane, and it is hydrogenated for 8 hours on palladium/carbon (10% Pd/C 2 g). Hydrogenating catalyst is filtered out, and the filtrate is evaporated to the dry state. The residue is recrystallized from acetone/diethyl ether.

Yield: 30.39 g (73% of theory) of a waxy, colorless solid.

Elementary analysis: Cld: C, 30.47; H, 2.68; F, 40.96; N, 3.55; S, 4.07. Fnd: C, 30.61; H, 2.75; F, 41.10; N, 3.46; S, 4.12.

b) Production of a formulation that consists of metal complex I and 1-O-α-D-[(1-perfluorooctylsulfonylpiperazine-4-carbonyl-)-methyl]-mannopyranose 4.71 g (5.97 mmol) of the title compound of Example 80a is added to 32 ml of a solution of metal complex I (280 mmol/L), dissolved in 0.45% aqueous common salt solution (pH 7.4; 0.25 mg/L of CaNa$_3$DTPA), and it is made up with a 0.9% aqueous common salt solution to a total of 55 ml. It is heated for 2 hours at 60° C. in an ultrasound bath. The solution is cooled to room temperature and set at pH 7.4 with aqueous 2N, sodium hydroxide solution. It is filtered with a 0.2 μm filter, and the filtrate is decanted into vials. A thus produced solution can be used directly for biological experiments. (The concentration is 200 mmol of Gd/L.)

EXAMPLE 81 a) 3-Oxa-2H,2H,4H,4H,5H,5H-perfluorotridecanoic acid, sodium salt 20 g (38.3 mmol) of 3-oxa-2H,2H,4H,4H,5H,5H-perfluorotridecanoic acid (production described in DE 196 03 033) is dissolved in 300 ml of ethanol, and 7.7 ml of 5N aqueous sodium hydroxide solution is added. It is evaporated to the dry state, and the residue is dried in a vacuum drying oven (8 hours, 60° C.).

Yield: 20.85 g (quantitative) of a colorless, crystalline powder.

Elementary analysis: Cld: C, 26.49; H, 1.11; F, 59.35; Na, 4.22. Fnd: C, 26.60; H, 1.19; F, 59.47; Na, 4.30.

b) Production of a formulation that consists of metal complex I and 3-oxa-2H,2H,4H,4H,5H,5H-perfluorotridecanoic acid, sodium salt 2.09 g (3.84 mmol) of the title compound of Example 81 a is added to 32 ml of a solution of metal complex I (280 mmol/L), dissolved in 0.45% aqueous common salt solution (pH 7.4; 0.25 mg/L of CaNa$_3$DTPA), and it is made up with a 0.9% aqueous common salt solution to a total of 90 ml. It is heated for 2 hours at 60° C. in an ultrasound bath. The solution is cooled to room temperature and set at pH 7.4 with aqueous 2N, sodium hydroxide solution. It is filtered with a 0.2 μm filter, and the filtrate is decanted into vials. A thus produced solution can be used directly for biological experiments. (The concentration is 100 mmol of Gd/L.)

c) Production of a formulation that consists of metal complex I and 3-oxa-2H,2H,4H,4H,5H,5H-perfluorotridecanoic acid, sodium salt 1.00 g.(1.84 mmol) of the title compound of Example 81a is added to 32 ml of a solution of metal complex I (280 mmol/L), dissolved in 0.45% aqueous common salt solution (pH 7.4; 0.25 mg/L of CaNa$_3$DTPA), and it is made up with a 0.9% aqueous common salt solution to a total of 90 ml. It is heated for 2 hours at 60° C. in an ultrasound bath. The solution is cooled to room temperature and set at pH 7.4 with aqueous 2N, sodium hydroxide solution. It is filtered with a 0.2 μm filter, and the filtrate is decanted into vials. A thus produced solution can be used directly for biological experiments. (The concentration is 100 mmol of Gd/L.)

d) Production of a formulation that consists of metal complex I and 3-oxa-2H,2H,4H,4H,5H,5H-perfluorotridecanoic acid, sodium salt 0.54 g (1.0 mmol) of the title compound of Example 81a is added to 32 ml of a solution of metal complex I (280 mmol/L), dissolved in 0.45% aqueous common salt solution (pH 7.4; 0.25 mg/L of CaNa$_3$DTPA), and it is made up with a 0.9% aqueous common salt solution to a total of 90 ml. It is heated for 2 hours at 60° C. in an ultrasound bath. The solution is cooled to room temperature and set at pH 7.4 with aqueous 2N, sodium hydroxide solution. It is filtered with a 0.2 am filter, and the filtrate is decanted into vials. A thus produced solution can be used directly for biological experiments. (The concentration is 100 mmol of Gd/L.)

EXAMPLE 82 a) 1-Perfluorooctylsulfonyl-4-(3,6,9,12,15-pentaoxahexadecanoyl)-piperazine 20 g (35.2 mmol) of perfluorooctylsulfonylpiperazine (see Example 80a) is dissolved in 300 ml of dichloromethane, and 5.06 g (50 mmol) of triethylamine is added. It is cooled to 0° C. and 14.24 g (50 mmol) of 3,6,9,12,15-pentaoxahexanoic acid chloride is added in drops within 20 minutes, and it is stirred for 3 hours at 0° C. 400 ml of 5% aqueous hydrochloric acid is added, and it is thoroughly stirred. The organic phase is separated, dried on magnesium sulfate and evaporated to the dry state in a vacuum. The residue is chromatographed on silica gel (mobile solvent= dichloromethane/methanol: 15:1).

Yield: 26.44 (92% of theory) of a waxy solid.

Elementary analysis: Cld: C, 33.83; H, 3.58; N, 3.43; F, 39.55; S, 3.93. Fnd: C, 33.96; H, 3.66; N, 3.50; F, 39.67; S, 3.82.

b) Production of a formulation that consists of metal complex I and 1-perfluorooctylsulfonyl-4-(3,6,9,12,15-pentaoxahexadecanoyl)-piperazine 4.61 g (5.64 mmol) of the title compound of Example 82a is added to 47 ml of a solution of metal complex I (280 mmol/L), dissolved in 0.45% aqueous common salt solution (pH 7.4; 0.25 mg/L of $CaNa_3DTPA$), and it is made up with a 0.9% aqueous common salt solution to a total of 66 ml. It is heated for 2 hours at 60° C. in an ultrasound bath. The solution is cooled to room temperature and set at pH 7.4 with aqueous 2N sodium hydroxide solution. It is filtered with a 0.2 μm filter, and the filtrate is decanted into vials. A thus produced solution can be used directly for biological experiments. (The concentration is 200 mmol of Gd/L.)

EXAMPLE 83 a) 1H,1H,2H,2H-Perfluorodecyl-p-toluenesulfonic acid ester 20 g (43.1 mmol) of 1H,1H,2H,2H-perfluorodecanol is dissolved in 200 ml of pyridine, and 9.53 g (50 mmol) of p-toluenesulfonic acid chloride is added in portions at 0° C. It is stirred for 5 hours at room temperature. The solution is poured into 1000 ml of ice water and stirred for 10 minutes. The precipitate is filtered off, washed with a lot of water and then recrystallized from acetone.

Yield: 22.04 g (97% of theory) of a colorless, crystalline solid.

Elementary analysis: Cld: C, 22.78; H, 0.76; F, 61.26; S, 6.08. Fnd: C, 22.89; H, 0.70; F, 61.39; S, 6.15.

b) $C_{18}$–$C_{25}$-Heptadeca-fluoro-3,6,9,12,15-pentaoxa-pentacosan-1-ol 20 g (37.94 mmol) of the title compound of Example 83a, 35.74 g (150 mmol) of pentaethylene glycol and 1 g of 18-crown-6 are dissolved in 300 ml of tetrahydrofuran, and 10.1 g (180 mmol) of fine-powder potassium hydroxide is added. It is stirred for 10 hours at room temperature. Solid is filtered out, and the filtrate is evaporated to the dry state in a vacuum. The residue is chromatographed on silica gel (mobile solvent: dichloromethane/methanol=15:1).

Yield: 5.45 g (21% of theory) of a colorless, viscous oil.

Elementary analysis: Cld: C, 35.10; H, 3.68; F, 47.19. Fnd: C, 35.22; H, 3.77; F, 47.10.

c) Production of a formulation that consists of the title compound of Example 69 and $C_{18}$–$C_{25}$-heptadeca-fluoro-3,6,9,12,15-pentaoxa-pentacosan-1-ol 44.98 g (65.72 mmol) of the title compound of Example 83b) is added to 53 ml of a solution of the title compound of Example 69 (310 mmol/L), dissolved in 0.45% aqueous sodium chloride solution, and it is heated for 10 minutes in the microwave. The solution is cooled to room temperature, filtered with a 0.2 μm filter, and the filtrate is decanted into vials. A thus produced solution can be used directly for biological experiments. (The concentration is 310 mmol of Gd/L.)

EXAMPLE 84 a) N,N-Bis(8-hydroxy-3,6-dioxa-octyl)-perfluorooctylsulfonic acid amide 15 g (29.23 mmol) of perfluorooctylsulfonic acid amide and 22.16 g (87.7 ml) of 9-(tetrahydropyran-2-yl)-3,6,9-trioxa-nonyl chloride are dissolved in 200 ml of acetonitrile. 41.46 g (300 mmol) of potassium carbonate and 1 g (6 mmol) of potassium iodide are added, and it is refluxed for 10 hours. The solid is filtered off, and the filtrate is evaporated to the dry state in a vacuum. The residue is dissolved in 400 ml of ethanol, and 30 ml of 10% aqueous hydrochloric acid is added. It is stirred for 2 hours at room temperature. It is set at pH 7 with sodium hydroxide solution, and the solution is concentrated by evaporation in a vacuum. The residue is chromatographed on silica gel (mobile solvent: dichloromethanemethanol=10:1).

Yield: 11.38 g (51% of theory) of a colorless, viscous oil.

Elementary analysis: Cld: C, 31.46; H, 3.43; N, 1.83; F, 42.30; S, 4.20. Fnd: C, 31.59; H, 3.50; N, 1.90; F, 42.46; S, 4.08.

b) Production of a formulation that consists of metal complex I and N,N-bis(8-hydroxy-3,6,-dioxa-octyl)-perfluorooctylsulfonic acid amide 7.91 g (10.36 mmol) of the title compound of Example 84a is added to 37 ml of a solution of metal complex I (280 mmol/L), dissolved in 0.45% aqueous common salt solution (pH 7.4; 0.25 mg/L of $CaNa_3DTPA$), and it is made up with a 0.9% aqueous common salt solution to a total of 104 ml. It is heated for 2 hours at 60° C. in an ultrasound bath. The solution is cooled to room temperature and set at pH 7.4 with aqueous 2N, sodium hydroxide solution. It is filtered with a 0.2 μm filter, and the filtrate is decanted into vials. A thus produced solution can be used directly for biological experiments. (The concentration is 100 mmol of Gd/L.)

EXAMPLE 85 a) N,N-Bis(t-butyloxycarbonylmethyl)-perfluorooctylsulfonic acid amide 20 g (38.97 mmol) of perfluorooctylsulfonic acid amide and 20.73 g (150 mol) of potassium carbonate are suspended in 200 ml of acetone, and 17.56 g (90 mmol) of bromoacetic acid-tert-butyl ester is added. It is refluxed for 3 hours. The solid is filtered off, and the filtrate is evaporated to the dry state in a vacuum. The residue is chromatographed on silica gel (mobile solvent: n-hexane/ethyl acetate=10:1).

Yield: 23.53 g (83% of theory) of a colorless, waxy solid.

Elementary analysis: Cld: C, 33.02; H, 3.05; F, 44.40; N, 1.93; S, 4.41. Fnd: C, 33.19; H, 3.11; F, 44.30; N, 1.99; S, 4.32.

b) N,N-Bis(carboxymethyl)-perfluorooctylsulfonic acid amide, disodium salt 23 g (31.62 mmol) of the title compound of Example 85a is dissolved in 300 ml of trifluoroacetic acid and stirred for 5 hours at room temperature. It is evaporated to the dry state in a vacuum, and the residue is recrystallized from acetone. The crystals are suctioned off and dried at 50° C. in a vacuum.

Yield: 17.7 g (91% of theory) of a colorless, crystalline powder.

17 g (27.63 mmol) of the thus obtained dioic acid is dissolved in 100 ml of water/300 ml of ethanol, and 9.2 ml of 3N, aqueous sodium hydroxide solution is added. It is stirred for 20 minutes at room temperature and then evaporated to the dry state in a vacuum. The residue is dried in a vacuum (60° C./8 hours).

Yield: 18.2 g of colorless, crystalline powder.

Elementary analysis: Cld: C, 21.87; H, 0.61; N, 2.12; F, 49.00; S, 4.86; Na, 6.98. Fnd: C, 22.00; H, 0.70; N, 2.20; F, 49.17; S, 4.93; Na, 7.10.

c) Production of a formulation that consists of metal complex II and N,N-bis(carboxymethyl)-perfluorooctylsulfonic acid amide, disodium salt 2.89 g (4.39 mmol) of the title compound of Example 85b is added to 41 ml of a solution of metal complex II (250 mmol/L), dissolved in 0.45% aqueous common salt solution (pH 7.4; 0.25 mg/L of CaNa₃DTPA, and it is made up with a 0.9% aqueous common salt solution to a total of 52 ml. It is heated for 2 hours at 60° C. in an ultrasound bath. The solution is cooled to room temperature and set at pH 7.4 with aqueous 2N sodium hydroxide solution. It is filtered with a 0.2 μm filter, and the filtrate is decanted into vials. A thus produced solution can be used directly for biological experiments. (The concentration is 200 mmol of Gd/L.)

EXAMPLE 86 a) 1H,1H,2H,2H-Perfluorododecyl-sulfuric acid monoester, sodium salt 10 g (17.73 mmol) of 1H,1H,2H,2H-perfluorododecanol is dissolved in 300 ml of chloroform, and 2.82 g (17.73 mmol) of sulfur trioxide-pyridine complex is added at 0° C. It is stirred for one hour at 0° C. and then evaporated to the dry state in a vacuum. The residue is dissolved in 300 ml of ethanol and mixed with 17.8 ml of 1N aqueous sodium hydroxide solution. The solution is evaporated to the dry state, and the residue is dried in a vacuum (60° C./2 hours).

Yield: 11.81 g (quantitative).

Elementary analysis: Cld: C, 21.64; H, 0.61; F, 59.89; Na, 3.45; S, 4.81. Fnd: C, 21.70; H, 0.72; F, 60.00; Na, 3.57; S, 4.92.

b) Production of a formulation that consists of metal complex VI and 1H,1H,2H,2H-perfluorododecyl-sulfuric acid monoester, sodium salt 4.90 g (7.35 mmol) of the title compound of Example 86a is added to 38 ml of a solution of metal complex VI (290 mmol/L), dissolved in 0.45% aqueous sodium chloride solution), and it is heated for 10 minutes in the microwave. The solution is cooled to room temperature, filtered with a 0.2 μm filter, and the filtrate is decanted into vials. A thus produced solution can be used directly for biological experiments. (The concentration is 290 mmol of Gd/L.)

EXAMPLE 87 a) 2H,2H,4H,4H,5H,5H-3-Oxa-perfluoropentadecanoic acid, sodium salt 10 g (16.07 mmol) of 2H,2H,4H,4H,5H,5H-3-oxa-perfluoropentadecanoic acid is dissolved in 300 ml of ethanol, and it is mixed with 16.1 ml of 1N aqueous sodium hydroxide solution. The solution is evaporated to the dry state, and the residue is dried in a vacuum (60° C./2 hours).

Yield: 10.35 g (quantitative) of a colorless, amorphous powder.

Elementary analysis: Cld: C, 26.10; H, 0.94; F, 61.94; Na, 3.57. Fnd: C, 26.22; H, 1.00; F, 62.05; Na, 3.66.

b) Production of a formulation that consists of the title compound of Example 66 and 2H,2H,4H,4H,5H,5H-3-oxa-perfluoropentadecanoic acid, sodium salt A solution that consists of 3.36 g (5.21 mmol) of the title compound of Example 87a, dissolved in 200 ml of ethanol, is added to 45 ml of a solution of the title compound of Example 66 (270 mmol/L), dissolved in 0.45% sodium chloride solution (pH, 7.4/0.25 mg/L of CaNa₃DTPA), and it is stirred for 2 hours at 50° C. The solution is evaporated to the dry state in a vacuum, and the residue is made up with distilled water to a total of 122 ml. It is stirred for 10 minutes at 40° C. and filtered with a 0.2 μm filter. The filtrate is decanted into vials. A thus produced solution can be used directly for biological experiments. (The concentration is 100 mmol of Gd/L.)

EXAMPLE 88 a) Ethylenediamine-N,N-tetraacetic acid-N-(1H,1H,2H,2H,4H,4H,5H,5H-3-oxa-perfluorotridecyl)-monoamide 10.14 g (20 mmol) of 1H,1H,2H,2H,4H,4H,5H,5H-3-oxa-perfluorotridecylamine is added in portions at 50° C. to 30 g (117.1 mmol) of EDTA-bisanhydride, suspended in 200 ml of dimethylformamide, and 50 ml of pyridine, and it is stirred for 6 hours at 50° C. 10 ml of water is added, it is stirred for 10 minutes at 50° C., and the residue is evaporated to the dry state. The residue is taken up in a little water and brought to pH, 4 with glacial acetic acid. The insoluble precipitate is filtered off and chromatographed on RP-18 (mobile solvent: acetonitrile/water/gradient).

Yield: 9.58 g (61% of theory) of a colorless solid.

Water content: 8%.

Elementary analysis: Cld: C, 33.64; H,3.59; N, 5.35; F,41.12. Fnd: C, 33.51; H,3.69; N, 5.44; F,41.24.

b) Ethylenediamine-N,N-tetraacetic acid-N-(1H,1H,2H,2H, 4H,4H,5H,5H-3-oxa-perfluorotridecyl)-monoamide, calcium salt, sodium salt 9.0 g (11.46 mmol) of the title substance of Example 88a is suspended in 300 ml of water, and 11.4 ml of 1N aqueous sodium hydroxide solution is added. Then, 1.15 g (11.46 mmol) of calcium carbonate is added, and it is stirred for 5 hours at 50° C. The solution is filtered, and the filtrate is freeze-dried.

Yield: 9.7 g (100% of theory) of a colorless, amorphous solid.

Water content: 7.5%.

Elementary analysis: Cld: C, 31.25; H, 2.98; N, 4.97; F, 38.20; Na, 2.72; Ca, 4.74. Fnd: C, 31.40; H, 3.09; N, 5.10; F, 38.07; Na, 2.81; Ca, 4.82.

c) Production of a formulation that consists of metal complex I and ethylenediamine-N,N-tetraacetic acid-N-(1H,1H, 2H,2H,4H,4H,5H,5H-3-oxa-perfluorotridecyl)-monoamide, calcium salt, sodium salt 2.54 g (3.01 mmol) of the title compound of Example 88b is added to 43 ml of a solution of metal complex I (280 mmol/L), dissolved in 0.45% aqueous common salt solution (pH, 7.4; 0.25 mg/L of CaNa₃DTPA), and it is made up with a 0.9% aqueous common salt solution to a total of 121 ml. It is heated for 2 hours at 60° C. in an ultrasound bath. The solution is cooled to room temperature and set at pH, 7.4 with aqueous 2N sodium hydroxide solution. It is filtered with a 0.2 μm filter, and the filtrate is decanted into vials. A thus produced solution can be used directly for biological experiments. (The concentration is 100 mmol of Gd/L.)

EXAMPLE 89 a) 1H,1H,2H,2H-Perfluorodecyl-(2,2-dimethyl-5-hydroxy-1,3-dioxepan-6-yl)-ether 30 g (64.64 mmol) of 1H,1H,2H,2H-perfluorodecanol is dissolved in 200 ml of tetrahydrofuran, and 1.68 g (70 mmol) of sodium hydride is added at 0° C. It is stirred for 2 hours at room temperature, then for 4 hours at 60° C. The solution is added to a metal autoclave, then 9.31 g (64.64 mmol) of 2,2-dimethyl-1,3,6-trioxabicyclo[5.1.0]octane is added and then heated for 10 hours to 150° C. The reaction solution is poured onto ice water and extracted 2 times with diethyl ether. The combined organic phases are evaporated to the dry state, and the residue is chromatographed on silica gel (mobile solvent: dichloromethane/acetone=10:1.)

Yield: 16.12 g (41% of theory) of a colorless solid.

Elementary analysis: Cld: C, 33.57; H, 2.82; F, 53.10. Fnd: C, 33.69; H, 2.90; F, 53.35.

b) 1H,1H,2H,2H-Perfluorodecyl-(1-hydroxymethyl-2,3-dihydroxypropyl)-ether 15 g (24.66 mmol) of the title compound of Example 89a is dissolved in 300 ml of ethanol, and 30 ml of 10% aqueous hydrochloric acid is added. It is refluxed for 5 hours. It is set at pH, 7 with sodium hydroxide solution, then evaporated to the dry state, and the residue is chromatographed on RP-18 (mobile solvent: acetonitrile/water/gradient).

Yield: 12.75 g (91% of theory) of a colorless solid.
Water content: 4.5%.
Elementary analysis: Cld: C, 29.59; H, 2.31; F, 56.84. Fnd: C, 29.48; H, 2.37; F, 56.99.

c) Production of a formulation that consists of the title compound of Example 12 of WO 99/01161 (1,4,7-tris{1,4,7-tris(N-carboxylatomethyl)-10-(N-1-methyl-3-aza-2,5-dioxo-pentane-1,5-diyl]-1,4,7,10-tetraazacyclododecane, Gd complex}-10-[2-(N-ethyl-N-perfluorooctylsulfonyl)-amino]-acetyl-1,4,7,10-tetraazacyclododecane) and 1H,1H,2H,2H-perfluorodecyl-(1-hydroxymethyl-2,3-dihydroxypropyl)-ether 9.46 g (16.65 mmol) of the title compound of Example 89b is added to 37 ml of a solution of 1,4,7-tris{1,4,7-tris(N-carboxylatomethyl)-10-(N-1-methyl-3-aza-2,5-dioxo-pentane-1,5-diyl]-1,4,7,10-tetraazacyclododecane, Gd complex}-10-[2-(N-ethyl-N-perfluorooctylsulfonyl)-amino]-acetyl-1,4,7,10-tetraazacyclododecane (300 mmol/L), dissolved in 0.45% aqueous common salt solution (pH, 7.4; 0.25 mg/L of $CaNa_3DTPA$), and it is made up with a 0.9% aqueous common salt solution to a total of 111 ml. It is heated for 2 hours at 60° C. in an ultrasound bath. The solution is cooled to room temperature and set at pH, 7.4 with aqueous 2N sodium hydroxide solution. It is filtered with a 0.2 $\mu$m filter, and the filtrate is decanted into vials. A thus produced solution can be used directly for biological experiments. (The concentration is 100 mmol of Gd/L.)

EXAMPLE 90 a) 1H,1H,2H,2H-Perfluorodecyl-[1,2-bis(2,2-dimethyl-1,3-dioxolan-4-yl)-2-hydroxyethyl]-ether 30 g (64.64 mmol) of 1H,1H,2H,2H-perfluorodecanol is dissolved in 200 ml of tetrahydrofuran, and 1.68 g (70 mmol) of sodium hydride is added at 0° C. It is stirred for 2 hours at room temperature, then for 4 hours at 60° C. The solution is added to a metal autoclave, then 15.78 g (64.64 mmol) of 1,2-bis-(2,2-dimethyl-1,3-dioxolan-4-yl)-oxiran is added, and then it is heated for 10 hours to 150° C. The reaction solution is poured onto ice water and extracted 2 times with diethyl ether. The combined organic phases are evaporated to the dry state, and the residue is chromatographed on silica gel (mobile solvent: dichloromethane/acetone=10:1).

Yield: 14.2 g (31% of theory) of a colorless solid.
Elementary analysis: Cld: C, 37.30; H, 3.56; F, 45.59. Fnd: C, 37.48; H, 3.66; F, 45.71.

b) 1H,1H,2H,2H-Perfluorodecyl-[1,2-bis(1,2-dihydroxy-ethyl)-2-hydroxyethyl]-ether 14 g (19.76 mmol) of the title compound of Example 90a is dissolved in 300 ml of ethanol, and 30 ml of 10% aqueous hydrochloric acid is added. It is refluxed for 5 hours. It is set at pH, 7 with sodium hydroxide solution, then it is evaporated to the dry state, and the residue is chromatographed on RP-18 (mobile solvent: acetonitrile/water/gradient).

Yield: 10.55 g (85% of theory) of a colorless solid.
Water content: 3.2%.
Elementary analysis: Cld: C, 30.59; H, 2.73; F, 51.41. Fnd: C, 30.73; H, 2.81; F, 51.58.

c) Production of a formulation that consists of metal complex II and 1H,1H,2H,2H-perfluorodecyl-[1,2-bis(1,2-dihydroxy-ethyl)-2-hydroxyethyl]-ether 11.98 g (19.07 mmol) of the title compound of Example 90b is added to 41 ml of a solution of metal complex II (300 mmol/L), dissolved in 0.45% aqueous common salt solution (pH, 7.4; 0.25 mg/L of $CaNa_3DTPA$), and it is made up with a 0.9% aqueous common salt solution to a total of 64 ml. It is heated for 2 hours at 60° C. in an ultrasound bath. The solution is cooled to room temperature and set at pH, 7.4 with aqueous 2N sodium hydroxide solution. It is filtered with a 0.2 $\mu$m filter, and the filtrate is decanted into vials. A thus produced solution can be used directly for biological experiments. (The concentration is 200 mmol of Gd/L.)

EXAMPLE 91 a) Perfluorooctylsulfonic acid-N,N-bis[[(8-sulfuric acid-monoester, sodium salt)-3,6-dioxaoctyl]-amide 13.54 g (17.73 mmol) of the title compound of Example 84a is dissolved in 300 ml of chloroform, and 2.82 g (17.73 mmol) of sulfur trioxide-pyridine complex is added at 0° C. It is stirred for one hour at 0° C., and then it is evaporated to the dry state in a vacuum. The residue is dissolved in 300 ml of ethanol and mixed with 17.8 ml of 1N aqueous sodium hydroxide solution. The solution is evaporated to the dry state, and the residue is dried in a vacuum (60° C./2 hours).

Yield: 17.15 g (quantitative).
Elementary analysis: Cld: C, 24.83; H, 2.50; F, 33.83; N, 1.45; S, 9.94; Na, 4.75. Fnd: C, 24.96; H, 2.62; F, 33.97; N, 1.53; S, 10.05; Na, 4.86.

b) Production of a formulation that consists of metal complex I and perfluorooctylsulfonic acid-N,N-bis[[(8-sulfuric acid-monoester, sodium salt)-3,6-dioxaoctyl]-amide 142.29 g (147.06 mmol) of the title compound of Example 91a is added to 43 ml of a solution of metal complex I (380 mmol/L), dissolved in 0.45% aqueous common salt solution (pH, 7.4; 0.25 mg/L of $CaNa_3DTPA$), and it is made up with a 0.9% aqueous common salt solution to a total of 164 ml. It is heated for 2 hours at 60° C. in an ultrasound bath. The solution is cooled to room temperature and set at pH, 7.4 with aqueous 2N sodium hydroxide solution. It is filtered with a 0.2 $\mu$m filter, and the filtrate is decanted into vials. A thus produced solution can be used directly for biological experiments. (The concentration is 100 mmol of Gd/L.)

EXAMPLE 92 a) 2-(2H,2H,3H,3H,5,5H,6H,6H-1,4-Dioxaperfluorotetradec-1-yl)-succinic acid-diethyl ester 30 g (59.03 mmol) of 1H,1H,2H,2H,4H,4H,5H,5H-3-oxa-perfluorotridecanol is added to 300 ml of tetrahydrofuran, and at 0° C., 1.68 g (70 mmol) of sodium hydride is added. It is stirred for one hour at 0° C., then for 5 hours at 40° C. In this 40° C. solution, 20.25 g (80 mmol) of bromosuccinic acid diethyl ester is added in drops within 10 minutes, and it is then stirred for 12 hours at this temperature. 500 ml of ice water is added, and it is extracted 2 times with 300 ml of diethyl ether. The combined organic phases are evaporated to the dry state in a vacuum, and the residue is chromatographed on silica gel (mobile solvent: n-hexane/ethanol=20:1).

Yield: 12.05 g (30% of theory).
Elementary analysis: Cld: C, 35.31; H, 3.11; F, 47.47. Fnd: C, 35.19; H, 3.20; F, 47.59.

b) 2-(2H,2H,3H,3H,5H,5H,6H,6H-1,4-Dioxa-perfluorotetradec-1-yl)-succinic acid, disodium salt 50 ml of 3N aqueous sodium hydroxide solution is added to 11.5 g (16.90 mmol) of the title compound of Example 92a, dissolved in 300 ml of methanol, and it is refluxed for 8 hours. It is evaporated to the dry state, and the residue is taken up in 300 ml of water. The aqueous phase is extracted 2 times with 300 ml of diethyl ether. The aqueous phase is acidified with concentrated hydrochloric acid to pH 1 and extracted 2 times with 300 ml of chloroform. The combined chloroform phases are dried on magnesium sulfate and evaporated to the dry state. The residue is dissolved in 300 ml of water and set at pH 7.4 with 5% aqueous sodium hydroxide solution. Then, it is freeze-dried.

Yield: 10.50 g (93% of theory) of a colorless, amorphous solid.

Water content: 5.7%.

Elementary analysis: Cld: C, 28.76; H, 1.66; F, 48.33; Na, 6.88. Fnd: C, 28.88; H, 1.71; F, 48.25; Na, 6.95.

c) Production of a formulation that consists of metal complex II and 2-(2H,2H,3H,3H,5H,5H,6H,6H-1,4-dioxa-perfluorotetradec-1-yl)-succinic acid, disodium salt 1.14 g (1.71 mmol) of the title compound of Example 92b is added to 57 ml of a solution of metal complex II (300 mmol/L), dissolved in 0.45% aqueous common salt solution (pH 7.4; 0.25 mg/L of $CaNa_3DTPA$), and it is made up with a 0.9% aqueous common salt solution to a total of 154 ml. It is heated for 2 hours at 60° C. in an ultrasound bath. The solution is cooled to room temperature and set at pH 7.4 with aqueous 2N sodium hydroxide solution. It is filtered with a 0.2 μm filter, and the filtrate is decanted into vials. A thus produced solution can be used directly for biological experiments. (The concentration is 100 mmol of Gd/L.)

EXAMPLE 93 a) 2H,2H,4H,4H,5H,5H-3-Oxa-perfluorotridecanoic acid-N-(succin-2-yl)-amide 16.51 g (80 mmol) of N,N'-dicyclohexylcarbodiimide is added at 0° C. to 20 g (38.30 mmol) of 2H,2H,4H,4H,5H,5H-3-oxa-perfluorotridecanoic acid and 9.21 g (80 mmol) of N-hydroxysuccinimide, dissolved in 150 ml of dimethylformamide, and it is stirred for 3 hours at this temperature. A solution, cooled to 0° C., of 5.10 g (38.30 mmol) of L-asparaginic acid, dissolved in 300 ml of 5% aqueous sodium carbonate solution, is added to the thus produced active ester solution, and it is stirred for 2 hours at 0° C. It is poured onto 500 ml of ice water, precipitated dicyclohexylurea is filtered out, and it is set at pH 1 with concentrated hydrochloric acid. It is extracted 3 times with 300 ml of chloroform. The combined, organic phases are evaporated to the dry state, and the residue is chromatographed on RP-18 (mobile solvent: acetonitrile/water/gradient). The thus obtained dioic acid is dissolved in 400 ml of water and set at pH 7.4 with 1N aqueous sodium hydroxide solution. It is filtered, and the filtrate is freeze-dried.

Water content: 6.3%.

Yield: 21.13 g (81% of theory) of a colorless, amorphous powder.

Elementary analysis: Cld: C, 28.21; H, 1.48; N, 2.06; F, 47.41; Na, 6.75. Fnd: C, 28.30; H, 1.53; N, 2.11; F, 47.53; Na, 6.83.

b) Production of a Formulation that Consists of Metal Complex XIV and 2H,2H,4H,4H,5H,5H-3-oxa-perfluorotridecanoic acid-N-(succin-2-yl)-amide 422 mg (0.62 mmol) of the title compound of Example 93a is added to 37 ml of a solution of metal complex XIV (300 mmol/L), dissolved in 0.45% aqueous common salt solution (pH 7.4; 0.25 mg/L of $CaNa_3DTPA$), and it is made up with a 0.9% aqueous common salt solution to a total of 111 ml. It is heated for 2 hours at 60° C. in an ultrasound bath. The solution is cooled to room temperature and set at pH 7.4 with aqueous 2N sodium hydroxide solution. It is filtered with a 0.2 μm filter, and the filtrate is decanted into vials. A thus produced solution can be used directly for biological experiments. (The concentration is 100 mmol of Gd/L.)

EXAMPLE 94

Production of a Formulation that Consists of the Title Compound of Example 67 and Perfluorooctanesulfonic Acid, Sodium Salt A solution that consists of 1.34 g (2.69 mmol) of perfluorooctanesulfonic acid, sodium salt, dissolved in 200 ml of ethanol, is added to 43 ml of a solution of the title compound of Example 67 (250 mmol/L), dissolved in 0.45% sodium chloride solution (pH 7.4/0.25 mg(L of $CaNa_3DTPA$), and it is stirred for 2 hours at 50° C. The solution is evaporated to the dry state in a vacuum, and the residue is made to up a total of 108 ml with distilled water. It is stirred for 10 minutes at 40° C. and filtered with a 0.2 μm filter. The filtrate is decanted into vials. A thus produced solution can be used directly for biological experiments. (The concentration is 100 mmol of Gd/L.)

EXAMPLE 95

Production of a Formulation that Consists of the Title Compound of Example 68 and Perfluorodecanesulfonic Acid, Sodium Salt 3.03 g (5.06 mmol) of perfluorodecanesulfonic acid, sodium salt, is added to 49 ml of a solution of the title compound of Example 68 (310 mmol/L), dissolved in 0.45% aqueous sodium chloride solution, and it is heated for 10 minutes in a microwave. The solution is cooled to room temperature, filtered with a 0.2 μm filter, and the filtrate is decanted into vials. A thus produced solution can be used directly for biological experiments. (The concentration is 310 mmol of Gd/L.)

EXAMPLE 96 a) (1H,1H,2H,2H-Perfluorodecyl)-5-[(1,3-dicarboxy, disodium salt)-phenyl]-ether 42.5 g (80.62 mmol) of the title compound of Example 14a is added to 20 g (80.62 mmol) of trisodium salt of 5-hydroxy-isophthalic acid in 300 ml of dimethylformamide, and it is stirred for 10 hours at 60° C. It is poured onto 1500 ml of ice water and set at pH 1 with concentrated hydrochloric acid. It is extracted 3 times with 300 ml of chloroform. The combined, organic phases are concentrated by evaporation, and the residue is chromatographed on RP-18 (mobile solvent: acetonitrile/water/gradient). The dioic acid that is purified in such a way is dissolved in 400 ml of water, and the pH is brought to 7.4 with 1N aqueous sodium hydroxide solution. It is filtered, and the filtrate is freeze-dried.

Yield: 20.05 g (37% of theory) of a colorless, amorphous solid.

Water content: 5.0%.

Elementary analysis: Cld: C, 32.16; H, 1.05; F, 48.05; Na, 6.84. Fnd: C, 32.30; H, 1.15; F, 48.20; Na, 6.95.

b) Production of a Formulation that Consists of the Title Compound of Example 12 of WO 99/01161 (1,4,7-tris{1,4,7-tris(N-carboxylatomethyl)-10-(N-1-methyl-3-aza-2,5-dioxo-pentane-1,5-diyl]-1,4,7,10-tetraazacyclododecane, Gd complex}-10-[2-(N-ethyl-N-perfluorooctylsulfonyl)-amino]-acetyl-1,4,7,10-tetraazacyclododecane) and (1H,1H,2H,2H-perfluorodecyl)-5-[(1,3-dicarboxy, disodium salt)-phenyl]-ether 6.86 g (10.2 mmol) of the title compound of Example 96a is added to 51 ml of a solution of 1,4,7-tris{1,4,7-tris(N-carboxylatomethyl)-10-(N-1-methyl-3-aza-2,5-dioxo-pentane-1,5-diyl]-1,4,7,10-tetraazacyclododecane, Gd complex}-10-[2-(N-ethyl-N-perfluorooctylsulfonyl)-amino]-acetyl-1,4,7,10-tetraazacyclododecane (300 mmol/L), dissolved in 0.45% aqueous common salt solution (pH 7.4; 0.25 mg/L of $CaNa_3DTPA$), and it is made up with a 0.9% aqueous common salt solution to a total of 153 ml. It is heated for 2 hours at 60° C. in an ultrasound bath. The solution is cooled to room temperature and set at pH 7.4 with aqueous 2N sodium hydroxide solution. It is filtered with a 0.2 μm filter, and the filtrate is decanted into vials. A thus produced solution can be used directly for biological experiments. (The concentration is 100 mmol of Gd/L.)

EXAMPLE 97

Production of a Formulation that Consists of Metal Complex XIV and 3-oxa-2H,2H,4H,4H,5H,5H-perfluorotridecanoic acid, sodium salt 434 mg (0.55 mmol) of the title compound of Example 80a is added to 4 ml of a solution of metal complex XIV (320 mmol/L), dissolved in 0.45% aqueous common salt solution (pH 7.4; 0.25 mg/L of $CaNa_3DTPA$), and it is made up with a 0.9% aqueous common salt solution to a total of 12.8 ml. It is heated for 2 hours at 60° C. in an ultrasound bath. The solution is cooled to room temperature and set at pH 7.4 with aqueous 2N sodium hydroxide solution. It is filtered with a 0.2 μm filter, and the filtrate is decanted into vials. A thus produced solution can be used directly for biological experiments. (The concentration is 100 mmol of Gd/L.)

EXAMPLE 98 a) (Adamant-1-yl)-3-oxa-propionic acid-t-butylester 29.26 g (150 mmol) of bromoacetic acid-tert-butyl ester is added at 0° C. to 15.22 g (100 mmol) of 1-adamantanol in 300 ml of 50% aqueous potassium hydroxide solution, 200 ml of toluene, and it is vigorously and thoroughly stirred for 2 hours. It is poured onto 1500 ml of water and extracted 2 times with 300 ml of diethyl ether. The combined organic phases are dried on magnesium sulfate and evaporated to the dry state in a vacuum. The residue is chromatographed on silica gel (mobile solvent: n-hexane/diethyl ether 20:1).

Yield: 21.58 g (81% of theory) of a viscous, colorless oil.

Elementary analysis: Cld: C, 72.14; H, 9.84. Fnd: C, 72.26; H, 9.95.

b) (Adamant-1-yl)-3-oxa-propionic acid 20 g (75 mmol) of the title compound of Example 98a is dissolved at 0° C. in 200 ml of trifluoroacetic acid, and it is stirred for 8 hours at room temperature. It is evaporated to the dry state, and the residue is recrystallized from diisopropyl ether.

Yield: 14.68 g (93% of theory) of colorless flakes.

Elementary analysis: Cld: C, 68.55; H, 8.63. Fnd: C, 68.41; H, 8.74.

c) 1-(Perfluorooctylsulfonyl)-4-[(adamant-1-yl)-oxapropionyl]-piperazine 14 g (66.6 mmol) of the title compound of Example 98b and 37.50 g (66.6 mmol) of 1-perfluorooctylsulfonyl-piperazine are dissolved in 300 ml of tetrahydrofuran, and 32.15 g (130 mmol) of 1,2 dihydro-2-ethoxyquinoline-1-carboxylic acid ethyl ester (=EEDQ) is added at 0° C. It is stirred for 5 hours at room temperature. The solution is evaporated to the dry state in a vacuum, and the residue is chromatographed on silica gel (mobile solvent: dichloromethane/diethyl ether=30:1).

Yield: 43.05 g (85% of theory) of a colorless solid.

Elementary analysis: Cld: C, 37.90; H, 3.31; N, 3.68; S, 4.22; F, 42.47. Fnd: C, 38.04; H, 3.42; N, 3.49; S, 4.11; F, 42.30.

d) Preparation that Consists of 0.5 Part of Metal Complex I and 0.5 Part of an Inclusion Compound of β-cyclodextrin-hydrate and 1-(perfluorooctylsulfonyl)-4-[(adamant-1-yl)-oxapropionyl]-piperazine 6.81 g (8.96 mmol) of the title compound of Example 98c and 10.33 g (8.96) of β-cyclodextrin monohydrate are added to 32 ml of a solution of metal complex I (280 mmol/L), dissolved in 0.45% aqueous common salt solution (pH 7.4; 0.25 mg/L of $CaNa_3DTPA$), and it is made up with a 0.9% aqueous common salt solution to a total of 98 ml. It is heated for 2 hours at 60° C. in an ultrasound bath. The solution is cooled to room temperature and set at pH 7.4 with aqueous 2N sodium hydroxide solution. It is filtered with a 0.2 μm filter, and the filtrate is decanted into vials. A thus produced solution can be used directly for biological experiments. (The Gd concentration is 100 mmol of Gd/L.)

EXAMPLE 99 a) 3-Oxa-2H,2H,4H,4H,5H,5H-perfluorotridecanoic acid-N-(1-adamantyl)-amide 30.95 g (150 mmol) of N,N-dicyclohexylcarbodiimide is added at 0° C. to 15.12 g (100 mmol) of 1-amino-adamantane, 52.21 (100 mmol) of 3-oxa-2H,2H,4H, 4H,5H, 5H-perfluorotridecanoic acid and 11.51 g (100 mmol) of N-hydroxysuccinimide, dissolved in 300 ml of tetrahydrofuran. It is stirred for 2 hours at 0° C., then for 6 hours at room temperature. Precipitated urea is filtered out, the filtrate is evaporated to the dry state, and the residue is chromatographed on silica gel (mobile solvent: dichloromethane/acetone=30:1).

Yield: 54.4 g (83% of theory) of a waxy solid.

Elementary analysis: Cld: C, 40.32; H, 3.38; N, 2.14; F, 49.28. Fnd: C, 40.47; H, 3.49; N, 2.03; F, 49.09.

b) Preparation that Consists of 0.6 Part of Metal Complex II and 0.4 Part of an Inclusion Compound that Consists of β-cyclodextrin-hydrate and 3-oxa-2H,2H,4H,4H,5H,5H-perfluorotridecanoic acid-N-(1-adamantyl)-amide 4.48 g (6.83 mmol) of the title compound of Example 99a and 7.87 g (6.83 mmol) of β-cyclodextrin monohydrate are added to 41 ml of a solution of metal complex II (250 mmol/L), dissolved in 0.45% aqueous common salt solution (pH 7.4; 0.25 mg/L of $CaNa_3DTPA$), and it is made up with a 0.9% aqueous common salt solution to a total of 103 ml. It is heated for 2 hours at 60° C. in an ultrasound bath. The solution is cooled to room temperature and set at pH 7.4 with aqueous 2N sodium hydroxide solution. It is filtered with a 0.2 μm filter, and the filtrate is decanted into vials. A thus produced solution can be used directly for biological experiments. (The Gd concentration is 100 mmol of Gd/L.)

EXAMPLE 100 a) 2-[N-(Ethyl)-N-(perfluorooctylsulfonyl)-amino]-acetic acid-N-(adamantyl)-amide 30.95 g (150 mmol) of N,N-dicyclohexylcarbodiimide is added at 0° C. to 15.12 g (100 mmol) of 1-aminoadamantane, 58.52 g (100 mmol) of N-(ethyl)N-(perfluorooctylsulfonyl)-aminoacetic acid and 11.51 g (100 mmol) of N-hydroxysuccinimide, dissolved in 300 ml of tetrahydrofuran. It is stirred for 2 hours at 0° C., then for 6 hours at room temperature. Precipitated urea is filtered out, the filtrate is evaporated to the dry state, and the residue is chromatographed on silica gel (mobile solvent: dichloromethane/acetone=30:1).

Yield: 55.65 g (79% of theory) of an amorphous solid.

Elementary analysis: Cld: C, 37.51; H, 3.29; F, 45.85; N, 1.99; S, 4.55. Fnd: C, 37.64; H, 3.41; F, 45.99; N, 2.12; S, 4.43.

b) Preparation that consists of 0.6 part of metal complex I and 0.4 part of an inclusion compound that consists of β-cyclodextrin-hydrate and 2-[N-(ethyl)-N-(perfluoroacetylsulfonyl)-amino]-acetic acid-N-(1-adamantyl)-amide 4.20 g (5.97 mmol) of the title compound of Example 100a and 6.88 g (5.97 mmol) of β-cyclodextrin monohydrate are added to 32 ml of a solution of metal complex I (280 mmol/L), dissolved in 0.45% aqueous common salt solution (pH 7.4; 0.25 mg/L of $CaNa_3DTPA$), and it is made up with a 0.9% aqueous common salt solution to a total of 90 ml. It is heated for 2 hours at 60° C. in an ultrasound bath. The solution is cooled to room temperature and set at pH 7.4 with aqueous 2N sodium hydroxide solution. It is filtered with a 0.2 μm filter, and the filtrate is decanted into vials. A thus produced solution can be used directly for biological experiments. (The Gd concentration is 100 mmol of Gd/L.)

EXAMPLE 101 a) 6-N-a)Benzyloxycarbonyl-2-N-(3,6,9,12-tetraoxatridecanoyl)-lysine[1-(4-perfluorooctylsulfonyl)-piperazine]-amide A solution that consists of 16.85 g (70 mmol) of 3,6,9,12-tetraoxatridecanoic acid chloride in 50 ml of dichloromethane is added in drops at 0° C. to 50 g (60.20 mmol) of the title compound of Example 1c and 7.10 g (70 mmol) of triethylamine, dissolved in 350 ml of dichloromethane, and it is stirred for 3 hours at 0° C. 200 ml of 5% aqueous hydrochloric acid is added, and it is stirred for 5 minutes at room temperature. The organic phase is separated, dried on magnesium sulfate and evaporated to the dry state in a vacuum. The residue is chromatographed on silica gel (mobile solvent: dichloromethane/acetone=15:1).

Yield: 30.94 g (92% of theory) of a colorless, viscous oil.
Elementary analysis: Cld.: C, 40.63; H, 4.19; F, 31.21; N, 5.41; S, 3.10. Fnd.: C, 40.75; H, 4.08; F, 31.29; N, 5.58; S, 3.25.

b) 2-N(3,6,9,12-Tetraoxatridecanoyl)-lysine[1-(4-perfluorooctylsulfonyl)-piperazine]

53.96 g (52.15 mmol) of the title compound of Example 101a is dissolved in 500 ml of ethanol, and 6 g of palladium catalyst (10% Pd/C) is added. It is hydrogenated at room temperature. Catalyst is filtered out, and the filtrate is evaporated to the dry state in a vacuum.

Yield: 43.0 g (quantitative) of a colorless solid.
Elementary analysis: Cld.: C, 36.01; H, 4.14; F, 35.86; N, 6.22; S, 3.56. Fnd.: C, 36.20; H, 4.23; F, 35.99; N, 6.38; S, 3.71.

c) 6N-[1,4,7-Tris(carboxylatomethyl)-1,4,7,10-tetraazacyclododecane-10-(pentanoyl-3-aza-4-oxo-5-methyl-5-yl)]-2-N-(3,6,9,12-tetraoxatridecanoyl)-lysine[1-(4-perfluorooctylsulfonyl)-piperazine]-amide, Gd complex 21.84 (24.25 mmol) of the title compound of Example 101b, 2.79 g (24.25 mmol) of N-hydroxysuccinimide, 2.12 g (50 mmol) of lithium chloride and 15.27 g (24.25 mmol) of 1,4,7-tris(carboxylatomethyl)-10-[(3-aza-4-oxo-5-methyl-5-yl)]-pentanoic acid]-1,4,7,10-tetraazacyclododecane, Gd complex, are dissolved in 200 ml of dimethyl sulfoxide while being heated slightly. At 10° C., 8.25 g (40 mmol) of N,N-dicyclohexylcarbodiimide is added and then stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 28.21 g (81% of theory) of a colorless solid.
Water content: 11.0%.
Elementary analysis (relative to anhydrous substance): Cld.: C, 36.53; H, 4.33; F, 21.36; N, 8.34; S, 2.12; Gd, 10.40. Fnd.: C, 36.64; H, 4.48; F, 21.39; N, 8.29; S, 2.15; Gd, 10.57.

EXAMPLE 102 a) 6-N-Benzyloxycarbonyl-2-N-(propyl-3-sulfonic acid)-lysine[1-(4-perfluorooctyl-sulfonyl)-piperazine]-amide A solution that consists of 7.33 g (60 mol) of propanesultone in 50 ml of tetrahydrofuran is added in drops at 50° C. to 50 g (60.20 mmol) of the title compound of Example 1c and 7.10 g (70 mmol) of triethylamine, dissolved in 250 ml of dry tetrahydrofuran, and it is stirred for 3 hours at 60° C. 200 ml of 5% aqueous hydrochloric acid is added, and it is stirred for 5 minutes at room temperature. The organic phase is separated, dried on magnesium sulfate and evaporated to the dry state in a vacuum. The residue is chromatographed on silica gel (mobile solvent: dichloromethane/acetone=15:1).

Yield: 45.16 g (79% of theory) of a colorless, viscous oil.
Elementary analysis: Cld.: C, 36.56; H, 3.49; F, 33.90; N, 5.88; S, 6.73. Fnd.: C, 36.72; H, 3.35; F, 33.79; N, 5.78; S, 6.75.

b) 2-N-(Propyl-3-sulfonic acid)-lysine[1-(4-perfluorooctylsulfonyl)-piperazine]-amide 49.68 g (52.15 mmol) of the title compound of Example 102a is dissolved in 500 ml of ethanol, and 6 g of palladium catalyst (10% Pd/C) is added. It is hydrogenated at room temperature. Catalyst is filtered out, and the filtrate is evaporated to the dry state in a vacuum.

Yield: 42.69 g (quantitative) of a colorless solid.
Elementary analysis: Cld.: C, 30.81; H, 3.32; F, 39.46; N, 6.84; S, 7.83. Fnd.: C, 30.64; H, 4.1; F, 39.29; N, 6.68; S, 7.89.

c) 6N-[1,4,7-Tris(carboxylatomethyl)-1,4,7,10-tetraazacyclododecane-10-(pentanoyl-3-aza4-oxo-5-methyl-5-yl)]-2-N-(propyl-3-sulfonic acid)-lysine[1-(4-perfluorooctylsulfonyl)-piperazine]-amide, Gd complex 19.85 g (24.25 mmol) of the title compound of Example 102b, 2.79 g (24.25 mmol) of N-hydroxysuccinimide, 2.12 g (50 mmol) of lithium chloride, and 15.27 g (24.25 mmol) of 1,4,7-tris(carboxylatomethyl)-10-[(3-aza-4-oxo-5-methyl-5-yl)]-pentanoic acid]-1,4,7,10-tetraazacyclododecane, Gd complex, are dissolved in 200 ml of dimethyl sulfoxide while being heated slightly. At 10° C., 8.25 g (40 mmol) of N,N-dicyclohexylcarbodiimide is added, and then it is stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 28.13 g (81% of theory) of a colorless solid.
Water content: 11.0%.
Elementary analysis (relative to anhydrous substance): Cld.: C, 33.27; H, 3.70; F, 22.36; N, 8.73; S, 4.44; Gd, 10.89. Fnd.: C, 32.41; H, 3.88; F, 22.49; N, 8.69; S, 4.35; Gd, 10.97.

EXAMPLE 103 a) 6-N-Benzyloxycarbonyl-2-N,N-bis (propyl-3-sulfonic acid)-lysine[1-4-perfluorooctylsulfonyl)-piperazine]-amide A solution that consists of 14.65 g (120 mmol) of 1,3-propanesultone in 100 ml of tetrahydrofuran is added in drops at 50° C. to 50 g (60.20 mmol) of the title compound of Example 1c and 12.14 g (120 mmol) of triethylamine, dissolved in 250 ml of dry tetrahydrofuran, and it is stirred for 3 hours at 60° C. 400 ml of 5% aqueous hydrochloric acid is added, it is stirred for 5 minutes at room temperature, mixed with sodium chloride, the organic phase is separated, it is dried on magnesium sulfate and evaporated to the dry sttate in a vacuum. The residue is chromatographed on silica gel (mobile solvent: dichloromethane/acetone 15:1).

Yield: 52.24 g (81% of theory) of a colorless, viscous oil.
Elementary analysis: Cld.: C, 35.76; H, 3.66; F, 30.05; N, 5.21; S, 8.95. Fnd.: C, 35.75; H, 3.55; F, 30.19; N, 5.08; S, 9.04.

b) 2-N,N Bis(propyl-3-sulfonic acid)-lysine[1-(4-perfluorooctylsulfonyl)-piperazine]-amide 53.74 g (52.15 mmol) of the title compound of Example 103a is dissolved in 500 ml of ethanol, and 6 g of palladium catalyst (10% Pd/C) is added. It is hydrogenated at room temperature. Catalyst is filtered out, and the filtrate is evaporated to the dry state in a vacuum.

Yield: 49.06 g (quantitative) of a colorless solid.

Elementary analysis: Cld.: C, 30.64; H, 3.54; F, 34.33; N, 5.96; S, 10.23. Fnd.: C, 30.69; H, 3.71; F, 34.19; N, 6.08; S, 10.38.

c) 6-N-[1,4,7-Tris(carboxylatomethyl)-1,4,7,10-tetraazacyclododecane-10-(pentanoyl-3-aza-4-oxo-5-methyl-5-yl)]-2-N,N bis(propyl-3-sulfonic acid)-lysine[1-(4-perfluorooctylsulfonyl)-piperazine]-amide, Gd complex, disodium salt 38.76 g (24.25 mmol) of the title compound of Example 103b, 2.79 g (24.25 mmol) of N-hydroxysuccinimide, 2.12 g (50 mmol) of lithium chloride and 15.27 g (24.25 mmol) of 1,4,7-tris(carboxylatomethyl)-10-[(3-aza-4-oxo-5-methyl-5-yl)]-pentanoic acid]-1,4,7,10-tetraazacyclododecane, Gd complex, are dissolved in 200 ml of dimethyl sulfoxide while being heated slightly. At 10° C., 8.25 g (40 mmol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 31.63 g (81% of theory) of a colorless solid.

Water content: 11.0%.

Elementary analysis (relative to anhydrous substance): Cld.: C, 32.07; H, 3.57; F, 20.06; N, 7.83; S, 5.97; Gd, 9.76; Na, 2.86. Fnd.: C, 31.94; H, 3.48; F, 20.19; N, 7.69; S, 5.85; Gd, 9.87; Na, 2.99.

EXAMPLE 104 a) N-Trifluoroacetyl-L-glutamic acid-5-benzylester 100 g (421.5 mmol) of L-glutamic acid-5-benzylester is dissolved in a mixture that consists of 1000 ml of trifluoroacetic acid ethyl ester/500 ml of ethanol, and it is stirred for 24 hours at room temperature. It is evaporated to the dry state, and the residue is crystallized from diisopropyl ether.

Yield: 140.47 g (96% of theory) of a colorless, crystalline powder.

Elementary analysis: Cld.: C, 50.46; H, 4.23; F, 17.10; N, 4.20. Fnd.: C, 51.35; H, 4.18; F, 17.03; N, 4.28.

b) 2-N-Trifluoroacetyl-L-glutamic acid-5-benzylester-N-bis(2-hydroxyethyl)-amide 8.25 g (40 mmol) of N,N-dicyclohexylcarbodiimide is added at 0° C. to a solution that consists of 24.9 g (24.08 mmol) of the title compound of Example 104a, 2.53 g (24.08 mmol) of diethanolamine and 2.77 g (24.08 mmol) of N-hydroxysuccinimide, dissolved in 150 ml of dimethylformamide. It is stirred for 3 hours at 0° C., then overnight at room temperature. Precipitated urea is filtered out, the filtrate is evaporated to the dry state in a vacuum, and it is chromatographed on silica gel (mobile solvent: dichloromethane/ethanol=20:1).

Yield: 9.11 g (90% of theory) of a viscous oil.

Elementary analysis: Cld.: C, 51.43; H, 5.51; F, 13.56; N, 6.66. Fnd.: C, 51.22; H, 5.41; F, 13.40; N, 6.75.

c) N-Trifluoroacetyl-L-glutamic acid-N bis(2-hydroxyethyl)-monoamide 21.92 g (52.15 mmol) of the title compound of Example 104b is dissolved in 500 ml of ethanol, and 3 g of palladium catalyst (10% Pd/C) is added. It is hydrogenated at room temperature. Catalyst is filtered out, and the filtrate is evaporated to the dry state in a vacuum.

Yield: 43.0 g (quantitative) of a colorless solid.

Elementary analysis: Cld.: C, 40.01; H, 5.19; F, 17.26; N, 8.48. Fnd.: C, 39.84; H, 5.13; F, 17.09; N, 8.68.

c) Trifluoroacetyl-L-glutamic acid-N-bis(2-hydroxyethyl)-amide-5-[1-(4-perfluorooctylsulfonyl)-piperazine]-amide 16.42 g (66.4 mmol) of EEDQ (2-ethoxy-1,2-dihydroquinoline-1-carboxylic acid ethyl ester) is added at 0° C. to 10.96 g (33.2 mmol) of the title compound of Example 104a and 18.87 g (33.2 mmol) of 1-perfluorooctylsulfonyl-piperazine (produced according to DE 19603033) in 80 ml of tetrahydrofuran, and it is stirred overnight at room temperature. It is evaporated to the dry state in a vacuum, and it is chromatographed on silica gel (mobile solvent: dichloromethane/methanol=20:1).

Yield: 30.93 g (93% of theory) of a colorless solid.

Elementary analysis: Cld.: C, 39.61; H, 2.89; F, 35.66; N, 6.19; S, 3.54. Fnd.: C, 39.68; H, 2.74; F, 35.81; N, 6.13; S, 3.40.

e) L-Glutamic acid-N-bis(2-hydroxyethyl)-amide-5-[1-(4-perfluorooctylsulfonyl)-piperazine]-amide Ammonia gas is introduced at 0° C. for one hour into 200 ml of ethanol. It is then stirred for 4 hours at 0° C. It is evaporated to the dry state, and the residue is absorptively precipitated from water. The solid is filtered off and dried in a vacuum (50° C.).

Yield: 26.55 g (97% of theory) of an amorphous solid.

Elementary analysis: Cld.: C, 41.12; H, 2.89; F, 35.66; N, 6.19; S, 3.54. Fnd.: C, 41.15H2.83; F, 35.78; N, 6.28; S, 3.71.

f) N-[1,4,7-Tris(carboxylatomethyl-1,4,7,10-tetraazacyclododecane-10-(pentanoyl-3-aza4-oxo-5-methyl-5-yl)]-L-glutamic acid-N-bis(2-hydroxyethyl)-amide-5-[1-(4-perfluorooctylsulfonyl)-piperazine]-amide, Gd complex 211.96 g (24.25 mmol) of the title compound of Example 104e, 2.79 g (24.25 mmol) of N-hydroxysuccinimide, 2.12 g (50 mmol) of lithium chloride and 15.27 g (24.25 mmol) of 1,4,7-tris(carboxylatomethyl)-10-[(3-aza-4-oxo-5-methyl-5-yl)]-pentanoic acid]-1,4,7,10-tetraazacyclododecane, Gd complex, are dissolved in 200 ml of dimethyl sulfoxide while being heated slightly. At 10° C., 8.25 g (40 mmol) of N,N-dicyclohexylcarbodiimide is added, and it then is stirred overnight at room temperature. The solution is poured into 3000 ml of acetone, and it is stirred for 10 minutes. The precipitated solid is filtered off and then purified by chromatography (silica gel RP-18, mobile solvent: gradient that consists of water/ethanol/acetonitrile).

Yield: 27.43 g (81% of theory) of a colorless solid.

Water content: 11.0%.

Elementary analysis (relative to anhydrous substance): Cld.: C, 34.41; H, 3.83; F, 23.13; N, 9.03; S, 2.30; Gd, 11.26. Fnd.: C, 34.34; H, 3.98; F, 23.29; N, 9.19; S, 2.15; Gd, 11.07.

EXAMPLE 105 a) N-Trifluoroacetyl-L-glutamic acid-5-benzylester-N-dimethyl-bis(1,1-dihydroxymethyl)-amide 8.25 g (40 mmol) of N,N-dicyclohexylcarbodiimide is added at 0° C. to a solution that consists of 8.03 g (24.08 mmol) of the title compound of Example 104a, 3.98 g (24.08 mmol) of dimethyl-bis(1,1-dihydroxymethyl)-amine and 2.77 g (24.08 mmol) of N-hydroxysuccinimide, dissolved in 150 ml of dimethylformamide. It is stirred for 3 hours at 0° C., then overnight at room temperature. Precipitated urea is filtered out, the filtrate is evaporated to the dry state in a vacuum, and it is chromatographed on silica gel (mobile solvent: dichloromethane/ethanol=20:1).

Yield: 110.53 g (91% of theory) of a viscous oil.

Elementary analysis: Cld.: C, 50.00; H, 5.66; F, 11.86; N, 7.18. Fnd.: C, 50.17; H, 5.82; F, 11.80; N, 7.15.

b) N-Trifluoroacetyl-L-glutamic acid-5-benzylester-[1-(4-perfluorooctylsulfonyl)-piperazine]-amide 25.05 g (52.15 mmol) of the title compound of Example 105a is dissolved in 500 ml of ethanol, and 6 g of palladium catalyst (10% Pd/C) is added, hydrogenated at room temperature. Catalyst is filtered out, and the filtrate is evaporated to the dry state in a vacuum.

Yield: 20.36 g (quantitative) of a colorless solid.

Elementary analysis: Cld.: C, 40.00; H, 5.42; F, 14.60; N, 7.18. Fnd.: C, 40.10; H, 5.53; F, 14.69; N, 7.28.

c) N-Trifluoroacetyl-L-glutamic acid-N-dimethyl-bis(1,1-dihydroxymethyl)-amide-5-[ 1-(4-perfluorooctylsulfonyl)piperazine]-amide 16.42 g (66.4 mmol) of EEDQ (2-ethoxy-1,2-dihydroquinoline-1-carboxylic acid ethyl ester) is added at 0° C. to 12.96 g (33.2 mmol) of the title compound of Example 105b and 18.87 g (33.2 mmol) of 1-perfluorooctylsulfonyl-piperazine (produced according to DE 19603033) in 800 ml of tetrahydrofuran, and it is stirred overnight at room temperature. It is evaporated to the dry state in a vacuum and chromatographed on silica gel (mobile solvent: dichloromethane/methanol=20:1).

Yield: 28.42 g (91% of theory) of a colorless solid.

Elementary analysis: Cld.: C, 31.93; H, 3.00; F, 40.40; N, 5.96; S, 3.41. Fnd.: C, 32.08; H, 2.94; F, 40.57; N, 5.88; S, 3.31.

d) LGlutamic acid-N-[dimethyl-bis(1,1-dihydroxymethyl)]-amide-5-[(1-4-perfluorooctylsulfonyl)-piperazinc]-amide Ammonia gas is introduced at 0° C. for one hour into a solution that consists of 28.41 g (30.2 mmol) of the title compound of Example 105c in 200 ml of ethanol. It then is stirred for 4 hours at 0° C. It is evaporated to the dry state, and the residue is absorptively precipitated from water. The solid is filtered off and dried in a vacuum (50° C.).

Yield: 24.74 g (97% of theory) of an amorphous solid.

Elementary analysis: Cld.: C, 32.71; H, 3.46; F, 38.24; N, 6.63; S, 3.80. Fnd.: C, 32.75; H, 3.33; F, 38.38; N, 6.68; S, 3.81.

e) 2-N-[1,4,7-Tris(carboxylatomethyl)-1,4,7,10-tetraazacyclododecane-10-(pentanoyl-3-aza4-oxo-5-methyl-5-yl)]-L-glutamic acid-N-[dimethyl-bis(1,1-dihydroxymethyl)-amide]-5-[1-(4-perfluorooctylsulfonyl)-piperazine]-amide, Gd complex 20.48 g (24.25 mmol) of the title compound of Example 105d, 2.79 g (24.25 mmol) of N-hydroxysuccinimide, 2.12 g (50 mmol) of lithium chloride and 15.27 g (24.25 mmol) of 1,4,7-tris(carboxylatomethyl)-10-[(3-aza-4-oxo-5-methyl-5-yl)]-pentanoic acid]-1,4,7,10-tetraazacyclododecane, Gd complex, are dissolved in 200 ml of dimethyl sulfoxide while being heated slightly. At 10° C., 8.25 g (40 mmol) of N,N-dicyclohexylcarbodiimide is added, and it then is stirred overnight at room temperature. The solution is poured into 3000 ml of acetone and stirred for 10 minutes. The precipitated filtrate is filtered off and then purified by chromatography (silica gel RP-18, mobile solvent: gradient that consists of water/ethanol/acetonitrile).

Yield: 29.05 g (83% of theory) of a colorless solid.

Water content: 11.0%.

Elementary analysis (relative to anhydrous substance): Cld.: C, 34.12; H, 3.91; F, 22.38; N, 8.73; S, 2.22; Gd, 10.90. Fnd.: C, 34.24; H, 3.98; F, 22.39; N, 8.69; S, 2.15; Gd, 10.87.

EXAMPLE 106 a) N-Trifluoromethylacetyl-L-glutamic acid-5-benzylester-[1-(4-perfluorooctylsulfonyl)-piperazine]-amide 16.42 g (66.4 mmol) of EEDQ (2-ethoxy-1,2-dihydroquinoline-1-carboxylic acid ethyl ester) is added at 0° C. to 11.06 g (33.2 mmol) of the title compound of Example 104a and 18.87 g (33.2 mmol) of 1-perfluorooctylsulfonyl-piperazine (produced according to DE 19603033) in 80 ml of tetrahydrofuran, and it is stirred overnight at room temperature. It is evaporated to the dry state in a vacuum and chromatographed on silica gel (mobile solvent: dichloromethane/methanol=20:1).

Yield: 27.28 g (93% of theory) of a colorless solid.

Elementary analysis: Cld.: C, 35.35; H, 2.40; F, 43.01; N, 4.76; S, 3.63. Fnd.: C, 35.48; H, 2.51; F, 42.87; N, 4.73; S, 3.50.

b) N-Trifluoroacetyl-L-glutarnic acid-5-[1-[4-perfluorooctylsulfonyl)-piperazine]-amide 21.92 g (52.15 mmol) of the title compound of Example 106a is dissolved in 500 ml of ethanol, and 3 g of palladium catalyst (10% Pd/C) is added. It is hydrogenated at room temperature. Catalyst is filtered out, and the filtrate is evaporated to the dry state in a vacuum.

Yield: 41.37 g (quantitative) of a colorless solid.

Elementary analysis: Cld.: C, 28.76; H, 1.91; F, 47.89; N, 5.30; S, 4.40. Fnd.: C, 28.84; H, 2.03; F, 47.79; N, 5.28; S, 4.19.

c) N-Trifluoroacetyl-L-glutarmic acid-N-bis(2-hydroxyethyl)-amide-5-[-(4-perfluorooctylsulfonyl)-piperazine]-amide 8.25 g (40 mmol) of N,N-dicyclohexylcarbodiimide is added at 0° C. to a solution that consists of 24.9 g (24.08 mmol) of the title compound of Example 106a, 2.53 g (24.08 mmol) of diethanolamine and 2.77 g (24.08 mmol) of N-hydroxysuccinimide, dissolved in 150 ml of dimethylformamide. It is stirred for 3 hours at 0° C., then overnight at room temperature. Precipitated urea is filtered out, the filtrate is evaporated to the dry state in a vacuum and chromatographed on silica gel (mobile solvent:= dichloromethane/ethanol=20:1).

Yield: 9.11 g (90% of theory) of a viscous oil.

Elementary analysis: Cld.: C, 31.37; H, 2.75; F, 43.15; N, 6.36; S, 3.64. Fnd.: C, 31.22; H, 2.61; F, 43.30; N, 6.25; S, 3.81.

d) L-Glutamic acid-N-bis(2-hydroxyethyl)-amide-5-[1-(4-perfluorooctylsulfonyl)-piperazine]-amide Ammonia gas is introduced at 0° C. for one hour into a solution that consists of 26.61 g (30.22 mmol) of the title compound of Example 106c in 200 ml of ethanol. It then is stirred for 4 hours at 0° C. It is evaporated to the dry state, and the residue is absorptively precipitated from water. The solid is filtered off and dried in a vacuum (50° C.).

Yield: 23.93 g (97% of theory) of an amorphous solid.

Elementary analysis: Cld.: C, 30.89; H, 3.09; F, 39.56; N, 6.86; S, 3.93. Fnd.: C, 30.75; H, 3.13F39.78; N, 6.75; S, 3.81.

e) N-[1,4,7-Tris(carboxylatomethyl)-1,4,7,10-tetraazacyclododecane-10-(pentanoyl-3-aza-4-oxo-5-methyl-5-yl)]-L-glutamic acid-N-bis(2-hydroxyethyl)-amide-5-[1-(4-perfluorooctylsulfonyl)-piperazine]-amide, Gd complex 16.43 g (24.25 mmol) of the title compound of Example 106d, 2.79 g (24.25 mmol) of N-hydroxysuccinimide, 2.12 g (50 mmol) of lithium chloride and 15.27 g (24.25 mmol) of 1,4,7-tris(carboxylatomethyl)-10-[(3-aza-4-oxo-5-methyl-5-yl)]-pentanoic acid]-1,4,7,10-tetraazacyclododecane, Gd complex, are dissolved in 200 ml of dimethyl sulfoxide while being heated slightly. At 10° C., 8.25 g (40 mmol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 28.10 g (83% of theory) of a colorless solid.

Water content: 11.0%.

Elementary analysis (relative to anhydrous substance): Cld.: C, 34.41; H, 3.83; F, 23.13; N, 9.03; S, 2.30; Gd, 11.26. Fnd.: C, 34.44; H, 4.98; F, 23.19; N, 8.89; S, 2.15; Gd, 11.17.

EXAMPLE 107 a) N-Trifluoroacetyl-glutamic acid-5-benzylester-[1-(4-perfluorooctylsulfonyl)-piperazine]-amide 16.42 g (66.4 mmol) of EEDQ (2-ethoxy-1,2-dihydroquinoline-1-carboxylic acid ethyl ester) is added at 0° C. to 11.06 g (33.2 mmol) of the title compound of Example 104a and 18.87 g (33.2 mmol) of 1-perfluorooctylsulfonyl-piperazine (produced according to DE 19603033) in 80 ml of tetrahydrofuran, and it is stirred overnight at room temperature. It is evaporated to the dry state in a vacuum and chromatographed on silica gel (mobile solvent: dichloromethane/methanol=20:1).

Yield: 27.28 g (93% of theory) of a colorless solid.

Elementary analysis: Cld.: C, 33.35; H, 2.40; F, 43.01; N, 4.76; S, 3.63. Fnd.: C, 35.48; H, 2.54; F, 42.87; N, 4.73; S, 3.40.

b) N-Trifluoroacetyl-L-glutamic acid-5-[1-[4-perfluorooctylsulfonyl)-piperazine]-amide 21.92 g (52.15 mmol) of the title compound of Example 107a is dissolved in 500 ml of ethanol, and 3 g of palladium catalyst (10% Pd/C) is added. It is hydrogenated at room temperature. Catalyst is filtered out, and the filtrate is evaporated to the dry state in a vacuum.

Yield: 41.37 g (quantitative) of a colorless solid.

Elementary analysis: Cld.: C, 28.76; H, 1.91; F, 47.89; N, 5.30; S, 4.04. Fnd.: C, 28.84; H, 1.81; F, 47.79; N, 5.28; S, 4.16.

EXAMPLE 108 a) 6-N-Benzyloxycarbonyl-2-N-(2,3,4,5-pentahydroxy-hexanoyl)L-lysine-[1-(4-perfluorooctylsulfonyl)-piperazine]-amide A solution that consists of 21.45 g (120.4 mol) of 5-gluoconolactone in 50 ml of tetrahydrofuran is added in drops at 50° C. to a solution that consists of 100.0 g (120.4 mol) of the title compound of Example 21c), in 500 ml of dry tetrahydrofuran. It is stirred for 3 hours at 60° C. and then overnight at room temperature. It is evaporated to the dry state in a vacuum, and the residue is chromatographed on silica gel. (Mobile solvent: dichloromethane/ethanol=20:1).

Yield: 98.37 g (82% of theory) of a viscous oil).

Elementary analysis: Cld.: C, 38.10; H, 3.70; F, 32.02; N, 5.55; S, 3.18. Fnd.: C, 38.22; H, 3.79; F, 32.02; N, 5.42; S, 3.29.

b) 2-N-2,3,4,5-Pentahydroxy-hexanoyl)-L-lysine-1-[(4-perfluorooctylsulfonyl)-piperazine]-amide 100.9 g (100.0 mmol) of the title compound of Example 108a) is dissolved in 2000 ml of ethanol, and 10.0 g of palladium catalyst (10% Pd/C) is added thereto. It is hydrogenated for 12 hours at room temperature. Catalyst is filtered out, and the filtrate is evaporated to the dry state in a vacuum.

Yield: 87.46 g (quantitative) of a colorless solid.

Elementary analysis: Cld.: C, 32.96; H, 3.57; N, 6.41; S, 3.67; F, 36.93. Fnd.: C, 32.91; H, 3.72; N, 6.34; S, 3.50; F, 36.78.

f) 6-N-[1,4,7-Tris(carboxylatomethyl)]-1,4,7,10-tetraazacyclododecane-10-N-(pentanoyl-3-aza-4-oxo-5-methyl-5-yl)]-2-N-[1-O-α-D-carbonymethyl-mannopyranose]-L-lysine-[1-(4-perfluorooctylsulfonyl)-piperazine]-amide, Gd complex 50.0 g (54.55 mmol) of the title compound of Example 21e), 6.28 g (54.55 mmol) of N-hydroxysuccinimide, 4.62 g (109.0 mmol) of lithium chloride and 34.35 g (54.55 mol) of 1,4,7-tris (carboxylatomethyl)-10-(carboxy-3-aza-4-ox6-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (RP-18 mobile solvent: gradient that consists of water/ethanol/acetonitrile).

Yield: 75.9 g (91.0% of theory) of a colorless solid.

Water content: 8.6%.

Elementary analysis (relative to anhydrous substance): Cld.: C, 35.34; H, 4.09; N, 8.24; S, 2.10; F, 21.12; Gd, 10.28. Fnd.: C, 35.28; H, 4.15; N, 8.19; S, 2.15; F, 21.03; Gd, 10.14.

EXAMPLE 109 a) 6-N-Benzyloxycarbonyl-2-N-(2,3,4,5-pentahydroxy-hexanoyl)L-lysine-1-(4-perfluorooctylsulfonyl)-piperazine]-amide A solution that consists of 21.45 g (120.4 mol) of 5-gluconolactone in 50 ml of tetrahydrofuran is added in drops at 50° C. to a solution that consists of 100.0 g (120.4 mmol) of the title compound of Example 21c) and 12.18 g (120.4 mmol) of triethylamine in 500 ml of dry tetrahydrofuran. It is stirred for 3 hours at 60° C. and then overnight at room temperature. Then, 400 ml of 5% aqueous hydrochloric acid is added thereto, it is stirred for 5 minutes at room temperature, mixed with sodium chloride, the organic phase is separated, it is dried on magnesium sulfate, evaporated to the dry state in a vacuum, and the residue is chromatographed on silica gel. (Mobile solvent: dichloromethane/ethanol=20:1).

Yield: 100.97 g (82% of theory) of a viscous oil.

Elementary analysis: Cld.: C, 37.58; H, 3.45; F, 31.58; N, 5.48; S, 3.14. Fnd.: C, 37.72; H, 3.59; F, 31.72; N, 5.42; S, 3.29.

b) 2-N-(2,3,4,5-Pentahydroxy-hexanoyl)-L-lysine-1-[(4-perfluorooctylsulfonyl)-piperazine]-amide 100.9 g (100.0 mmol) of the title compound of Example 108a) is dissolved in 2000 ml of ethanol, and 10.0 g of palladium catalyst (10% Pd/C) is added thereto. It is hydrogenated for 12 hours at room temperature. Catalyst is filtered out, and the filtrate is evaporated to the dry state in a vacuum.

Yield: 87.46 g (quantitative) of a colorless solid.

Elementary analysis: Cld.: C, 32.96; H, 3.57; N, 6.41; S, 3.67; F, 36.93. Fnd.: C, 32.91; H, 3.72; N, 6.34; S, 3.50; F, 36.78.

c) 6-N-[1,4,7-Tris(carboxylatomethyl)]-1,4,7,10-tetraazacyclododecane-10-N-(pentanoyl-3-aza-4-oxo-5-methyl-5-yl)]-2-N-[1-O-α-D-carbonylmethyl-mannopyranose]-L-lysine-[1-(4-perfluorooctylsulfonyl)-piperazine]-amide, Gd complex 50.0 g (54.55 mmol) of the title compound of Example 21e), 6.28 g (54.55 mmol) of N-hydroxysuccinimide, 4.62 g (109.0 mol) of lithium chloride and 34.35 g (54.55 mol) of 1,4,7-tris(carboxylatomethyl)-10-(carboxy-3-aza-4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (RP-18 mobile solvent: gradient that consists of water/ethanol/acetonitrile).

Yield: 75.9 g (91.0% of theory) of a colorless solid.

Water content: 8.6%.

Elementary analysis (relative to anhydrous substance): Cld.: C, 35.34; H, 4.09; N, 8.24; S, 2.10; F, 21.12; Gd, 10.28. Fnd.: C, 35.28; H, 4.15; N, 8.19; S, 2.15; F, 21.03; Gd, 10.14.

EXAMPLE 110 a) 6-N-Benzyloxycarbonyl-2-N-[1-O-α-D-carbonylmethyl-(2,3,4,6-tetra-O-benzyl glucopyranose]-L-lysine-[1-(4-perfluorooctylsulfonyl)-piperazine]-amide 41.27 g (200.0 mmol) of N,N-dicyclohexylcarbodiimide is added at 0° C. to a solution that consists of 100.0 g (120.4 mol) of the title compound of Example 21c), 72.1 g (120.4 mol) of 1-O-α-D-carbonylmethyl-2,3,4,6-tetra-O-benzyl-glucopyranose and 13.86 g (120.4 mol) of N-hydroxysuccinimide, dissolved in 500 ml of dimethylformamide. It is stirred for 3 hours at 0° C. and then overnight at room temperature. Precipitated urea is filtered out, the filtrate is evaporated to the dry state in a vacuum, and it is chromatographed on silica gel. (Mobile solvent: dichloromethane/ethanol=20:1).

Yield: 136.1 g (87% of theory) of a viscous oil.

Elementary analysis: Cld.: C, 57.32; H, 4.89; N, 4.31; F, 24.86; S, 2.47. Fnd.: C, 57.48; H, 5.04; N, 4.20; F, 24.69; S, 2.38.

b) 2-N-[1-O-α-D-Carbonylmethylglucopyranose]-L-lysine-1-[(4-perfluorooctylsulfonyl)-piperazine]-amide 130.0 g (100.0 mmol) of the title compound of Example 110a) is dissolved in 2000 ml of ethanol, and 10.0 g of palladium catalyst (10% Pd/C) is added thereto. It is hydrogenated for 12 hours at room temperature. Catalyst is filtered out, and the filtrate is evaporated to the dry state in a vacuum.

Yield: 9.17 g (quantitative) of a colorless solid.

Elementary analysis: Cld.: C, 34.07; H, 3.63; N, 6.11; S, 3.50; F, 35.24. Fnd.: C, 33.92; H, 3.71; N, 6.02; S, 3.42; F, 35.33.

c) 6-N-[1,4,7-Tris(carboxylatomethyl)]-1,4,7,10-tetraazacyclododecane-10-N-(pentanoyl-3-aza-4-oxo-5-methyl-5-yl)]-2-N-[1-O-α-D-carbonylmethyl-glucopyranose]-L-lysine-[144-perfluorooctylsulfonyl)-piperazine]-amide, Gd complex 50.0 g (54.55 mmol) of the title compound of Example 110b), 6.28 g (54.55 mmol) of N-hydroxysuccinimide, 4.62 g (109.0 mol) of lithium chloride and 34.35 g (54.55 mol) of 1,4,7-tris(carboxylatomethyl)-10-(carboxy-3-aza4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added and then stirred overnight at room temperature. The solution is poured into 3000 ml of acetone and stirred for 10 minutes. The precipitated solid is filtered off and then purified by chromatography (RP-18 mobile solvent: gradient that consists of water/ethanol/acetonitrile).

Yield: 75.9 g (91.0% of theory) of a colorless solid.

Water content: 8.6%.

Elementary analysis (relative to anhydrous substance): Cld.: C, 35.34; H, 4.09; N, 8.24; S, 2.10; F, 21.12; Gd, 10.28. Fnd.: C, 35.26; H, 4.18; N, 8.14; S, 2.158; F, 21.01; Gd, 10.13.

EXAMPLE 111 a) 6-N-Benzyloxycarbonyl-2-N-[1-O-α-D-carbonylmethyl-(2,3,4,6-tetra-O-benzyl-galactopyranose]-L-lysine-[1-(4-perfluorooctylsulfonyl)-piperazine]-amide 20.64 g (100.0 mmol) of N,N-dicyclohexylcarbodiimide is added at 0° C. to a solution that consists of 50.0 g (60.2 mol) of the title compound of Example 21c), 36.05 g (60.2 mmol) of 1-O-α-D-carbonymethyl-2,3,4,6-tetra-O-benzyl-galactopyranose and 6.93 g (60.2 mmol) of N-hydroxysuccinimide, dissolved in 500 ml of dimethylformamide. It is stirred for 3 hours at 0° C. and then overnight at room temperature. Precipitated urea is filtered out, the filtrate is evaporated to the dry state in a vacuum, and it is chromatographed on silica gel. (Mobile solvent: dichloromethane/ethanol=20:1).

Yield: 68.1 g (87% of theory) of a viscous oil.

Elementary analysis: Cld.: C, 57.32; H, 4.89; N, 4.31; F, 24.86; S, 2.47. Fnd.: C, 57.47; H, 5.50; N, 4.19; F, 24.72; S, 2.29.

b) 2-N-[1-O-α-D-Carbonylmethyl-galactopyranose]-L-lysine-1-[(4-perfluorooctylsulfonyl)-piperazine]-amide 65.0 g (50.0 mmol) of the title compound of Example 111a) is dissolved in 1000 ml of ethanol, and 5.0 g of palladium catalyst (10% Pd/C) is added. It is hydrogenated for 12 hours at room temperature. Catalyst is filtered out, and the filtrate is evaporated to the dry state in a vacuum.

Yield: 45.85 g (quantitative) of a colorless solid.

Elementary analysis: Cld.: C, 34.07; H, 3.63; N, 6.11; S, 3.50; F, 35.24. Fnd.: C, 33.93; H, 3.74; N, 6.01; S, 3.39; F, 35.05.

c) 6-N-[1,4,7-Tris(carboxylatomethyl)]-1,4,7,10-tetraazacyclododecane-10-N-(pentanoyl-3-aza-4-oxo-5-methyl-5-yl)]-2-N-[1-O-α-D-carbonylmethyl-galactopyranose]-L-lysine-[1-(4-perfluorooctylsulfonyl)-piperazine]-amide, Gd complex 50.0 g (54.55 mmol) of the title compound of Example 111b), 6.28 g (54.55 mmol) of N-hydroxysuccinimide, 4.62 g (109.0 mol) of lithium chloride and 34.35 g (54.55 mol) of 1,4,7-tris(carboxylatomethyl)-10-(carboxy-3-aza4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added, and it then is stirred overnight at room temperature. The solution is poured into 3000 ml of acetone and stirred for 10 minutes. The precipitated solid is filtered off and then purified by chromatography (RP-18 mobile solvent: gradient that consists of water/ethanol/acetonitrile).

Yield: 37.95 g (91.0% of theory) of a colorless solid.

Water content: 8.6%.

Elementary analysis (relative to anhydrous substance): Cld.: C, 35.34; H, 4.09; N, 8.24; S, 2.10; F, 21.12; Gd, 10.28. Fnd.: C, 35.22; H, 4.17; N, 8.18; S, 2.19; F, 20.91; Gd, 10.12.

EXAMPLE 112 a) N-Trifluoroacetyl-L-glutamic acid-mono-benzyl ester 100 g (421.5 mmol) of L-glutamic acid-mono-benzyl ester is dissolved in a mixture that consists of 1000 ml of trifluoroacetic acid ethyl ester/500 ml of ethanol, and it is stirred for 24 hours at room temperature. It is evaporated to the dry state, and the residue is crystallized from diisopropyl ether.

Yield: 140.47 g (96% of theory) of a colorless, crystalline powder.

Elementary analysis: Cld.: C, 50.46; H, 4.23; F, 17.10; N, 4.20. Fnd.: C, 51.35; H, 4.18; F, 17.03; N, 4.28.

b) 2-N-Trifluoroacetyl-L-glutamic acid-mono-benzylester-5-N-(methyl)-N-(2,3,4,5,6-pentahydroxyhexyl)-amide 8.25 g (40 mmol) of N,N-dicyclohexylcarbodiimide is added at 0° C. to a solution that consists of 24.9 g (24.08 mmol) of the title compound of Example 112a), 2×g (24.08 mmol) of N-methylglucamine and 2.77 g (24.08 mmol) of N-hydroxysuccinimide, dissolved in 150 ml of dimethylformamide. It is stirred for 3 hours at 0° C., then overnight at room temperature. Precipitated urea is filtered out, the filtrate is evaporated to the dry state in a vacuum and chromatographed on silica gel (mobile solvent:= dichloromethane/ethanol=20:1).

Yield: 9.×g (89% of theory) of a viscous oil.

Elementary analysis: Cld.: C, 51.43; H, 5.51; F, 13.56; N, 6.66. Fnd.: C, 51.22; H, 5.41; F, 13.40; N, 6.75.

c) N-Trifluoroacetyl-L-glutamic acid-N-(methyl)-N-(2,3,4,5,6-pentahydroxyhexyl)-amide 21.9×g (52.15 mmol) of the title compound of Example 112b is dissolved in 500 ml of ethanol, and 3 g of palladium catalyst (10% Pd/C) is added. It is hydrogenated at room temperature. Catalyst is filtered out, and the filtrate is evaporated to the dry state in a vacuum.

Yield: 43.0 g (quantitative) of a colorless solid.

Elementary analysis: Cld.: C, 40.01; H, 5.19; F, 17.26; N, 8.48. Fnd.: C, 39.84; H, 5.13; F, 17.09; N, 8.68.

d) Trifluoroacetyl-L-glutamic acid-5-N-(methyl)-N-(2,3,4,5,6-pentahydroxyhexy])-amide-[1-(4-perfluorooctylsulfonyl)-piperazine]-amidepiperazine]-amide 16.42 g (66.4 mmol) of EEDQ (2-ethoxy-1,2-dihydroquinoline-1-carboxylic acid ethyl ester) is added at 0° C. to 10.96 g (33.2 mmol) of the title compound of Example 112c and 18.87 g (33.2 mmol) of 1-perfluorooctylsulfonyl-piperazine (produced according to DE 19603033) in 80 ml of tetrahydrofuran, and it is stirred overnight at room temperature. It is evaporated to the dry state in a vacuum and chromatographed on silica gel (mobile solvent: dichloromethane/methanol=20:1).

Yield: 28.67 g (92% of theory) of a colorless solid.

Elementary analysis: Cld.: C, 39.61; H, 2.89; F, 35.66; N, 6.19; S, 3.54. Fnd.: C, 39.68; H, 2.74; F, 35.81; N, 6.13; S, 3.40.

e) L-Glutamic acid-5-N-(methyl)-N-2,3,4,5,6-pentahydroxyhexyl)-amide-[1-(4-perfluorooctylsulfonyl)-piperazine]-amide Ammonia gas is introduced at 0° C. for one hour into a solution that consists of 28.36 g (30.22 mmol) of the title compound of Example 112d in 200 ml of ethanol. It then is stirred for 4 hours at 0° C. It is evaporated to the dry state, and the residue is absorptively precipitated from water. The solid is filtered off and dried in a vacuum (50° C.).

Yield: 24.19 g (95% of theory) of an amorphous solid.

Elementary analysis: Cld.: C, 41.12; H, 2.89; F, 35.66; N, 6.19; S, 3.54. Fnd.: C, 41.15; H, 2.83; F, 35.78; N, 6.28; S, 3.71.

f) N-[1,4,7-Tris(carboxylatomethyl)-1,4,7,10-tetraazacyclododecane-10-(pentanoyl-3-aza-4-oxo-5-methyl-5-yl)]-L-glutamic acid-5-N-(methyl)-N-(2,3,4,5,6-pentahydroxyhexyl)-amide-[1-(4-perfluorooctylsulfonyl)-piperazine]-amide, Gd complex 20.43 g (24.25 mmol) of the title compound of Example 112e, 2.79 g (24.25 mmol) of N-hydroxysuccinimide, 2.12 g (50 mmol) of lithium chloride and 15.27 g (24.25 mmol) of 1,4,7-tris(carboxylatomethyl)-O-[(3-aza-4-oxo-5-methyl-5-yl)]-pentanoic acid]-1,4,7,10-tetraazacyclododecane, Gd complex are dissolved in 200 ml of dimethyl sulfoxide while being heated slightly. At 10° C., 8.25 g (40 mmol) of N,N-dicyclohexylcarbodiimide is added and then stirred overnight at room temperature. The solution is poured into 3000 ml of acetone and stirred for 10 minutes. The precipitated solid is filtered off and then purified by chromatography (silica gel RP-18, mobile solvent: gradient that consists of water/ethanol/acetonitrile).

Yield: 28.45 g (79% of theory) of a colorless solid.

Water content: 11.0%.

Elementary analysis (relative to anhydrous substance): Cld.: C, 34.41; H, 13.83; F, 23.13; N, 9.03; S, 2.30; Gd, 11.26. Fnd.: C, 34.34; H, 3.98; F, 23.29; N, 9.19; S, 2.15; Gd, 11.07.

EXAMPLE 113 a) 6-N-Benzyloxycarbonyl-2-N-[-O-α-D-carbonylmethyl-(2,3,4-tri-O-benzyl-glucuronic acid-benzylester]-L-lysinc-[1-(4-perfluorooctylsulfonyl)-piperazine]-amide 41.27 g (200.0 mmol) of N,N-dicyclohexylcarbodiimide is added at 0° C. to a solution that consists of 100.0 g (120.4 mol) of the title compound of Example 21c), 73.77 g (120.4 mol) of 1-O-α-D-carbonylmethyl-2,3,4-tri-O-benzyl-glucuronic acid-benzylester and 13.86 g (120.4 mol) of N-hydroxysuccinimide, dissolved in 500 ml of dimethylformamide. It is stirred for 3 hours at 0° C. and then overnight at room temperature. Precipitated urea is filtered out, the filtrate is evaporated to the dry state in a vacuum and chromatographed on silica gel. (Mobile solvent: dichloromethane/ethanol=20:1).

Yield: 147.58 g (86% of theory) of a viscous oil.

Elementary analysis: Cld.: C, 52.25; H, 4.31; N, 3.93; F, 22.66; S, 2.45. Fnd.: C, 52.38; H, 4.17; N, 4.12; F, 22.78; S, 2.39.

b) 2-N-[1-O-α-D-Carbonylmethyl-glucuronic acid]-L-lysine-1-[(4-perfluorooctylsulfonyl)-piperazine]-amide 142.52 g (100.0 mmol) of the title compound of Example 113a) is dissolved in 2000 ml of ethanol, and 10.0 g of palladium catalyst (10% Pd/C) is added thereto. It is hydrogenated for 12 hours at room temperature. Catalyst is filtered out, and the filtrate is evaporated to the dry state in a vacuum.

Yield: 93.06 g (quantitative) of a colorless solid.

Elementary analysis: Cld.: C, 33.56; H, 3.36; N, 6.02; S, 3.45; F, 34.71. Fnd.: C, 33.31; H, 3.42; N, 6.04; S, 3.40; F, 35.51.

c) 6-N-[1,4,7-Tris(carboxylatomethyl)]-1,4,7,10-tetraazacyclododecane-10-N-(pentanoyl-3-aza-4-oxo-5-methyl-5-yl)]-2-N-[1-O-α-D-carbonylmethyl-glucuronic acid]-L-lysine-[1-(4-perfluorooctylsulfonyl)-piperazine]-amide, Gd complex, sodium salt 50.76 g (54.55 mmol) of the title compound of Example 113b), 6.28 g (54.55 mmol) of N-hydroxysuccinimide, 4.62 g (109.0 mol) of lithium chloride and 34.35 g (54.55 mol) of 1,4,7-tris(carboxylatomethyl)-10-(carboxy-3-aza4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added, and it then is stirred overnight at room temperature. The solution is poured into 3000 ml of acetone, and it is stirred for 10 minutes. The precipitated solid is filtered off and then purified by chromatography (RP-18 mobile solvent: gradient that consists of water/ethanol/acetonitrile).

Yield: 75.149 g (88.0% of theory) of a colorless solid.

Water content: 8.6%.

Elementary analysis (relative to anhydrous substance): Cld.: C, 34.53; H, 3.80; N, 8.05; Na, 1.47; S, 2.05; F, 20.63; Gd, 10.05. Fnd.: C, 34.38; H, 3.95; N, 8.19; Na, 1.63; S, 2.15; F, 20.83; Gd, 10.14.

EXAMPLE 114 a) 6-N-Benzyloxycarbonyl)-2-[2-(N-ethyl-N-perfluorooctylsulfonyl]-amino]-acetyl-L-lysine 49.46 g (200.0 mmol) of EEDQ (2-ethoxy-1,2-dihydroquinoline-1-carboxylic acid ethyl ester) is added at 0° C. to 31.820 g (113.5 mmol) of 6-N-benzyloxycarbonyl)-L-lysine and 66.42 g (113.5 mmol) of 2-(N-ethyl-N-perfluorooctylsulfonyl)-aminoacetic acid (produced according to DE 196 03 033) in 300 ml of tetrahydrofuran, and it is stirred overnight at room temperature. It is evaporated to the dry state in a vacuum and chromatographed on silica gel (mobile solvent: dichloromethanelmethanol=20:1).

Yield: 55.79 g (58% of theory) of a colorless solid.

Elementary analysis: Cld.: C, 36.85; H, 3.09; N, 4.96; F, 38.11; S, 3.78. Fnd.: C, 36.85; H, 3.19; N, 4.87; F, 38.28; S, 3.95.

b) 6-N-Benzyloxycarbonyl-2-N-[2-(N-ethyl-N-perfluorooctylsulfonyl)-amino]-acetyl-L-lysine-N-methyl-N-(2,3,4,5,6-pentahydroxy-hexyl)-amide 20.64 g (100.0 mmol) of N,N-dicyclohexylcarbodiimide is added at 0° C. to a solution that consists of 51.02 g (60.2 mol) of the title compound of Example 114a), 11.75 g (60.2 mol) of N-methyl-glucamine and 6.93 g (60.2 mol) of N-hydroxysuccinimide, dissolved in 250 ml of dimethylformamide. It is stirred for 3 hours at 0° C. and then overnight at room temperature. Precipitated urea is filtered out, the filtrate is evaporated to the dry state in a vacuum, and it is chromatographed on silica gel. (Mobile solvent: dichloromethane/ethanol=20:1).

Yield: 53.05 g (86% of theory) of a viscous oil.

Elementary analysis: Cld.: C, 38.68; H, 4.03; N, 5.47; F, 31.52; S, 3.13. Fnd.: C, 38.49; H, 4.17; N, 5.32; F, 31.70; S, 3.29.

c) 2-N-[2-(N-Ethyl-N-perfluorooctylsulfonyl)-amino]-acetyl-L-lysine-N-methyl-N-(2,3,4,5,6-pentahydroxy-hexyl)-amide 102.48 g (100.0 mmol) of the title compound of Example 114b) is dissolved in 2000 ml of ethanol, and 10.0 g of palladium catalyst (10% Pd/C) is added thereto. It is hydrogenated for 12 hours at room temperature. Catalyst is filtered out, and the filtrate is evaporated to the dry state in a vacuum.

Yield: 89.06 g (quantitative) of a colorless solid.

Elementary analysis: Cld.: C, 33.72; H, 3.96; N, 6.29; S, 3.60; F, 36.26. Fnd.: C, 33.91; H, 3.82; N, 6.14; S, 3.47; F, 36.31.

d) 6-N-[1,4,7-Tris(carboxylatomethyl)]-1,4,7,10-tetraazacyclododecane-10-N-(pentanoyl-3-aza-4-oxo-5-methyl-5-yl)]-2-N-[2-(N-ethyl-N-perfluorooctyl-sulfonyl)-amino]-acetyl-L-lysine-N-methyl-N-(2,3,4,5,6-pentahydroxy-hexyl)-amide, Gd complex 48.58 g (54.55 mmol) of the title compound of Example 114), 6.28 g (54.55 mmol) of N-hydroxysuccinimide, 4.62 g (109.0 mol) of lithium chloride and 34.35 g (54.55 mol) of 1,4,7-tris(carboxylatomethyl)-10-(carboxy-3-aza-4-oxo-5-methyl-pent-5-yl)-1,4,7,10-tetraazacyclododecane, Gd complex, are dissolved in 400 ml of dimethyl sulfoxide while being heated slightly. At 10° C., 16.88 g (81.8 mol) of N,N-dicyclohexylcarbodiimide is added and then stirred overnight at room temperature. The solution is poured into 3000 ml of acetone and stirred for 10 minutes. The precipitated solid is filtered off and then purified by chromatography (RP-18 mobile solvent: gradient that consists of water/ethanol/acetonitrile).

Yield: 73.27 g (89.4% of theory) of a colorless solid.

Water content: 8.6%.

Elementary analysis (relative to anhydrous substance): Cld.: C, 35.18; H, 4.23; N, 4.23; S, 21.3; F, 21.50; Gd, 10.47. Fnd.: C, 35.28; H, 4.15; N, 4.19; S, 2.18; F, 21.33; Gd, 10.61.

EXAMPLE 115

MRT-Visualization of Arteriosclerotic Plaque After Intravenous Administration of Metal Complexes According to the Invention In rabbits with genetically induced arteriosclerosis (Watanabe rabbits), it was possible to observe a significant enhancement in the arteriosclerotic plaque 5–60 minutes as well as 24 hours and 48 hours after intravenous administration of 25 μmol of Gd/kg of body weight of the compounds according to the invention in T1-weighted gradient-echo images (TR 11.1 ms, TE 4.3 ms, 15° flip angle α). The healthy vessel wall showed only little or no contrast medium image and therefore also indicated only little or no signal rise in the $T_1$-weighted images. Based on the contrast between the plaque with strong signals and the healthy vessel wall with little or no signals, a diagnosis of the arteriosclerotic vessel wall changes was possible.

The pictures in FIG. 1 show MR images of the aorta before, as well as 24 hours and 48 hours after intravenous administration of 25 μmol of Gd/kg of body weight of metal complex XV in Watanabe rabbits (genetically induced arteriosclerosis). The $T_1$-weighted gradient-echo images (1.5 T; TR: 11.1 ms, TE: 4.3 ms; NA: 2; matrix: 213*256; layer thickness: 1.0 mm) illustrate a strong signal rise in the arteriosclerotic plaque. The localization of the plaque, especially in aortic arches and in vascular passages, was confirmed by means of Sudan-III-staining.

EXAMPLE 116

Figure 2A:
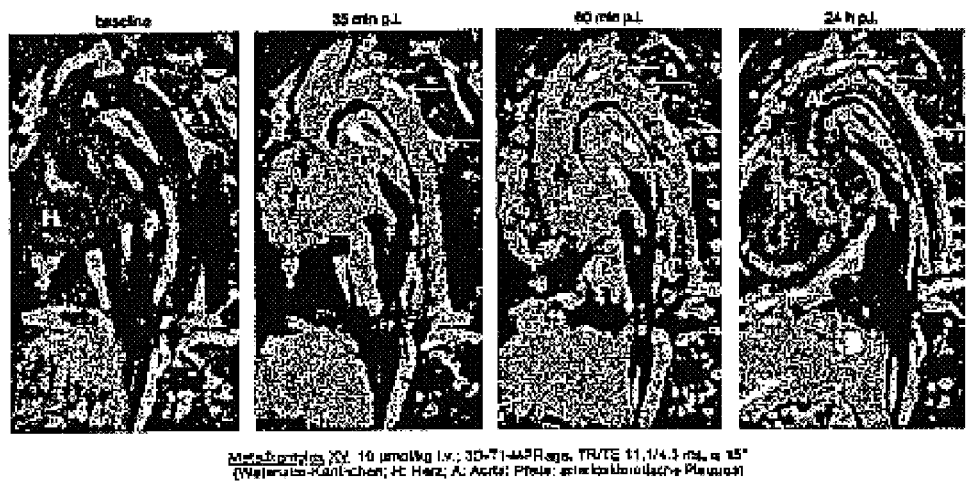
FIG. 2A presents MR images of the aorta at baseline and after 35 min., 60 min. and 24 hours, with visualization after administration of metal complex XV 10 µmol/kg i.v.; 3D-T1-MPRage, TR/TE 11.1/4.3 ms, α 15°. (Watanabe rabbits; A:Aorta; H: Heart; Arrow: arteriosclerotic plaque; MPR Projection: Histology after Sudan-III staining)
Figure 2B:
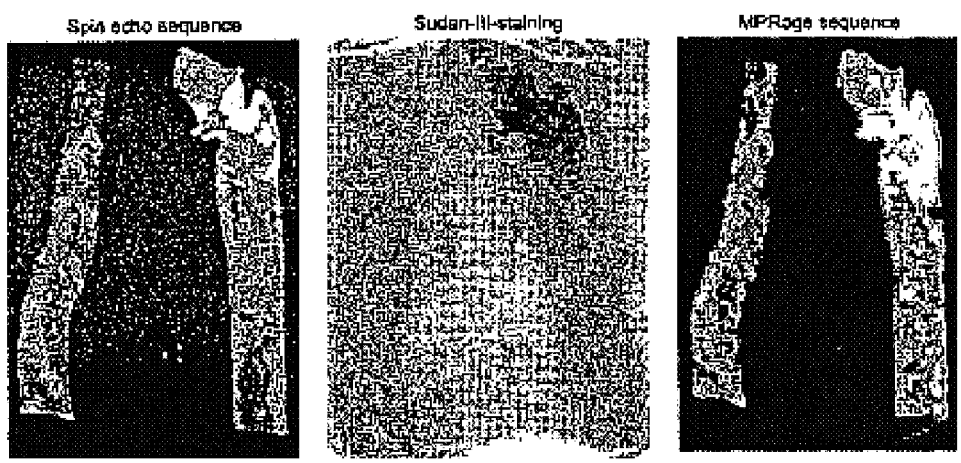
FIG. 2B depicts post mortem MRI of agar-embedded aorta with visualization after administration of metal complex XV 10 µmol/kg i.v.; SE, TR/TE 400/15 ms, and 3D-T1-MPRage, TR/TE 11.1/4.3 ms α 15°. (Watanabe rabbits; 24 hour p.i. preparation of Aorta; Histology after Sudan-III staining)

MRT-Visualization of Arteriosclerotic Plaque After Intravenous Administration of Metal Complex XV in Rats, and Correlation of the Post Mortem Image With Sudan-III-staining The pictures in FIGS. 2a and 2b show MR images of the aorta before as well as 35 minutes, 60 minutes and 24 hours after intravenous administration of 10 μmol of Gd/kg of body weight of gadolinium metal complex XV in Watanabe rabbits (genetically induced arteriosclerosis). The $T_1$-weighted gradient-echo-images (MPRage; 1.5T; TR: 11.1 ms, TE: 4.3 ms; NA: 2; matrix: 213*256; layer thickness: 1.0 mm) illustrate a strong signal rise in arteriosclerotic plaque. The localization of the plaque, especially in aortic arches as well as in vascular passages, was confirmed by means of Sudan-III-staining. Then, the MR-imaging of the agar-embedded preparation was again examined with a $T_1$-weighted gradientecho sequence (MPRage; 1.5 T; TR 11.1 ms, TE 4.3 ms, 15° flip angle α; NA: 2; matrix: 213*256) and a spin-echo sequence (1.5 T; TR: 400 ms, TE: 15 ms; NA: 16; matrix: 256*256) (post mortem image). In this case, there was shown an excellent correlation of the aortic sections with strong signal rise and stained plaque, which confirms an uptake of the compounds according to the invention in the arteriosclerotic plaque.

EXAMPLE 117

Figure 3:
FIG. 3 shows myocardial infarction visualization 24 hours p.i. after administration of metal complex XV, 100 µmol/kg i.v.; T1-SE, TR/TE 400/6 ms.

Infarction Visualization (MRT) After Intravenous Administration of Metal Complex XV in Rats The pictures in FIG. 3 show MR images of the heart (in vivo and post mortem) 24 hours after intravenous administration of 100 μmol of Gd/kg of body weight of metal complex XV in rats with acutely induced myocardial infarction. The $T_1$-weighted spin-echo images (1.5 T; TR: 400 ms, TE: 6 ms; NA: 4; matrix: 128*128; layer thickness: 2.5 mm) illustrate the strong signal rise in the infarction area. The successful induction of an acute myocardial infarction was confirmed by means of NBT-staining.

Metal complex XV, 100 μmol/kg i.v.; T1-SE, TR/TE 400/6 ms; arrow: myocardial infarction.

EXAMPLE 118

Figure 4:
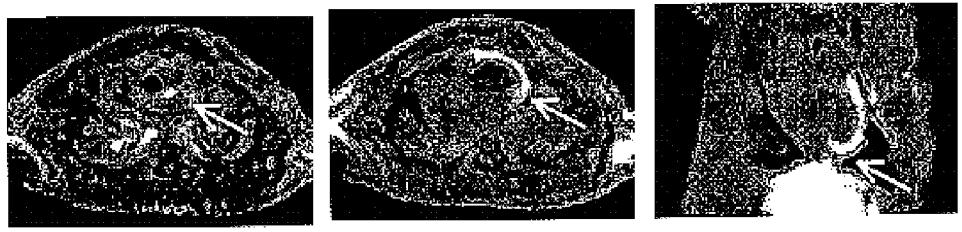
FIG. 4 shows myocardial infarction visualization 24 hours p.i. after administration of metal complex I, 100 µmol/kg i.v.; SE, , TR/TE 400/6 ms.

Infarction Visualization (MRT) After Intravenous Administration of Metal Complex I in Rats The pictures in FIG. 4 show MR images of the heart (in vivo and post mortem) 24 hours after intravenous administration of 100 μmol of Gd/kg of body weight of metal complex I in rats with acutely induced myocardial infarction. The $T_1$-weighted spin-echo images (1.5 T; TR: 400 ms, TE: 6 ms; NA: 4; matrix: 128*128; layer thickness: 2.5 mm) illustrate the strong signal rise in the infarction area. The successful induction of an acute myocardial infarction was confirmed by means of NBT-staining.

Figure 5A:
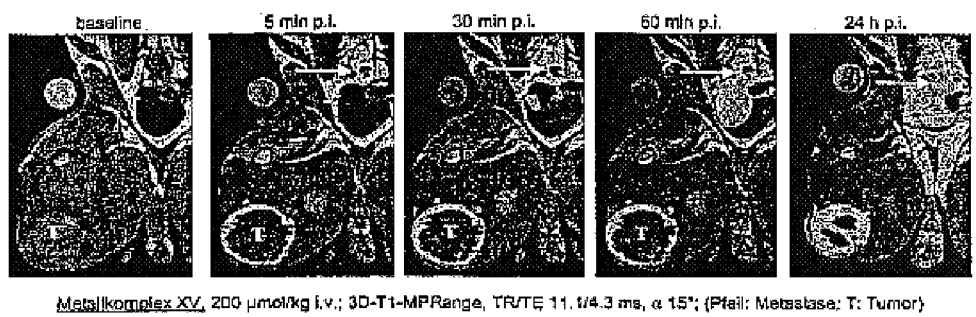
FIG. 5A arrow points to metastasis. Visualization is after administration of metal complex XV, 200 µmol/kg i.v.; 3D-T1-MPRange, TR/TE 11.1/4.3 ms, α 150°, T: tumor.
Figure 5B:
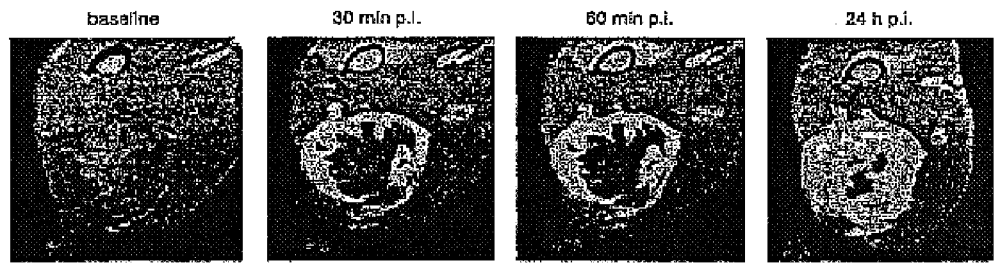
FIG. 5B arrow points to metastasis, with visualization after administration of metal complex XV, 200 µmol/kg i.v.; TR/TE 11.1/4.3 ms, α 15°.

EXAMPLE 119
Lymph Node Visualization (MRT) After Intravenous Administration of Metal Complex XV in VX2-tumor-carrying Rabbits The pictures in FIG. 5a and 5b show MR images of iliac lymph nodes precontrast and up to 24 hours after intravenous administration of 200 μmol of Gd/kg of body weight of metal complex XV in rabbits with VX2-tumors implanted i.m. The $T_1$-weighted gradient-echo images (1.5 T; sequence: MPRange; TR 11.1 ms, TE 4.3 ms, α 15°) illustrate the strong signal rise in healthy lymph node tissue. Zones without signal rise within the lymph node were diagnosed as metastases and confirmed histologically (H/E-staining of the lymph node section). Later (24 hours) after contrast medium administration, however, a signal reversal was observed, surprisingly enough. The signal rise in healthy lymph node tissue was reduced, while the metastasis now exhibited a considerable signal rise.

Surprisingly enough, even immediately after administration, a considerable enhancement of the primary tumor (especially the periphery) could be observed. Later (24 hours p.i.), this enhancement also propagates out from the center of the tumor.

Figure 6:
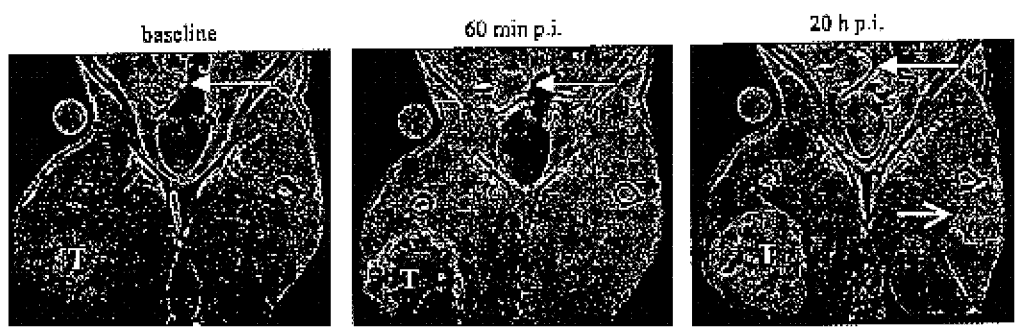
FIG. 6 closed arrow points to lymph nodes and open arrow points to late enhancement, with visualization after administration of metal complex I, 100 µmol/kg i.v.; 3D-T1-MPRange, TR/TE 11.1/4.3 ms, α 15°.

EXAMPLE 120
Tumor Visualization (MRT) After Intravenous Administration of Metal Complex I in VX2-tumor-carrying Rabbits The pictures of FIG. 6 show MR images of an iliac lymph node and of a primary tumor (VX2-tumor implanted i.m.) precontrast, 60 minutes and 20 hours after intravenous administration of 100 μmol of Gd/kg of body weight of metal complex I in rabbits. The $T_1$-weighted gradient-echo images (1.5 T; sequence: MPRange; TR 11.1 ms, TE 4.3 ms, α 15°) illustrate the strong signal rise in healthy lymph node tissue.

Shortly after administration (60 minutes p.i.), a considerable enhancement of the primary tumor (especially the periphery) can be observed. Subsequently (20 hours p.i.), the signal rise is also propagated in the more central region of the tumor.

The enhancement of a pathological structure (optionally secondary tumor or necrosis) on the contralateral side, which shows up only in late images ("late enhancement") is especially noteworthy.
Metal Complex X

Figure 7:
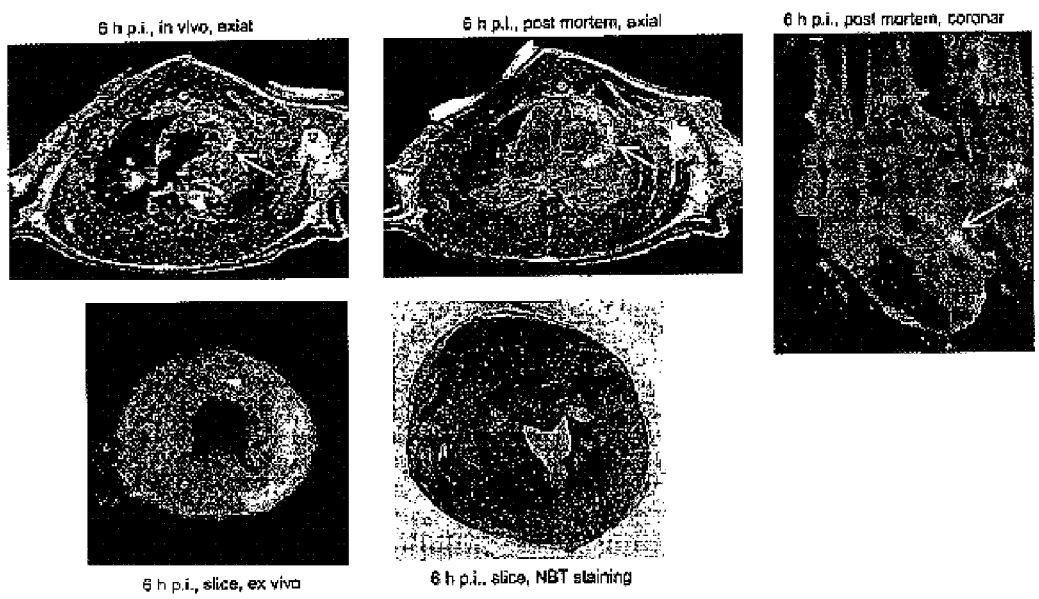
FIG. 7 depicts imaging of myocardial infarct, with visualization after administration of metal complex X;, 100 µmol/kg i.v.; SE, , TR/TE 400/12 ms .

EXAMPLE 121
Infarction Visualization (MRT) After Intravenous Administration of the Contrast Medium in Rats The pictures in FIG. 7 show MR images of the heart (in vivo and post mortem) 6 hours after intravenous administration of 100 μmol of Gd/kg of body weight of a polar Gd-chelate with perfluorinated side chains (metal complex X) in rats with acutely induced myocardial infarction. The $T_1$-weighted, EKG-triggered spin-echo images (1.5 T; TR(effective): 400 ms, TE: 12 ms; NA: 4; matrix: 128*128; layer thickness: 2.5 mm) illustrate the strong signal rise in the infarction area. The successful induction of an acute myocardial infarction was confirmed by means of NBT-staining.

EXAMPLE 122
Organ Distribution (Including Lymph Node Concentration) After Intravenous Administration of the Contrast Medium in Rats After intravenous administration of 100 μmol of total gadolinium/kg of body weight of a polar Gd-chelate with perfluorinated side chains (metal complex X) in rats, the metal content in various organs as well as in the lymph nodes (pooled as mesenteric and peripheral lymph nodes) was determined 24 hours after administration (MW, n=2).

| Organ | μmol Gd/L | % Dose |
|---|---|---|
| Liver | 104 | 2.34 |
| Femur | 3 | 0.01 |
| Kidneys | 150 | 0.65 |
| Brain | 1 | 0.01 |
| Carcass | 192 | 34.01 |
| Blood | 1 | 0.01 |
| Stomach | 49 | 0.18 |
| Intestine | 65 | 1.22 |
| Spleen | 54 | 0.07 |
| Pancreas | 6 | 0.02 |
| Heart | 3 | 0.01 |
| Lung | 18 | 0.05 |
| Muscle | 1 | 0.00 |
| Mesenteric lymph nodes | 19 | 0.01 |
| Peripheral lymph nodes | 11 | 0.01 |
| Total | | 38.58 |

Figure 8:
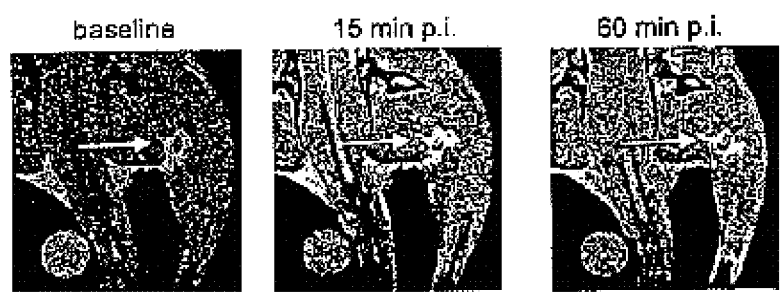
FIG. 8 depicts the visualization of popliteal lymph nodes after administration of metal complex X, 100 µmol/kg i.v.; 3D-T1-MPRange, TR/TE 11.1/4.3 ms, α 15°.

EXAMPLE 123
Lymph Node Visualization (MRT) After Intravenous Administration of the Contrast Medium in Rats By way of example, the pictures in FIG. 8 show MR images of iliac lymph nodes precontrast and up to 60 minutes after intravenous administration of 100 μmol of Gd/kg of body weight of metal complex X in rats. The $T_1$-weighted gradient-echo images (1.5 T; sequence: MPRange; TR 11.1 ms, TE 4.3 ms, a 15°) illustrate the strong signal rise in healthy lymph node tissue even very shortly after injection. The enhancement was thus 263% at the time of 15 minutes p.i. and 254% at the time of 60 minutes p.i.

Figure 9:
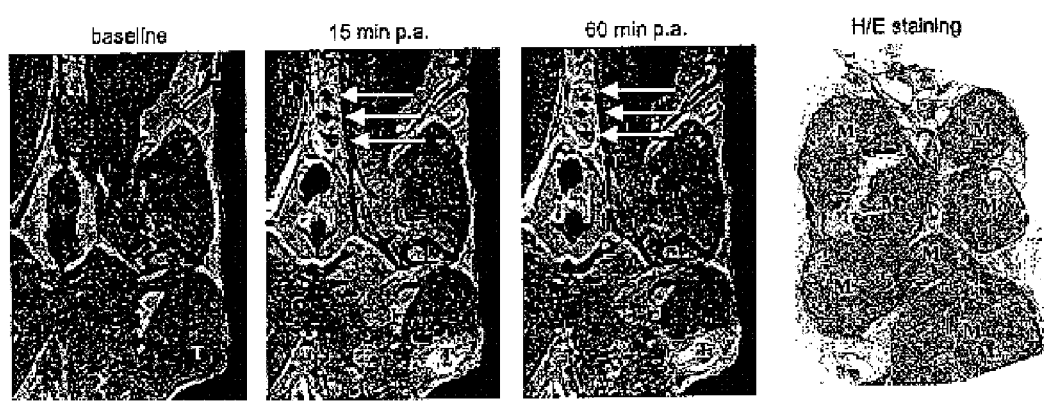
FIG. 9 depicts the visualization of metastases and tumors after administration of metal complex X, 200 µmol/kg i.v.; 3D-T1-MPRange, TR/TE 11.1/4.3 ms , α 15°.

EXAMPLE 124
Lymph Node Visualization (MRT) After Intravenous Administration of the Contrast Medium in VX2-tumor-bearing Rabbits By way of example, the pictures in FIG. 9 show MR images of iliac lymph nodes precontrast and up to 60 minutes after intravenous administration of 200 μmol of Gd/kg of body weight of metal complex X in rabbits with VX2-tumors implanted i.m. The $T_1$-weighted gradient-echo images (1.5 T; sequence: MPRange; TR 11.1 ms, TE 4.3 ms, α 15°) illustrate the strong signal rise in healthy lymph node tissue. The enhancement in the healthy lymph node tissue was 382% at the time of 15 minutes p.i. and 419% at the time of 60 minutes p.i. Zones without signal rise within the lymph node were diagnosed as metastases and confirmed histologically (H/E-staining of the lymph node section). The ratio of signal intensities of healthy lymph node tissue to metastasis was 3.0 at the time of 15 minutes p.i. and 3.4 at the time of 60 minutes p.i.

Surprisingly enough, even immediately after administration, a considerable enhancement not only of the lymph nodes but also of the primary tumor (especially the periphery) could be observed (15 minutes p.i.: 277%). Later (up to 24 hours p.i.), this enhancement also propagates out from the center of the tumor (24 hours p.i.: 217%).
Metal Complex V

Figure 10:
FIG. 10 depicts the visualization of myocardial infarct after administration of metal complex V, 100 µmol/kg i.v.; SE, TR/TE 400/12 ms.

EXAMPLE 125
Infarction Visualization (MRT) After Intravenous Administration of the Contrast Medium in Rats The pictures in FIG. 10 show MR images of the heart (in vivo and post mortem) 24 hours after intravenous administration of 100 μmol of Gd/kg of body weight of a polar Gd-chelate with perfluorinated side chains (metal complex V) in rats with acutely induced myocardial infarction. The $T_1$-weighted, EKG-triggered spin-echo images (1.5 T; TR (effective): 400 ms, TE: 12 ms; NA: 4; matrix: 128*128; layer thickness: 2.5 mm) illustrate the strong signal rise in the infarction area. The successful induction of an acute myocardial infarction was confirmed by means of NBT-staining.

EXAMPLE 126
Organ Distribution (Including Lymph Node Concentration) After Intravenous Administration of the Contrast Medium in Rats After intravenous administration of 200 μmol of total gadolinium/kg of body weight of a polar Gd-chelate with perfluorinated side chains (metal complex V) in rats, the metal content in various organs as well as in the lymph nodes (pooled as mesenteric and peripheral lymph nodes) was determined 24 hours after administration (MW, n=2).

| Organ | μmol Gd/L | % Dose |
|---|---|---|
| Liver | 344 | 6.34 |
| Femur | 13 | 0.05 |
| Kidneys | 436 | 1.77 |
| Brain | 4 | 0.02 |
| Carcass | 268 | 37.93 |
| Blood | 15 | 0.18 |
| Stomach | 28 | 0.08 |
| Intestine | 113 | 1.56 |
| Spleen | 116 | 0.17 |
| Pancreas | 30 | 0.05 |
| Heart | 14 | 0.02 |
| Lung | 62 | 0.17 |
| Muscle | 9 | 0.02 |
| Mesenteric lymph nodes | 70 | 0.05 |
| Peripheral lymph nodes | 44 | 0.02 |
| Total | | 48.43 |

Figure 11:
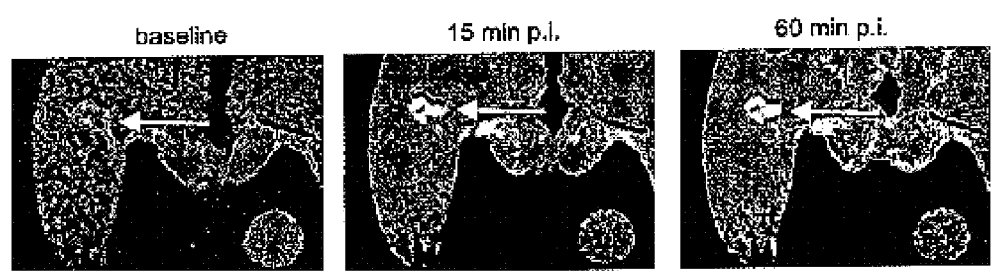
FIG. 11 depicts the visualization of popliteal lymph nodes after administration of metal complex III, 200 µmol/kg i.v.; 3D-T1-MPRange, TR/TE 11.1/4.3 ms, α 15°.

EXAMPLE 127
Lymph Node Visualization (MRT) After Intravenous Administration of the Contrast Medium in Rats By way of example, the pictures in FIG. 11 show MR images of iliac lymph nodes precontrast and up to 60 minutes after intravenous administration of 200 μmol of Gd/kg of body weight of metal complex V in rats. The $T_1$-weighted gradient-echo images (1.5 T; sequence: MPRange; TR 11.1 ms, TE 4.3 ms, α 15°) illustrate the strong signal rise in healthy lymph node tissue even very shortly after injection. The enhancement was thus 147% at the time of 15 minutes p.i. and 230% at the time of 60 minutes p.i.

Figure 12:
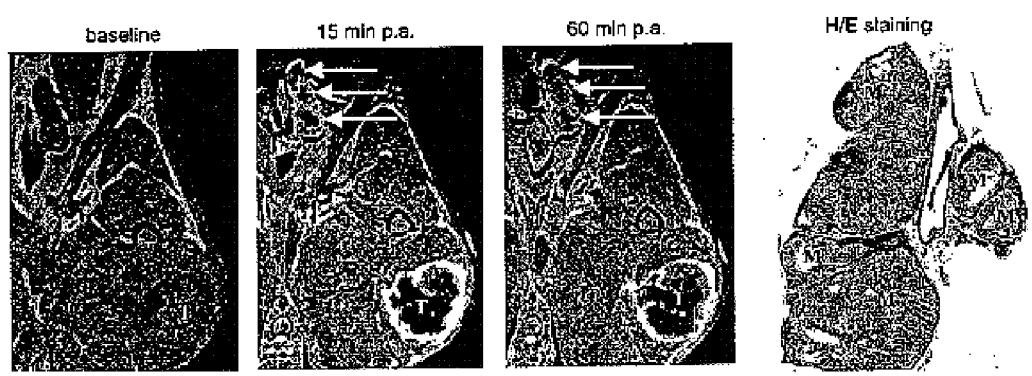
FIG. 12 depicts the visualization of metastasis after administration of metal complex V, 200 µmol/kg i.v.; 3D-T1-MPRange, TR/TE 11.1/4.3 ms, α 15°., T: tumor.

EXAMPLE 128
Lymph Node Visualization (MRT) After Intravenous Administration of the Contrast Medium in VX2-tumor-bearing Rabbits By way of example, the pictures in FIG. 12 show MR images of iliac lymph nodes precontrast and up to 60 minutes after intravenous administration of 200 μmol of Gd/kg of body weight of metal complex V in rabbits with VX2-tumors implanted i.m. The $T_1$-weighted gradient-echo images (1.5 T; sequence: MPRange; TR 11.1 ms, TE 4.3 ms, a 15°) illustrate the strong signal rise in healthy lymph node tissue. The enhancement in the healthy lymph node tissue was 246% at the time of 15 minutes p.i. and 282% at the time of 60 minutes p.i. Zones without signal rise within the lymph node were diagnosed as metastases and confirmed histologically (H/E-staining of the lymph node section). The ratio of signal intensities of healthy lymph node tissue to metastasis was 2.5 at the time of 15 minutes p.i. and 1.7 at the time of 60 minutes p.i.

Surprisingly enough, even immediately after administration, a considerable enhancement not only of the lymph nodes but also of the primary tumor (especially the periphery) could be observed (15 minutes p.i.: 350%). Later (up to 24 hours p.i.), this enhancement also propagates out from the center of the tumor (24 hours p.i.: 106%).

Metal Complex XIV

Figure 13:
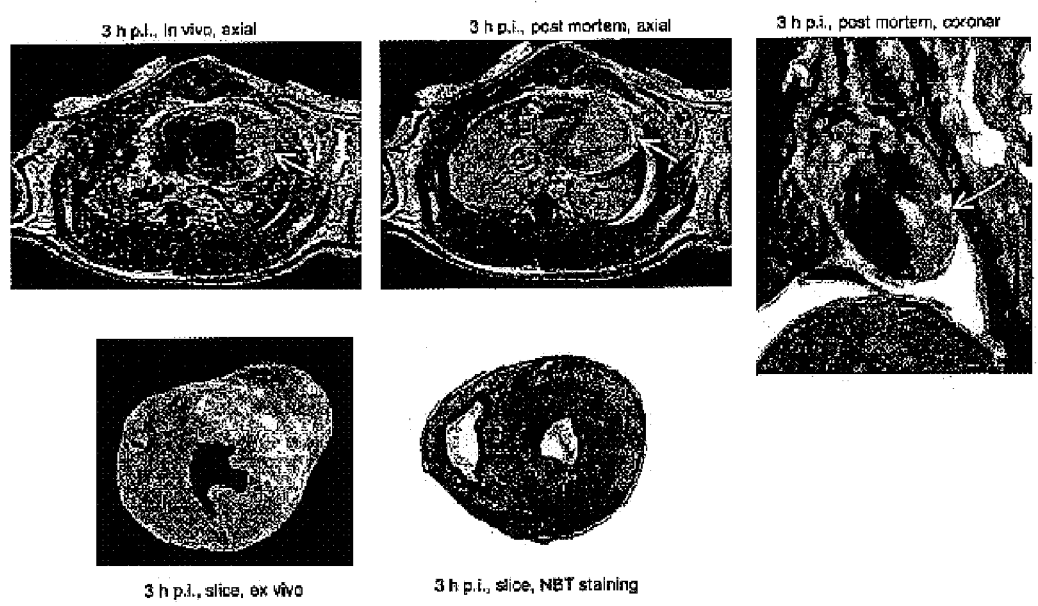
FIG. 13 depicts the visualization of myocardial infarct after administration of metal complex XIV, 100 µmol/kg i.v.; SE,, TR/TE 400/12 ms.

EXAMPLE 129
Infarction Visualization (MRT) After Intravenous administration of the Contrast Medium in Rats The pictures in FIG. 13 show MR images of the heart (in vivo and post mortem) 3 hours after intravenous administration of 100 μmol of Gd/kg of body weight of a polar Gd-chelate with perfluorinated side chains (metal complex XIV) in rats with acutely induced myocardial infarction. The $T_1$-weighted, EKG-triggered spin-echo images (1.5 T; TR (effective): 400 ms, TE: 12 ms; NA: 4; matrix: 128*128; layer thickness: 2.5 mm) illustrate the strong signal rise in the infarction area. The successful induction of an acute myocardial infarction was confirmed by means of NBT-staining.

EXAMPLE 130
Organ Distribution (Including Tumor and Lymph Node Concentration) After Intravenous Administration of the Contrast Medium in Prostate/cancer-bearing Rats After intravenous administration of 200 μmol of total gadolinium/kg of body weight of a polar Gd-chelate with perfluorinated side chains (metal complex XIV) in rats (Cop-inbreeding with Dunning R3327 MAT-Lu prostate cancer i.m.-implanted 12 days earlier), the metal content in various organs, in tumors, as well as in the lymph nodes (pooled as mesenteric and peripheral lymph nodes) was determined 10 minutes, 1 hour and 24 hours after administration (MW±SD, n=3).

| | Metal complex XIV | | | | | |
|---|---|---|---|---|---|---|
| | Gd concentration [µmol/l] | | | % Dose | | |
| | 10 min p.i. | 1 h p.i. | 24 h p.i. | 10 min p.i. | 1 h p.i. | 24 h p.i. |
| Liver | 192 ± 12 | 147 ± 7 | 64 ± 4 | 2.62 ± 0.11 | 2.04 ± 0.15 | 0.96 ± 0.05 |
| Spleen | 200 ± 13 | 123 ± 10 | 69 ± 5 | 0.13 ± 0.01 | 0.08 ± 0.01 | 0.06 ± 0.00 |
| Pancreas | 191 ± 14 | 139 ± 26 | 25 ± 1 | 0.35 ± 0.02 | 0.21 ± 0.05 | 0.03 ± 0.01 |
| Kidney | 761 ± 60 | 1181 ± 232 | 338 ± 49 | 1.76 ± 0.14 | 2.84 ± 0.61 | 0.81 ± 0.09 |
| Lung | 603 ± 30 | 415 ± 39 | 44 ± 4 | 1.04 ± 0.02 | 0.80 ± 0.06 | 0.09 ± 0.01 |
| Heart | 320 ± 8 | 190 ± 15 | 19 ± 0 | 0.32 ± 0.01 | 0.19 ± 0.01 | 0.02 ± 0.00 |
| Brain | 38 ± 6 | 22 ± 2 | 4 ± 4 | 0.10 ± 0.03 | 0.06 ± 0.00 | 0.01 ± 0.01 |
| Muscle**** | 93 ± 5 | 56 ± 3 | 8 ± 1 | 0.06 ± 0.02 | 0.04 ± 0.00 | 0.00 ± 0.00 |
| Tumor | 246 ± 25 | 266 ± 87 | 56 ± 4 | 0.25 ± 0.05 | 0.37 ± 0.14 | 0.04 ± 0.01 |
| Femur | 115 ± 3 | 81 ± 10 | 9 ± 1 | 0.39 ± 0.02 | 0.28 ± 0.03 | 0.03 ± 0.00 |
| Mesentric lymph nodes | 291 ± 29 | 179 ± 16 | 50 ± 6 | 0.08 ± 0.01 | 0.05 ± 0.01 | 0.02 ± 0.00 |
| Peripheral lymph nodes | 284 ± 19 | 254 ± 14 | 51 ± 5 | 0.13 ± 0.00 | 0.14 ± 0.02 | 0.02 ± 0.00 |
| Stomach (empty) | 244 ± 17 | 165 ± 21 | 19 ± 2 | 0.56 ± 0.07 | 0.40 ± 0.05 | 0.05 ± 0.00 |
| Intestine (empty) | 242 ± 15 | 201 ± 32 | 36 ± 5 | 1.55 ± 0.09 | 1.16 ± 0.22 | 0.26 ± 0.04 |
| Blood** | 957 ± 38 | 575 ± 56 | 22 ± 1 | 26.73 ± 0.84 | 16.13 ± 1.77 | 0.61 ± 0.03 |
| The remainder of the body* | 419 ± 27 | 392 ± 25 | 42 ± 0 | 70.71 ± 2.74 | 64.27 ± 5.50 | 6.81 ± 0.16 |
| Urine 0–24 h | — | — | 619 ± 19 | — | — | 79.86 ± 3.13 |
| Feces 0–24 h | — | — | 781 ± 611 | — | — | 6.00 ± 4.91 |
| | | | =Sum of the organs*** | 80.06 ± 2.84 | 72.94 ± 5.83 | 9.21 ± 0.27 |
| | | | Balance** | | | 95.07 ± 2.41 |

*Blood samples are contained in the remainder of the body
**58 ml Blut/kg KGW = 58 ml of blood/kg of body weight
Balance without blood values, since the latter [are] contained in the remainder of the body
Only tissue aliquot

Figure 14:
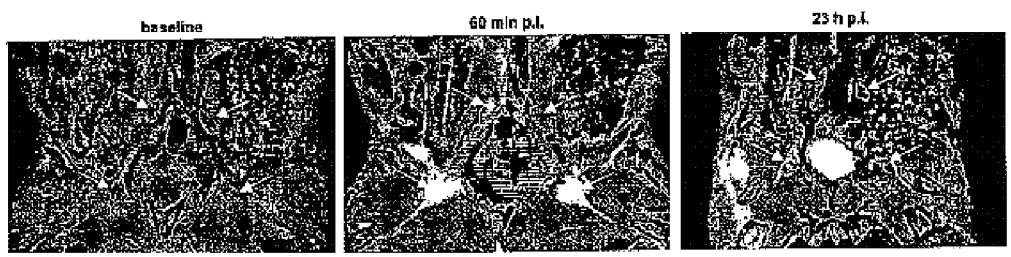
FIG. 14 closed arrow points to inguinal and iliacal lymph nodes. Visualization after administration of metal complex XIV, flash outphase, TR/TE 10/5 ms, α 40°.

EXAMPLE 131
Lymph Node Visualization (MRT) After Intravenous Administration of the Contrast Medium in Guinea Pigs By way of example, the pictures in FIG. 14 show MR images of iliac and inguinal lymph nodes precontrast and up to 24 hours after intravenous administration of 200 µmol of Gd/kg of body weight of metal complex XIV in guinea pigs with stimulated lymph nodes (Freund adjuvant). The $T_1$-weighted gradient-echo images (2.0 T; TR 10 ms, TE 5 ms, a 40°) illustrate the strong signal rise in healthy lymph node tissue even very shortly after injection. The enhancement was 127% at the time of 60 minutes p.i.

Figure 15:
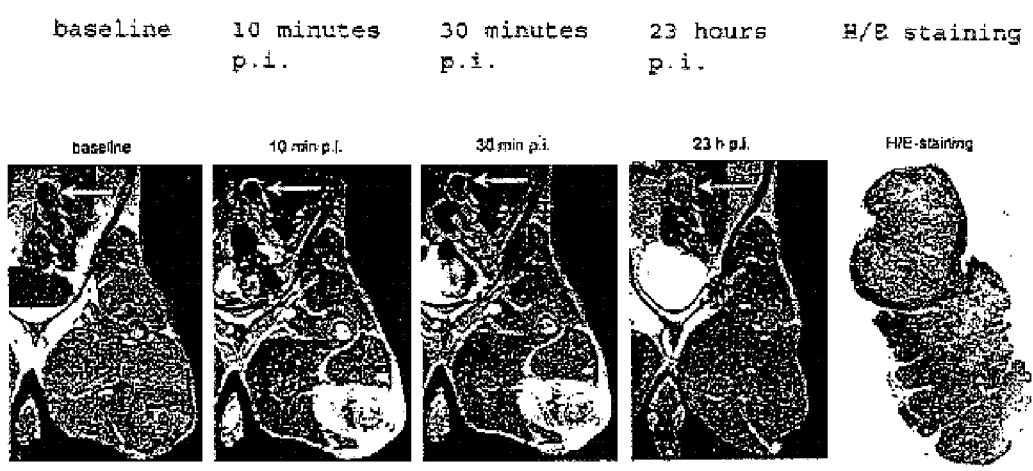
FIG. 15 depicts the visualization of inguinal and iliacal lymph nodes after administration of metal complex XIV, flash outphase, TR/TE 10/5 ms , α 40°.

EXAMPLE 132
Lymph Node Visualization (MRT) After Intravenous Administration of the Contrast Medium in VX2-t-tumor-bearing Rabbits By way of example, the pictures in FIG. 15 show MR images of iliac lymph nodes precontrast and up to 23 hours after intravenous administration of 200 µmol of Gd/kg of body weight of metal complex XIV in rabbits with VX2-tumors implanted i.m. The $T_1$-weighted gradient-echo images (1.5 T; sequence: MPRange; TR 11.1 ms, TE 4.3 ms, α 15°) illustrate the strong signal rise in healthy lymph node tissue. The enhancement in the healthy lymph node tissue was 297% at the time of 10 minutes p.i. and 269% at the time of 60 minutes p.i. Zones without signal rise within the lymph node were diagnosed as metastases and confirmed histologically (H/E-staining of the lymph node section). The ratio of signal intensities of healthy lymph node tissue to metastasis was 5.1 at the time of 10 minutes p.i. and 1.9 at the time of 60 minutes p.i.

Surprisingly enough, even immediately after administration, a considerable enhancement not only of the lymph nodes but also of the primary tumor (especially the periphery) could be observed (15 minutes p.i.: 594%). Later (up to 24 hours p.i.), this enhancement also propagates out from the center of the tumor (120 hours p.i.: 162%).

Metal Complex III

EXAMPLE 133

Figure 16:
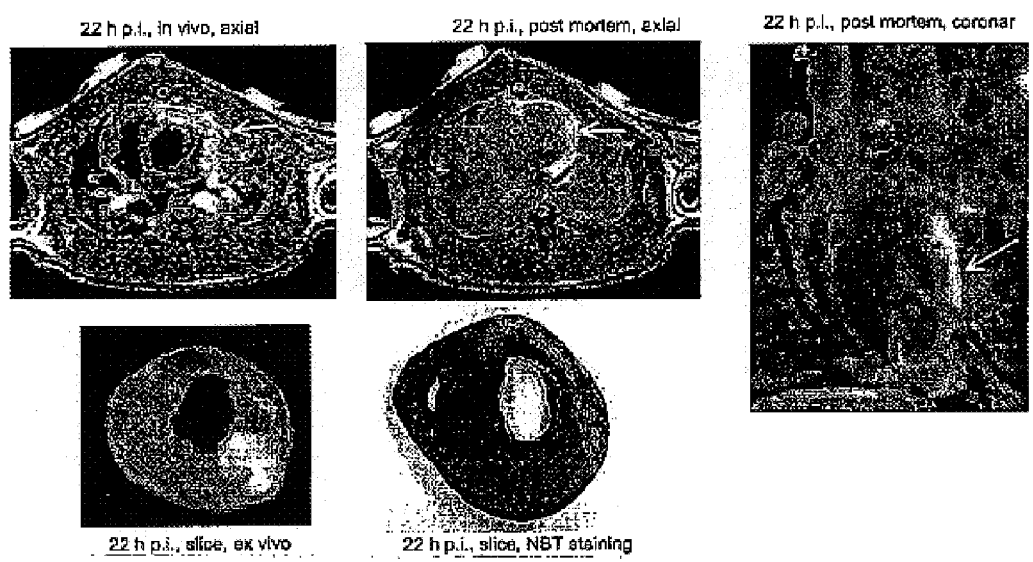
FIG. 16 depicts the visualization of myocardial infarct after administration of metal complex III, 100 µmol/kg i.v.; SE, , TR/TE 400/12 ms.

Infarction Visualization (MRT) After Intravenous Administration of the Contrast Medium in Rats The pictures in FIG. 16 show MR images of the heart (in vivo and post mortem) 22 hours after intravenous administration of 100 µmol of Gd/kg of body weight of a polar Gd-chelate with perfluorinated side chains (metal complex III) in rats with acutely induced myocardial infarction. The $T_1$-weighted, EKG-triggered spin-echo images (1.5 T; TR (effective): 400 ms, TE: 12 ms; NA: 4; matrix: 128*128; layer thickness: 2.5 mm) illustrate the strong signal rise in the infarction area. The successful induction of an acute myocardial infarction was confirmed by means of NBT-staining.

EXAMPLE 134

Organ Distribution (Including Lymph Node Concentration) After Intravenous Administration of the Contrast Medium in Rats After intravenous administration of 200 µmol of total gadolinium/kg of body weight of a polar Gd-chelate with perfluorinated side chains (metal complex III) in rats, the metal content in various organs as well as in the lymph nodes (pooled as mesenteric and peripheral lymph nodes) was determined 24 hours after administration (MW, n=2).

| Oragn | μmol Gd/L | % Dose |
|---|---|---|
| Liver | 1222 | 26.28 |
| Femur | 76 | 0.32 |
| Kidneys | 489 | 1.97 |
| Brain | 10 | 0.05 |
| Carcass | 242 | 36.30 |
| Blood | 83 | 1.15 |
| Stomach | 165 | 0.57 |
| Intestine | 230 | 3.56 |
| Spleen | 464 | 0.89 |
| Pancreas | 203 | 0.48 |
| Heart | 82 | 0.13 |
| Lung | 338 | 0.96 |
| Muscle | 28 | 0.04 |
| Mesenteric lymph nodes | 455 | 0.33 |
| Peripheral lymph nodes | 279 | 0.18 |
| Total | | 73.20 |

Figure 17:
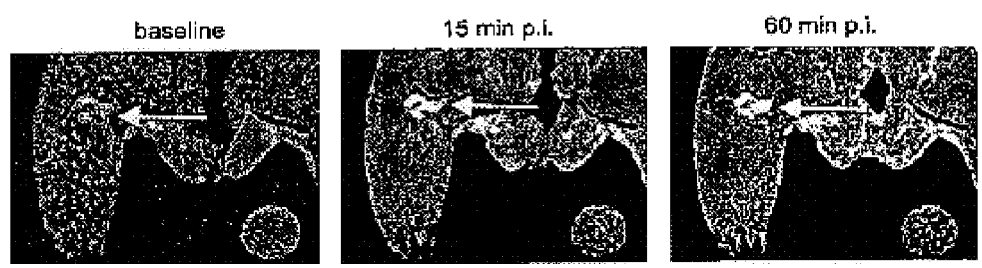
FIG. 17 depicts the visualization of popliteal lymph nodes after administration of metal complex III, 200 µmol/kg i.v.; 3D-T1-MPRange, TR/TE 11.1/4.3 ms, α 15°.

EXAMPLE 135
Lymph Node Visualization (MRT) After Intravenous Administration of the Contrast Medium in Rats By way of example, the pictures in FIG. 17 show MR images of iliac lymph nodes precontrast and up to 60 minutes after intravenous administration of 200 μmol of Gd/kg of body weight of metal complex III in rats. The $T_1$-weighted gradient-echo images (1.5 T; sequence: MPRange; TR 11.1 ms, TE 4.3 ms, α 15°) illustrate the strong signal rise in healthy lymph node tissue even very shortly after injection. The enhancement was thus 320% at the time of 15 minutes p.i. and 401% at the time of 60 minutes p.i.

Figure 18:
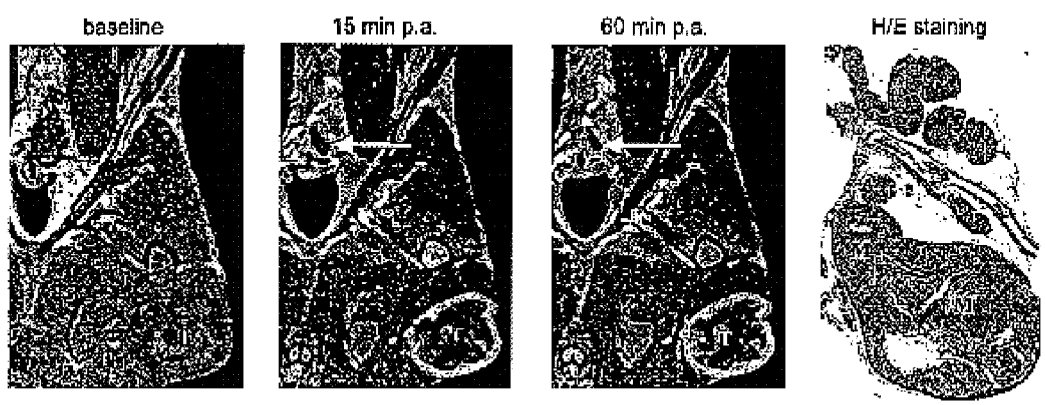
FIG. 18 depicts visualization of matastases and tumors after administration of metal complex III, 200 µmol/kg i.v.; 3D-T1-MPRange, TR/TE 11.1/4.3 ms, α 15°.

EXAMPLE 136
Lymph Node Visualization (MRT) After Intravenous Administration of the Contrast Medium in VX2-tumor-bearing Rabbits By way of example, the pictures in FIG. 18 show MR images of iliac lymph nodes precontrast and up to 60 minutes after intravenous administration of 200 μmol of Gd/kg of body weight of metal complex III in rabbits with VX2-tumors implanted i.m. The $T_1$-weighted gradient-echo images (1.5 T; sequence: MPRange; TR 11.1 ms, TE 4.3 ms, α 15°) illustrate the strong signal rise in healthy lymph node tissue. The enhancement in the healthy lymph node tissue was 195% at the time of 15 minutes p.i. and 233% at the time of 60 minutes p.i. Zones without signal rise within the lymph node were diagnosed as metastases and confirmed histologically (H/E-staining of the lymph node section). The ratio of signal intensities of healthy lymph node tissue to metastasis was 1.9 at the time of 15 minutes p.i. and 1.8 at the time of 60 minutes p.i. Surprisingly enough, even immediately after administration, a considerable enhancement not only of the lymph nodes but also of the primary tumor (especially the periphery) could be observed (15 minutes p.i.: 232%).

What is claimed is:

1. A method for MRI imaging comprising:
administering to a patient an MRI contrast agent, comprising a perfluoroalkyl-containing metal complex that has a critical micelle formation concentration $<10^{-3}$ mol/l, a hydrodynamic micelle diameter (2 Rh)>1 nm and a proton relaxivity in plasma ($R^1$)>10 l/mmol·s, allowing the uptake of contrast agent in tissue, conducting MRI imaging, and visualizing plaque in which contrast agent is uptaken, or independently simultaneously visualizing necroses and tumors in which contrast agent is uptaken.

2. A method according to claim 1, wherein the metal complex has a micelle formation concentration of $<10^{-4}$ mol/l.

3. A method according to claim 1, wherein the metal complex has a hydrodynamic micelle diameter of >3 nm.

4. A method according to claim 1, wherein the metal complex has a proton relaxivity in plasma of >13 l/mmol·s.

5. A method according to claim 1, wherein the perfluoroalkyl-containing metal complex is a compound of formula I $$R^F\text{—}L\text{—}K \qquad\qquad I$$

in which $R^F$ is a perfluorinated, straight-chain or branched carbon chain with formula —$C_nF_{2n}$E, in which
E is a terminal fluorine, chlorine, bromine, iodine or hydrogen atom and n is a number from 4–30, L is a direct bond, a methylene group, an —NHCO— group, a group

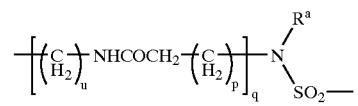

whereby p is a number from 0 to 10, and q and n, independently of one another, are 0 or 1, and $R^a$ is a hydrogen atom, a methyl group, a —$CH_2$—OH group, a —$CH_2$—$CO_2$H group or a $C_2$-$C_{15}$ alkyl, which optionally is interrupted by 1 to 3 oxygen atoms, 1 to 2 CO groups or an optionally substituted aryl group and/or is substituted with 1 to 4 hydroxyl groups, 1 to 2 $C_1$-$C_4$ alkoxy groups, 1 to 2 carboxy groups, or a group —$SO_3$H, or L is a straight-chain, branched, saturated or unsaturated $C_2$-$C_{30}$ carbon chain, which optionally contains 1 to 10 oxygen atoms, 1 to 3 —$NR^a$ groups, 1 to 2 sulfur atoms, a piperazine group, a —$CONR^a$ group, an —$NR^aCO$ group, an —$SO_2$ group, an —$NR^a$—$CO_2$ group, 1 to 2 CO groups, a group —CO—N—T—N($R^a$)—$SO_2$—$R^F$, or 1 to 2 optionally substituted aryls and/or is interrupted by these groups and/or is optionally substituted with 1 to 3 —$OR^a$ groups, 1 to 2 oxo groups, 1 to 2 —NH—$COR^a$ groups, 1 to 2 —$CONHR^a$ groups, 1 to 2 —$(CH_2)_p$—$CO_2$H groups, 1 to 2 groups —$(CH_2)_p$—$(O)_q$—$CH_2CH_2$—$R^F$, whereby $R^a$, $R^F$ and p and q have the above-indicated meanings, and T is a $C_2$-$C_{10}$ chain, which optionally is interrupted by 1 to 2 oxygen atoms or 1 to 2 —NHCO groups, K is a complexing agent or metal complex of formula II

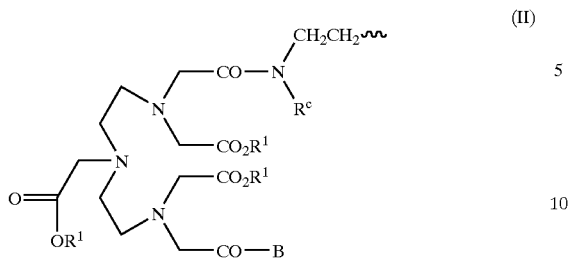
(II)

in which $R^c$, $R^1$ and B are independent of one another, and
$R^c$ is $R^a$ or is —$(CH_2)$m-L—RF, whereby m is 0, 1 or 2, and L and $R^F$ have the above-mentioned meaning,
$R^1$, independently of one another, is a hydrogen atom or a metal ion equivalent of atomic numbers 22–29, 42–46 or 58–70,
B is —$OR^1$,

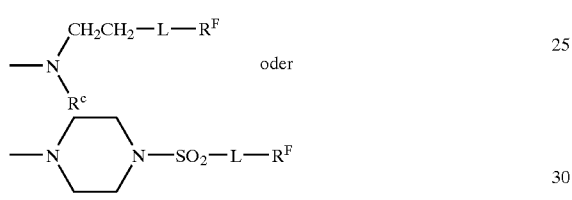
oder whereby $R^1$, L, $R^F$ and $R^c$ have the above-mentioned meanings, or K is a complexing agent or complex of formula III

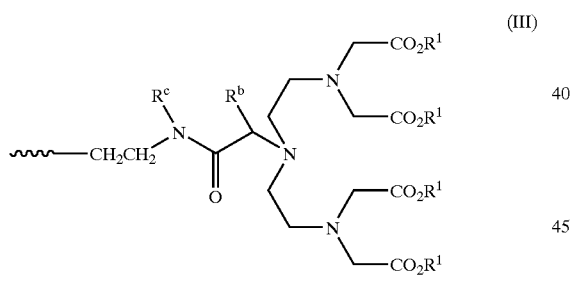
(III)

in which $R^c$ and $R^1$ have the above-mentioned meanings and $R^b$ has the meaning of $R^a$
or
K is a complexing agent or complex of formula IV

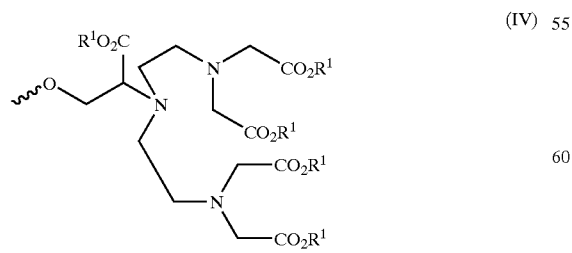
(IV)

in which $R^1$ has the above-mentioned meaning
or

K is a complexing agent or complex of formula V

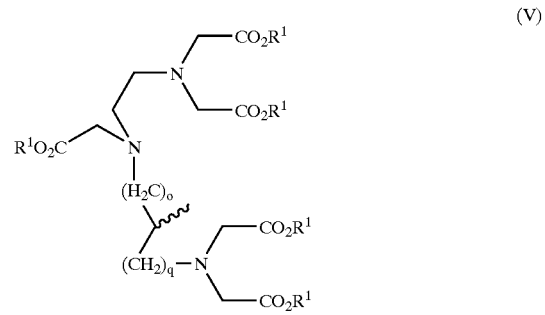
(V)

in which $R^1$ has the above-mentioned meaning, and o and q stand for numbers 0 or 1, and yields the sum o+q=1,
or
K is a complexing agent or complex of formula VI

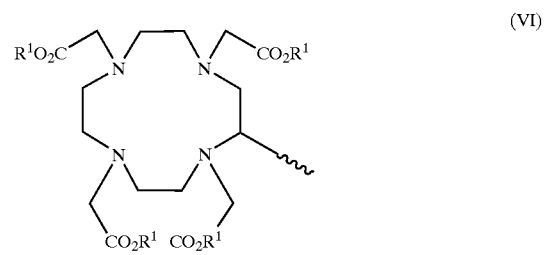
(VI)

in which $R^1$ has the above-mentioned meaning
or
K is a complexing agent or complex of formula VII

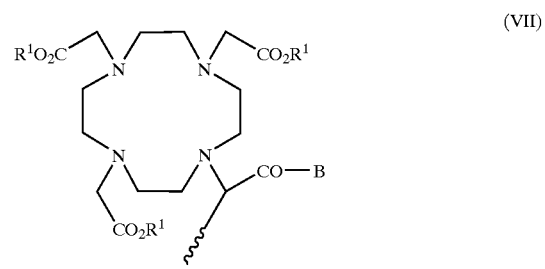
(VII)

in which $R^1$ and B have the above-mentioned meanings
or
K is a complexing agent or complex of formula VIII

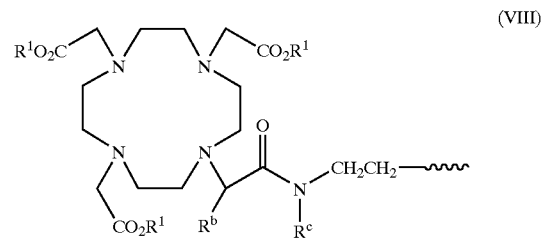
(VIII)

in which $R^c$ and $R^1$ have the above-mentioned meanings, and $R^b$ is $R^a$
or K is a complexing agent or complex of formula IX

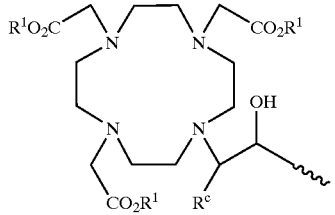
(IX)

in which $R^c$ and $R^1$ have the above-mentioned meanings,
or
K is a complexing agent or complex of formula X

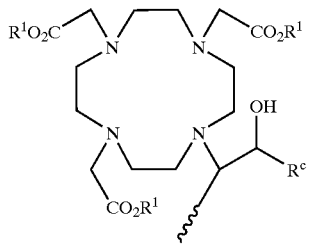
(X)

in which $R^c$ and $R^1$ have the above-mentioned meanings,
or
K is a complexing agent or complex of formula XI

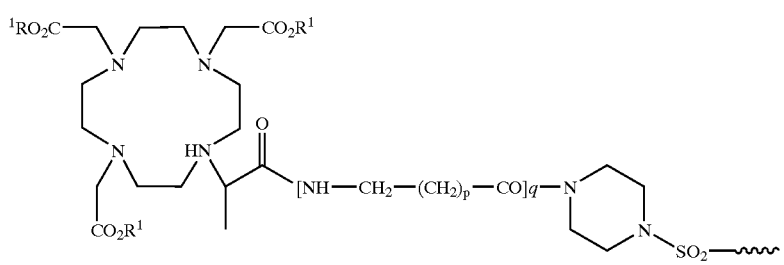
(XI)

in which $R^1$, p and q have the above-mentioned meanings,
and $R^b$ has the meaning of $R^a$,
or
K is a complexing agent or complex of formula XII

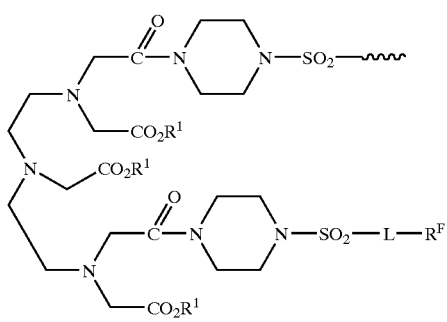
(XII)

in which L, $R^F$ and $Z^1$ have the above-mentioned meanings,
or

K is a complexing agent or complex of formula XIII

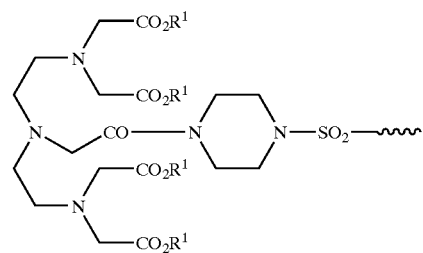
(XIII)

in which $R^1$ has the above-mentioned meaning, or
K is a salt of one of the complexing agents or complexes of formula II to XIII with an organic and/or inorganic base or amino acid or amino acid amide.

6. A method according to claim 5, wherein in the compound of formula I,
L is
$\alpha$-$CH_2$-$\beta$
$\alpha$-$CH_2CH_2$-$\beta$
$\alpha$-$(CH_2)_s$-$\beta$ s=3–15
$\alpha$-$CH_2$—O—$CH_2CH_2$-$\beta$
$\alpha$-$CH_2$—(O—$CH_2$—$CH_2$—)$_t$-$\beta$ t=2–6
$\alpha$-$CH_2$—NH—CO-$\beta$
$\alpha$-$CH_2$—NH—CO—$CH_2$—N($CH_2COOH$)—$SO_2$-$\beta$
$\alpha$-$CH_2$—NH—CO—$CH_2$—N($C_2H_5$)—$SO_2$-$\beta$
$\alpha$-$CH_2$—NH—CO—$CH_2$—N($C_{10}H_{21}$)—$SO_2$-$\beta$ $\alpha$-$CH_2$—NH—CO—$CH_2$—N($C_6H_{13}$)—$SO_2$-$\beta$
$\alpha$-$CH_2$—NH—CO—$(CH_2)_{10}$—N($C_2H_5$)—$SO_2$-$\beta$
$\alpha$-$CH_2$—NH—CO—$CH_2$—N(—$CH_2$-$C_6H_5$)—$SO_2$-$\beta$
$\alpha$-$CH_2$—NH—CO—$CH_2$—N(—$CH_2$-$CH_2$—OH) $SO_2$-$\beta$
$\alpha$-$(CH_2$—NHCO—$(CH_2)_{10}$—S—$CH_2CH_2$-$\beta$
$\alpha$-$CH_2NHCOCH_2$—O—$CH_2CH_2$-$\beta$
$\alpha$-$CH_2NHCO(CH_2)_{10}$—$CH_2CH_2$-$\beta$
$\alpha$-$CH_2$—$C_6H_4$—O—$CH_2CH_2$-$\beta$
$\alpha$-$CH_2$—O—$CH_2$—C($CH_2$—$OCH_2CH_2$—$C_6F_{13}$)$_2$—$CH_2$—$OCH_2$-$CH_2$-$\beta$
$\alpha$-$CH_2$—$NHCOCH_2CH_2CON$—$CH_2CH_2NHCOCH_2N$ ($C_2H_5$)$SO_2C_8F_{17}$ $CH_2$—$CH_2NHCOCH_2N(C_2H_5)$—$SO_2$-$\beta$
$\alpha$-$CH_2$—O—$CH_2$—$CH(OC_{10}OH_{21})$—$CH_2$—O—$CH_2CH_2$-$\beta$
$\alpha$-$(CH_2NHCO)_4$—$CH_2$—$CH_2CH_2$-$\beta$
$\alpha$-$(CH_2NHCO)_3$—$CH_2$—$CH_2CH_2$-$\beta$
$\alpha$-$CH_2$—$OCH_2C(CH_2OH)_2$—$CH_2$—O—$CH_2CH_2$-$\beta$ $\alpha$-CH$_2$-O-[benzene ring with CH$_2$-O-$\beta$ and COOH substituents]

α-CH$_2$NHCOCH$_2$N(C$_6$H$_5$)SO$_2$-β
α-NHCO—CH$_2$—CH$_2$-β
α-NHCO—CH$_2$—O—CH$_2$CH$_2$-β
α-NH—CO-β
α-NH—CO—CH$_2$—N(CH$_2$COOH)—SO$_2$-β
α-NH—CO—CH$_2$—N(C$_2$H$_5$)—SO$_2$-β
α-NH—CO—CH$_2$—N(C$_{10}$H$_{21}$)—SO$_2$-β
α-NH—CO—CH$_2$—N(C$_6$H$_{13}$)—SO$_2$-β
α-NH—CO—(CH$_2$)$_{10}$—N(C$_2$H$_5$)—SO$_2$-β
α-NH—CO—CH$_2$—N(—CH$_2$—C$_6$H$_5$)—SO$_2$-β
α-NH—CO—CH$_2$—N(—CH$_2$—CH$_2$—OH)SO$_2$-β
α-NH—CO—CH$_2$-β
α-CH$_2$—O—C$_6$H$_4$—O—CH$_2$—CH$_2$-β
α-CH$_2$—C$_6$H$_4$—O—CH$_2$—CH$_2$-β
α-N(C$_2$H$_5$)—SO$_2$-β
α-N(C$_6$H$_5$)—SO$_2$-β
α-N(C$_{10}$H$_{21}$)—SO$_2$-β
α-N(C$_6$H$_{13}$)—SO$_2$-β
α-N(C$_2$H$_4$OH)—SO$_2$-β
α-N(CH$_2$COOH)—SO$_2$-β
α-N(CH$_2$C$_6$H$_5$)—SO$_2$-β
α-N-[CH(CH$_2$OH)$_2$]—SO$_2$-β or
α-N-[CH(CH$_2$OH)CH(CH$_2$OH)]—SO$_2$-β, in which α is the binding site to the complexing agent or metal complex K, and β is the binding site to the fluorine radical.

7. A method according to claim 5, wherein the compound of formula I, is a compound in which n in formula —C$_n$F$_{2n}$E is a number from 4–15 and/or E is a fluorine atom.

8. A method according to claim 5, wherein the compound of formula I is:

Gadolinium complex of 10-[1-methyl-2-oxo-3-aza-5-oxo-{4-perfluorooctylsulfonyl-piperazin-1-yl}-pentyl]-1,4,7-tris(carbonylmethyl)-1,4,7,10-tetraazacyclododecane, Gadolinium complex of 10-[2-hydroxy-4-aza-5-oxo-7-oxa-10,10,11,11,12,12,13,13,14,14,15,15,16,16,17,17-heptadecafluoroheptadecyl]-1,4,7-tris(carbonylmethyl)-1,4,7,10-tetraazacyclododecane, Gadolinium complex of 10-[$_2$-hydroxy4-aza-5,9-dioxo-9-{4-perfluorooctyl)-piperazin-1-yl}-nonyl]-1,4,7-tris(carbonylmethyl)-1,4,7,10-tetraazacyclododecane, Gadolinium complex of 10-[$_2$-hydroxy4-aza-5-oxo-7-aza-7-(perfluorooctyl-sulfonyl)-nonyl]-1,4,7-tris(carboxymethyl)-1,4,7,10-tetraazacyclododecane, Gadolinium complex of 10-[$_2$-hydroxy-4-oxa-1H,1H,2H,3H,3H,5H,5H,6H,6H-perfluorotetradecyl]-1,4,7-tris(carboxymethyl)-1,4,7,10-tetraazacyclododecane, Gadolinium complex of 10-[$_2$-hydroxy-4-aza-5-oxo-7-oxa-10,10,11,11,12,12,13,13,14,14,15,15,16,16,17,17,18,18,19,19-henicosafluoro-nonadecyl]-1,4,7-tris(carboxymethyl)-1,4,7,10-tetraazacyclododecane, Gadolinium complex of 10-[$_2$-hydroxy-4-aza-5-oxo-1-aza-11-(perfluorooctylsulfonyl)-tridecyl]-1,4,7-tris(carboxymethyl)-1,4,7,10-tetraazacyclododecane, or Gadolinium complex of 10-[$_2$-hydroxy-4-aza-5-oxo-7-aza-7-(perfluorooctylsulfonyl)-8-phenyl-octyl]-1,4,7-tris(carboxymethyl)-1,4,7,10-tetraaza-cyclododecane.

9. A method according to claim 1, wherein the perfluoroalkyl-containing metal complex, is a compound of formula Ia $$A—R^F \qquad (Ia)$$

in which
A is a group that contains 2 to 6 metal complexes, which are bonded directly or via a linker to a nitrogen atom of an annular skeleton chain, and
$R^F$ is a perfluorinated, straight-chain or branched carbon chain with formula —C$_n$F$_{2n}$E, in which
E is a terminal fluorine, chlorine, bromine, iodine or hydrogen atom, and n is a number from 4–30,
whereby A has the following structure:

[cyclic structure with N atoms bearing K—V— substituents and N—D—X— substituent, with q$^1$ group]

whereby
$q^1$ is 0, 1, 2 or 3,
K is a complexing agent or metal complex or a salts thereof with an organic and/or inorganic base or amino acid or amino acid amide,
X as the point of attachment to $R^F$, is a direct bond, a phenylene group or a C$_1$–C$_{10}$ alkylene chain, which optionally contains 1–15 oxygen atoms, 1–5 sulfur atoms, 1–10 carbonyl groups, 10-10 (NR$^d$) groups, 1–2 NR$^d$SO$_2$ groups, 1–10 CONR$^d$ groups, 1 piperidine group, 1–3 SO$_2$ groups and/or 1–2 phenylene groups or optionally is substituted by 1–3 radicals $R^F$, in which $R^d$ is a hydrogen atom, a phenyl group, benzyl group or a C$_1$–C$_{15}$ alkyl group, which optionally contains 1–2 NHCO, 1–2 CO groups, 1–5 oxygen atoms and optionally is substituted by 1–5 hydroxy, 1–5 methoxy, 1–3 carboxy, or 1–3 $R^F$ radicals,
V is a direct bond or a chain of formula IIa or IIIa:

$$\beta—\underset{\underset{R^e}{|}}{N}—(CH_2)_k—(W)_t—(CH_2)_m—\overset{O}{\overset{\|}{C}}—\alpha \qquad (IIa)$$

(IIIa)
[structure showing β—N(H)—CH$_2$—C(O)—N(H)— attached to benzene ring with (CH$_2$)$_{0-5}$—C(O)—α and K—N(H)—CH$_2$—C(O)—N(H)— substituent]

in which
$R^e$ is a hydrogen atom, a phenyl group, a benzyl group or a C$_1$–C$_7$ alkyl group, which optionally is substituted with a carboxy group, a methoxy group or a hydroxy group, W is a direct bond, a polyglycol ether group with up to 5 glycol units, or a group of formula IVa —CH(R$^b$)— (IVa)

in which R$^h$ is a C$_1$–C$_7$ carboxylic acid, a phenyl group, a benzyl group or a —(CH$_2$)$_{1-5}$—NH—K group, α is the binding to the nitrogen atom of the skeleton chain, β is the binding to complexing agent or metal complex K, and in which variables k and m stand for natural numbers between 0 and 10, and l is 0 or 1 and whereby

D is a CO or SO$_2$ group.

10. A method according to claim 9, wherein the compound of formula Ia is a compound in which q$^1$ is the number 1.

11. A method according to claim 9, wherein the compound of formula Ia is a compound in which X is an alkylene chain, which contains 1–10 —CH$_2$CH$_2$O— groups or 1–5 —COCH$_2$NH— groups, a direct bond or one of the following structures

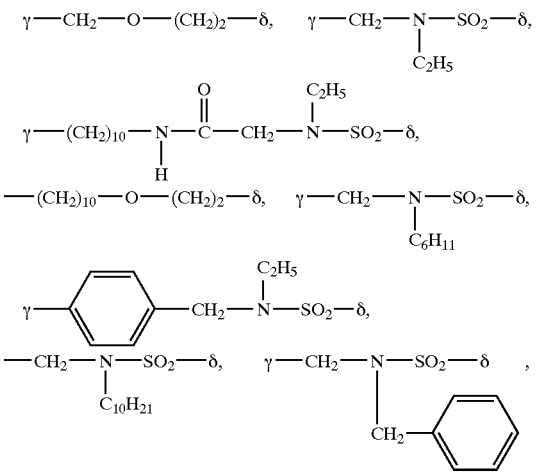

whereby

γ binds to D, and δ binds to R$^F$.

12. A method according to claim 9, wherein the compound of formula Ia, is a compound in which V is a group with one of the following structures

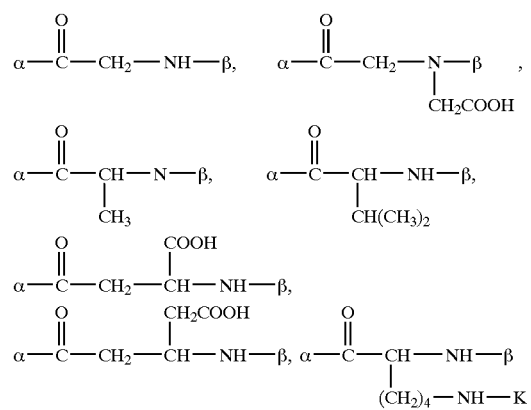

13. A method according to claim 9, wherein the compound of formula Ia, is a compound in which K is a complexing agent or complex of formula Va, VIa, VIIa or VIIIa,

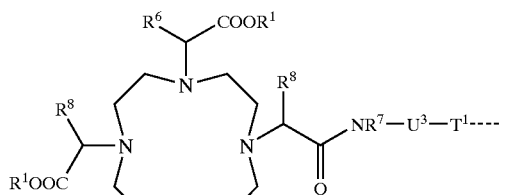

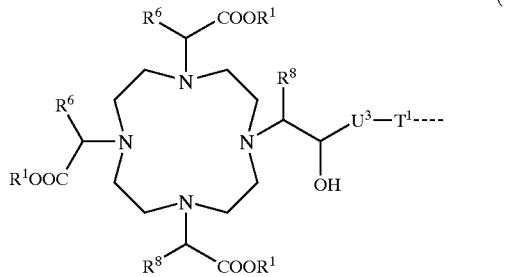

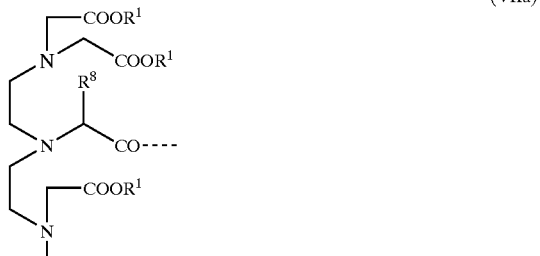

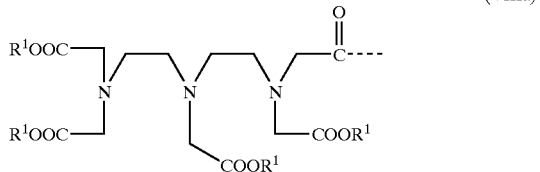

whereby

R$^1$, independently of one another, are a hydrogen atom or a metal ion equivalent of the elements of atomic numbers 23–29, 42–46 or 58–70, R$^8$ is a hydrogen atom or a straight-chain, branched, saturated or unsaturated C$_1$–C$_{30}$ alkyl chain, which optionally is substituted by 1–5 hydroxy, 1–3 carboxy or 1 phenyl group(s) and/or optionally is interrupted by 1–10 oxygen atoms, 1 phenylene group or 1 phenylenoxy group, R$^6$ are independently a hydrogen atom, a straight-chain or branched C$_1$–C$_7$ alkyl radical, a phenyl radical or benzyl radical, R$^7$ is a hydrogen atom, a methyl group or ethyl group, which optionally is substituted by a hydroxy group or carboxy group, U$^3$ is a straight-chain, branched, saturated or unsaturated C$_1$–C$_{20}$ alkylene group optionally containing 1–5 imino groups, 1–3 phenylene groups, 1–3 phenylenoxy groups, 1–3 phenylenimino groups, 1–5 amide groups, 1–2 hydrazide groups, 1–5 carbonyl groups, 1–5 ethylenoxy groups, 1 urea group, 1 thiourea group, 1–2 carboxyalkylimino groups, 1–2 ester groups, 1-1-0 oxygen atoms, 1–5 sulfur atoms and/or 1–5 nitrogen atoms, and/or optionally substituted by 1–5 hydroxy groups, 1–2 mercapto groups, 1–5 oxo groups, 1–5 thioxo groups, 1–3 carboxy groups, 1–5 carboxyalkyl groups, 1–5 ester groups and/or 1–3 amino groups, whereby the optionally contained phenylene groups can be substituted by 1–2 carboxy groups, 1–2 sulfone groups or 1–2 hydroxy groups $T^1$ is a -CO—β, —NHCO-β or —NHCS-β group, whereby β is the binding site to V.

14. A method according to claim 13, wherein the $C_1$–$C_{20}$ alkylene chain that is $U^3$ contains the group —$CH_2NHCO$—, —$NHCOCH_2O$—, —$NHCOCH_2OC_6H_4$—, —$N(CH_2CO_2H)$—, —$CH_2OCH_2$—, —$NHCOCH_2C_6H_4$—, —$NHCSNHC_6H_4$—, —$CH_2OC_6H_4$—, or —$CH_2CH_2O$— and/or is substituted by the group —COOH and/or —$CH_2COOH$.

15. A method according to claim 13, wherein $U^3$ is a —$CH_2$—, —$CH_2CH_2$—, —$CH_2CH_2CH_2$—, —$CH_4$—, —$C_6H_{10}$—, —$CH_2C_6H_4$—, —$CH_2NHCOCH_2CH(CH_2CO_2H)$—$C_6H_4$—, —$CH_2NHCOCH_2OCH_2$—, or —$CH_2NHCOCH_2C_6H_4$— group.

16. A method according to claim 9, wherein the compound of formula Ia, is a compound in which K has one of the following structures:

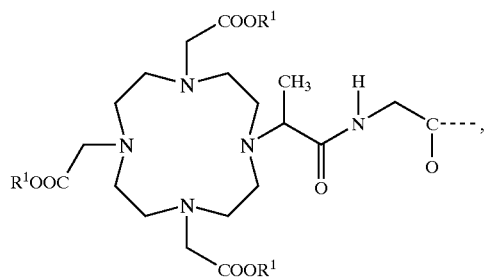

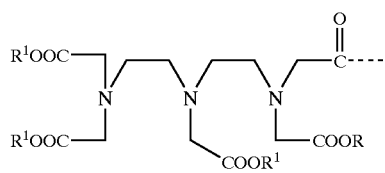

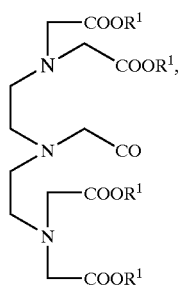

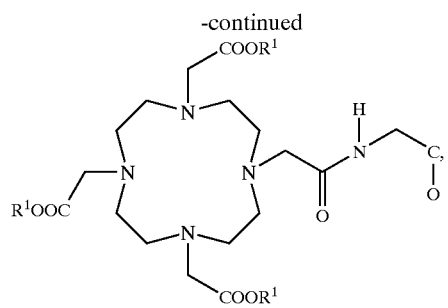

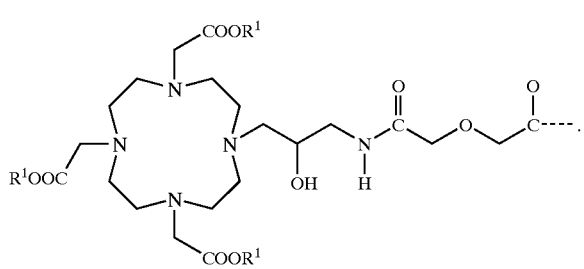

17. A method according to claim 9, wherein the compound of formula Ia, is a compound in which the perfluoroalkyl chain is $R^F$ is —$C_6F_{13}$, —$C_8F_{17}$, —$C_{10}F_{21}$ or —$C_{12}F_{25}$.

18. A method according to claim 9, wherein the compound of formula Ia is a gadolinium complex of 1,4,7-tris{1,4,7-tris(N-(carboxylatomethyl)-10-[N-1-methyl-3,6-diaza-2,5,8-trioxooctane-1,8-diyl)]-1,4,7,10-tetraazacyclododecane, Gd complex}-10-[N-2H,2H, 4H,4H, 5H,5H-3-oxa-perfluorotridecanoyl]-1,4,7,10-tetraazacyclododecane.

19. A method according to claim 1, wherein the perfluoroalkyl-containing metal complex, is a compound of formula Ib

in which

K is a complexing agent or a metal complex of formula IIb

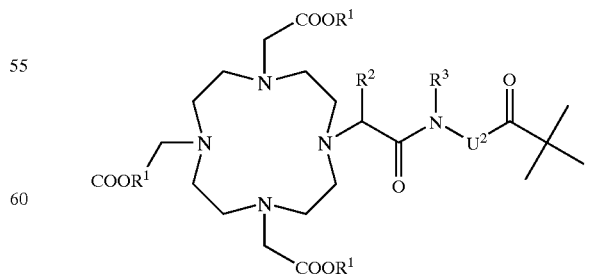

whereby $R^1$ is a hydogenatom or a metal ion equivalent of atomic numbers 23–29, 42–46 or 58–70, R² and R³ are independently a hydrogen atom, a $C_1$–$C_7$ alkyl group, a benzyl group, a phenyl group, —$CH_2OH$ or —$CH_2$—$OCH_3$, U² is radical L¹, whereby L¹ and U², independently of one another, can be the same or different, A¹ is a hydrogen atom, a straight-chain or branched $C_1$–$C_{30}$ alkyl group, which optionally is interrupted by 1–15 oxygen atoms, and/or optionally is substituted with 1–10 hydroxy groups, 1–2 COOH groups, a phenyl group, a benzyl group and/or 1–5 —OR⁹ groups, with R⁹ having the meaning of a hydrogen atom or a $C_1$–$C_7$ alkyl radical, or —L¹—$R^F$, L¹ is a straight-chain or branched $C_1$–$C_{30}$ alkylene group, which optionally is interrupted by 1–10 oxygen atoms, 1–5 —NH—CO groups, 1–5 —CO—NH groups, by a phenylene group optionally substituted by a COOH— group, 1–3 sulfur atoms, 1–2 —N(B¹)—$SO_2$ groups and/or 1–2 —$SO_2$—N(B¹)groups with B¹ in the meaning of A¹, an NHCO group, a CONH group, an N(B¹)—$SO_2$ group or an —$SO_2$—N(B¹) group and/or optionally is substituted with radical $R^F$, and $R^F$ is a straight-chain or branched perfluorinated alkyl radical of formula $C_nF_{2n}E$, whereby n is number 4–30, and E is a terminal fluorine atom, chlorine atom, bromine atom, iodine atom or a hydrogen atom, and optionally present acid groups optionally can be present as salts of organic and/or inorganic bases or amino acids or amino acid amides.

20. A method according to claim 19, wherein the compound of formula Ib, is a compound in which R², R³ and R⁹, independently of one another, mean hydrogen or a $C_1$–$C_4$ alkyl group.

21. A method according to claim 19, wherein the compound of formula Ib, is a compound in which A¹ is hydrogen, a $C_1$–$C_5$ alkyl radical, or the radicals $C_2H_4$—O—$CH_3$, $C_3H_6$—O—$CH_3$,
$C_2H_4$—O—($C_2H_4$—O)$_t$—$C_2H_4$—OH,
$C_2H_4$—O—($C_2H_4$—O)$_t$—$C_2H_4$—$OCH_3$,$C_2H_4OH$,
$C_3H_6OH$, $C_4H_8OH$, $C_5H_{10}OH$, $C_6H_{12}OH$, $C_7H_4OH$,
CH(OH)$CH_2OH$,
CH(OH)CH(OH)$CH_2OH$, $CH_2$[CH(OH)]$_{u^1}CH_2OH$,
CH[$CH_2$(OH)]CH(OH)$CH_2OH$,
$C_2H_4$CH(OH)$CH_2OH$,
($CH_2$)$_s$COOH,
$C_2H_4$—O—($C_2H_4$—O)$_t$—$CH_2$COOH, or
$C_2H_4$—O—($C_2H_4$—O)$_t$—$C_2H_4$—$C_nF_{2n}E$
whereby
s is integers 1 to 15,
t is integers 0 to 13,
u¹ is integers 1 to 10,
n is integers 4 to 20, and
E is hydrogen, fluorine, chlorine, bromine or iodine atoms, and optionally, their branched isomers.

22. A method according to claim 19, wherein the compound of formula Ib, is a compound in which A¹ is hydrogen, $C_1$–$C_{10}$ alkyl, $C_2H_4$—O—$CH_3$, $C_3H_6$—O—$CH_3$,
$C_2H_4$—O—($C_2H_4$—O)$_x$—$C_2H_4$—OH, $C_2H_4$—O—($C_2H_4$—O)$_x$—$C_2H_4$—$OCH_3$,
$C_2H_4OH$, $C_3H_6OH$,
$CH_2$[CH(OH)]$_y$$CH_2OH$,
CH[$CH_2$(OH)]CH(OH)$CH_2OH$,
($CH_2$)$_w$COOH,
$C_2H_4$—O—($C_2H_4$—O)$_x$—$CH_2$COOH or
$C_2H_4$—O—($C_2H_4$—O)$_x$—$C_2H_4$—$C_nF_{2n}E$,
whereby
x is integers 0 to 5,
y is integers 1 to 6,
w is integers 1 to 10,
n is integers 4 to 15, and
E is a fluorine atom, and, optionally, their branched isomers.

23. A method according to claim 19, wherein the compound of formula Ib, is a compound in which L¹ is α-($CH_2$)$_s$-β
α-$CH_2$—$CH_2$—(O—$CH_2$—$CH_2$—)$_y$-β
α-$CH_2$—(O—$CH_2$—$CH_2$—)$_y$-β,
α-$CH_2$—NH—CO-β
α-$CH_2$—$CH_2$—NH—$SO_2$-β
α-$CH_2$—NH—CO—$CH_2$—N($CH_2$COOH)—$SO_2$-β
α-$CH_2$—NH—CO—$CH_2$—N($C_2H_5$)—$SO_2$-β
α-$CH_2$—NH—CO—$CH_2$—N($C_{10}H_{21}$)—$SO_2$-β
α-$CH_2$—NH—CO—$CH_2$—N($C_6H_{13}$)—$SO_2$-β
α-$CH_2$—NH—CO—($CH_2$)$_{10}$—N($C_2H_5$)—$SO_2$-β,
α-$CH_2$—NH—CO—$CH_2$—N(—$CH_2$—$C_6H_5$)—$SO_2$-β
α-$CH_2$—NH—CO—$CH_2$—N(—$CH_2$—$CH_2$—OH)$SO_2$-β
α-$CH_2$—NHCO—($CH_2$)$_{10}$—S—$CH_2CH_2$-β
α-$CH_2$NHCO$CH_2$—O—$CH_2CH_2$-β
α-$CH_2$—$CH_2$NHCO$CH_2$—O—$CH_2CH_2$-β
α-$CH_2$-($CH_2$—$CH_2$—O)$_r$—($CH_2$)$_3$NHCO—$CH_2$—O—$CH_2CH_2$-β
α-$CH_2$NHCO($CH_2$)$_{10}$—O—$CH_2CH_2$-β
α-$CH_2$$CH_2$NHCO($CH_2$)$_{10}$—O—$CH_2CH_2$-β
α-$CH_2$-$C_6H_4$—O—$CH_2CH_2$-β whereby the phenylene group 1,4 or 1,3 is linked
α-$CH_2$—O—$CH_2$-C($CH_2$—$OCH_2CH_2$-$C_6F_{13}$)$_2$—$CH_2$—$OCH_2$—$CH_2$-β
α-$CH_2$—NHCO$CH_2CH_2$CON—$CH_2CH_2$NHCOC$H_2$N($C_2H_5$)$SO_2C_8F_{17}$β
α-$CH_2$—$CH_2$NHCO$CH_2$N($C_2H_5$)—$SO_2$-β
α-$CH_2$—O—$CH_2$—CH(O$C_{10}OH_{21}$)—$CH_2$—O—$CH_2CH_2$-β
α-($CH_2$NHCO)$_4$—$CH_2$—$CH_2CH_2$-β
α-($CH_2$NHCO)$_3$—$CH_2$O—$CH_2CH_2$-β
α-$CH_2$—$OCH_2$C($CH_2$OH)$_2$—$CH_2$—O—$CH_2CH_2$-β

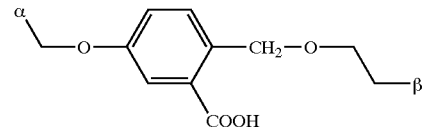

α-$CH_2$NHCOC$H_2$N($C_6H_5$)—$SO_2$-β
α-NHCO—$CH_2$—$CH_2$-β
α-NHCO—$CH_2$—O—$CH_2CH_2$-β
α-NH—CO-β
α-NH—CO—$CH_2$—N($CH_2$COOH)—$SO_2$-β
α-NH—CO—$CH_2$—N($C_2H_5$)—$SO_2$-β
α-NH—CO—$CH_2$—N($C_{10}H_{21}$)—$SO_2$-β
α-NH—CO—$CH_2$—N($C_6H_{13}$)—$SO_2$-β

α-NH—CO—(CH$_2$)$_{10}$—N(C$_2$H$_5$)—SO$_2$-β
α-NH—CO—CH$_2$—N(—CH$_2$—C$_6$H$_5$)—SO$_2$-β
α-NH—CO—CH$_2$—N(—CH$_2$—CH$_2$—OH)SO$_2$-β
α-NH—CO—CH$_2$-β
α-CH$_2$—O—C$_6$H$_4$—O—CH$_2$—CH$_2$-β
α-CH$_2$-C$_6$H$_4$—O—CH$_2$—CH$_2$-β
α-N(C$_2$H$_5$)—SO$_2$-β
α-N(C$_6$H$_5$)—SO$_2$-β
α-N(C$_{10}$H21)—SO$_2$-β
α-N(C$_6$H$_{13}$)—SO$_2$-β
α-N(C$_2$H$_4$OH)—SO$_2$-β
α-N(CH$_2$COOH)—SO$_2$-β
α-N(CH$_2$C$_6$H$_5$)—SO$_2$-β
α-N-[CH(CH$_2$OH)$_2$]—SO$_2$-β, or
α-N-[CH(CH$_2$OH)CH(OH)(CH$_2$OH)]—SO$_2$-β
whereby
s is integers 1 to 15 and
y is integers 1 to 6.

24. A method according to claim 19, wherein the compound of formula Ib, is a compound in which L$^1$ is
α-CH$_2$—O—CH$_2$CH$_2$-β,
α-CH$_2$—CH$_2$—(O—CH$_2$—CH$_2$)$_y$-β,
α-CH$_2$—(O—CH$_2$—CH$_2$—)$_y$-β,
α-CH$_2$—CH$_2$—NH—SO$_2$-β,
α-CH$_2$NHCOCH$_2$—O—CH$_2$CH$_2$-β
α-CH$_2$—CH$_2$NHCOCH$_2$—O—OH$_2$CH$_2$-β
α-CH$_2$—(CH$_2$—CH$_2$—O)$_y$—CH$_2$) $_3$NHCO—CH$_2$—O—CH$_2$CH$_2$-β
α-CH$_2$NHCO(CH$_2$)$_{10}$—O—CH$_2$CH$_2$-β
α-CH$_2$CH$_2$NHCO(CH$_2$)$_{10}$—O—CH$_2$CH$_2$-β
α-CH$_2$—O—CH$_2$—CH(OC$_{10}$OH$_{21}$)—CH$_2$—O—CH$_2$CH$_2$-β
α-CH$_2$—O—C$_6$H$_4$—O—CH$_2$—CH$_2$-β or
α-CH$_2$-C$_6$H$_4$—O—CH$_2$—CH$_2$-β
whereby
y is an interger from 1 to 6.

25. A method according to claim 19, wherein the compound of formula Ib, is a compound in which R$^F$ is a straight-chain or branched perfluorinated alkyl radical of formula C$_n$F$_{2n}$E, whereby n is a number from 4 to 15 and E stands for a terminal fluorine atom.

26. A method according to claim 19, wherein the compound of formula Ib is a:

1,4,7-Tris(carboxylatomethyl)-10-(3-aza4-oxo-hexan-5-ylic)-acid-(2,3-dihydroxypropyl)-N-(1H,1H,2H,2H, 4H,4H, 5H,5H-3-oxa)-perfluorotridecyl)-amide]-1,4,7, 10-tetraazacyclododecane, gadolinium complex, 1,4,7-Tris(carboxylatomethyl)-10-{(3-aza4-oxo-hexan-5-ylic)acid-N-(3,6,9,12,15-pentaoxa)-hexadecyl)-(1H, 1H,2H,2H, 4H,4H,5H,5H-3-oxa)-perfluorotridecyl]-amide}-1,4,7,10-tetraazacyclododecane, gadolinium complex, 1,4,7-Tris(carboxylatomethyl)-10-{(3-aza4-oxo-hexan-5-ylic)-acid-N-5-hydroxy-3-oxa-pentyl)—N-(1H,1H,2H, 2H, 4H,4H,5H,5H-3-oxa)-perfluorotridecyl]-amide}-1,4,7,10-tetraazacyclododecane, gadolinium complex, 1,4,7-Tris(carboxylatomethyl)-10-{(3-aza4-oxo-hexan-5-ylic)-acid-[N-3,6,9,15-tetraoxa-12-aza-15-oxo-C$_7$-C$_{26}$-hepta-decafluor)hexacosyl]-amide }-1,4,7,10-tetraazacyclododecane, gadolinium complex, or 1,4,7-Tris(carboxylatomethyl)-10-[(3-aza-4-oxo-hexan-5-ylic]-acid—N-(2-methoxyethyl)—N-(1H,1H,2H,2H, 4H,4H,5H,5H-3-oxa)-perfluorotridecyl]-amide -1,4,7, 10-tetraazacyclododecane, gadolinium complex.

27. A method according to claim 5, wherein the perfluoroalkyl-containing metal complex is in a galenical formulation that contains a paramagnetic, perfluoroalkyl-containing metal complex of formula I, and a diamagnetic perfluoroalkyl-containing substance, optionally dissolved in an aqueous solvent, wherein the diamagnetic perfluoroalkyl-containing substance is a compound of formula XX $$R^F—L^2—B^2 \quad (XX)$$

in which R$^F$ is a straight-chain or branched perfluoroalkyl radical with 4 to 30 carbon atoms, L$^2$ is a linker and B$^2$ is a hydrophilic group.

28. A method according to claim 27, wherein linker L$^2$ is a direct bond, an —SO$_2$ group, or a straight-chain or branched carbon chain with 1 to 20 carbon atoms, which can be substituted with one or more —OH, —COO, —SO$_3$ groups and/or optionally contains one or more —O—, —S—, —CO—, —CONH—, —NHCO—, —CONR$^9$, —NR$^9$CO—, —SO$_2$—, —PO$_4$—, —NH— or —NR$^9$ groups, an aryl ring or a piperazine, whereby R$^9$ is a C$_1$ to C$_{20}$ alkyl radical, which in turn can contain one or more 0 atoms, and/or can be substituted with —COO— or SO$_3$ groups.

29. A method according to claim 27, wherein hydrophilic group B$^2$ is a mono- or disaccharide, with one or more adjacent —COO$^-$ or —SO$_3$ groups, a dicarboxylic acid, an isophthalic acid, a picolinic acid, a benzenesulfonic acid, a tetrahydropyrandicarboxylic acid, a 2,6-pyridinedicarboxylic acid, a quaternary ammonium ion, an aminopolycarboxylic acid, an aminodipolyethylene glycol-sulfonic acid, an aminopolyethylene glycol group, an SO$_2$—(CH$_2$)$_2$—OH group, a polyhydroxyalkyl chain with at least two hydroxyl groups or one or more polyethylene glycol chains with at least two glycol units, whereby the polyethylene glycol chains are terminated by an —OH or —OCH$_3$ group.

30. A method according to claim 3, wherein the metal complex has a hydrodynamic micelle diameter of >4 nm.

31. A method according to claim 4, wherein the metal complex has a proton relaxivity in plasma of >15 l/mmol·s.

32. A method according to claim 9, wherein the perfluoroalkyl-containing metal complex is in a galenical formulation that contains a paramagnetic, perfluoroalkyl-containing metal complex of formula Ia and diamagnetic perfluoroalkyl-containing substance, optionally dissolved in an aqueous solvent.

33. A method according to claim 19, wherein the perfluoroalkyl-containing metal complex is in a galenical formulations that contains a paramagnetic, perfluoroalkyl-containing metal complex of formula Ib, and a diamagnetic perfluoroalkyl-containing substance, optionally dissolved in an aqueous solvent.

34. A method according to claim 1, wherein plaque in which contrast agent is uptaken is visualized.

35. A method according to claim 1, wherein necroses and tumors in which contrast agent is uptaken are independently and simultaneously visualized.

* * * * *

UNITED STATES PATENT AND TRADEMARK OFFICE
CERTIFICATE OF CORRECTION

PATENT NO. : 6,818,203 B2
APPLICATION NO. : 09/925618
DATED : November 16, 2004
INVENTOR(S) : Johannes Platzek et al.

It is certified that error appears in the above-identified patent and that said Letters Patent is hereby corrected as shown below:

Column 183, line 17, reads "-$(CH_2)$m-L-RF," should read -- "-$(CH_2)$m-L-$R^F$, --
Column 183, line 25, reads "oder" should read -- or --
Column 185, line 30, reads "$^1RO_2C$" should read -- $R^1O_2C$ --
Column 186, line 52, reads "α-$(CH_2$" should read -- α-$CH_2$ --
Column 186, line 54, reads "α-$CH_2NHCO(CH_2)_{10}$-$CH_2CH_2$-β" should read
-- α-$CH_2NHCO(CH_2)_{10}$-O-$CH_2CH_2$-β --
Column 186, line 63, reads "$(OC_{10}OH_{21})$" should read -- $(OC_{10}H_{21})$ --
Column 186, line 65, reads "-$CH_2$-$CH_2CH_2$-β" should read -- -$CH_2$O-$CH_2CH_2$-β --
Column 186, line 66, reads "-$CH_2$-$CH_2CH_2$-β" should read -- -$CH_2$O-$CH_2CH_2$-β --
Column 187, line 8, reads "$C_6H_5)SO_2$-β" should read -- $C_6H_5$)-$SO_2$-β --
Column 187, line 18, reads "OH)$SO_2$-β" should read -- OH)-$SO_2$-β --
Column 187, line 35, reads "formula I, is" should read -- formula I is --
Column 187, line 41, reads "(carbonylmethyl)" should read -- (carboxymethyl) --
Column 187, line 46, reads "(carbonylmethyl)" should read -- (carboxymethyl) --
Column 187, line 47, reads "10-[$_2$-hydroxy4-aza" should read -- 10-[2-hydroxy-4-aza --
Column 187, line 49, reads "(carbonylmethyl)" should read -- (carboxymethyl) --
Column 187, line 51, reads "10-[$_2$-hydroxy4-aza" should read -- 10-[2-hydroxy-4-aza --
Column 187, line 54, reads "10-[$_2$-hydroxy-4-aza" should read -- 10-[2-hydroxy-4-aza --
Column 187, line 57, reads "10-[$_2$-hydroxy-4-aza" should read -- 10-[2-hydroxy-4-aza --
Column 187, line 62, reads "10-[$_2$-hydroxy-4-aza" should read -- 10-[2-hydroxy-4-aza --
Column 187, line 62, reads "5-oxo-1-" should read -- 5-oxo-11- --
Column 187, line 64, reads "tetraazacyclododecanc," should read
-- tetraazacyclododecane, --
Column 187, line 65, reads "10-[$_2$-hydroxy-4-aza" should read -- 10-[2-hydroxy-4-aza --
Column 189, line 4, reads "-CH($R^b$)-" should read -- -CH($R^h$)- --
Column 189, line 12, reads "and 1 is 0 or 1" should read -- and I is 0 or 1 --
Column 189, line 20, reads "-$CH_2CH_{20}$- groups" should read -- -$CH_2CH_2$O- groups --
Column 190, line 9, reads "$R^8$" should read -- $R^6$ --
Column 190, line 26, reads "$R^8$" should read -- $R^6$ --
Column 191, line 1, reads "I urea group," should read -- 1 urea group, --
Column 191, line 2, reads "1-1-0" should read -- 1-10 --

UNITED STATES PATENT AND TRADEMARK OFFICE
CERTIFICATE OF CORRECTION

PATENT NO.       : 6,818,203 B2
APPLICATION NO. : 09/925618
DATED            : November 16, 2004
INVENTOR(S)      : Johannes Platzek et al.

It is certified that error appears in the above-identified patent and that said Letters Patent is hereby corrected as shown below:

Column 191, line 25, reads "-$CH_4$-," should read -- -$C_6H_4$ --
Column 191, line 31, reads "formula Ia, is" should read -- formula Ia is --
Column 191, line 52, reads "COOR" should read -- $COOR^1$ --
Column 192, line 29, reads "chain is $R^F$ is" should read -- chain $R^F$ is --
Column 192, line 66, reads "hydrogenatom" should read -- hydrogen atom --
Column 193, line 18, reads "-$SO_2$-N($B^1$)groups" should read -- -$SO_2$-N($B^1$)- groups" --
Column 193, line 32, reads "formula Ib, is" should read -- formula Ib is --
Column 193, line 41, reads "$C_4H_{80}H$," should read -- $C_4H_8OH$, --
Column 193, line 59, reads "formula Ib, is" should read -- formula Ib is --
Column 194, line 14, reads "formula Ib, is" should read -- formula Ib is --
Column 194, line 38, reads "α-$CH_2$-$C_6H_4$-O-$CH_2CH_2$-βwhereby" should read
-- α-$CH_2$-$C_6H_4$-O-$CH_2CH_2$-β whereby --
Column 194, line 48, reads "α-$(CH_2NHCO)_4$-$CH_2$-$CH_2CH_2$-β" should read
-- α-$(CH_2NHCO)_4$-$CH_2$O-$CH_2CH_2$-β --
Column 195, line 11, reads "α-N($C_{10}$H21)-$SO_2$-β" should read -- α-N($C_{10}H_{21}$)-$SO_2$-β --
Column 195, line 23, reads "formula Ib, is" should read -- formula Ib is --
Column 195, line 30, reads "α-$CH_2$-$CH_2NHCOCH_2$-O-$OH_2CH_2$-β" should read
-- α-$CH_2$-$CH_2NHCOCH_2$-O-$CH_2CH_2$-β --
Column 195, line 31, reads "α-$CH_2$-$(CH_2$-$CH_2$-O$)_y$-$CH_2$)" should read
-- α-$CH_2$-$(CH_2$-$CH_2$-O$)_y$-$(CH_2)$ --
Column 195, line 36, reads "($OC_{10}OH_{21}$)" should read -- ($OC_{10}H_{21}$) --
Column 195, line 38, reads "βor" should read -- β or --
Column 195, line 42, reads "an interger" should read -- an integer --
Column 195, line 44, reads "formula Ib, is" should read -- formula Ib is --
Column 196, line 1, reads "$C_7$-$C_{26}$" should read -- $C_{17}$-$C_{26}$ --
Column 196, line 5, reads "-amide –1,4,7," should read -- -amide}-1,4,7, --
Column 196, line 24, reads "-$CONR^9$," should read -- -$CONR^9$-, --
Column 196, line 25, reads "-$NR^9$" should read -- -$NR^9$- --
Column 196, line 26, reads "one or more 0" should read -- one or more O --

UNITED STATES PATENT AND TRADEMARK OFFICE
CERTIFICATE OF CORRECTION

PATENT NO. : 6,818,203 B2
APPLICATION NO. : 09/925618
DATED : November 16, 2004
INVENTOR(S) : Johannes Platzek et al.

It is certified that error appears in the above-identified patent and that said Letters Patent is hereby corrected as shown below:

Column 196, line 55, reads "formulations that contains" should read -- formulation that contains --

Signed and Sealed this

Fifteenth Day of December, 2009

David J. Kappos
*Director of the United States Patent and Trademark Office*